United States Patent
Li et al.

(10) Patent No.: US 12,186,343 B2
(45) Date of Patent: Jan. 7, 2025

(54) METHOD AND COMPOSITION FOR TREATING TUMORS

(71) Applicant: CRAGE medical Co., Limited, Hong Kong (CN)

(72) Inventors: Zonghai Li, Shanghai (CN); Huamao Wang, Shanghai (CN); Min Zhou, Shanghai (CN)

(73) Assignee: CRAGE MEDICAL CO., LIMITED, Hong Kong (CN)

( * ) Notice: Subject to any disclaimer, the term of this patent is extended or adjusted under 35 U.S.C. 154(b) by 957 days.

(21) Appl. No.: 16/979,102

(22) PCT Filed: Mar. 8, 2019

(86) PCT No.: PCT/CN2019/077529
§ 371 (c)(1),
(2) Date: Sep. 8, 2020

(87) PCT Pub. No.: WO2019/170147
PCT Pub. Date: Sep. 12, 2019

(65) Prior Publication Data
US 2022/0110973 A1    Apr. 14, 2022

(30) Foreign Application Priority Data

| Mar. 9, 2018 | (CN) | 201810196524.0 |
| Jul. 20, 2018 | (CN) | 201810806560.4 |
| Sep. 6, 2018 | (CN) | 201811039594.1 |
| Dec. 7, 2018 | (CN) | 201811495012.0 |

(51) Int. Cl.
| *A61K 35/17* | (2015.01) |
| *A61K 31/337* | (2006.01) |
| *A61K 31/675* | (2006.01) |
| *A61K 31/7076* | (2006.01) |
| *A61K 38/17* | (2006.01) |
| *A61K 47/64* | (2017.01) |
| *A61P 35/00* | (2006.01) |
| *C07K 16/46* | (2006.01) |
| *A61K 39/00* | (2006.01) |

(52) U.S. Cl.
CPC ............ *A61K 35/17* (2013.01); *A61K 31/337* (2013.01); *A61K 31/675* (2013.01); *A61K 31/7076* (2013.01); *A61K 38/1774* (2013.01); *A61K 47/643* (2017.08); *A61P 35/00* (2018.01); *A61K 39/4611* (2023.05); *A61K 39/4631* (2023.05); *A61K 2039/545* (2013.01); *A61K 2239/38* (2023.05)

(58) Field of Classification Search
CPC .... A61K 2039/5156; A61K 2039/5158; A61K 35/17; A61K 2039/545
See application file for complete search history.

(56) References Cited

U.S. PATENT DOCUMENTS

| 6,040,177 | A | 3/2000 | Riddell et al. | |
| 7,446,190 | B2 | 11/2008 | Sadelain et al. | |
| 9,175,308 | B2 | 11/2015 | Shiku et al. | |
| 10,377,822 | B2 | 8/2019 | Wang et al. | |
| 11,111,295 | B2* | 9/2021 | Wang | C12N 5/10 |
| 11,198,729 | B2 | 12/2021 | Wang et al. | |
| 2007/0186437 | A1 | 8/2007 | Gasteyer et al. | |
| 2016/0206656 | A1* | 7/2016 | Gilbert | A61K 45/06 |
| 2017/0204177 | A1 | 7/2017 | Wang et al. | |

FOREIGN PATENT DOCUMENTS

| CN | 103483453 A | 1/2014 |
| CN | 103820393 A | 5/2014 |
| CN | 105194661 A | 12/2015 |
| CN | 105315375 A | 2/2016 |
| CN | 105331585 A | 2/2016 |
| CN | 105713881 A | 6/2016 |
| CN | 106146666 A | 11/2016 |
| CN | 106397593 A | 2/2017 |
| CN | 106467573 A | 3/2017 |
| CN | 106519037 A | 3/2017 |
| CN | 106554414 A | 4/2017 |
| CN | 107058354 A | 8/2017 |
| CN | 107106610 A | 8/2017 |
| CN | 107460201 A | 12/2017 |
| CN | 107893052 A | 4/2018 |
| JP | 2006502117 A | 1/2006 |
| JP | 2009517354 A | 4/2009 |
| JP | 2017522024 A | 8/2017 |
| JP | 2017533904 A | 11/2017 |
| WO | WO-8909622 A1 | 10/1989 |
| WO | WO-9007861 A1 | 7/1990 |
| WO | WO-9110741 A1 | 7/1991 |
| WO | WO-9208796 A1 | 5/1992 |
| WO | WO-9402602 A1 | 2/1994 |

(Continued)

OTHER PUBLICATIONS

Paul, Fundamental Immunology, 3rd Edition, 1993, pp. 292-295.*
Rudikoff et al, Proc. Natl. Acad. Sci. USA, 1982, 79(6):1979-1983.*
Colman, Research in Immunology, 1994, 145:33-36.*
Bendig, Methods: A Companion to Methods in Enzymology, 1995; 8:83-93.*
Khantasup et al., Monoclonal Antibodies in Immunodiagnosis and Immunotherapy, 2015, 34(6): 404-417.*
Murphy et al., Journal of Immunological Methods, vol. 463, p. 127-133, 2018.*

(Continued)

*Primary Examiner* — Hong Sang
(74) *Attorney, Agent, or Firm* — WILSON SONSINI GOODRICH & ROSATI

(57) ABSTRACT

Provided in the present invention are a composition of immune effector cells and a treatment kit including the composition of immune effector cells, wherein the composition of immune effector cells comprises an initial dose of immune effector cells and a subsequent dose of immune effector cells.

20 Claims, 7 Drawing Sheets

Specification includes a Sequence Listing.

(56) References Cited

FOREIGN PATENT DOCUMENTS

| WO | WO-9428143 A1 | 12/1994 | |
|---|---|---|---|
| WO | WO-9633735 A1 | 10/1996 | |
| WO | WO-2005113587 A2 | 12/2005 | |
| WO | WO-2007059997 A1 | 5/2007 | |
| WO | WO-2012038055 A1 | 3/2012 | |
| WO | WO-2013051718 A1 | 4/2013 | |
| WO | WO-2014055668 A1 | 4/2014 | |
| WO | WO-2014075788 A1 | 5/2014 | |
| WO | WO-2014180306 A1 | 11/2014 | |
| WO | WO-2015113576 A1 | 8/2015 | |
| WO | WO-2016008405 A1 | 1/2016 | |
| WO | WO-2015172339 A8 | 2/2016 | |
| WO | WO-2016064929 A1 | 4/2016 | |
| WO | WO-2016160621 A2 | 10/2016 | |
| WO | WO-2016180468 A1 * | 11/2016 | ......... A61K 39/0011 |
| WO | WO-2016180782 A1 * | 11/2016 | ......... A61K 39/0011 |
| WO | WO-2016191756 A1 * | 12/2016 | ............ A61K 31/664 |
| WO | 2017/165571 A1 | 9/2017 | |
| WO | WO-2017186121 A1 * | 11/2017 | ............. A61K 35/17 |
| WO | WO-2018006882 A1 * | 1/2018 | ............ A61K 31/282 |
| WO | WO-2019047932 A1 * | 3/2019 | ............. A61K 35/17 |

OTHER PUBLICATIONS

English Translation of the International Search Report mailed Jun. 17, 2019 corresponding to PCT/CN2019/077529 filed Mar. 8, 2019; 4 pages.
Alonso-Camino et al.: CARbodies: Human Antibodies Against Cell Surface Tumor Antigens Selected From Repertoires Displayed on T Cell Chimeric Antigen Receptors. Mol. Ther. Nucleic Acids. 2(5):e93 (2013).
Beatty et al. Chimeric antigen receptor T cells are vulnerable to immunosuppressive mechanisms present within the tumor microenvironment. Oncoimmunology 3(11):e970027 (2014).
Brash, Douglas E et al. Strontium Phosphate Transfection of Human Cells in Primary Culture: Stable Expression of the Simian Virus 40 Large-t-antigen Gene in Primary Human Bronchial Epithelial Cells. Molecular and Cellular Biology vol. 7,5: pp. 2031-2034 (1987).
Brentjens, et al. CAR T Update Part 2: Challenges and Opportunities in Solid Tumors. Published by the Memorial Sloan Kettering Cancer Center, New York, NY. at https://www.mskcc.org/clinical-updates/car-update-part-2-challenges-and-opportunities-solid-tumors . 16 pages as printed. (Year: 2020).
Brown, Christine, et al., Regression of Glioblastoma after Chimeric Antigen Receptor T-Cell Therapy. The New England Journal of Medicine 375(26):2561-9 (2016).
Carlens et al.: Ex vivo T lymphoccyte expansion for retroviral transduction: Influence of serum-free media on variations in cell expansion rates and lymphocyte subset distribution. Exp. Hematol. 28(10):1137-1146 (2000).
Carpenito et al. Control of large, established tumor xenografts with genetically retargeted human T cells containing CD28 and CD137 domains. PNAS USA 106(9):3360-3365 (2009).
Cartellieri, et al., Chimeric antigen receptor-engineered T cells for immunotherapy of Cancer, J Biomed Biotechnol, 2010, 1-10. Doi : 10.1155/2010/956304.
Casucci, Monica, et al., Overcoming the toxicity hurdles of genetically targeted T cells. Cancer Immunology 64(1):123-30 (2015).
Cavaletti, Guido, et al., Chemotherapy-induced Peripheral Neurotoxicity. Nature Reviews. Neurology 6(12):657-666 (2010).
Cavalieri, et al., Human T lymphocytes transduced by lentiviral vectors in the absence of TCR activation maintain an intact immune competence. Blood 102(2):497-505 (2003).
Chicaybam, Leonardo, et al., An Efficient Low Cost Method for Gene Transfer to T Lymphocytes. PloS one 8(3):e60298 (2013).
Citation in opposition procedure—D1—WO2015/113576 A1 + sequence listing. Opposition by BioNTech Cell & Gene Therapies GmbH filed Jun. 4, 2020 against EP3170842 Application No. 15821331.4. Consolidated List of Cited Opposition Documents reference D1. BioNTech Cell & Gene Therapies GmbH reference D3. 134 pages.
Citation in opposition procedure—D10—English machine translation of D6. Opposition by BioNTech Cell & Gene Therapies GmbH filed Jun. 4, 2020 against EP3170842 Application No. 15821331.4. Consolidated List of Cited Opposition Documents reference D10. BioNTech Cell & Gene Therapies GmbH reference D6a. 33 pages.
Citation in opposition procedure—D11—Sadelain et al. 2013, Cancer Discovery 3: 388-398. Opposition by BioNTech Cell & Gene Therapies GmbH filed Jun. 4, 2020 against EP3170842 Application No. 15821331.4. Consolidated List of Cited Opposition Documents reference D11. BioNTech Cell & Gene Therapies GmbH reference D7. 11 pages.
Citation in opposition procedure—D12—EP3170842 (opposed patent). Opposition by BioNTech Cell & Gene Therapies GmbH filed Jun. 4, 2020 against EP3170842 Application No. 15821331.4. Consolidated List of Cited Opposition Documents reference D12. BioNTech Cell & Gene Therapies GmbH reference D8. 53 pages.
Citation in opposition procedure—D13—English-language translation of the application as filed PCT/CN2015/084023 (published in Chinese as WO 2016/008405), as filed by the Patentee at the European Patent Office on Jan. 30, 2017. Opposition by BioNTech Cell & Gene Therapies GmbH filed Jun. 4, 2020 against EP3170842 Application No. 15821331.4. Consolidated List of Cited Opposition Documents reference D13. BioNTech Cell & Gene Therapies GmbH reference D8a. 57 pages.
Citation in opposition procedure—D14—CN201410341504. Opposition by BioNTech Cell & Gene Therapies GmbH filed Jun. 4, 2020 against EP3170842 Application No. 15821331.4. Consolidated List of Cited Opposition Documents reference D14. BioNTech Cell & Gene Therapies GmbH reference D9. 51 pages.
Citation in opposition procedure—D15—WO 2016/180782 A1 + sequence listing. Opposition by BioNTech Cell & Gene Therapies GmbH filed Jun. 4, 2020 against EP3170842 Application No. 15821331.4. Consolidated List of Cited Opposition Documents reference D15. BioNTech Cell & Gene Therapies GmbH reference D10. 164 pages.
Citation in opposition procedure—D16—WO 2016/180468 (priority document of D10). Opposition by BioNTech Cell & Gene Therapies GmbH filed Jun. 4, 2020 against EP3170842 Application No. 15821331.4. Consolidated List of Cited Opposition Documents reference D16. BioNTech Cell & Gene Therapies GmbH reference D10a. 160 pages.
Citation in opposition procedure—D17—EP3294333, publication of regional phase of D10. Opposition by BioNTech Cell & Gene Therapies GmbH filed Jun. 4, 2020 against EP3170842 Application No. 15821331.4. Consolidated List of Cited Opposition Documents reference D17. BioNTech Cell & Gene Therapies GmbH reference D10b. 1 page.
Citation in opposition procedure—D18—Annex to D10 showing a sequence alignment between SEQ ID No. 6 and SEQ ID No. 41 of D10. Opposition by BioNTech Cell & Gene Therapies GmbH filed Jun. 4, 2020 against EP3170842 Application No. 15821331.4. Consolidated List of Cited Opposition Documents reference D18. BioNTech Cell & Gene Therapies GmbH reference D10c. 1 page.
Citation in opposition procedure—D19—Annex to D10 showing the NCBI reference sequence for human CD28. Opposition by BioNTech Cell & Gene Therapies GmbH filed Jun. 4, 2020 against EP3170842 Application No. 15821331.4. Consolidated List of Cited Opposition Documents reference D19. BioNTech Cell & Gene Therapies GmbH reference D10d. 3 pages.
Citation in opposition procedure—D2—Annex to D3 showing a a sequence alignment of SEQ ID No. 6 with SEQ ID Nos. 2-4 of D3. Opposition by BioNTech Cell & Gene Therapies GmbH filed Jun. 4, 2020 against EP3170842 Application No. 15821331.4. Consolidated List of Cited Opposition Documents reference D2. BioNTech Cell & Gene Therapies GmbH reference D3a. 1 page.
Citation in opposition procedure—D20—Annex to D10 showing the NCBI reference sequence for human CD3£. Opposition by BioNTech Cell & Gene Therapies GmbH filed Jun. 4, 2020 against EP3170842 Application No. 15821331.4. Consolidated List of

(56) References Cited

OTHER PUBLICATIONS

Cited Opposition Documents reference D20. BioNTech Cell & Gene Therapies GmbH reference D10e. 3 pages.
Citation in opposition procedure—D3—EP3099706, publication of regional phase of D3. Opposition by BioNTech Cell & Gene Therapies GmbH filed Jun. 4, 2020 against EP3170842 Application No. 15821331.4. Consolidated List of Cited Opposition Documents reference D3. BioNTech Cell & Gene Therapies GmbH reference D3b. 1 page.
Citation in opposition procedure—D4—EP2765193 (WO2013/051718). Opposition by BioNTech Cell & Gene Therapies GmbH filed Jun. 4, 2020 against EP3170842 Application No. 15821331.4. Consolidated List of Cited Opposition Documents reference D4. BioNTech Cell & Gene Therapies GmbH reference D4. 62 pages.
Citation in opposition procedure—D5—WO2014/075788A1 + sequence listing. Opposition by BioNTech Cell & Gene Therapies GmbH filed Jun. 4, 2020 against EP3170842 Application No. 15821331.4. Consolidated List of Cited Opposition Documents reference D5. BioNTech Cell & Gene Therapies GmbH reference D5. 349 pages.
Citation in opposition procedure—D6—Annex to D5 showing a sequence alignment of SEQ ID No. 6 with SEQ ID Nos. 8, 15 and 46 of D5. Opposition by BioNTech Cell & Gene Therapies GmbH filed Jun. 4, 2020 against EP3170842 Application No. 15821331.4. Consolidated List of Cited Opposition Documents reference D6. BioNTech Cell & Gene Therapies GmbH reference D5a. 1 page.
Citation in opposition procedure—D7—Annex to D5 showing a sequence alignment of SEQ ID No. 6 with SEQ ID No. 38 of D5. Opposition by BioNTech Cell & Gene Therapies GmbH filed Jun. 4, 2020 against EP3170842 Application No. 15821331.4. Consolidated List of Cited Opposition Documents reference D7. BioNTech Cell & Gene Therapies GmbH reference D5b. 1 page.
Citation in opposition procedure—D8—Annex to D5 showing a sequence alignment of SEQ ID No. 4 with SEQ ID Nos. 6, 11 and 46 of D5. Opposition by BioNTech Cell & Gene Therapies GmbH filed Jun. 4, 2020 against EP3170842 Application No. 15821331.4. Consolidated List of Cited Opposition Documents reference D8. BioNTech Cell & Gene Therapies GmbH reference D5c. 1 page.
Citation in opposition procedure—D9—CN103483453, cited in the ISR as D3. Opposition by BioNTech Cell & Gene Therapies GmbH filed Jun. 4, 2020 against EP3170842 Application No. 15821331.4. Consolidated List of Cited Opposition Documents reference D9. BioNTech Cell & Gene Therapies GmbH reference D6. 58 pages.
Citation in opposition procedure—Exhibit A—Alignment SEQ ID_19 with eGFP+SEQID 4. Amino acid sequences contributing to the extracellular binding region of SEQ ID No. 19-22. Opposition by BioNTech Cell & Gene Therapies GmbH filed Jun. 4, 2020 against EP3170842 Application No. 15821331.4. 2 pages.
Citation in opposition procedure—Exhibit B—Alignment SEQ ID_20 with eGFP+SEQID 4. Amino acid sequences contributing to the extracellular binding region of SEQ ID No. 19-22. Opposition by BioNTech Cell & Gene Therapies GmbH filed Jun. 4, 2020 against EP3170842 Application No. 15821331.4. 2 pages.
Citation in opposition procedure—Exhibit C—Alignment SEQ ID_21 with eGFP+SEQID 6. Amino acid sequences contributing to the extracellular binding region of SEQ ID No. 19-22. Opposition by BioNTech Cell & Gene Therapies GmbH filed Jun. 4, 2020 against EP3170842 Application No. 15821331.4. 2 pages.
Citation in opposition procedure—Exhibit D—Alignment SEQ ID_22 with eGFP+SEQID 6. Amino acid sequences contributing to the extracellular binding region of SEQ ID No. 19-22. Opposition by BioNTech Cell & Gene Therapies GmbH filed Jun. 4, 2020 against EP3170842 Application No. 15821331.4. 2 pages.
Consolidated list of cited opposition documents. Opposition by BioNTech Cell & Gene Therapies GmbH filed Jun. 4, 2020 against EP3170842 Application No. 15821331.4. Consolidated List of Cited Opposition Documents references D1-D20. 1 page.
Cooper, et al. T-cell clones can be rendered specific for CD19: toward the selective augmentation of the graft-versus-B-lineage leukemia effect. Blood. Feb. 15, 2003;101(4):1637-44. Epub Oct. 10, 2002.

Davies, et al. Combining CD19 redirection and alloanergization to generate tumor-specific human T cells for allogeneic cell therapy of B-cell malignancies. Cancer Res, 2010, 70(10):3915-24.
Grupp, et al., Adoptive cellular therapy, Curr Top Microbiol Immunol., 2011, 344:149-172.
Harmsen et al. Properties, production, and applications of camelid single-domain antibody fragments. Appl. Microbiol. Biotechnol. 77:13-22 (2007).
Hermans et al. The VITAL assay: a versatile fluorometric technique for assessing CTL- and NKT-mediated cytotoxicity against multiple targets in vitro and in vivo. Journal of Immunological Methods 285 (2004) 25-40.
Huang, Xin, et al., DNA Transposons for Modification of Human Primary T Lymphocytes. Methods in Molecular Biology 506:115-126 (2009).
International search report and written opinion dated Jan. 21, 2016 for PCT/CN2015/084023.
Johnston SA, et al. Biolistic Transformation: Microbes to Mice. Nature vol. 346,6286: pp. 776-777 (1990).
Kim, et al. Enhancement of LFA-1-Mediated T Cell Adhesion by Human T Lymphotropic Virus Type 1 p12. Journal of Immunology, 176(9):5463-70. Year: 2006.
Klebanoff et al. Sorting through subsets: Which T cell poulations mediate highly effective adoptive immunotherapy? J Immunother 35(9):651-660 (2012).
Kochenderfer et al.: Construction and preclinical evaluation of an anti-CD19 chimeric antigen receptor. Journal of Immunotherapy 32:689-702 (2009).
Koste L., et al., T-cell Receptor Transfer Into Human T Cells With Ecotropic Retroviral Vectors. Gene Therapy 21(5):533-538 (2014).
Lupton, Stephen D, et al., Dominant Positive and Negative Selection Using a Hygromycin Phosphotransferase-Thymidine Kinase Fusion Gene. Molecular and Cellular Biology 11(6):3374-3378 (1991).
Ma, et al. Current Progress in CAR-T Cell Therapy for Solid Tumors. Int J Biol Sci. 2019; 15(12): 2548-2560. Published online Sep. 7, 2019. doi: 10.7150/ijbs.34213.
Manuri, Pallavi V. et al.: piggyBac Transposon/Transposase System to Generate CD19-Specific T Cells for the Treatment of B-Lineage Malignancies. Hum Gene Ther. 21(4):427-437 (2010). doi: 10.1089/hum.2009.114.
Morgan, R.A., et al., Case report of a serious adverse event following the administration of T cells transduced with a chimeric antigen receptor recognizing ERBB2. Molecular Therapy, Apr. 18, 2010. pp. 843-851 vol. 18, No. 4. e-pub Feb. 23, 2010.
Mullen et al.: Transfer of the bacterial gene for cytosine deaminase to mammalian cells confers lethal sensitivity to 5-fluorocytosine: a negative selection system. Proc Natl Acad Sci U S A. 89(1): 33-37 (1992).
Nakazawa, Y. Gene-modified T-cell Therapy Using Chimeric Antigen Receptor. The Shinshu Medical Journal. 2013. vol. 61. Issue 4. pp. 197-203, Released Sep. 25, 2013. https://doi.org/10.11441/shinshumedj.61.197.
Ngo, et al., Ex vivo gene transfer for improved adoptive immunotherapy of cancer Human Molecular Genetics, 2011, 20(1): R93-99.
Notice of opposition dated Jun. 9, 2020 against EP3170842 Application No. 15821331.4 by BioNTech Cell & Gene Therapies GmbH filed Jun. 4, 2020 with non patent literature (D7) Sadelain at al., "The Basic Principles of Chimeric Antigen Receptor Design" Cancer Discovery, vol. 3, 2013. 44 pages.
Park et al., Treating cancer with genetically engineered T cells. Trends Biotechnol., 29(11):550-557 (2011).
Remington: The Science and Practice of Pharmacy. 21st Edition, Lippincott Williams & Wilkins: 4 Pages (2005).
Riddell S R, et al., Phase I Study of Cellular Adoptive Immunotherapy Using Genetically Modified Cd8+ Hiv-specific T Cells for Hiv Seropositive Patients Undergoing Allogeneic Bone Marrow Transplant. The Fred Hutchinson Cancer Research Center and the University of Washington School of Medicine, Department of Medicine, Division of Oncology. Human Gene Therapy 3(3):319-338 (1992).
Sadelain et al. The basic principles of chimeric antigen receptor design. Cancer Discov. 3(4):388-98 (2013).

(56) References Cited

OTHER PUBLICATIONS

Sahin, et al. Claudin-18 Splice Variant 2 Is a Pan-Cancer Target Suitable for Therapeutic Antibody Development. Human Cancer Biology. vol. 14. No. 23. pp. 2-13. Dec. 1, 2008.
Savoldo, et al., CD28 costimulation improves expansion and persistence of chimeric antigen receptor modified T cells in lymphoma patients, J Clin Invest, May 2011, 121 (5):1822-1826.
Sharma, Nynne, et al., Efficient Sleeping Beauty DNA Transposition From DNA Minicircles. Molecular Therapy. Nucleic Acids 2(2):e74 (2013).
Stoter, et al., Treatment of metastatic renal cell carcinoma with autologous T-lymphocytes genetically retargeted against carbonic anhydrase IX: first clinical experience, J. Clin. Oncol, 2006, 24(13): e20-e22.
Swartz, et al. Tumor microenvironment complexity: emerging roles in cancer therapy. Cancer Res. May 15, 2012;72(10):2473-80. doi: 10.1158/0008-5472.CAN-12-0122. Epub Mar. 13, 2012.
Tendeloo, Van et al., High-level transgene expression in primary human T lymphocytes and adult bone marrow CD34+ cells via electroporation-mediated gene delivery, Gene Therapy vol. 7, pp. 1431-1437; Published: Aug. 21, 2000.
Terakura et al., Generation of CD19-chimeric antigen receptor modified CD8+ T cells derived from virus-specific central memory T cells. Blood 119:72-82 (2012).
U.S. Appl. No. 15/326,974 Notice of allowance dated Apr. 12, 2019.
U.S. Appl. No. 16/448,053 Notice of Allowance dated Sep. 13, 2021.
U.S. Appl. No. 16/448,053 Office action dated Jan. 6, 2021.
U.S. Appl. No. 15/326,974 Office action dated Jan. 30, 2019.
U.S. Appl. No. 16/448,053 Office action dated Aug. 5, 2021.
U.S. Appl. No. 15/326,974 Office action dated Sep. 20, 2018.
U.S. Appl. No. 17/522,284 Notice of Allowance dated Jun. 5, 2024.
U.S. Appl. No. 17/522,284 Office Action dated Feb. 14, 2024.
Verhoeyen et al., Lentiviral Vector Gene Transfer into Human T Cells, Methods in Molecular Biology, Methods and Protocols 506:97-114, 2009.
Wang et al.: Phenotypic and Functional Attributes of Lentivirus-modified CD19-specific Human CD8+ Central Memory T Cells Manufactured at Clinical Scale. J. Immunother. 35(9):689-701 (2012).
Wigler, Michael et al. Transfer of Purified Herpes Virus Thymidine Kinase Gene to Cultured Mouse Cells. Cell 11(1):223-232 (1977).
Zhang, et al., Chimeric NKG2D-modified T cells inhibit systemic T-cell lymphoma growth in a manner involving multiple cytokines and cytotoxic pathways, Can Res 2007, 67 (22): 11029-11036.

* cited by examiner

METHOD AND COMPOSITION FOR TREATING TUMORS

TECHNICAL FIELD

The present invention belongs to the field of immunotherapy; and in particular, the present invention relates to the immune cell therapy targeting and recognizing an tumor antigen, triggering the activation of immune effector cells, and exerting anti-tumor effects.

REFERENCE TO A "SEQUENCE LISTING"

The Sequence Listing.txt, modified on Sep. 17, 2020 (79,363 bytes in size), machine format IBM-PC, MS-Windows operating system, is hereby incorporated by reference in its entirety for all purposes.

BACKGROUND

The immunotherapy for tumor has received extensive attention and applied in recent years, and especially, a milestone development in the control of human tumor has been achieved with the emergence of CAR-T technology.

Cancer cells in a solid tumor can form a tumor microenvironment around them to support the growth and metastasis of cancer cells. The tumor microenvironment is the cellular environment in which tumors exist, including surrounding blood vessels, immune cells, fibroblasts, other cells, soluble factors, signal transduction molecules, extracellular matrix and promoting tumor transformation, supporting tumor growth and invasion, protecting tumors from immunity of the host, cultivating resistance against the treatment, and providing a mechanical cue of the microenvironment for dormant, transfer and growth. A tumor is closely related to and constantly interacts with its surrounding microenvironment. A tumor can affect its microenvironment by releasing extracellular signals, promoting tumor angiogenesis and inducing peripheral immune tolerance. See Swarts et al., "Tumor Microenvironment Complexity: Emerging Roles in Cancer Therapy" Cancer Res, Volume 72, Pages 2473-2480, 2012. Therefore, when CAR-T technology is applied into the treatment of a solid tumor, good therapeutic effects are usually difficult to be achieved. For example, it is currently reported in most literature that CD19 CAR T cell therapy can bring good clinical therapeutic effects to patients with a hematological tumor. However, satisfactory results have not been achieved by CAR T cell therapy in the treatment of solid tumors.

Therefore, there is an urgent need in the art for technical means with significant anti-tumor capabilities in the tumor microenvironment of solid tumors.

SUMMARY OF THE INVENTION

The purpose of the present invention is to provide a technical means exhibiting excellent killing effects on CLD18 positive solid tumors.

In the first aspect, the present invention provides a method for treating CLD18-positive tumors, comprising administering a first dose of immune effector cells to a subject in need thereof, wherein said immune effector cells express a chimeric antigen receptor (CAR) and specifically recognizes CLD18, and the first dose contains not more than about $2\times10^{10}$ cells/kg of subject's body weight or the total amount of cells does not exceed about $1\times10^{12}$ cells. Preferably, the first dose contains not more than about $2\times10^{9}$ cells/kg of subject's body weight or the total amount does not exceed about $1\times10^{11}$ cells. Preferably, the first dose contains not more than about $2.5\times10^{8}$ cells/kg of subject's body weight or the total amount of cells does not exceed about $1\times10^{10}$ cells. Preferably, the first dose contains not more than about $5\times10^{7}$ cells/kg of the subject's body weight or a total of not more than about $1\times10^{10}$ cells. More preferably, the first dose contains not more than about $3\times10^{7}$ cells/kg of the subject's body weight or the total amount does not exceed about $5\times10^{9}$ or about $2\times10^{9}$ cells.

In a preferred embodiment, the first dose is not less than $1\times10^{5}$ cells/kg of the subject's body weight.

In a specific embodiment, the CLD18 is CLD18A2.

In a specific embodiment, after the first dose of immune effector cells is administered, at least one subsequent dose of immune effector cells expressing a chimeric antigen receptor (CAR) and specifically recognizing CLD18 is administered.

In a preferred embodiment, the subsequent dose of immune effector cells is administered under the safety for the patient.

In a preferred embodiment, the first dose of immune effector cells is the same as the subsequent dose of immune effector cells.

In a preferred embodiment, both of the first dose of immune effector cells and the subsequent doses of immune effector cells recognize CLD18A2, but contain different chimeric antigen receptors. For example, the chimeric antigen receptors are different in the extracellular segments, however, all of them recognize CLD18A2, or the extracellular segments of the chimeric antigen receptors are the same, while the transmembrane domain or intracellular domain is different.

In a specific embodiment, after the first dose of immune effector cells is no longer detected in vivo, the subsequent dose of immune effector cells is administered.

In a preferred embodiment, the immune effector cells are detected by, such as qPCR.

In a specific embodiment, the subsequent dose of immune effector cells is administered at about 21 to 80 days after the first dose is administered; preferably, the subsequent dose of immune effector cells is administered at about 25 to 60 days after the first dose is administered; and more preferably, the subsequent dose of immune effector cells is administered at about 25 to 50 days after the first dose is administered.

In a preferred embodiment, the subsequent dose is less than or equal to or higher than the first dose.

In a preferred embodiment, the subsequent dose is equivalent to the first dose.

In a preferred embodiment, the subsequent dose is less than the first dose.

In a preferred embodiment, the subsequent dose is higher than the first dose.

In a specific embodiment, the subsequent dose is higher than the first dose; and preferably, the subsequent dose is at least 2 times, 5 times, 7 times or 10 times the first dose.

In a specific embodiment, the subsequent dose contains not more than about $2\times10^{10}$ cells/kg of subject's body weight or the total amount of cells does not exceed about $1\times10^{12}$ cells.

In a preferred embodiment, the subsequent dose contains not more than about $2\times10^{9}$ cells/kg of subject's body weight or the total amount of cells does not exceed about $1\times10^{11}$ cells.

In a preferred embodiment, the subsequent dose contains not more than about $2.5\times10^{8}$ cells/kg of subject's body weight or the total amount of cells does not exceed about $1\times10^{10}$ cells.

In a preferred embodiment, the subsequent dose contains not more than about $5 \times 10^7$ cells/kg of subject's body weight or the total amount of cells does not exceed about $1 \times 10^{10}$ cells.

In a preferred embodiment, the subsequent dose contains not more than about $3 \times 10^7$ cells/kg of subject's body weight or the total amount of cells does not exceed $5 \times 10^9$ or is about $2 \times 10^9$ cells.

In a preferred embodiment, the subsequent dose is not less than $1 \times 10^5$ cells/kg of subject's body weight.

In a specific embodiment, the first dose or subsequent dose is administered in N times within 20 days, and N is a natural number not less than 1.

In a preferred embodiment, the first dose or subsequent dose is administered in N times within 3-15 days, and N is a natural number not less than 1.

In a preferred embodiment, N is 1, 2, 3, or 4.

In a preferred embodiment, N is 2 or 3.

In a specific embodiment, when a subsequent dose is administered, the subject exhibits any of the following characteristics:
  (i) The fold of the serum level of the factor indicative of cytokine release syndrome (CRS) in the subject is about 10 times, about 25 times, and/or about 50 times smaller than the level in the subject immediately before the first dose is administered;
  (ii) neurotoxicity of grade 3 or higher is not shown;
  (iii) The neurotoxicity or CRS level is reduced compared with the peak level of neurotoxicity or CRS after the first dose of immune effector cells is administered; or
  (iv) The subject does not exhibit a detectable humoral or cell-mediated immune response to the CAR expressed by the first dose of cells.

In a specific embodiment, when the above-mentioned subsequent dose is administered and the subject exhibits characteristic (iii), the CRS level is reduced by at least 50%, preferably at least 20%, more preferably, at least 5% compared with the peak CRS level after the first dose of immune effector cells is administered, or the CRS level is equivalent to the CRS level before the first dose of immune effector cells is administered.

In a preferred embodiment, the CRS level can be assessed according to the following information: fever, hypotension, hypoxia, neurological disorder, or serum levels of inflammatory cytokines or C-reactive protein (CRP).

In a preferred embodiment, the symptoms related to the clinical risk of neurotoxicity and/or grade 3 or higher neurotoxicity are selected from confusion, delirium, expressive aphasia, unresponsiveness, myoclonus, lethargy, altered mental state, convulsions, epileptic-like activity, epilepsy (optionally confirmed by EEG), elevated levels of amyloid β (Aβ), elevated glutamate levels or elevated oxygen free radical levels.

In a specific embodiment, the method further includes pretreatment performed before administering the immune effector cells, and the pretreatment includes administering a chemotherapeutic agent to the subject, irradiating the subject on the whole body, or performing local radiation therapy on the subject, or a combination thereof.

In a preferred embodiment, the pretreatment is performed before the first dose or between the first dose and the subsequent dose; and more preferably, the pretreatment is performed before the first dose and the subsequent dose.

In a preferred embodiment, the pretreatment is performed before the first dose of immune effector cells is administered, and the pretreatment is not required before the subsequent dose of immune effector cells is administered.

In a preferred embodiment, the pretreatment is required before the first dose of immune effector cells is administered and before the subsequent dose of immune effector cells is administered.

In a preferred embodiment, the pretreatment is performed for lymphocyte depletion.

In a preferred embodiment, the pretreatment is performed to stabilize the tumor burden or reduce the tumor burden, especially to maintain the tumor burden or reduce the tumor burden before the immune effector cell therapy is administered.

In a preferred embodiment, a lymphatic depleting agent, such as cyclophosphamide and fludarabine is administered to the subject for lymphocyte depletion.

In a specific embodiment, the pretreatment is performed 4-12 days before the immune effector cells are administered.

In a specific embodiment, the chemotherapeutic agent is any chemotherapeutic drug selected from the following group or a combination: cyclophosphamide, fludarabine, a taxane compound, and a pyrimidine anti-tumor drug.

In a preferred embodiment, the taxane compound includes but not limited to paclitaxel, albumin-bound paclitaxel or docetaxel, preferably albumin-bound paclitaxel; and the pyrimidine anti-tumor drug includes but not limited to 5-Fluorouracil, gemepyrimidine, ottiracil potassium, difurfurouracil, carmofur, deoxyfluridine, capecitabine.

In a specific embodiment, the chemotherapeutic agent is a combination of cyclophosphamide and fludarabine; or a combination of cyclophosphamide, fludarabine, and albumin-bound paclitaxel.

In a preferred embodiment, the amount of administered fludarabine is about 10-50 mg/m$^2$/day, or about 15-40 mg/m$^2$/day, or about 15-30 mg/m$^2$/day, or about 20-30 mg/m$^2$/day.

In a preferred embodiment, the amount of administered cyclophosphamide is about 300-700 mg/m$^2$/day, or about 400-650 mg/m$^2$/day, or about 450-600 mg/m$^2$/day, or about 450-550 mg/m$^2$/day, or about 490-550 mg/m$^2$/day.

In a preferred embodiment, the amount of administered albumin-bound paclitaxel is not higher than about 300 mg/m$^2$/day, or not higher than about 200 mg/m$^2$/day, or not higher than about 150 mg/m$^2$/day, or not higher than about 100 mg/m$^2$/day, or not higher than about 80 mg/m$^2$/day, or not higher than about 70 mg/m$^2$/day.

In a specific embodiment, the chemotherapeutic agent is continuously used for not more than 4 days.

In a specific embodiment, the cyclophosphamide and/or fludarabine are continuously used for not more than 4 days, and the albumin-bound paclitaxel is administered once.

In a preferred embodiment, pretreatment is performed, especially before the first dose and subsequent dose are administered, and the dose of the immune effector cells administered subsequently can be reduced accordingly.

In a specific embodiment, the tumor is a CLD18A2 positive tumor; preferably, the tumor is a CLD18A2 positive digestive tract tumor; more preferably, the digestive tract tumor is adenocarcinoma; and the most preferably, the digestive tract tumor is pancreatic cancer or gastric adenocarcinoma.

In a specific embodiment, the chimeric antigen receptor comprises an extracellular domain, a transmembrane domain and an intracellular domain. The extracellular domain is an antibody or a fragment thereof specifically binding to CLD18A2.

In a preferred embodiment, the transmembrane domain of the chimeric antigen receptor is the transmembrane region of CD28 or CD8.

In a preferred embodiment, the intracellular domain of the chimeric antigen receptor is a fusion peptide of the costimulatory signal domain of CD28 and CD3ζ, or a fusion peptide of the costimulatory signal domain of CD137 and CD3ζ, or a fusion peptide of the costimulatory signal domain of CD28, costimulatory signal domain of CD137 and CD3ζ.

In a specific embodiment, the chimeric antigen receptor comprises an antibody specifically binding to CLD18A2 or a fragment thereof, a transmembrane domain and an intracellular domain, and the antibody has:
HCDR1 as shown in SEQ ID NO:1, HCDR2 as shown in SEQ ID NO:2, HCDR3 as shown in SEQ ID NO:3, LCDR1 as shown in SEQ ID NO:4, LCDR2 as shown in SEQ ID NO:5, LCDR3 as shown in SEQ ID NO: 6; or
HCDR1 as shown in SEQ ID NO:1, HCDR2 as shown in SEQ ID NO:7, HCDR3 as shown in SEQ ID NO:3, LCDR1 as shown in SEQ ID NO:4, LCDR2 as shown in SEQ ID NO:5, LCDR3 as shown in SEQ ID NO: 6; or
HCDR1 as shown in SEQ ID NO:8, HCDR2 as shown in SEQ ID NO:9 or 68, HCDR3 as shown in SEQ ID NO:10, LCDR1 as shown in SEQ ID NO:11, LCDR2 as shown in SEQ ID NO: 12, LCDR3 as shown in SEQ ID NO: 13.

In a specific embodiment, the antibody or a fragment thereof has:
a heavy chain variable region as shown in SEQ ID NO: 14 and a light chain variable region as shown in SEQ ID NO: 16; or
a heavy chain variable region as shown in SEQ ID NO: 18 and a light chain variable region as shown in SEQ ID NO: 16; or
a heavy chain variable region as shown in SEQ ID NO: 22 and a light chain variable region as shown in SEQ ID NO: 20; or
a heavy chain variable region as shown in SEQ ID NO:53 and a light chain variable region as shown in SEQ ID NO:52.

Preferably, the antibody or a fragment thereof has the sequence as shown in SEQ ID NO: 54, 56, 57 or 58.

In a preferred embodiment, the antibody or a fragment thereof has a heavy chain variable region as shown in SEQ ID NO: 14 and a light chain variable region as shown in SEQ ID NO: 16.

In a specific embodiment, the chimeric antigen receptor has an amino acid sequence as shown in any one of SEQ ID NO: 24, 25, 26, 27, 28, 29, 30, 31 and 32; preferably, sequence as shown in SEQ ID NO: 24, 25 or 26.

In a preferred embodiment, the chimeric antigen receptor has an amino acid sequence as shown in any one of SEQ ID NO: 24, 25, and 26.

In a preferred example, the chimeric antigen receptor has the amino acid sequence as shown in SEQ ID NO:24.

In a specific embodiment, the immune effector cell is a T lymphocyte, NK cell or NKT lymphocyte.

In a preferred embodiment, the preferred immune effector cell is a T lymphocyte.

In a preferred embodiment, the T lymphocyte is derived from the subject himself.

In a preferred embodiment, the T lymphocyte is allogeneic.

In a specific embodiment, two or more subsequent doses of immune effector cells are administered, and the interval between each subsequent dose of immune effector cells is about 21 to about 80 days, or about 25 to about 60 days, or about 25 to 50 days, with end-points being included.

In a preferred embodiment, the subsequent dose of immune effector cells administered later results in a stable or reduced tumor burden in the subject compared with the subsequent dose of immune effector cells administered earlier.

In a specific embodiment, the number of immune cells administered in each subsequent dose is substantially the same.

In a specific embodiment, the number of immune effector cells administered in the later subsequent dose is higher than the number of immune cells administered in the earlier subsequent dose.

In a specific embodiment, the number of immune effector cells administered in the later subsequent dose is less than the number of immune cells administered in the earlier subsequent dose.

In a specific embodiment, before the immune effector cells are administered, the subject has not received treatment with immune cells expressing chimeric antigen receptors targeting CLD18.

In a specific embodiment, the subsequent dose is the number of cells sufficient to stabilize or reduce the tumor burden in the subject.

In a specific embodiment, before the first dose is administered, the subject is subjected to a surgical treatment, chemotherapy, or immunotherapy other than that described in the first aspect.

In a specific embodiment, before the first dose is administered, or after the first dose is administered and before the subsequent dose is administered, the subject is evaluated for the serum levels of a factor indicative of CRS, a factor indicative of neurotoxicity, a factor indicative of tumor burden, and/or a factor indicative of the anti-CAR immune response of the host.

In a specific embodiment, the factor indicative of tumor burden is: the total amount of tumor cells in the subject, or the total amount of tumor cells in the organ of the subject, or the total amount of tumor cells in the tissue of the subject, or the mass or volume of the tumor, or the extent of tumor metastasis, or the number of tumors.

In a specific embodiment, the method for treating a tumor includes:
i) evaluating a factor indicative of the tumor burden before the subsequent dose is administered; and
ii) determining the continuous dose of cells to be administered to the subject, based on the results of the evaluation, and
iii) if it is determined by the evaluation that the subject's tumor mass or volume is stable or reduced, administering the subject with a subsequent dose comprising the number of cells less than or more than the number of CAR-expressing cells in the first dose or approximately the same number of CAR-expressing cells as that in the first dose.

In a specific embodiment, the number of cells administered in the first dose or the subsequent doses is about $1.1 \times 10^6$ cells/kg to $2.8 \times 10^7$ cells/kg, and about $2.9 \times 10^6$ cells/kg to $2.6 \times 10^7$ cells/kg, or about $3.3 \times 10^6$ cells/kg to $1.3 \times 10^7$ cells/kg or about $1.3 \times 10^7$ cells/kg to $1.8 \times 10^7$ cells/kg, with end-points being included.

In a specific embodiment, the number of CAR-expressing cells administered in the subsequent dose comprises about $1.1 \times 10^7$ cells/kg (cells/kg) of body weight to about $5.1 \times 10^7$ cells/kg, and about $1.3 \times 10^7$ cells/kg to about $3.7 \times 10^7$ cells/kg, about $1.6 \times 10^7$ cells/kg to about $2.2 \times 10^7$ cells/kg, about $1.9 \times 10^7$ cells/kg to about $2.2 \times 10^7$ cells/kg, about $2.2 \times 10^7$ cells/kg to about $2.7 \times 10^7$ cells/kg, with end-points being included.

In a specific embodiment, after the first dose or subsequent doses of immune effector cells are administered, the subject does not exhibit cytokine release syndrome (CRS), severe CRS, neurotoxicity, severe neurotoxicity, or neurotoxicity above grade 3.

In a specific embodiment, after the first dose or subsequent doses of immune effector cells are administered, the immune effector cells proliferate in the subject.

In a preferred embodiment, the proliferation is represented by: (i) the increased serum CRP level after the first dose and/or subsequent dose is administered, compared with that immediately before the administration, and/or (ii) the increased level of CAR-encoding nucleic acid in the serum after the first dose and/or subsequent dose is administered, compared with that immediately before the administration, as measured by qPCR.

In a specific embodiment, after the first dose of immune effector cells is administered, the subject's tumor burden is stable or reduced. In a specific embodiment, the stable or reduced tumor burden is represented by one or more stable or reduced factors indicative of tumor burden.

In a preferred embodiment, after the subsequent dose of immune effector cells is administered, the tumor burden is stable or further reduced compared with the tumor burden after the first dose of immune effector cells is administered.

In a specific embodiment, when the subsequent dose is administered, there is no relapse in the subject, and/or one or more factors indicative of tumor burden are not increased after being reduced.

In a specific embodiment, the stable or reduced burden and/or further reduced burden means that the total amount of diseased cells in the subject, the organ of the subject, the tissue of the subject, or the body fluid of the subject is stabilized or reduced, and/or the mass or volume of the tumor is stabilized or reduced, and/or the number and/or degree of metastasis is stabilized or reduced, and/or tumor markers are stabilized or reduced, and/or the common complications of advanced cancer disappear or are weaken.

In a specific embodiment, the tumor markers include: alpha-fetoprotein (AFP), CA125, CA15-3, squamous cell carcinoma antigen (SCC), soluble fragment of cytokeratin 19 (CYFRA21-1), carcinoembryonic Antigen (CEA), CA199, CA724, etc.

In a specific embodiment, the common complications of advanced cancer include: cancer pain, infection, and cancerous pleural and ascites.

In a specific embodiment, the mass or volume of the tumor is measured by PET (positron emission computed tomography) and CT (computed tomography).

In the second aspect of the present invention, another method of tumor treatment is also provided, which includes: the subject has received chemotherapy, radiotherapy, immunotherapy, or a combination thereof, before any of the methods described above is administered.

In a preferred embodiment, the immunotherapy includes administering a checkpoint inhibitor or an immune effector cell therapy not targeting CLD18.

In a preferred embodiment, the immunotherapy does not include the immune effector cell therapy targeting CLD18.

In a preferred embodiment, the subject receives an immune effector cell therapy not targeting CLD 18.2.

In a preferred embodiment, after the subject receives chemotherapy, radiotherapy, other immunotherapy, or a combination thereof, the tumor burden does not remain stable or reduced.

In a specific embodiment, the tumor is a relapsed and refractory tumor.

In the third aspect of the present invention, the use of a composition comprising immune effector cells expressing a chimeric antigen receptor specifically recognizing CLD18 is provided for preparing a medicament for treating CLD18A2 positive tumors in a subject who is previously treated with CLD18A2-CAR T cells, wherein, when used, the first dose of immune effector cells expressing a chimeric antigen receptor (CAR) and specifically recognizing CLD18 is administered to a subject in need thereof, and the first dose contains not more than about $2 \times 10^{10}$ cells/kg of subject's body weight or the total amount of cells does not exceed about $1 \times 10^{12}$ cells. Preferably, the first dose contains not more than about $2 \times 10^9$ cells/kg of subject's body weight or the total amount of cells does not exceed about $1 \times 10^{11}$ cells. Preferably, the first dose contains not more than about $2.5 \times 10^8$ cells/kg of subject's body weight or the total amount of cells does not exceed about $1 \times 10^{10}$ cells. Preferably, the first dose contains not more than about $5 \times 10^7$ cells/kg of subject's body weight or the total amount of cells does not exceed about $1 \times 10^{10}$ cells. More preferably, the first dose contains not more than about $3 \times 10^7$ cells/kg of subject's body weight or the total amount of cells does not exceed $5 \times 10^9$ or about $2 \times 10^9$ cells.

In a specific embodiment, the CLD18 is CLD18A2.

In a specific embodiment, after the first dose of immune effector cells is administered, at least one subsequent dose of immune effector cells expressing chimeric antigen receptor (CAR) and specifically recognizing CLD18 is administered.

In a preferred embodiment, the subsequent dose of immune effector cells is administered under the safety for the patient.

In a preferred embodiment, the first dose of immune effector cells is the same as the subsequent dose of immune effector cells.

In a preferred embodiment, both of the first dose of immune effector cells and the subsequent doses of immune effector cells recognize CLD18A2, but contain different chimeric antigen receptors. For example, the chimeric antigen receptors are different in the extracellular segments, however, all of them recognize CLD18A2, or the extracellular segments of the chimeric antigen receptors are the same, while the transmembrane domain or intracellular domain is different.

In a specific embodiment, after the first dose of immune effector cells is no longer detected in vivo, the subsequent dose of immune effector cells is administered.

In a preferred embodiment, the immune effector cells are detected by, such as qPCR. In a specific embodiment, the subsequent dose of immune effector cells is administered at about 21 to 80 days after the first dose is administered; preferably, the subsequent dose of immune effector cells is administered at about 25 to 60 days after the first dose is administered; and more preferably, the subsequent dose of immune effector cells is administered at about 25 to 50 days after the first dose is administered.

In a preferred embodiment, the subsequent dose is equivalent to the first dose.

In a preferred embodiment, the subsequent dose is lower than the first dose.

In a preferred embodiment, the subsequent dose is higher than the first dose.

In a specific embodiment, the subsequent dose is higher than the first dose; and preferably, the subsequent dose is at least 2 times, 5 times, 7 times or 10 times the first dose.

In a specific embodiment, the subsequent dose contains not more than about $2 \times 10^{10}$ cells/kg of subject's body weight or the total amount of cells does not exceed about $1 \times 10^{12}$ cells.

In a preferred embodiment, the subsequent dose contains not more than about $2 \times 10^9$ cells/kg of subject's body weight or the total amount of cells does not exceed about $1 \times 10^{11}$ cells.

In a preferred embodiment, the subsequent dose contains not more than about $2.5 \times 10^8$ cells/kg of subject's body weight or the total amount of cells does not exceed about $1 \times 10^{10}$ cells.

In a preferred embodiment, the subsequent dose contains not more than about $5 \times 10^7$ cells/kg of subject's body weight or the total amount of cells does not exceed about $1 \times 10^{10}$ cells.

In a preferred embodiment, the subsequent dose contains not more than about $3 \times 10^7$ cells/kg of subject's body weight or the total amount of cells does not exceed $5 \times 10^9$ or is about $2 \times 10^9$ cells.

In a specific embodiment, the first dose or subsequent dose is administered in N times within 20 days, and N is a natural number not less than 1.

In a preferred embodiment, the first dose or subsequent dose is administered in N times within 3-15 days, and N is a natural number not less than 1.

In a preferred embodiment, N is 1, 2, 3, or 4.

In a preferred embodiment, N is 2 or 3.

In a specific embodiment, when a subsequent dose is administered, the subject exhibits any of the following characteristics:
 (i) The fold of the serum level of the factor indicative of cytokine release syndrome (CRS) in the subject is about 10 times, about 25 times, and/or about 50 times smaller than the level in the subject immediately before the first dose is administered;
 (ii) neurotoxicity of grade 3 or higher is not shown;
 (iii) The neurotoxicity or CRS level is reduced compared with the peak level of neurotoxicity or CRS after the first dose of immune effector cells is administered; or
 (iv) The subject does not exhibits a detectable humoral or cell-mediated immune response to the CAR expressed by the first dose of cells.

In a specific embodiment, when the above-mentioned subsequent dose is administered and the subject exhibits characteristic (iii), the CRS level is reduced by at least 50%, preferably at least 20%, more preferably, at least 5% compared with the peak CRS level after the first dose of immune effector cells is administered, or the CRS level is equivalent to the CRS level before the first dose of immune effector cells is administered.

In a preferred embodiment, the CRS level can be assessed according to the following information: fever, hypotension, hypoxia, neurological disorder, or serum levels of inflammatory cytokines or C-reactive protein (CRP).

In a preferred embodiment, the symptoms related to the clinical risk of neurotoxicity and/or grade 3 or higher neurotoxicity are selected from confusion, delirium, expressive aphasia, unresponsiveness, myoclonus, lethargy, altered mental state, convulsions, epileptic-like activity, epilepsy (optionally confirmed by EEG), elevated levels of amyloid β (Aβ), elevated glutamate levels or elevated oxygen free radical levels.

In a specific embodiment, the method further includes pretreatment performed before administering the immune effector cells, and the pretreatment includes administering a chemotherapeutic agent to the subject, irradiating the subject on the whole body, or performing local radiation therapy on the subject, or a combination thereof.

In a preferred embodiment, the pretreatment is performed before the first dose of immune effector cells is administered, and the pretreatment is not required before the subsequent dose of immune effector cells is embodiment, the pretreatment is required before the first dose of immune effector cells is administered and before the subsequent dose of immune effector cells is administered.

In a preferred embodiment, the pretreatment is performed for lymphocyte depletion.

In a preferred embodiment, the pretreatment is performed to stabilize the tumor burden or reduce the tumor burden, especially to maintain the tumor burden or reduce the tumor burden before the immune effector cell therapy is administered.

In a preferred embodiment, a lymphatic depleting agent, such as cyclophosphamide and fludarabine is administered to the subject for lymphocyte depletion.

In a specific embodiment, the pretreatment is performed 4-12 days before the immune effector cells are administered.

In a specific embodiment, the chemotherapeutic agent is any chemotherapeutic drug selected from the following group or a combination: cyclophosphamide, fludarabine, a taxane compound, and a pyrimidine anti-tumor drug. In a specific embodiment, the chemotherapeutic agent is a combination of cyclophosphamide and fludarabine; or a combination of cyclophosphamide, fludarabine, and albumin-bound paclitaxel.

In a preferred embodiment, the amount of administered fludarabine is about 10-50 mg/m$^2$/day, or about 15-40 mg/m$^2$/day, or about 15-30 mg/m$^2$/day, or about 20-30 mg/m$^2$/day.

In a preferred embodiment, the amount of administered cyclophosphamide is about 300-700 mg/m$^2$/day, or about 400-650 mg/m$^2$/day, or about 450-600 mg/m$^2$/day, or about 450-550 mg/m$^2$/day, or about 490-550 mg/m$^2$/day.

In a preferred embodiment, the amount of administered albumin-bound paclitaxel is not higher than about 300 mg/m$^2$/day, or not higher than about 200 mg/m$^2$/day, or not higher than about 150 mg/m$^2$/day, or not higher than about 100 mg/m$^2$/day, or not higher than about 80 mg/m$^2$/day, or not higher than about 70 mg/m$^2$/day.

In a specific embodiment, the chemotherapeutic agent is continuously used for not more than 4 days.

In a specific embodiment, the cyclophosphamide and the fludarabine are continuously used for not more than 4 days, and the albumin-bound paclitaxel is administered once.

In a specific embodiment, the tumor is a CLD18A2 positive tumor; preferably, the tumor is a CLD18A2 positive digestive tract tumor; more preferably, the digestive tract tumor is adenocarcinoma; and most preferably, the digestive tract tumor is pancreatic cancer or gastric adenocarcinoma.

In a specific embodiment, the chimeric antigen receptor comprises an extracellular domain, a transmembrane domain and an intracellular domain. The extracellular domain is an antibody or a fragment thereof specifically binding to CLD18A2.

In a preferred embodiment, the transmembrane domain of the chimeric antigen receptor is the transmembrane region of CD28 or CD8.

In a preferred embodiment, the intracellular domain of the chimeric antigen receptor is a fusion peptide of the costimulatory signal domain of CD28 and CD34, or a fusion peptide of the costimulatory signal domain of CD137 and CD3ζ, or a fusion peptide of the costimulatory signal domain of CD28, costimulatory signal domain of CD137 and CD3ζ.

In a specific embodiment, the chimeric antigen receptor comprises an antibody specifically binding to CLD18A2 or a fragment thereof, a transmembrane domain and an intracellular domain, and the antibody has:

HCDR1 as shown in SEQ ID NO:1, HCDR2 as shown in SEQ ID NO:2, HCDR3 as shown in SEQ ID NO:3, LCDR1 as shown in SEQ ID NO:4, LCDR2 as shown in SEQ ID NO:5, LCDR3 as shown in SEQ ID NO: 6; or HCDR1 as shown in SEQ ID NO:1, HCDR2 as shown in SEQ ID NO:7, HCDR3 as shown in SEQ ID NO:3, LCDR1 as shown in SEQ ID NO:4, LCDR2 as shown in SEQ ID NO:5, LCDR3 as shown in SEQ ID NO: 6; or HCDR1 as shown in SEQ ID NO:8, HCDR2 as shown in SEQ ID NO:9 or 68, HCDR3 as shown in SEQ ID NO: 10, LCDR1 as shown in SEQ ID NO:11, LCDR2 as shown in SEQ ID NO: 12, LCDR3 as shown in SEQ ID NO: 13.

In a specific embodiment, the antibody or a fragment thereof has:

a heavy chain variable region as shown in SEQ ID NO: 14 and a light chain variable region as shown in SEQ ID NO: 16; or a heavy chain variable region as shown in SEQ ID NO: 18 and a light chain variable region as shown in SEQ ID NO: 16; or a heavy chain variable region as shown in SEQ ID NO: 22 and a light chain variable region as shown in SEQ ID NO: 20.

In a preferred embodiment, the antibody or a fragment thereof has a heavy chain variable region as shown in SEQ ID NO: 14 and a light chain variable region as shown in SEQ ID NO: 16.

In a specific embodiment, the chimeric antigen receptor has an amino acid sequence as shown in any one of SEQ ID NO: 24, 25, 26, 27, 28, 29, 30, 31 and 32.

In a preferred embodiment, the chimeric antigen receptor has an amino acid sequence as shown in any one of SEQ ID NO: 24, 25, and 26.

In a preferred example, the chimeric antigen receptor has the amino acid sequence as shown in SEQ ID NO:24.

In a specific embodiment, the immune effector cell is a T lymphocyte, NK cell or NKT lymphocyte.

In a preferred embodiment, the preferred immune effector cell is a T lymphocyte.

In a preferred embodiment, the T lymphocyte is derived from the subject himself.

In a preferred embodiment, the T lymphocyte is allogeneic.

In a specific embodiment, two or more subsequent doses of immune effector cells are administered, and the interval between each subsequent dose of immune effector cells is about 21 to about 80 days, or about 25 to about 60 days, or about 25 to 50 days, with end-points being included.

In a preferred embodiment, the subsequent dose of immune effector cells administered later results in a stable or reduced tumor burden in the subject compared with the subsequent dose of immune effector cells administered earlier.

In a specific embodiment, the number of immune cells administered in each subsequent dose is substantially the same.

In a specific embodiment, the number of immune effector cells administered in the later subsequent dose is higher than the number of immune cells administered in the earlier subsequent dose.

In a specific embodiment, the number of immune effector cells administered in the later subsequent dose is less than the number of immune cells administered in the earlier subsequent dose.

In a specific embodiment, before the immune effector cells are administered, the subject has not received treatment with immune cells expressing chimeric antigen receptors targeting CLD18.

In a specific embodiment, the subsequent dose is the number of cells sufficient to stabilize or reduce the tumor burden in the subject.

In a specific embodiment, before the first dose is administered, the subject is subjected to a surgical treatment, chemotherapy, or immunotherapy other than that described in the first aspect.

In a specific embodiment, before the first dose is administered, or after the first dose is administered and before the subsequent dose is administered, the subject is evaluated for the serum levels of a factor indicative of CRS, a factor indicative of neurotoxicity, a factor indicative of tumor burden, and/or a factor indicative of the anti-CAR immune response of the host.

In a specific embodiment, the factor indicative of tumor burden is: the total amount of tumor cells in the subject, or the total amount of tumor cells in the organ of the subject, or the total amount of tumor cells in the tissue of the subject, or the mass or volume of the tumor, or the extent of tumor metastasis, or the number of tumors.

In a specific embodiment, the method for treating a tumor includes:

i) evaluating a factor indicative of the tumor burden before the subsequent dose is administered; and ii) determining the continuous doses of cells to be administered to the subject, based on the results of the evaluation, and iii) if it is determined by the evaluation that the subject's tumor mass or volume is stable or reduced, administering the subject with a subsequent dose comprising the number of cells less than or more than the number of CAR-expressing cells in the first dose or approximately the same number of CAR-expressing cells as that in the first dose.

In a specific embodiment, the number of cells administered in the first dose or the subsequent doses is about $1.1 \times 10^6$ cells/kg of subject's body weight to $2.8 \times 10^7$ cells/kg, and about $2.9 \times 10^6$ cells/kg to $2.6 \times 10^7$ cells/kg, or about $3.3 \times 10^6$ cells/kg to $1.3 \times 10^7$ cells/kg, with end-points being included.

In a specific embodiment, the number of CAR-expressing cells administered in the subsequent dose comprises about $1.1 \times 10^7$ cells/kg (cells/kg) of body weight to about $5.1 \times 10^7$ cells/kg, and about $1.3 \times 10^7$ cells/kg to about $3.7 \times 10^7$ cells/kg, about $1.6 \times 10^7$ cells/kg to about $2.2 \times 10^7$ cells/kg, about $1.9 \times 10^7$ cells/kg to about $2.2 \times 10^7$ cells/kg, with end-points being included.

In a specific embodiment, after the first dose or subsequent doses of immune effector cells are administered, the subject does not exhibit cytokine release syndrome (CRS), severe CRS, neurotoxicity, severe neurotoxicity, or neurotoxicity above grade 3.

In a specific embodiment, after the first dose or subsequent doses of immune effector cells are administered, the immune effector cells proliferate in the subject.

In a preferred embodiment, the proliferation is represented by: (i) the increased serum CRP level after the first dose and/or subsequent dose is administered, compared with that immediately before the administration, and/or (ii) the increased level of CAR-encoding nucleic acid in the serum after the first dose and/or subsequent dose is administered, compared with that immediately before the administration, as measured by qPCR.

In a specific embodiment, after the first dose of immune effector cells is administered, the subject's tumor burden is stable or reduced. In a specific embodiment, the stable or reduced tumor burden is represented by one or more stable or reduced factors indicative of tumor burden.

In a preferred embodiment, after the subsequent dose of immune effector cells is administered, the tumor burden is stable or further reduced compared with the tumor burden after the first dose of immune effector cells is administered.

In a specific embodiment, when the subsequent dose is administered, there is no relapse in the subject, and/or one or more factors indicative of tumor burden are not increased after being reduced.

In a specific embodiment, the stable or reduced burden and/or further reduced burden means that the total amount of diseased cells in the subject, the organ of the subject, the tissue of the subject, or the body fluid of the subject is stabilized or reduced, and/or the mass or volume of the tumor is stabilized or reduced, and/or the number and/or degree of metastasis is stabilized or reduced, and/or tumor markers are stabilized or reduced, and/or the common complications of advanced cancer disappear or are weaken.

In a specific embodiment, the tumor markers include: alpha-fetoprotein (AFP), CA125, CA15-3, squamous cell carcinoma antigen (SCC), soluble fragment of cytokeratin 19 (CYFRA21-1), carcinoembryonic Antigen (CEA), CA199, CA724, etc.

In a specific embodiment, the common complications of advanced cancer include: cancer pain, infection, and cancerous pleural and ascites.

In a specific embodiment, the mass or volume of the tumor is measured by PET (positron emission computed tomography) and CT (computed tomography).

In the fourth aspect of the present invention, a composition is also provided, comprising cyclophosphamide, fludarabine, taxane compound and/or pyrimidine antitumor drug.

In a preferred embodiment, the taxane compound includes but not limited to paclitaxel, albumin-bound paclitaxel or docetaxel, preferably albumin-bound paclitaxel; and the pyrimidine anti-tumor drug includes but not limited to 5-Fluorouracil, gemepyrimidine, ottiracil potassium, difurfurouracil, carmofur, deoxyfluridine, capecitabine.

In a specific embodiment, the composition comprises cyclophosphamide, fludarabine and paclitaxel.

In a specific embodiment, the composition comprises cyclophosphamide, fludarabine and albumin-bound paclitaxel.

In a preferred embodiment, the composition is administered to a subject before the subject receiving immune effector cell therapy receives the immune effector cells, preferably before each time the subject receiving immune effector cell therapy receives the immune effector cells.

In a preferred embodiment, the amount of administered fludarabine is about 10-50 mg/m$^2$/day, or about 15-40 mg/m$^2$/day, or about 15-30 mg/m$^2$/day, or about 20-30 mg/m$^2$/day; and/or the amount of administered cyclophosphamide is about 300-700 mg/m$^2$/day, or about 400-650 mg/m$^2$/day, or about 450-600 mg/m$^2$/day, or about 450-550 mg/m$^2$/day, or about 490-550 mg/m$^2$/day; and/or the amount of administered albumin-bound paclitaxel is not higher than about 300 mg/m$^2$/day, or not higher than about 200 mg/m$^2$/day, or not higher than about 150 mg/m$^2$/day, or not higher than about 100 mg/m$^2$/day, or not higher than about 80 mg/m$^2$/day, or not higher than about 70 mg/m$^2$/day.

In a specific embodiment, a pretreatment is administered about 30 days; preferably, about 20 days; more preferably, about 12 days; and most preferably, about 7 days before the immune cell therapy is administered.

In a specific embodiment, the cyclophosphamide, fludarabine and/or albumin-bound paclitaxel are continuously used for not more than 4 days; and preferably, the albumin-bound paclitaxel is administered once.

In a specific embodiment, it is used for anti-tumor therapy; preferably, it is used for anti-tumor targeted therapy; and most preferably, it is used for anti-tumor chimeric antigen receptor targeted therapy.

In a specific embodiment, the immune effector cells are CAR T cells.

In a specific embodiment, the CAR T cell specifically recognizes CLD18A2.

In a specific embodiment, the tumor is a CLD18A2 positive digestive tract tumor; more preferably, the digestive tract tumor is adenocarcinoma; and most preferably, the digestive tract tumor is pancreatic cancer or gastric adenocarcinoma.

In the fifth aspect of the present invention, a method for treating tumors in combination with immune effector cell therapy is also provided, comprising: administering cyclophosphamide, fludarabine and a taxane compound before administering immune effector cell therapy to the subject for pretreatment.

In a preferred embodiment, the tumor is a solid tumor.

In a preferred embodiment, the solid tumor is breast cancer, colon cancer, rectal cancer, renal cell carcinoma, liver cancer, lung cancer, gastric cancer, small bowel cancer, esophageal cancer, melanoma, bone cancer, pancreatic cancer, skin cancer, Head and neck cancer, uterine cancer, ovarian cancer, anal cancer, testicular cancer, uterine cancer, fallopian tube cancer, endometrial cancer, cervical cancer, vaginal cancer, Hodgkin's lymphoma, non-Hodgkin's lymphoma, endocrine system cancer, Thyroid cancer, parathyroid cancer, adrenal cancer, soft tissue sarcoma, urethral cancer, penile cancer, bladder cancer, kidney or ureter cancer, renal pelvis cancer, central nervous system (CNS) tumor, primary CNS lymphoma, spinal tumor, brain Stem glioma, pituitary adenoma, Kaposi's sarcoma, epidermoid carcinoma, squamous cell carcinoma.

In a preferred embodiment, the taxane compound is selected from paclitaxel, albumin-bound paclitaxel, or docetaxel.

In a preferred embodiment, the taxane compound is selected from albumin-bound paclitaxel.

In a specific embodiment, the amount of administered fludarabine is about 10-50 mg/m$^2$/day, or about 15-40 mg/m$^2$/day, or about 15-30 mg/m$^2$/day, or about 20-30 mg/m$^2$/day; and/or the amount of administered cyclophosphamide is about 300-700 mg/m$^2$/day, or about 400-650 mg/m$^2$/day, or about 450-600 mg/m$^2$/day, or about 450-550 mg/m$^2$/day, or about 490-550 mg/m$^2$/day; and/or the amount of administered albumin-bound paclitaxel is not higher than about 300 mg/m$^2$/day, or not higher than about 200 mg/m$^2$/day, or not higher than about 150 mg/m$^2$/day, or not higher than about 100 mg/m$^2$/day, or not higher than about 80 mg/m$^2$/day, or not higher than about 70 mg/m$^2$/day.

In a specific embodiment, a pretreatment is administered about 30 days; preferably, about 20 days; more preferably, about 12 days; and most preferably, about 7 days before the immune cell therapy is administered.

In a specific embodiment, the cyclophosphamide, fludarabine and/or albumin-bound paclitaxel are continuously used for not more than 4 days; and preferably, the albumin-bound paclitaxel is administered once.

In a specific embodiment, the immune effector cells are immune effector cells modified with chimeric antigen receptors, such as CAR-T cells, CAR-NK cells, CAR-NKT cells and the like.

In the sixth aspect of the present invention, a use of immune effector cells containing CLD18A2-CAR in the preparation of a medicament is also provided, the medicament containing the cells and cyclophosphamide, fludarabine as well as a taxane compound (preferably paclitaxel, more preferably albumin-bound paclitaxel) for treating CLD18 positive tumors, wherein the cells and cyclophosphamide, fludarabine as well as taxane compound are formulated to provide therapeutic effects greater than the sum of the effects produced by the respective reagents.

In a specific embodiment, a first dose of immune effector cells is administered to a subject in need thereof, and the first dose does not exceed about $3\times10^7$ cells/kg of the subject's body weight or the total amount of cells does not exceed about $2\times10^9$ cell.

In a specific embodiment, after the first dose of immune effector cells is administered, at least one subsequent dose of the immune effector cells is administered, and the subsequent dose contains not more than about $3\times10^7$ cells/kg of the subject's body weight or the total amount of the cells does not exceed about $5\times10^9$ cells.

In a specific embodiment, the subsequent dose of immune effector cells is administered at about 21 to 80 days after the first dose is administered; preferably, the subsequent dose of immune effector cells is administered at about 25 to 60 days after the first dose is administered; and more preferably, the subsequent dose of immune effector cells is administered at about 25 to 50 days after the first dose is administered.

In a specific embodiment, the cyclophosphamide, fludarabine and taxane compound are administered 4-12 days before the immune effector cells are administered.

In a specific embodiment, the amount of administered fludarabine is about 10-50 mg/m$^2$/day, or about 15-40 mg/m$^2$/day, or about 15-30 mg/m$^2$/day, or about 20-30 mg/m$^2$/day; and/or
the amount of administered cyclophosphamide is about 300-700 mg/m$^2$/day, or about 400-650 mg/m$^2$/day, or about 450-600 mg/m$^2$/day, or about 450-550 mg/m$^2$/day, or about 490-550 mg/m$^2$/day; and/or
the amount of administered taxane compound is not higher than about 300 mg/m$^2$/day, or not higher than about 200 mg/m$^2$/day, or not higher than about 150 mg/m$^2$/day, or not higher than about 100 mg/m$^2$/day, or not higher than about 80 mg/m$^2$/day, or not higher than about 70 mg/m$^2$/day.

In a specific embodiment, the cyclophosphamide and/or fludarabine are continuously used for not more than 4 days, and the taxane compound is administered once.

In a specific embodiment, the chimeric antigen receptor has an amino acid sequence as shown in any one of SEQ ID NO: 24, 25, 26, 27, 28, 29, 30, 31, and 32; and preferably, the sequence as shown in SEQ ID NO: 24, 25, or 26.

Corresponding to the sixth aspect, the present invention also provides a kit for treating CLD18-positive tumors, wherein the kit comprises:

1) immune effector cells containing CLD18A2-CAR;
2) Cyclophosphamide;
3) Fludarabine;
4) a Taxane compound, preferably paclitaxel, more preferably albumin-bound paclitaxel;
5) containers for containing the substances described in 1)-4); and
6) an instruction for using the kit to treat CLD18 positive tumors;
wherein the cells and cyclophosphamide, fludarabine as well as taxane compound are formulated to provide therapeutic effects greater than the sum of the effects produced by the respective agents.

In a specific embodiment, it is described in the instruction that the first dose of the immune effector cells is administered to a subject in need thereof, and the first dose does not exceed about $3\times10^7$ cells/kg of the subject's body weight or the total amount of cells does not exceed about $2\times10^9$ cells.

In a specific embodiment, it is described in the instruction that after the first dose of immune effector cells is administered, at least one subsequent dose of the immune effector cells is administered, and the subsequent dose contains not more than about $3\times10^7$ cells/kg of the subject's body weight or the total amount of the cells does not exceed about $5\times10^9$ cells.

In a specific embodiment, it is described in the instruction that the subsequent dose of immune effector cells is administered at about 21 to 80 days after the first dose is administered; preferably, the subsequent dose of immune effector cells is administered at about 25 to 60 days after the first dose is administered; and more preferably, the subsequent dose of immune effector cells is administered at about 25 to 50 days after the first dose is administered.

In a specific embodiment, the cyclophosphamide, fludarabine and taxane compound are administered 4-12 days before the immune effector cells are administered.

In a specific embodiment, it is described in the instruction that:
the amount of administered fludarabine is about 10-50 mg/m$^2$/day, or about 15-40 mg/m$^2$/day, or about 15-30 mg/m$^2$/day, or about 20-30 mg/m$^2$/day; and/or
the amount of administered cyclophosphamide is about 300-700 mg/m$^2$/day, or about 400-650 mg/m$^2$/day, or about 450-600 mg/m$^2$/day, or about 450-550 mg/m$^2$/day, or about 490-550 mg/m$^2$/day; and/or
the amount of administered taxane compound is not higher than about 300 mg/m$^2$/day, or not higher than about 200 mg/m$^2$/day, or not higher than about 150 mg/m$^2$/day, or not higher than about 100 mg/m$^2$/day, or not higher than about 80 mg/m$^2$/day, or not higher than about 70 mg/m$^2$/day.

In a specific embodiment, it is described in the instruction that:
the cyclophosphamide and/or fludarabine are continuously used for not more than 4 days, and the taxane compound is administered once.

In a specific embodiment, the chimeric antigen receptor has an amino acid sequence as shown in any one of SEQ ID NO: 24, 25, 26, 27, 28, 29, 30, 31, and 32; and preferably, the sequence as shown in SEQ ID NO: 24, 25, or 26.

A person skilled in the art will know that the kit may contain each component in a dosage compatible with the description of the instruction.

In one aspect of the present invention, a method for treating a tumor is provided, including administering immune effector cells and a tubulin inhibitor to an individual suffering from a tumor, wherein the immune effector cells express a receptor recognizing a tumor antigen. In some embodiments, the present invention provides a method for reducing the growth, survival, or viability or all of the growth, survival and viability of cancer cells, comprising administering immune effector cells and a tubulin inhibitor to an individual suffering from a tumor, wherein the immune effector cells express a receptor recognizing a tumor antigen. In some embodiments, the tubulin inhibitor is a taxane compound. In some embodiments, the taxane compound is selected from: paclitaxel, albumin-bound paclitaxel (nab-paclitaxel, Abraxane), docetaxel (docetaxel), and a derivative with a taxane skeleton structure.

In another embodiment, the antibody that specifically recognizes a tumor antigen has HCDR1 as shown in SEQ ID NO:1, HCDR2 as shown in SEQ ID NO:2, HCDR3 as shown in SEQ ID NO:3, LCDR1 as shown in SEQ ID NO: 4, LCDR2 as shown in SEQ ID NO: 5, LCDR3 as shown in SEQ ID NO: 6; or HCDR1 as shown in SEQ ID NO:1, HCDR2 as shown in SEQ ID NO:7, HCDR3 as shown in SEQ ID NO:3, LCDR1 as shown in SEQ ID NO:4, LCDR2 as shown in SEQ ID NO:5, LCDR3 as shown in SEQ ID NO: 6; or HCDR1 as shown in SEQ ID NO:8, HCDR2 as shown in SEQ ID NO:9 or 68, HCDR3 as shown in SEQ ID NO: 10, LCDR1 as shown in SEQ ID NO: 11, LCDR2 as shown in SEQ ID NO: 12, LCDR3 as shown in SEQ ID NO: 13.

In another embodiment, the antibody that specifically recognizes a tumor antigen has a heavy chain variable region as shown in SEQ ID NO: 14 and a light chain variable region as shown in SEQ ID NO: 16; or a heavy chain variable region as shown in SEQ ID NO: 18 and a light chain variable region as shown in SEQ ID NO: 16; or a heavy chain variable region as shown in SEQ ID NO: 22 and a light chain variable region as shown in SEQ ID NO: 20; or a heavy chain variable region as shown in SEQ ID NO:53 and a light chain variable region as shown in SEQ ID NO:52.

In another embodiment, the antibody specifically recognizing a tumor antigen has an amino acid sequence as shown in SEQ ID NO: 54, 56, 57, or 58, preferably, as shown in SEQ ID NO: 54.

In another embodiment, no pretreatment or lymphocyte depletion is performed on the subject. The present invention also provides a use of immune effector cells expressing a receptor that recognize a tumor antigen in the preparation of a medicament, wherein the medicament contains the immune effector cells and a taxane compound, and the medicament is used for treating a tumor. In some embodiments, the immune effector cells and the taxane compound contained in the medicament provide therapeutic effects greater than the sum of their respective effects. In one aspect of the present invention, a kit for treating tumors is provided, comprising: 1) immune effector cells expressing a receptor that recognize a tumor antigen; 2) a taxane compound; 3) containers for containing the substances of 1) and 2); and 4) an instruction for using the kit to treat tumors.

It should be understood that within the scope of the present invention, the above-mentioned technical features of the present invention and the technical features specifically described in the following (such as in the Examples) can be combined with each other to form a new or preferred technical solution, which will not be repeated due to the length of the present specification.

DESCRIPTION OF DRAWINGS

FIG. 6A and FIG. 6B are CCK8 experiments detecting the toxicity of Abraxane on pancreatic cancer cells and CAR-T cells, respectively.

FIGS. 7A and B show an in vivo experiment observing the inhibitory effects of Abraxane in combination with CAR T cells on pancreatic cancer in mice and the change of body weight in mice.

FIGS. 8A to 8C show the survival period of mice after being treated with the method of the present invention.

FIG. 9 is a body weight change curve of a mouse model after being treated with the method of the present invention.

MODES FOR CARRYING OUT THE INVENTION

Figure 1:
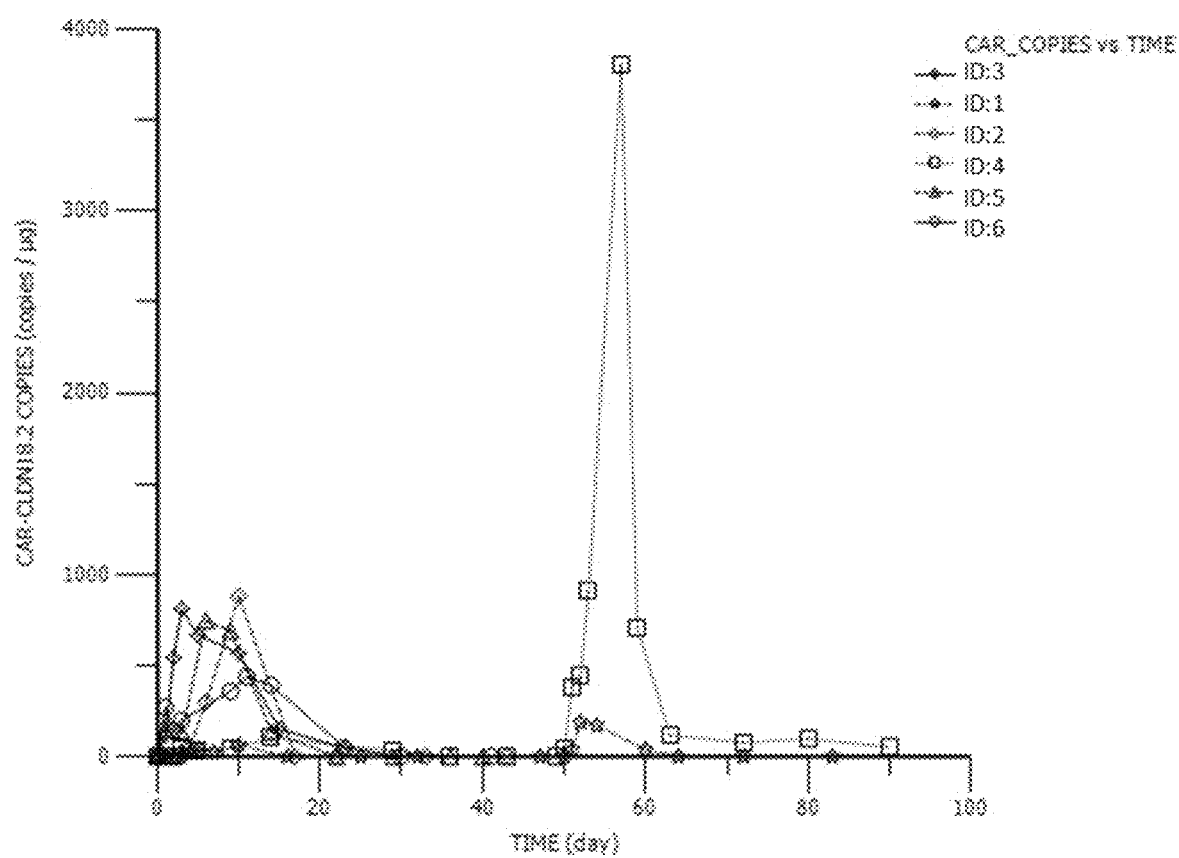
FIG. 1 shows the detection of the copy number of CAR-T.

After extensive and in-depth research, the inventors unexpectedly discovered that immune effector cells expressing chimeric antigen receptors (CAR) or other transgenic receptors, such as T cell receptors (TCR), can be administered in a specific amount and according to a specific time parameter, thereby significantly improving the therapeutic efficacy for tumor treatment by using immune effector cells and improving the effects of immune effector cells applied in solid tumors. At least partially based on this discovery, the present invention is completed.

Unless otherwise defined, all technical terms, symbols, and other technical and scientific terms or proprietary words used herein are intended to have the same meaning as commonly understood by a skilled person to which the present invention belongs. In some cases, for the purpose of clarification and/or ease of reference, terms with conventionally understood meanings are further defined herein, and such definitions included herein shall not be construed as indicating that they are substantively different from the conventional understanding in the art.

All publications mentioned in the present invention, including patent documents, academic papers, and databases, are incorporated in their entirety by reference for all purposes to the same extent that each individual publication is independently incorporated by reference. If the definition shown herein is different from the definition shown in the patents, published applications, and other publications incorporated herein by reference, or is otherwise inconsistent, the definitions herein control.

As used herein, the singular "a", "an" and "the" include plural forms, unless clearly indicates otherwise. For example, "a" or "an" means "at least one" or "one or more".

In this disclosure, all aspects of the claimed subject matter are presented in a range format. It should be understood that the description in a range format is merely for convenience and brevity, and should not be construed as an inflexible limitation on the scope of the claimed subject matter. Therefore, the description of a range should be considered to have specifically disclosed all possible subranges and individual values within that range. For example, where a range of values is provided, it should be understood that every intermediate value between the upper limit and lower limit of the range and any other stated or intermediate values within the range are included in the claims. And the upper and lower limits of the scope also belong to the scope of the claimed subject. The upper and lower limits of these smaller ranges can be independently included in the smaller range, and they also belong to the scope of the claimed subject matter, unless the upper and lower limits of the range are explicitly excluded. When the set range includes one or two limit values, the claimed subject matter also includes a range that excludes one or two of the limit values. This principle applies regardless of the scope of the range.

The term "about" used herein refers to the usual error range of each value easily known by a skilled person. The reference to "about" a value or parameter herein includes (and describes) an embodiment that refers to the value or parameter itself. For example, description of "about X" includes description of "X". For example, "about" may mean within 1 or more than 1 according to the actual standard deviation in the field. Or "about" can mean a range of up to 10% (i.e., +10%). For example, about 5 mg can include any number between 4.5 mg and 5.5 mg. When a specific value or composition is provided in the application and the scope of the patent application, "about" should be assumed to be within the acceptable error range of the specific value or composition, unless otherwise indicated.

When describing an amino acid or nucleic acid sequence, "having" a specific sequence should be understood to encompass variants of the specific sequence. In some embodiments, the amino acid or nucleic acid sequence having a specific sequence means that the amino acid or nucleic acid sequence has more than 80%, 85%, 90%, 95%, or 99% sequence identity with the specific sequence.

Any concentration range, percentage range, ratio range, or integer range described herein should be understood to include any integer within the stated range, and where appropriate, its fraction (for example, one tenth of an integer and one hundredth of an integer), unless otherwise indicated.

As used herein, the "dosing interval" refers to the time between multiple courses of immune effector cell therapy administered to an individual (such as multiple courses of treatment including the first dose of immune effector cells and subsequent doses of immune effector cells) and between the administration of the pretreatment medication. Therefore, the dosing interval can be indicated as a range. In some aspects of the present invention, the present invention includes administering multiple courses of immune effector cell therapy to an individual, and in each course, a dose determined by a physician (such as the first dose and subsequent doses) is given. In some aspects of the present invention, the specific dose of immune effector cell therapy according to the present invention can be administered in two or more times, and the total dose administered in divided doses is equal to the total dose in the course of treatment determined by a physician.

The "dose" mentioned herein can be expressed as a dose calculated according to the weight or a dose calculated according to body surface area (BSA). The dose calculated according to the weight is the dose given to a patient calculated based on the weight of the patient, such as mg/kg, number of immune effector cells/kg, etc. The dose calculated according to BSA is the dose given to a patient calculated based on the surface area of the patient, such as $mg/m^2$, and the number of immune effector cells/$m^2$, etc.

The "number of administrations" as used herein refers to the frequency of administration of immune effector cells or pretreatment drug doses within a given time. The number of administrations can be indicated as the number of doses per given time. For example, fludarabine can be administered as follows: once a day for 4 consecutive days, once a day for 3 consecutive days, once a day for 2 consecutive days, or once a day. Cyclophosphamide can be administered as follows: once a day for 4 consecutive days, once a day for 3 consecutive days, once a day for 2 consecutive days, or once a day. The albumin-bound paclitaxel can be administered as follows: once a day for 4 consecutive days, once a day for 3 consecutive days, once a day for 2 consecutive days, or once a day for administration.

The composition as used herein refers to any mixture of two or more products, substances or compounds (including cells). It can be a solution, suspension, liquid, powder, paste, which can be aqueous, non-aqueous, or any combination thereof.

As used herein, "a cell or cell population is "positive" for a specific marker" refers to the detectable presence of a specific marker (usually a surface marker) on or in the cell. Regarding a surface marker, the term means that the presence of surface expression is detected by flow cytometry, for example, by staining with an antibody specifically binding to the marker, and detecting the antibody. The staining can be detected by flow cytometry at a certain level that is significantly higher than the staining level detected when the isotype-matched control is used to perform the same step under the same conditions, and/or substantially similar to the level of cells known to be positive for the marker, and/or significantly higher than the level of cells known to be negative for the marker.

As used herein, "a cell or cell population is "negative" for a specific marker" means that no specific marker, such as a surface marker is present on or in the cell, or the specific marker is substantially undetectable. Regarding a surface marker, the term means that surface expression is not detectable by flow cytometry, or although the presence of surface expression is detected, for example, when staining with an antibody specifically binding to the marker and detecting surface expression by detecting the antibody, the staining can be detected by flow cytometry at a certain level, which is significantly lower than the staining level detected when the isotype-matched control is used to perform the same step under the same conditions, and/or significantly lower than the level of cells known to be positive for the marker, and/or substantially similar to the level of cells known to be negative for the marker.

The term "vector" as used herein refers to a nucleic acid molecule capable of replicating another nucleic acid to which it is connected. The term includes a vector in a form of a self-replicating nucleic acid structure, as well as a vector introduced into the genome of a host cell. Certain vectors can direct the expression of nucleic acids operably linked to them. The vector is also referred to herein as an "expression vector".

The present application relates to adoptive cells or immune effector cells for treating a solid tumor, including the administration of multiple doses or repeated doses of cells, and methods of using the same, compositions, and products thereof. Cells generally express a chimeric antigen receptor (CAR) or other transgenic receptors such as T cell receptors (TCR).

Claudin 18 (Claudin 18, CLD18) molecule (Genbank accession number: splice variant 1 (CLD18A1): NP_057453, NM016369, and splice variant 2 (CLD18A2): NM_001002026, NP_001002026) is an intrinsic transmembrane protein with a molecular weight of approximately 27.9/27.72 kD. Claudin is an internal membrane protein located in the tight junction of epithelium and endothelium. A network of interconnected chains of particles in the tissue membrane tightly connected between adjacent cells. In tight junctions, occludin and claudin are the most important transmembrane protein components. They create a primary barrier that prevents and controls the paracellular transport of solutes and restricts the lateral diffusion of membrane lipids and proteins to maintain cell polarity due to their strong intercellular adhesion properties. The proteins that form tight junctions are critically involved in the structure of epithelial tissues.

CLD18A1 is selectively expressed in the epithelium of normal lung and stomach, while CLD18A2 is only expressed in gastric cells. Moreover, CLD18A2 is limited to differentiated short-lived gastric epithelial cells, but does not exist in the gastric stem cell area. Both variants are strongly expressed in several cancer types, including tumors of the stomach, esophagus, pancreas, and lung, as well as human cancer cell lines. The expression is mainly in the adenocarcinoma subtypes of these indications.

The present invention provides therapeutic methods and compositions for treating diseases (such as tumors) related to CLD18 expression.

The present invention provides a method for treating tumors, particularly solid tumors, in a subject using adoptive cells or immune effector cells expressing genetically engineered (recombined) chimeric receptors. The method includes a single course of reinfusion, or a multiple course of reinfusion of adoptive cells or immune effector cells. As used herein, "dose" refers to the total amount of adoptive cells or immune effector cells that are administered or reinfused in a course of treatment. In some embodiments, where multiple courses of treatment are included in the methods described herein, the dosage for each course of treatment is the same. In some embodiments, where multiple courses of treatment are included in the methods described herein, the dosage for each course of treatment is different. "Divided dose" refers to a single dose administered when the dose of the entire treatment course is divided into multiple doses and administered to a subject within a course of treatment. In some embodiments, in the case where the dose within a course of treatment is divided into multiple doses and administered to a subject, the divided dose for each administration is the same. In some embodiments, when the dose within a course of treatment is divided into multiple doses and administered to a subject, the divided dose for each administration is different. For the purposes of this article, unless otherwise specified, the dose refers to the total amount of adoptive cells or immune effector cells administered or reinfused within a course of treatment.

In some embodiments, the methods described herein include the reinfusion of the adoptive cells or immune effector cells in a single course of treatment. A single course of treatment refers to the reinfusion of a certain amount of adoptive cells or immune effector cells within a certain period of time. In some embodiments, a certain total amount of adoptive cells or immune effector cells is reinfused at one time during the course of treatment. In some embodiments, a certain total amount of adoptive cells or immune effector cells is reinfused in two or more times. In some embodiments, a certain total amount of adoptive cells or immune effector cells is reinfused in three or more times. In some embodiments, a certain total amount of adoptive cells or immune effector cells is reinfused in four or more times. In some embodiments, a certain total amount of adoptive cells or immune effector cells is reinfused in five or more times. In some embodiments, a certain total amount of adoptive cells or immune effector cells is reinfused in six or more times. In some embodiments, a certain total amount of adoptive cells or immune effector cells is reinfused in seven or more times. In some embodiments, a certain total amount of adoptive cells or immune effector cells is reinfused in eight or more times. In some embodiments, a certain total amount of adoptive cells or immune effector cells is reinfused in nine times or more. In some embodiments, a certain total amount of adoptive cells or immune effector cells is reinfused in ten or more times. In some embodiments, the adoptive cells or immune effector cells that are reinfused each time are aliquots of the adoptive cells or immune effector cells to be reinfused. In some embodiments, the adoptive cells or immune effector cells that are reinfused each time are non-aliquots of the adoptive cells or immune effector cells to be reinfused. In some embodiments, the amount of adoptive cells or immune effector cells to be reinfused each time is determined by a physician according to the specific conditions of the subject. The specific conditions of the subject may be, for example, the overall health of the subject, the severity of the disease, the response to the previous dose of the same course of treatment, the response to the previous course of treatment, the combined medication of the subject, the degree or likelihood of toxicity, complications, cancer metastasis, and any other factors considered by a physician which will affect the amount of adoptive cells or immune effector cells suitable for reinfusion in a subject. In some embodiments, among the total amount of adoptive cells or immune effector cells that are reinfused in multiple times, the amount of adoptive cells or immune effector cells that are reinfused each time shows an increasing trend. In some embodiments, among the total amount of adoptive cells or immune effector cells that are reinfused in multiple times, the amount of adoptive cells or immune effector cells that are reinfused each time shows a decreasing trend. In some embodiments, among the total amount of adoptive cells or immune effector cells that are reinfused in multiple times, the amount of adoptive cells or immune effector cells that are reinfused each time shows a trend which increases first and then decreases. In some embodiments, among the total amount of adoptive cells or immune effector cells that are reinfused in multiple times, the amount of adoptive cells or immune effector cells that are reinfused each time shows a trend which decreases firstly and then increases.

Multi-course reinfusion refers to multiple time-of-periods, and a certain total amount of adoptive cells or immune effector cells are reinfused in each time-of-period. In some embodiments, the lengths of the multiple time-of-periods are the same. In some embodiments, the lengths of the multiple time-of-periods are unequal. In some embodiments, the multiple courses of treatment refers to at least two time-of-periods. In some embodiments, the multiple courses of treatment refers to at least three time-of-periods. In some embodiments, the multiple courses of treatment refers to at least four time-of-periods. In some embodiments, the multiple courses of treatment refers to at least five time-of-periods. In some embodiments, the multiple courses of treatment refers at least six time-of-periods. In some embodiments, the multiple courses of treatment refers to at least seven time-of-periods. In some embodiments, the multiple courses of treatment refers to at least eight time-of-periods. In some embodiments, the multiple courses of treatment refers to at least nine time-of-periods. In some embodiments, the multiple courses of treatment refers to at least ten time-of-periods. In some embodiments, the multiple courses of treatment refers to more than ten such time-of-periods.

In some embodiments, a certain total amount of adoptive cells or immune effector cells is reinfused at one time in one of the multiple courses of treatment. In some embodiments, a certain total amount of adoptive cells or immune effector cells is reinfused in two or more times in one of the multiple courses of treatment. In some embodiments, a certain total amount of adoptive cells or immune effector cells is reinfused in three or more times in one of the multiple courses of treatment. In some embodiments, a certain total amount of adoptive cells or immune effector cells is reinfused in four or more times in one of the multiple courses of treatment. In some embodiments, a certain total amount of adoptive cells or immune effector cells is reinfused in five or more times in one of the multiple courses of treatment. In some embodiments, a certain total amount of adoptive cells or immune effector cells is reinfused in six or more times in one of the multiple courses of treatment. In some embodiments, a certain total amount of adoptive cells or immune effector cells is reinfused in seven or more times in one of the multiple courses of treatment. In some embodiments, a certain total amount of adoptive cells or immune effector cells is reinfused in eight or more times in one of the multiple courses of treatment. In some embodiments, a certain total amount of adoptive cells or immune effector cells is reinfused in nine or more times in one of the multiple courses of treatment. In some embodiments, a certain total amount of adoptive cells or immune effector cells is reinfused in ten or more times in one of the multiple courses of treatment. In some embodiments, in one of the multiple courses of treatment, the adoptive cells or immune effector cells to be reinfused each time are aliquots of the adoptive cells or immune effector cells to be reinfused. In some embodiments, in one of the multiple courses of treatment, the adoptive cells or immune effector cells to be reinfused each time are non-aliquots of the adoptive cells or immune effector cells to be reinfused. In some embodiments, the amount of adoptive cells or immune effector cells to be reinfused each time in one of the multiple courses of treatment is determined by a physician according to the specific conditions of a subject. The specific conditions of the subject may be, for example, the overall health of the subject, the severity of the disease, the response to the previous dose of the same course of treatment, the response to the previous course of treatment, the combined medication of the subject, the degree or likelihood of toxicity, complications, cancer metastasis, and any other factors considered by a physician which will affect the amount of adoptive cells or immune effector cells suitable for reinfusion in the subject. In some embodiments, a certain total amount of adoptive cells or immune effector cells are reinfused in the same number of times in each of the multiple courses of treatment. In some embodiments, a certain total amount of adoptive cells or immune effector cells are reinfused in the different times in each of the multiple courses of treatment. In some embodiments, a certain total amount of adoptive cells or immune effector cells are reinfused in the same number of times in each of the multiple courses of treatment. In some embodiments, the same certain total amount of adoptive cells or immune effector cells is reinfused in each of the multiple courses of treatment. In some embodiments, a different certain total amount of adoptive cells or immune effector cells is reinfused in each of the multiple courses of treatment.

In some embodiments, the total amount of the adoptive cells or immune effector cells in each of the multiple courses of treatment shows an increasing trend. In some embodiments, the total amount of the adoptive cells or immune effector cells in each of the multiple courses of treatment shows a decreasing trend. In some embodiments, the total amount of the adoptive cells or immune effector cells in each of the multiple courses of treatment shows a trend which increases first and then decreases. The total amount of the adoptive cells or immune effector cells in each of the multiple courses of treatment tends to decrease firstly and then increase.

In some embodiments, the first dose is a lower dose and/or a modified or reduced dose and/or the subsequent dose is a consolidated dose and/or a modified or reduced dose. Cells, compositions, and articles that can be used in such methods are also provided. In some embodiments, the chimeric receptor is a genetically engineered antigen receptor, such as a functional non-TCR antigen receptor, for another example, a chimeric antigen receptor (CAR) and other recombinant antigen receptors, such as genetically engineered T cell receptor (TCR). Receptors also include other recombinant chimeric receptors, such as those containing extracellular portions specifically binding to ligands or receptors or other binding partners and intracellular portions, such as the intracellular signal transduction portion of CAR. In some embodiments, the dose includes a lower first dose.

In some embodiments, the method comprises (a) administering a single course of chimeric antigen receptor (e.g., CAR)-expressing cells to a subject with a tumor; and (b) administering multiple courses of chimeric antigen receptor (e.g., CAR)-expressing cells to the subject. In other embodiments, one or more subsequent doses may be administered.

The term "CLD18" refers to claudin-18, and includes any variant of CLD18 (including CLD18A1 and CLD18A2), conformational variant, isoform, and species homologs that are naturally expressed by cells or expressed by cells transfected with CLD18 gene. Preferably, "CLD18" refers to human CLD18, particularly CLD18A2 (SEQ ID NO: 33) and/or CLD18A1 (SEQ ID NO: 34), more preferably CLD18A2.

The term "CLD18A1" includes any post-translational modified variants, isoforms and species homologs of human CLD18A1 that are naturally expressed by cells or expressed by cells transfected with CLD18A1 gene.

The term "CLD18A2" includes any post-translationally modified variants, isoforms and species homologs of human CLD18A2 that are naturally expressed by cells or expressed by cells transfected with CLD18A2 gene.

The term "CLD18 variant" shall include (i) CLD18 splice variants, (ii) CLD18 post-translational modification variants, especially including variants with different N glycosylation, (ii CLD18 conformational variants, especially including CLD18-conformational-1, CLD18-conformational-2 and CLD18-conformational-3, (iv) free CLD18 and homo/allo-associated variants at intercellular tight junctions, (v) CLD18 cancer-related variants and CLD18 non-cancer-related variants.

Method for Treating Tumor Using Cells Expressing Chimeric Antigen Receptor

The present invention provides methods, compositions and articles for cell therapy, for the treatment of diseases or disorders including various solid tumors. The method involves administering immune effector cells expressing chimeric receptors targeting and recognizing and/or specifically binding to tumor antigens and activate immune effector cells. The receptors include chimeric receptors, such as chimeric antigen receptor (CAR), T cell receptors (TCR), T cell fusion protein (TFP), and T cell antigen coupler (TAC).

In some embodiments, the method includes administering to the subject one or more subsequent doses of cells. The dose is usually given in a specific amount and according to specific time parameters. In some embodiments, the method generally includes administering a first dose of cells, followed by administering subsequent doses of cells during a specific time window relative to the first dose. In some embodiments, the number of cells administered and the duration of multiple doses are designed to improve one or more results, such as reducing the degree or likelihood of toxicity in the subject, and/or improving the therapeutic efficacy.

In some embodiments, the provided methods are based on the observation herein that increased exposure of a subject to the administered cells (e.g., increased cell number or duration) can improve the efficacy and effectiveness of immune effector cell therapy. Preliminary analysis after the administration of different CAR-T cells targeting CLD18A2 to subjects with various CLD18A2-positive cancers in multiple clinical trials showed a correlation between higher and/or longer exposure to CAR-T cells and the treatment outcome. These results include the patient's survival, remission, or stability of the disease. In some embodiments, the method described herein includes monitoring the subject's exposure to the adoptive cells or immune effector cells, and determining the dose and interval of subsequent divided administration or subsequent courses of treatment based on the exposure time. In some embodiments, the methods described herein include monitoring the subject's exposure to the adoptive cells or immune effector cells, and maintaining or reducing the subsequent divided administration or dose for subsequent courses of treatment and/or maintaining or extending subsequent divided administrations or the interval between subsequent courses of treatment according to the exposure level reaching or exceeding a certain level. In some embodiments, the methods described herein include monitoring the subject's exposure to the adoptive cells or immune effector cells, and maintaining or increasing subsequent divided administration or subsequent dose for subsequent courses of treatment and/or maintaining or shortening subsequent divided administrations or the interval between subsequent courses of treatment according to the exposure level lower than a certain level.

In some embodiments, the method described herein includes monitoring the degree or risk of the toxic response of a subject to the adoptive cells or immune effector cells, and determining the subsequent divided administration or the dose and interval for subsequent courses of treatment based on the degree of toxicity or risk. In some embodiments, the degree of toxicity or risk includes, but is not limited to, for example, CRS, neurotoxicity, macrophage activation syndrome, tumor lysis syndrome, and the like.

In some embodiments, a subsequent dose is usually given, when the risk of toxicity response or symptoms or biochemical indicators (such as CRS or neurotoxicity, macrophage activation syndrome, or tumor lysis syndrome) is equal to or lower than an acceptable level after the first dose or the previous dose is administered. In some embodiments, the toxic response or symptoms or biochemical indicators include one or more of fever, hypotension, hypoxia, neurological disorders, inflammatory cytokines, and serum levels of C-reactive protein (CRP). Kind. In some embodiments, the acceptable level of the risk of the toxic response or symptoms or biochemical indicators refers to 95%, 90%, 85%, 80%, 75%, 70%, 65%, 60%, 55%, 50%, 45%, 40%, 35%, 30%, 25%, 20%, 15%, or 10% of the peak level after the first dose or the previous dose.

In some embodiments, a subsequent dose is given when the toxicity response reaches the peak level after the first dose or the previous dose and is decreasing. In some embodiments, a subsequent dose is administered after the first dose or the previous dose is administered and the toxicity response decreases to equal to or below an acceptable level. In some embodiments, a subsequent dose is administered after the first dose or the previous dose is administered and when the risk of the toxic response or symptoms or biochemical indicators is equal to or lower than 95%, 90%, 85%, 80%, 75%, 70%, 65%, 60%, 55%, 50%, 45%, 40%, 35%, 30%, 25%, 20%, 15%, or 10% of the peak level after the first dose or the previous dose is administered. Therefore, in some embodiments, a subsequent dose is administered at least 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 80 days after the first dose or the previous dose is administered. In some embodiments, the appropriate time is determined by monitoring and/or evaluating the presence of one or more symptoms or risks associated with a toxic event and determining the subsequent dose for infusion after the symptoms or risks are determined to be at or below an acceptable level.

In some embodiments, after the first dose, the subsequent dose is administered when the serum level of factors indicative of cytokine-release syndrome (CRS) in the subject does not exceed 5, 6, 7, 8, 9, 10, 11, 12, 13, 14, 15, 16, 17, 18, 19, 20, 21, 22, 23, 24, 25, 26, 27, 28, 29, 30 times of the subject's serum levels before the first dose is administered.

In some embodiments, the timing of the subsequent doses is selected to avoid the host immune response generated by the first dose or the previous dose, which may induce the decrease of the efficacy of the subsequent doses. In some aspects, the subsequent dose is administered before the appearance of a host immune response, such as adaptability or specificity to the administered cells and/or the expressed chimeric antigen receptor, such as a humoral or cell-mediated immune response. In some embodiments, the subsequent dose is administered before such a response can be detected, for example, by one or more specialized detection methods. One or more subsequent doses are usually given when the host adaptive immune response to the cells is not detected, not established, and/or does not reach a certain level or degree or stage. Therefore, in some embodiments, the subsequent dose is administered up to 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 80, 81, 82, 83, 84, 85, 86, 87, 88, 89, 90, 91, 92, 93, 94, 95, 96, 97, 98 or 99 days after the first or previous dose is administered.

Therefore, in some embodiments, the provided methods involve the administration of one or more subsequent doses, after the window of toxicity risk, after the tumor burden is stabilized or reduced with the first dose, while before the adaptive host immune response (i.e., the immune rejection to CAR-T cells produced in the body) is produced. Under this condition, the subsequent dose can safely and effectively provide immune monitoring, elimination or prevention of the proliferation or metastasis of residual tumor cells. Therefore, in some embodiments, the subsequent dose is a disease-consolidating dose.

The so-called tumor burden includes the size or degree of differentiation, or the type and stage of metastasis of the tumor, and/or the appearance and disappearance of common complications of advanced cancer, such as cancerous pleural effusion, and/or changes in the appearance or expression level of tumor markers, and/or the likelihood or incidence of toxic results in the subject, such as CRS, macrophage activation syndrome, tumor lysis syndrome, neurotoxicity and/or host immune responses for the administered cells and/or chimeric antigen. In some embodiments, the size of the tumor is measured by a scaler that comes with PET (positron emission computed tomography) and CT (computed tomography).

The tumor marker, also known as tumor label, refers to a substance that is characteristically present in malignant tumor cells, or is abnormally produced by malignant tumor cells, or is produced by a host in the response to tumor stimulation, and can reflect tumor occurrence and development and monitor tumor response to treatment. Tumor markers exist in the tissues, body fluids and excreta of cancer patients, and can be detected by immunological, biological and chemical methods, including alpha-fetoprotein (AFP), CA125, CA15-3, squamous cell carcinoma antigen (SCC), soluble fragments of cytokeratin 19 (CYFRA21-1), carcinoembryonic antigen (CEA), CA199, CA724, etc.

In some embodiments, the first dose includes cells in an amount sufficient to reduce the tumor burden of the subject, and the subsequent dose is administered, when the serum level of factors indicative of cytokine-release syndrome (CRS) in the subject does not exceed 10 or 25 times of the subject's serum level before the first dose is administered, and/or the peak level of CRS-related results in the subject begins to decline after the first dose is administered, and there is no detectable adaptive host immune response specific for the chimeric receptor expressed by the cells of the first dose in the subject.

In some embodiments, the first dose contains less than about $2.5 \times 10^8$ cells/kg of subject's body weight, or less than about $1 \times 10^{12}$ cells, and the subsequent dose is administered between 21 days to about 80 days after the first dose is administered.

Administration of Cells in Immune Effector Cell Therapy

The method provided by the present invention includes administering multiple doses of immune effector cells expressing a chimeric antigen receptor, such as CAR, TCR, TFP, and TAC that recognize a tumor antigen, to a subject with a solid tumor expressing the tumor antigen.

The "tumor antigen" as used herein includes, but is not limited to Thyroid Stimulating Hormone Receptor (TSHR); CD171; CS-1; C-type lectin-like molecule-1; Ganglioside GD3; Tn antigen; CD19; CD20; CD 22; CD 30; CD 70; CD 123; CD 138; CD33; CD44; CD44v7/8; CD38; CD44v6; B7H3 (CD276), B7H6; KIT (CD117); interleukin 13 receptor subunit a (IL-13Ra)); interleukin 11 receptor α (IL-11Ra); prostate stem cell antigen (PSCA); prostate specific membrane antigen (PSMA); carcinoembryonic antigen (CEA); NY-ESO-1; HIV-1 Gag; MART-1; gp100; tyrosinase; mesothelin; EpCAM; protease serine 21 (PRSS21); vascular endothelial growth factor receptor; Lewis (Y) antigen; CD24; platelet-derived growth factor receptor β (PDGFR-β); stage Specific embryonic antigen-4 (SSEA-4); cell surface-related mucin 1 (MUC1), MUC6; epidermal growth factor receptor family and its mutants (EGFR, EGFR2, ERBB3, ERBB4, EGFRvIII); nerve cell adhesion Attachment molecule (NCAM); Carbonic anhydrase IX (CAIX); LMP2; Ephrin A receptor 2 (EphA2); Fucosyl GM1; Sialyl Lewis adhesion molecule (sLe); Ganglioside GM3 (aNeu5Ac(2-3)bDGalp(1-4)bDGlcp(1-1)Cer; TGS5; high molecular weight melanoma-associated antigen (HMWMAA); o-acetyl GD2 ganglioside (OAcGD2); folate receptor; Tumor vascular endothelial marker 1 (TEM1/CD248); Tumor vascular endothelial marker 7 related (TEM7R); Claudin 6, Claudin 18.2, Claudin 18.1; ASGPR1; CDH16; 5T4; 8H9; αvβ6 integrin; B cell maturation antigen (BCMA); CA9; kappa light chain; CSPG4; EGP2, EGP40; FAP; FAR; FBP; embryonic AchR; HLA-A1, HLA-A2; MAGEA1, MAGE3; KDR; MCSP; NKG2D ligand; PSC1; ROR1; Sp17; SURVIVIN; TAG72; TEM1; Fibronectin; Tenascin; Carcinoembryonic variant of tumor necrosis zone; G protein-coupled receptor class C group 5-member D (GPRC5D); X chromosome open reading Box 61 (CXORF61); CD97; CD179a; Anaplastic Lymphoma Kinase (ALK); Polysialic acid; Placenta specific 1 (PL AC1); the hexose part of globoH glycoceramide (GloboH); breast differentiation antigen (NY-BR-1); uroplakin 2 (UPK2); hepatitis A virus cell receptor 1 (HAVCR1); adrenergic receptor β3 (ADRB3); Pannexin 3 (PANX3); G protein coupled receptor 20 (GPR20); lymphocyte antigen 6 complex locus K9 (LY6K); olfactory receptor 51E2 (OR51E2); TCRγ alternating reading frame protein (TARP); Wilms Cell tumor protein (WT1); ETS translocation variant gene 6 (ETV6-AML); Sperm protein 17 (SPA17); X antigen family member 1A (XAGE1); Angiopoietin binds to cell surface receptor 2 (Tie2); Melanin Tumor cancer testis antigen-1 (MAD-CT-1); Melanoma cancer testis antigen-2 (MAD-CT-2); Fos-related antigen 1; p53 mutant; human telomerase reverse transcriptase (hTERT); Sarcoma translocation breakpoint; melanoma inhibitor of apoptosis (ML-IAP); ERG (transmembrane protease serine 2 (TMPRSS2) ETS fusion gene); N-acetylglucosaminyl transferase V (NA17); Pairing box protein Pax-3 (PAX3); Androgen receptor; Cyclin B1; V-myc avian myeloidosis virus oncogene neuroblastoma-derived homolog (MYCN); Ras homolog family member C (RhoC); Cytochrome P450 1B1 (CYP1B1); CCCTC binding factor (zinc finger protein)-like (BORIS); Squamous cell carcinoma antigen 3 (SART3) recognized by T cells; Paired box protein Pax-5 (PAX5); Proacrosin binding protein sp32 (OYTES1); lymphocyte-specific protein tyrosine kinase (LCK); A kinase anchoring protein 4 (AKAP-4); synovial sarcoma, X breakpoint 2 (SSX2); CD79a; CD79b; CD72; Leukocyte-associated immunoglobulin-like receptor 1 (LAIR1); Fc fragment of IgA receptor (FCAR); Leukocyte immunoglobulin-like receptor subfamily member 2 (LILRA2); CD300 molecular-like family member f (CD300LF); C-type lectin domain family 12 member A (CLEC12A); bone marrow stromal cell antigen 2 (BST2); mucin-like hormone receptor-like 2 (EMR2) containing EGF-like modules; lymphocyte antigen 75 (LY75); phosphatidyl muscle Glycan-3 (GPC3); Fc receptor-like 5 (FCRL5); immunoglobulin lambda-like polypeptide 1

(IGLL1). In some embodiments, the tumor antigen is EGFR, EGFRVIII, Glypican 3, claudin 18.2 or BCMA.

"Subject" as used herein is a mammal, such as a human or other animal, and usually a human. In some embodiments, the subject has received tumor chemotherapy or radiation therapy before the first dose is administered and/or the subsequent dose is administered. In some aspects, the subject is refractory or non-responsive to other therapeutic agents.

In some embodiments, the tumor is persistent or recurrent, for example, after another therapeutic intervention, including chemotherapy and radiation is used. In some embodiments, the administration effectively treats the subject regardless of whether the subject is resistant to another therapy.

In some embodiments, the subject is responsive to other therapeutic agents and treatment with the therapeutic agent reduces the tumor burden. In some aspects, the subject is initially responsive to the therapeutic agent, but then shows tumor recurrence. In some embodiments, the subject is determined to be at risk of recurrence, for example at a high risk of recurrence, and the cells are thus prophylactically administered, for example, to reduce the likelihood of recurrence or prevent recurrence.

Such diseases include tumors, or other proliferative diseases or disorders. The tumors include but are not limited to: colon cancer, rectal cancer, renal cell carcinoma, liver cancer, non-small cell lung cancer, small bowel cancer, esophageal cancer, melanoma, bone cancer, pancreatic cancer, skin cancer, head and neck cancer, skin or intraocular malignant melanoma, uterine cancer, ovarian cancer, rectal cancer, anal cancer, stomach cancer, testicular cancer, uterine cancer, fallopian tube cancer, endometrial cancer, cervical cancer, vagina cancer, Hodgkin's disease, non-Hodgkin Lymphoma, endocrine system cancer, thyroid cancer, parathyroid cancer, adrenal cancer, soft tissue sarcoma, urethral cancer, penile cancer, childhood solid tumors, bladder cancer, renal or ureteral cancer, renal pelvis cancer, central nervous system (CNS) tumors, Primary CNS lymphoma, tumor angiogenesis, spinal tumor, brainstem glioma, pituitary adenoma, Kaposi's sarcoma, epidermoid carcinoma, squamous cell carcinoma, T cell lymphoma, environmentally induced cancer, a combination thereof and the metastatic foci thereof.

In some embodiments, the size of the dose and the reinfusion time are determined by the initial tumor burden of the subject. For example, in some cases, the number of cells in the first dose given to the subject is generally relatively low. In the case of low tumor burden, for solid tumors, tumor burden and/or minimal residual disease can be evaluated by detecting tumor markers, the initial dose may be relatively high. In other cases, in a subject with a higher tumor burden, the first dose can be divided into several continuous infusion, and the first dose is divided into 1, 2, 3, 4, 5, 6, 7, 8, 9 or 10 administrations, preferably 1 to 5 administrations, more preferably 2 to 3 administrations. There is an interval of 1, 2, 3, 4, 5, 6, 7, 8, 9, 10, 11, 12, 13, 14, 15, 16, 17, 18, 19 or 20 days or no interval between each administration. In some cases, the subsequent dose may be the same as or higher than or lower than the first dose.

The term "treatment" as used herein refers to the complete or partial mitigation or reduction of tumors or associated symptoms thereof. The desired therapeutic effects include, but are not limited to, preventing the occurrence or recurrence of tumors, mitigating symptoms, reducing any direct or indirect pathological results of the tumor, preventing metastasis, slowing the tumor progression, improving or mitigating tumor status, and reducing or improving prognosis. As used herein, "delaying the development of a tumor" means delaying, hindering, slowing, slowing down, stabilizing, restraining and/or limiting the development of a tumor. The delay can be of different lengths of time, depending on the history of the disease and/or the individual to be treated. A skilled person will understand that a sufficient or significant delay can encompass prevention (for individuals who have not developed the tumor). For example, advanced cancers, such as the development of metastases, can be delayed.

In some embodiments, the provided cells and compositions are used to delay tumor development or slow tumor progression.

As used herein, "inhibiting" a function or activity means a reduction in the function or activity when compared with the same disease under other conditions or compared with another disease.

In the context of administration, an "effective amount" of an agent, for example, a pharmaceutical preparation, cell, or composition refers to a certain amount that is effective to achieve the desired results, such as treating or preventing results in terms of a certain dose and a necessary length of time.

A "therapeutically effective amount" of an agent, for example, a pharmaceutical preparation or cell, refers to a certain amount that is effective in terms of dosage and necessary time course to achieve the desired therapeutic results, such as the treatment of tumors, and/or kinetic or pharmacokinetic effects of the treatment. The therapeutically effective amount can vary depending on various factors, such as disease state, age, sex, subject weight, and the administered cell population. In some embodiments, the provided methods involve administering an effective amount (e.g., a therapeutically effective amount) of the cell and/or composition.

A "prophylactically effective amount" refers to a certain amount that is conducive to achieving the desired preventive results in terms of a certain dose and necessary time course. Generally, the prophylactically effective dose will be less than the therapeutically effective dose, since the prophylactic dose is used in the subject at an early stage of the disease or before the disease. In the case of lower tumor burden, in some aspects, the prophylactically effective amount may be higher than the therapeutically effective amount.

Methods for administering cells for immune effector cell therapy are known and can be used in combination with the methods and compositions provided herein.

In some embodiments, the cell therapy, for example, adoptive T cell or immune effector cell therapy, is performed by autologous reinfusion. Therefore, in some aspects, the cells are derived from the subject in need of treatment and the cells, and are administered to the same subject after isolation and processing.

In some embodiments, the cell therapy, for example, adoptive T cell or immune effector cell therapy, is performed by allogeneic reinfusion, wherein the cells are isolated and/or in other cases extracted and prepared from the donor, and the donor is different from the subject for the reinfusion. In such embodiments, the cells are then administered to a subject with high genetic histocompatibility. In some embodiments, the donor and recipient are genetically identical. In some embodiments, the donor and recipient are genetically similar. In some embodiments, the recipient and donor are of the same HLA category or supertype.

The cells can be administered by any suitable means, for example, by injection, such as, intravenous or subcutaneous injection, intraocular injection, fundus injection, subretinal injection, intravitreal injection, counter-interval injection, subscleral injection, intrachoroidal injection, anterior chamber injection, subconjectval injection, subconjuntival injection, superscleral cavity injection, retrobulbar injection, periocular injection or perispheric delivery. In some embodiments, they are administered parenterally, intrapulmonarily, and intranasally, and if local treatment is desired, intralesional administration. Extraperitoneal infusion includes intramuscular, intravenous, intraarterial, intraperitoneal, or subcutaneous administration. In some embodiments, a given dose is administered by administering the cells in a single bolus injection. In some embodiments, the cells are administered by multiple boluses, for example, multiple administrations within not more than 20 days, or by continuous infusion of the cells.

For the prevention or treatment of diseases, the appropriate dose may depend on the type of disease to be treated, the type of chimeric antigen receptor or cell, the severity of the disease and the course of the disease, whether the cells are administered for preventive or therapeutic purposes, previous treatment, the clinical history and response to the cells of the subject, as well as the judgment of the attending physician. In some embodiments, the composition and cells are suitable for the administration to a subject at a time point or in a series of treatments.

In some embodiments, the immune effector cells are used as a part of a combination therapy, for example, with another interventional therapy, for example, with another therapeutic agent such as an antibody, engineered immune effector cells, receptors or reagents, cytotoxicity drugs or other treatments, simultaneously or sequentially, in any order. In some embodiments, immune effector cells are used in combination with one or more other treatment methods, or in combination with another interventional treatment method, simultaneously or sequentially in any order. In some cases, the immune effector cells are co-administered with another treatment at a sufficiently close time to produce therapeutic effects greater than those of the above-mentioned immune effector cell population or one or more other therapeutic drugs or methods, and vice versa. In some embodiments, the immune effector cells are administered before one or more other therapeutic agents are administered. In some embodiments, the immune effector cells are administered after one or more other therapeutic agents are administered. In some embodiments, one or more other therapeutic drugs include cytokines, such as IL-2, IL-12, to enhance persistence.

The other therapeutic agent may be administered by any suitable means, for example, by injection, for example, intravenous or subcutaneous injection, intraocular injection, fundus injection, subretinal injection, intravitreal injection, reverse septal injection, subscleral injection, intrachoroidal injections, anterior chamber injections, subconjectval injections, subconjuntival injections, supracleral injections, retrobulbar injections, periocular injections, or perispheric delivery. In some embodiments, they are delivered by parenteral, intrapulmonary, and intranasal route, and if local treatment is desired, they can be administered by intralesional route. Extraperitoneal infusion includes intramuscular, intravenous, intraarterial, intraperitoneal, or subcutaneous administration. In some embodiments, the therapeutic agent is administered by a single bolus injection to give a given dose. In some embodiments, the administration is multiple bolus injections, for example, multiple administrations within not more than 20 days, or by continuous infusion.

In some embodiments, the method of the present invention includes administering a tubulin inhibitor and the adoptive cell or immune effector cell to a subject. In some embodiments, the method of the present invention includes administering a tubulin inhibitor and immune effector cells to a subject within one course of treatment. In some embodiments, the method of the present invention includes administering a tubulin inhibitor to a subject and then administering immune effector cells. In some embodiments, the method of the present invention includes firstly administering immune effector cells to a subject and then administering a tubulin inhibitor. In some embodiments, the method of the present invention includes administering to a subject substantially simultaneously the tubulin inhibitor and immune effector cells. In some embodiments, the method of the present invention includes alternately administering a tubulin inhibitor and immune effector cells to a subject. In multiple courses of treatment, the tubulin inhibitor and immune effector cells can be the same or different.

The tubulin inhibitors described herein include a tubulin polymerization promoter and a tubulin polymerization inhibitor. The tubulin polymerization promoter includes, but not limited to, for example, taxanes, epothilones, sponge lactones, and Laulimalide, and the like. The tubulin polymerization inhibitor includes, but not limited to, for example, colchicine, Combretastatin A-4, BPR0L075, Plinabulin (NPI-2358), Nakiterpiosin, Vincristine, Nocodazole, Podophyllotoxin, Dolastatins 10, Indibulin (D-24851) and Eribulin, and the like.

Taxanes compounds include paclitaxel (Trade name: taxol), albumin-bound paclitaxel (nab-paclitaxel, Abraxane), docetaxel (docetaxel) and derivatives thereof. Tubulin inhibitors of Taxanes can promote the assembly of tubulin into microtubules and inhibit the depolymerization of microtubules, resulting in abnormal arrangement of microtubules and the formation of astroid bodies, thereby causing the spindle to lose its normal function and ultimately leading to cell death.

In some embodiments, the method of the present invention includes administering taxanes and immune effector cells to a subject within one course of treatment. In some embodiments, the method of the present invention includes administering taxanes to a subject and then administering immune effector cells within one course of treatment. In some embodiments, the method of the present invention includes firstly administering immune effector cells to a subject, and then administering taxanes within one course of treatment. In some embodiments, the method of the present invention includes substantially simultaneously administering taxanes and immune effector cells to a subject within one course of treatment. In some embodiments, the method of the present invention includes alternately administering taxanes and immune effector cells to a subject within one course of treatment.

In some embodiments, the method of the present invention includes administering taxanes and immune effector cells to a subject within multiple courses of treatment. In some embodiments, the method of the present invention includes administering taxanes to a subject and then administering immune effector cells within multiple courses of treatment. In some embodiments, the method of the present invention includes firstly administering immune effector cells to a subject, and then administering taxanes within multiple courses of treatment. In some embodiments, the method of the present invention includes substantially simultaneously administering taxanes and immune effector cells to a subject within multiple courses of treatment. In some embodiments, the method of the present invention includes alternately administering taxanes and immune effector cells to a subject within multiple courses of treatment. In some embodiments, the method of the present invention includes administering the same dose of taxanes and/or immune effector cells to a subject in different courses of treatment. In some embodiments, the method of the present invention includes administering different doses of taxanes and/or immune effector cells to a subject in different courses of treatment. The term "taxanes" refers to drugs, main components of which contain taxane compounds, and the taxane compounds have a bridge methylene benzocyclodecene core structure similar to taxanes. In some embodiments, an unsaturated bond is contained in the bridge methylene benzocyclodecene core structure of the taxane compound. In some embodiments, no unsaturated bond is contained in the bridge methylene benzocyclodecene core structure of the taxane compound. In some embodiments, the carbon atom on the bridge methylene benzocyclodecene core structure of the taxane is substituted with a heteroatom selected from N, O, S or P. In some embodiments, the taxane compound is administered by injection. In some embodiments, the method of the present invention can increase, enhance or prolong the activity and/or number of immune cells during cancer treatment, or produce a medically effective response. The term "increasing" or "enhancing" activities of immune cells means that the ability of a subject or tumor cells to respond to the treatment disclosed herein is improved. For example, the enhanced response may include 5%, 10%, 15%, 20%, 25%, 30%, 35%, 40%, 45%, 50%, 55%, 60%, 65%, 70%, 75%, 80%, 85%, 90%, 95%, or 98% or more increase in the responsiveness. As used herein, "enhancing" can also refer to increasing the number of subjects responding to a treatment, such as immune effector cell therapy. For example, an enhanced response can refer to the total percentage of subjects responding to a treatment, where the percentages are 5%, 10%, 15%, 20%, 25%, 30%, 35%, 40%, 45%, 50%, 55%, 60%, 65%, 70%, 75%, 80%, 85%, 90%, 95% or 98% or higher. In some embodiments, the dose of a taxane compound, such as Abraxane is not higher than 300 mg/m$^2$/time, or not higher than about 200 mg/m$^2$/time, preferably, 100 mg/m$^2$/time-200 mg/m$^2$/time. In some embodiments, the dose of a taxane compound, such as Abraxane is about 200, 195, 190, 185, 180, 175, 170, 165, 160, 155, 150, 145, 140, 135, 130, 125, 120, 115, 110, 105, 100, 95, 90, 85, 80, 75, 70, 65, 60, 55, 50, 45, 40, 35, 30, 25, 20, 15, 10, 8, 6, 4, 3, 2 or 1 mg/m$^2$/time, preferably, 100 mg/m$^2$/time-200 mg/m$^2$/time. In certain embodiments, the taxane compound, such as Abraxane is administered once via intravenous infusion approximately every 6 weeks, 5 weeks, 4 weeks, 3 weeks, 2 weeks, 1 week, 6 days, 5 days, 4 days, 3 days, 2 days, or 1 day. In some embodiments, a taxane compound, such as Abraxane is intravenously infused once per course of treatment. In certain embodiments, the immune effector cell therapy is administered 1 hour, 2 hours, 3 hours, 4 hours, 5 hours, 6 hours, 7 hours, 8 hours, 9 hours, 10 hours, 11 hours, 12 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 1 month or any combination thereof before the taxane compound is administered. In certain embodiments, the immune effector cell therapy is administered 1 hour, 2 hours, 3 hours, 4 hours, 5 hours, 6 hours, 7 hours, 8 hours, 9 hours, 10 hours, 11 hours, 12 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 1 month or any combination thereof after the taxane compound is administered.

In some embodiments, the method of the present invention includes administering pretreatment before the first dose or subsequent dose(s), for example, chemotherapeutic drugs (chemotherapeutics), whole body radiation, local radiation therapy, etc. or a combination thereof. In some embodiments, the method includes administering a pretreatment to a subject with one or more chemotherapeutic agents. In some embodiments, the method includes administering a pretreatment to a subject with a tubulin inhibitor and one or more other chemotherapeutic agents. Without being limited by theory, the effects of pretreatment are believed to include, but not limited to, lymphocyte clearance and reduction of tumor burden. In some embodiments, the methods described herein include not performing the pretreatment prior to administration of the first dose or subsequent dose(s). In some embodiments, not performing the pretreatment includes such a situation that not administering lymphocyte scavengers, whole body radiation therapy or a combination thereof or other means for pretreatment, and the lymphocyte clearance rate in the subject is still less than 50%, 55%, 60%, 65% or 70% after performing the pretreatment.

In some embodiments, the chemotherapeutic agents described herein refer to drugs used in chemotherapy, and refer to chemical drugs having preventive effects on microbial infections, parasitic diseases, and malignant tumors. Chemotherapeutics include, but are not limited to, synthetic antibacterial drugs, antibiotics, antiparasitic drugs, antifungal drugs, antiviral drugs, alkylating agents, antimetabolites, antituberculosis drugs, and antitumor drugs. For example, diterpene alkaloid compounds (such as taxane), cyclophosphamide, fludarabine, cyclosporine, rapamycin, mycophenolic acid, steroids, melphalan, bendamustine, asparaginase, busulfan, carboplatin, cisplatin, daunorubicin, doxorubicin, fluorouracil, hydroxyurea, methotrexate, rituximab, vinblastine, and/or vincristine, and the like. In some embodiments, the antimetabolites include, but are not limited to, antimetabolites such as carmofur, tegafur, pentostatin, deoxyfluridine, trimexate, fludarabine, capecitabine, gallopitabine, cytarabine stearyl sodium phosphate, fosteabine sodium hydrate, raltitrexed, paltitrexid, dipyriteflu, tiazofurin, norlatrexed, pemetrexed, nelzarabine, 2'-deoxy-2'-methylenecytidine, 2'-fluoromethylene-2'-deoxycytidine, N-[5-(2,3-dihydrogen-benzofuranyl) sulfonyl]-N'-(3,4-dichlorophenyl) urea, N6-[4-deoxy-4-[N2-[2(E),4(E)-tetradecadienoyl]glycylamino]-L-glycerol-BL-mannose-heptanosylpyranosyl]adenine, aplidine, ascidin, 4-[2-amino-4-oxo-4,6,7,8-tetrahydro-3H-pyrimido [5,4-b]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracycline (7.4.1.0.0)-tetradecano-2,4,6-triene-9-yl acetate, swainsonine, lometrisol, dexrazoxane, methioninase, 2'-cyano-2'-deoxy-N4-palmitoyl-1-B-D-arabinofuranosyl cytosine and 3-aminopyridine-2-aldehyde thiosemicarbazone, and the like. In some embodiments, the alkylating agent includes, but is not limited to, dacarbazine, chlorambucil, cyclophosphamide, temozolomide, chlorambucil, busulfan, chlorambucil and nitrosourea, and the like.

Pretreating a subject before the first dose or subsequent dose(s) is administered can improve the effects of immune effector cell therapy. The day of the first infusion of immune effector cells (such as CAR T cells) in each course of treatment is set as day 0. The pretreatment is administered before the infusion of immune effector cells. In some embodiments, the pretreatment is performed at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days before adoptive cells or immune effector cells are administered. In some embodiments, one chemotherapeutic agent is used for pretreatment. In some embodiments, two or more chemotherapeutic agents are used for pretreatment. In some embodiments, a microtubule inhibitor and one or more additional chemotherapeutic agents are used for pretreatment. In some embodiments, two microtubule inhibitors and one or more additional chemotherapeutic agents are used for pretreatment. In some embodiments, one microtubule inhibitor such as a tubulin polymerization promoter, one or more alkylating agents and one or more antimetabolites are used for pretreatment. In some embodiments, one or more taxols, one or more alkylating agents and one or more antimetabolites are used for pretreatment. In some embodiments, one microtubule inhibitor (such as paclitaxel, particularly albumin-bound paclitaxel) and two additional chemotherapeutics (such as fludarabine and cyclophosphamide) are used for pretreatment. For the purpose of convenience, in the following context, fludarabine and cyclophosphamide as representative chemotherapeutics, and (albumin-bound) paclitaxel as a representative microtubule inhibitor will be used to illustrate the specific embodiments using one microtubule inhibitor and two additional chemotherapeutics in the pretreatment. For example, in some embodiments, one, two or three selected from fludarabine, cyclophosphamide or albumin-bound paclitaxel used as the pretreatment is administered to the subject at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days, preferably at least 1, 2, 3, 4, 5, 6, 7, 8, 9, 10, 11, 12, 13, 14, 15, 16, 17, 18, 19 or 20 days, more preferably, at least 2, 3, 4, 5, 6, 7 or 8 days before the CAR-T cell infusion. In some embodiments, the pretreatment includes administering fludarabine and cyclophosphamide 6 days before CAR-T cell infusion. In some embodiments, pretreatment includes administering fludarabine and cyclophosphamide 7 days before CAR-T cell infusion. In some embodiments, pretreatment includes administering fludarabine and cyclophosphamide 5 days before CAR-T cell infusion. In some embodiments, pretreatment includes administering fludarabine, cyclophosphamide and albumin-bound paclitaxel 6 days before CAR-T cell infusion. In some embodiments, the pretreatment includes administering albumin-bound paclitaxel 4 days before CAR-T cell infusion.

As mentioned above, the day when the CAR T cell therapy is administered to a patient for each course of treatment is designated as day 0. In some embodiments, fludarabine, cyclophosphamide, and albumin-bound paclitaxel can be administered at any time before the CAR T cell therapy is administered. In some embodiments, fludarabine, cyclophosphate or albumin-bound paclitaxel is administered at least 7 days, at least 6 days, at least 5 days, at least 4 days, at least 3 days, at least 2 days, at least 1 day before the CAR T cell infusion is administered. In some embodiments, fludarabine, cyclophosphamide, or albumin-bound paclitaxel is administered at least 12 days, at least 11 days, at least 10 days, at least 9 days, or at least 8 days before the CAR T cell infusion is administered. In some embodiments, fludarabine, cyclophosphamide, or albumin-bound paclitaxel is administered 7 days before the CAR T cell infusion is administered. In some embodiments, fludarabine, cyclophosphamide, or albumin-bound paclitaxel is administered 6 days before the CAR T cell infusion is administered. In some embodiments, fludarabine, cyclophosphamide, or albumin-bound paclitaxel is administered 12 days before the CAR T cell infusion is administered. In some embodiments, fludarabine, cyclophosphamide, or albumin-bound paclitaxel is administered 5 days before the CAR T cell infusion is administered. In some embodiments, fludarabine, cyclophosphamide, or albumin-bound paclitaxel is administered 4 days before the CAR T cell infusion is administered.

In some embodiments, fludarabine is administered 7 days before the CAR T cell infusion, and cyclophosphamide is administered 7 days before the CAR T cell infusion. In some embodiments, fludarabine is administered 6 days before the CAR T cell infusion, and cyclophosphamide is administered 6 days before the CAR T cell infusion. In some embodiments, fludarabine is administered 5 days before the CAR T cell infusion, and cyclophosphamide is administered 5 days before the CAR T cell infusion. In some embodiments, fludarabine is administered 12 days before the CAR T cell infusion, and cyclophosphamide is administered 12 days before the CAR T cell infusion. In some embodiments, fludarabine is administered 5 days before CAR T cell infusion, cyclophosphamide is administered 5 days before CAR T cell infusion, and albumin-bound paclitaxel is administered 4 days before CAR T cell infusion. In some embodiments, fludarabine is administered 6 days before CAR T cell infusion, cyclophosphamide is administered 6 days before CAR T cell infusion, and albumin-bound paclitaxel is administered 5 days before CAR T cell infusion. In some embodiments, fludarabine is administered 12 days before CAR T cell infusion, cyclophosphamide is administered 12 days before CAR T cell infusion, and albumin-bound paclitaxel is administered 11 days before CAR T cell infusion.

The timing for administering components of the pretreatment can be adjusted to maximize the therapeutic effects of CAR T treatment. Generally, fludarabine, cyclophosphamide, and/or albumin-bound paclitaxel can be administered daily. In some embodiments, fludarabine, cyclophosphamide, and albumin-bound paclitaxel are administered daily for about 1 day, about 2 days, about 3 days, about 4 days, about 5 days, about 6 days, or about 7 days. In some embodiments, fludarabine is administered daily for 4 days, and cyclophosphamide is administered daily for 2 days. In some embodiments, fludarabine is administered daily for 2 days, and cyclophosphamide is administered daily for 3 days. In some embodiments, fludarabine is administered daily for 2 days, and cyclophosphamide is administered daily for 4 days. In some embodiments, fludarabine is administered daily for 1 day, and cyclophosphamide is administered daily for 3 days. In some embodiments, fludarabine is administered daily for 1 day, and cyclophosphamide is administered daily for 4 days. In some embodiments, fludarabine is administered daily for 4 days, and cyclophosphamide is administered daily for 2 days. In some embodiments, fludarabine is administered daily for 1 day, cyclophosphamide is administered daily for 3 days, and albumin-bound paclitaxel is administered daily for 1 day. In some embodiments, fludarabine is administered daily for 1 day, cyclophosphamide is administered daily for 4 days, and albumin-bound paclitaxel is administered daily for 1 day.

As mentioned above, in each round, the day when of CAR T cell therapy is administered to a patient is designated as day 0. In some embodiments, fludarabine is administered to a patient on day 4 before day 0 (i.e., day −4). In some embodiments, fludarabine is administered to a patient on day −5. In some embodiments, fludarabine is administered to a patient on day −6. In some embodiments, fludarabine is administered to a patient on day −12. In some embodiments, fludarabine is administered to a patient on days −6 and −5.

In some embodiments, fludarabine is administered to a patient on days −5 and −4. In some embodiments, fludarabine is administered to a patient on days −6, −5, −4, and −3. In some embodiments, fludarabine is administered to a patient on days −7, −6, −5, and −4. In some embodiments, cyclophosphamide is administered to a patient on days −6, −5, −4, and −3. In some embodiments, cyclophosphamide is administered to a patient on days −6, −5, and −4. In some embodiments, cyclophosphamide is administered to a patient on days −5, −4, and −2. In some embodiments, cyclophosphamide is administered to a patient on days −5, −4, and −3. In some embodiments, cyclophosphamide is administered to a patient on days −12, −11, and −10. In some embodiments, cyclophosphamide is administered to a patient on days −7 and −6. In some embodiments, cyclophosphamide is administered to a patient on days −6 and −5. In some embodiments, albumin-bound paclitaxel is administered to a patient on day −4. In some embodiments, albumin-bound paclitaxel is administered to a patient on day −5. In some embodiments, albumin-bound paclitaxel is administered to a patient on day −11. In some embodiments, albumin-bound paclitaxel is administered to a patient on days −5 and −4.

Fludarabine, cyclophosphamide, and albumin-bound paclitaxel can be administered on the same day or on different days. If fludarabine, cyclophosphamide, and albumin-bound paclitaxel are administered on the same day, cyclophosphamide and/or albumin-bound paclitaxel can be administered before or after fludarabine is administered; or fludarabine and/or albumin-bound paclitaxel can be administered before or after cyclophosphamide is administered; or cyclophosphamide and/or fludarabine can be administered before or after albumin-bound paclitaxel is administered. In some embodiments, fludarabine is administered to a patient on days −6, −5, −4, and −3, and cyclophosphamide is administered to the patient on days −6 and −5. In some embodiments, fludarabine is administered to a patient on days −7, −6, −5, and −4, and cyclophosphamide is administered to the patient on days −7 and −6. In some embodiments, fludarabine is administered to a patient on days −5 and −4, and cyclophosphamide is administered to the patient on days −5, −4, and −2. In some embodiments, fludarabine is administered to a patient on days −6 and −5, and cyclophosphamide is administered to the patient on days −6, −5, −4, and −3. In some embodiments, fludarabine is administered to a patient on day −5, and cyclophosphamide is administered to the patient on day −5, −4, and −3. In some embodiments, fludarabine is administered to a patient on day −6, and cyclophosphamide is administered to the patient on day −6, −5, and −4. In some embodiments, fludarabine is administered to a patient on day −6, and cyclophosphamide is administered to the patient on day −6, −5, −4, and −3. In some embodiments, fludarabine is administered to a patient on day −5, cyclophosphamide is administered to the patient on day −5, −4, and −3, and albumin-bound paclitaxel is administered on day −4. In some embodiments, fludarabine is administered to a patient on day −6, cyclophosphamide is administered to the patient on day −6, −5, and −4, and albumin-bound paclitaxel is administered on day −5. In some embodiments, fludarabine is administered to a patient on day −12, cyclophosphamide is administered to the patient on day −12, −11, and −10, and albumin-bound paclitaxel is administered on day −11. In some embodiments, fludarabine is administered to a patient on day −6, cyclophosphamide is administered to the patient on day −6, −5, −4, and −3, and the albumin-bound paclitaxel is administered on day −5.

In certain embodiments, fludarabine, cyclophosphamide, and albumin-bound paclitaxel can be administered simultaneously or sequentially. In some embodiments, cyclophosphamide is administered to a patient before fludarabine is administered. In some embodiments, cyclophosphamide is administered to a patient after fludarabine is administered. In some embodiments, albumin-bound paclitaxel is administered to a patient before fludarabine is administered. In some embodiments, albumin-bound paclitaxel is administered to a patient before or after fludarabine is administered. In some embodiments, albumin-bound paclitaxel is administered to a patient before cyclophosphamide is administered. In some embodiments, albumin-bound paclitaxel is administered to a patient after cyclophosphamide is administered.

Fludarabine, cyclophosphamide, and albumin-bound paclitaxel can be administered by any route, including intravenous injection (IV). In some embodiments, fludarabine is administered by IV within the following time: about 10 minutes, about 15 minutes, about 20 minutes, about 25 minutes, about 30 minutes, about 35 minutes, about 40 minutes, about 45 minutes, about 50 minutes, about 55 minutes, about 60 minutes, about 90 minutes, about 120 minutes. In some embodiments, cyclophosphamide is administered by IV within the following time: about 30 minutes, about 35 minutes, about 40 minutes, about 45 minutes, about 50 minutes, about 55 minutes, about 60 minutes, about 90 minutes, about 120 minutes. In some embodiments, the albumin-bound paclitaxel is administered by IV within the following time: about 10 minutes, about 15 minutes, about 20 minutes, about 25 minutes, about 30 minutes, about 35 minutes, about 40 minutes, about 45 minutes, about 50 minutes, about 55 minutes, about 60 minutes, about 90 minutes, about 120 minutes.

In some embodiments, T cell therapy is administered to a patient while fludarabine and cyclophosphamide, or fludarabine, cyclophosphamide, and albumin-bound paclitaxel are administered. In some embodiments, the T cell therapy includes adoptive cell therapy or immune effector cell therapy. In some embodiments, adoptive cell therapy or immune effector cell therapy is selected from tumor infiltrating lymphocyte (TIL) immunotherapy, autologous cell therapy, engineered autologous cell therapy (eACT), or allogeneic T cell transplantation. In some embodiments, eACT comprises the administration of engineered antigen-specific chimeric antigen receptor (CAR T) positive T cells. In some embodiments, eACT comprises the administration of engineered antigen-specific T cell receptor (TCR) positive T cells. In some embodiments, engineered T cells treat tumors in a patient.

In some embodiments, the pretreatment includes administering fludarabine at not higher than about 500, 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 85, 70, 65, 60, 55, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1 mg/m$^2$/day; and/or administering cyclophosphamide at not higher than about 1000, 950, 900, 850, 800, 750, 700, 690, 680, 670, 660, 650, 640, 630, 620, 610, 600, 595, 590, 585, 580, 579, 578, 576, 575, 574, 573, 572, 571, 570, 569, 568, 567, 566, 565, 564, 563, 562, 561, 560, 559, 558, 557, 556, 555, 554, 553, 552, 551, 550, 549, 548, 547, 546, 545, 544, 543, 542, 541, 540, 539, 538, 537, 536, 535, 534, 533, 532, 531, 530, 529, 528, 527, 526, 525, 524, 523, 522, 521, 520, 519, 518, 517, 516, 515, 514, 513, 512, 511, 510, 509, 508, 507, 506, 505, 504, 503, 502, 501, 500, 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, 70, 60, 50, 40, 30, 20 or 10 mg/m²/day; and/or administering albumin-bound paclitaxel at not higher than about 500, 450, 400, 350, 300, 290, 280, 270, 265, 260, 255, 250, 245, 240, 235, 230, 225, 220, 215, 210, 205, 200, 195, 190, 185, 180, 175, 170, 165, 160, 155, 150, 145, 140, 135, 130, 125, 120, 115, 110, 105, 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 49, 48, 47, 46, 45, 44, 43, 42, 41, 40, 35, 30, 25, 20, 15, 10, 5 or 1 mg/m²/day.

In some embodiments, the pretreatment includes administering fludarabine at a dose of about 10 mg/m²/day to 50 mg/m²/day and administering cyclophosphamide at a dose of about 300 to 700 mg/m²/day.

In some embodiments, the pretreatment includes administering fludarabine at a dose of about 10 mg/m²/day to 50 mg/m²/day, and administering cyclophosphamide at a dose of about 300 to 700 mg/m²/day, and administering albumin-bound paclitaxel at a dose not higher than about 300 mg/m²/day, not higher than about 200 mg/m²/day, not higher than about 150 mg/m²/day, 100 mg/m²/day, not higher than 80 mg/day m²/day or not higher than 70 mg/m²/day.

In some embodiments, the pretreatment includes administering fludarabine at a dose of about 15 mg/m²/day to 40 mg/m²/day and administering cyclophosphamide at a dose of about 400 to 650 mg/m²/day.

In some embodiments, the pretreatment includes administering fludarabine at a dose of about 15 mg/m²/day to 40 mg/m²/day and administering cyclophosphamide at a dose of about 400 to 650 mg/m²/day, and administering albumin-bound paclitaxel at a dose not higher than about 300 mg/m²/day, not higher than about 200 mg/m²/day, not higher than about 150 mg/m²/day, 100 mg/m²/day, not higher than 80 mg/m²/day or not more than 70 mg/m²/day.

In some embodiments, the pretreatment includes administering fludarabine at a dose of about 15 mg/m²/day to 30 mg/m²/day and administering cyclophosphamide at a dose of about 450 to 600, 450 to 550, or 490 to 550 mg/m²/day.

In some embodiments, the pretreatment includes administering fludarabine at a dose of about 15 mg/m²/day to 30 mg/m²/day and administering cyclophosphamide at a dose of about 450 to 600, 450 to 550, or 490 to 550 mg/m²/day, and administering albumin-bound paclitaxel at a dose not higher than about 300 mg/m²/day, not higher than about 200 mg/m²/day, not higher than about 150 mg/m²/day, 100 mg/m²/day, not higher than 80 mg/m²/day or not higher than 70 mg/m²/day.

In some embodiments, the pretreatment includes administering fludarabine at a dose of about 20 mg/m²/day to 30 mg/m²/day and administering cyclophosphamide at a dose of about 450 to 600, 450 to 550, or 490 to 550 mg/m²/day.

In some embodiments, the pretreatment includes administering fludarabine at a dose of about 20 mg/m²/day to 30 mg/m²/day and administering cyclophosphamide at a dose of about 450 to 600, 450 to 550, or 490 to 550 mg/m²/day, and administering albumin-bound paclitaxel at a dose not higher than about 300 mg/m²/day, not higher than about 200 mg/m²/day, not higher than about 150 mg/m²/day, 100 mg/m²/day, not higher than 80 mg/m²/day or not higher than 70 mg/m²/day.

In some embodiments, the pretreatment includes administering fludarabine at a dose of about 20 mg/m²/day to 25 mg/m²/day and administering cyclophosphamide at a dose of about 450 to 600, 450 to 550, or 490 to 550 mg/m²/day.

In some embodiments, the pretreatment includes administering fludarabine at a dose of about 15 mg/m²/day to 25 mg/m²/day and administering cyclophosphamide at a dose of about 450 to 600, 450 to 550, or 490 to 550 mg/m²/day, and administering albumin-bound paclitaxel at a dose not higher than about 300 mg/m²/day, not higher than about 200 mg/m²/day, not higher than about 150 mg/m²/day, 100 mg/m²/day, not higher than 80 mg/m²/day or not higher than 70 mg/m²/day.

In some embodiments, the present invention includes a pretreatment method before administering immune effector cells infusion, the method comprising administering fludarabine to a patient at a dose of about 20 mg/m²/day of and cyclophosphamide at a dose of about 500 mg/m²/day, in which fludarabine is administered on days −6, −5, −4, and −3, and cyclophosphamide is administered on days −6 and −5. In some embodiments, the present invention includes a pretreatment method before administering immune effector cells infusion, the method comprising administering fludarabine to a patient at a dose of about 20 mg/m²/day and cyclophosphamide at a dose of about 514 mg/m²/day, in which fludarabine is administered on days −7, −6, −5, and −4, and cyclophosphamide is administered on days −7 and −6. In some embodiments, the present invention includes a pretreatment method before administering immune effector cells infusion, the method comprising administering fludarabine to a patient at a dose of about 20 mg/m²/day and cyclophosphamide at a dose of about 514 mg/m²/day, in which fludarabine is administered on days −5 and −4, and cyclophosphamide is administered on days −5, −4, and −2. In some embodiments, the present invention includes a pretreatment method before administering immune effector cells infusion, the method comprising administering fludarabine to a patient at a dose of about 20 mg/m²/day of and cyclophosphamide at a dose of about 514 mg/m²/day, in which fludarabine is administered on −6, and −5 days, and cyclophosphamide is administered on −6, −5, −4, and −3 days. In some embodiments, the present invention includes a pretreatment method before administering immune effector cells infusion, the method comprising administering fludarabine to a patient at a dose of about 20 mg/m²/day and cyclophosphamide at a dose of about 510 mg/m²/day, in which fludarabine is administered on −6, and −5 days, and cyclophosphamide is administered on −6, −5, −4, and −3 days. In some embodiments, the present invention includes a pretreatment method before administering immune effector cells infusion, the method comprising administering fludarabine to a patient at a dose of about 20 mg/m²/day and cyclophosphamide at a dose of about 500 mg/m²/day, in which fludarabine is administered on day −5, and cyclophosphamide is administered on day −5, −4, and −3. In some embodiments, the present invention includes a pretreatment method before administering immune effector cells infusion, the method comprising administering fludarabine to a patient at a dose of about 20 mg/m²/day and cyclophosphamide at a dose of about 540 mg/m²/day, in which fludarabine is administered on day −6, and cyclophosphamide is administered on day −6, −5, and −4. In some embodiments, the present invention includes a pretreatment method before administering immune effector cells infusion, the method comprising administering fludarabine to a patient at a dose of about 20 mg/m²/day and cyclophosphamide at a dose of about 500 mg/m²/day, in which fludarabine is administered on day −6, and cyclophosphamide is administered on day −6, −5, and −4. In some embodiments, the present invention includes a pretreatment method before administering immune effector cells infusion, the method comprising administering fludarabine to a patient at a dose of about 20 mg/m²/day and cyclophosphamide at a dose of about 500 mg/m²/day, in which fludarabine is administered on day −6, and cyclophosphamide is administered on day −6, −5, −4, and −3. In some embodiments, the present invention includes a pretreatment method before administering immune effector cells infusion, the method comprising administering fludarabine to a patient at a dose of about 20 mg/m²/day and cyclophosphamide at a dose of about 500 mg/m²/day, in which fludarabine is administered on day −12, and cyclophosphamide is administered on day −12, −11 and −10. In some embodiments, the present invention includes a pretreatment method before administering immune effector cells infusion, the method comprising administering fludarabine to a patient at a dose of about 20 mg/m²/day, cyclophosphamide at a dose of about 500 mg/m²/day and albumin-bound paclitaxel at a dose of about 100 mg/m²/day, in which fludarabine is administered on day −5, and cyclophosphamide is administered on day −5, −4, and −3, and albumin-bound paclitaxel is administered on day −4. In some embodiments, the present invention includes a pretreatment method before administering immune effector cells infusion, the method comprising administering fludarabine to a patient at a dose of about 20 mg/m²/day, cyclophosphamide at a dose of about 540 mg/m²/day and albumin-bound paclitaxel at a dose of about 71 mg/m²/day, wherein fludarabine is administered on day −6, and cyclophosphamide is administered on day −6, −5, and −4, and albumin-bound paclitaxel is administered on day −5. In some embodiments, the present invention includes a pretreatment method before administering immune effector cells infusion, the method comprising administering fludarabine to a patient at a dose of about 20 mg/m²/day, cyclophosphamide at a dose of about 500 mg/m²/day and albumin-bound paclitaxel at a dose of about 71 mg/m²/day, wherein fludarabine is administered on day −12, cyclophosphamide is administered on day −12, −11, and −10, and albumin-bound paclitaxel is administered on day −11. In some embodiments, the present invention includes a pretreatment method before administering immune effector cells infusion, the method comprising administering fludarabine to a patient at a dose of about 20 mg/m²/day, cyclophosphamide at a dose of about 500 mg/m²/day and albumin-bound paclitaxel at a dose of about 100 mg/m²/day, wherein fludarabine is administered on day −6, cyclophosphamide is administered on day −6, −5, and −4, and albumin-bound paclitaxel is administered on day −5. In some embodiments, the present invention includes a pretreatment method before administering immune effector cells infusion, the method comprising administering fludarabine to a patient at a dose of about 20 mg/m²/day, cyclophosphamide at a dose of about 507 mg/m²/day and albumin-bound paclitaxel at a dose of about 68 mg/m²/day, wherein fludarabine is administered on day −6, cyclophosphamide is administered on day −6, −5, −4, and −3, and albumin-bound paclitaxel is administered on day −5. In some embodiments, the present invention includes a pretreatment method before administering immune effector cells infusion, the method comprising administering albumin-bound paclitaxel to a patient at a dose of about 137 mg/m²/day, wherein albumin-bound paclitaxel is administered on day −4.

Various other interventions can be included in the methods described herein. For example, cyclophosphamide and fludarabine may cause adverse events in a patient after administration. In the scope of the present invention, the administration of the composition to the patient is included to reduce some of these adverse events. In certain embodiments, the method comprises administering physiological saline to a patient. The physiological saline may be administered to a patient before or after cyclophosphamide and/or fludarabine, or before and after cyclophosphamide and/or fludarabine is administered. In some embodiments, the physiological saline normal saline is administered to a patient before cyclophosphamide and/or fludarabine is administered, and after cyclophosphamide and/or fludarabine is administered on each day of infusion. In addition, adjuvants and excipients can also be administered to a patient, such as Mesna (sodium 2-mercaptoethane sulfonate). In addition, exogenous cytokines can also be administered to a patient.

In some embodiments, the pretreatment is administered before the infusion of the first dose or subsequent dose(s) so as to improve the results of the treatment. For example, in some aspects, the pretreatment improves the therapeutic efficacy resulted from the first dose or subsequent dose(s), or increases the persistence of chimeric antigen receptor-expressing immune effector cells (e.g., CAR-expressing immune effector cells, such as CAR-expressing T cell) in a patient. In some embodiments, the pretreatment increases the stable period of disease.

Once the immune effector cells are administered to a subject (e.g., a human), in some aspects, biological activities of the engineered immune effector cell population can be measured by any of variety of known methods. The parameters used for evaluation include: specific binding of engineered or natural T cells or other immune cells to an antigen, in vivo (for example, by imaging) or ex vivo (for example, by ELISA or flow cytometry). In some embodiments, the ability of engineered immune effector cells to destroy target cells can be tested by any suitable method known in the art, such as the cytotoxicity assay described in the following literature, for example, Kochenderfer et al., J. Immunotherapy, 32 (7): 689-702 (2009) and Herman et al. J. Immunological Methods, 285 (1): 25-40 (2004). In some embodiments, biological activities of immune effector cells can also be measured by measuring the expression and/or secretion of certain cytokines, such as CD107a, IFNγ, IL-2 and TNF. In some aspects, the biological activity is assessed by clinical outcomes, such as tumor burden or reduction in burden. In some aspects, the reduction of tumor markers is assessed. In some aspects, the cells are assessed for their toxicity outcome, persistence and/or proliferation, and/or the presence of a host immune response.

Administration

In the present invention, the administration time and size of multiple doses of immune effector cells are generally designed to reduce risk or minimize toxic effects and/or improve efficacy, for example, by providing the subject with increased exposure to immune effector cells over time. The method involves administering the first dose within a specific time frame between different doses, usually before one or more subsequent doses.

In the case of immune effector cell therapy, the administration of a given "dose" includes the administration of a given amount or number of immune effector cells as a single composition and/or a single uninterrupted administration, such as a single injection or continuous infusion, and also includes the administration of a given amount or number of immune effector cells as multiple separate compositions or infusions, in divided doses within a specific period of time not exceeding 20, 19, 18, 17, 16, 15, 14, 13, 12, 11, 10, 9, 8, 7, 6, 5, 4, 3, or 2 days. Therefore, the first dose or subsequent doses are single or continuous administrations of a specified number of immune effector cells administered or started at a single time point. However, in some cases, the first dose or subsequent dose(s) is administered as multiple injections or infusions over a period of time not exceeding 20, 19, 18, 17, 16, 15, 14, 13, 12, 11, 10, 9, 8, 7, 6, 5, 4, 3 or 2 days, for example, once a day for three or two days, or multiple infusions within one day. In some aspects, the first dose of immune effector cells is administered as a single pharmaceutical composition. In some embodiments, the subsequent dose(s) of immune effector cells is administered as a single pharmaceutical composition. In some embodiments, the first dose of immune effector cells is administered in multiple compositions that collectively contain the first dose of immune effector cells. In some embodiments, the subsequent dose(s) of immune effector cells is administered in multiple compositions that collectively contain the subsequent dose(s) of immune effector cells. In some aspects, an additional subsequent dose(s) can be administered in multiple compositions over a period of time not exceeding 20, 19, 18, 17, 16, 15, 14, 13, 12, 11, 10, 9, 8, 7, 6, 5, 4, 3 or 2 days.

The term "divided dose" refers to an administration mode in which a part of a single dose is administered in divided doses, so that the single dose is administered to a subject over a period of more than one day. In some embodiments, the first dose and/or each subsequent dose can be administered in two or more divided doses. For example, in some embodiments, the dose can be administered to a subject within 3 days, 5 days, 14 days, or 15 days (the dose is the total dose of the first dose or the total dose of subsequent dose(s)). An exemplary method of divided administration includes administering a divided dose, which is 50% of the total dose, on day 0 (in each round, the day when of CAR T cell therapy is administered to a patient is designated as day 0), and administering a divided dose, which is 50% of the total dose, on day 2. In other embodiments, 10% of the total dose may be administered on day 0, 30% of the total dose on day 2, and 60% of the total dose on day 4. In some embodiments, a divided dose, which is 10% of the total dose, is administered on day 0, a divided dose, which is 30% of the total dose, is administered on day 1, and a divided dose, which is 60% of the total dose, on day 2. In some embodiments, a divided dose, which is ⅓ of the total dose, is administered on day 0, a divided dose, which is ⅓ of the total dose, is administered on day 11, and a divided dose, which is ⅓ of the total dose, is administered on day 14. In some embodiments, a divided dose, which is 46% of the total dose, is administered on day 0, a divided dose, which is 18% of the total dose, is administered on day 1, and a divided dose, which is 36% of the total dose, is administered on day 2. In some embodiments, a divided dose, which is 25% of the total dose, is administered on day 0, a divided dose, which is 25% of the total dose, is administered on day 2, a divided dose, which is 25% of the total dose, is administered on day 9, and a divided dose, which is 25% of the total dose, is administered on day 13. In some embodiments, the total period of time for a single dose to be administered in divided doses not extend beyond 15 days.

As used herein, "the first dose" is used to describe a total dose administered in the first course of treatment performed with the method described herein. This dose is equal to the total dose administered in the course of treatment during a single course of treatment, or the total dose administered in the first course of treatment during multiple courses of treatment. The term does not necessarily mean that the subject has never received immune effector cell therapy before receiving treatment with the method described herein, or the subject has not previously received a dose of the same immune effector cells expressing the same chimeric antigen receptor or targeting the same antigen.

With respect to the first dose, the term "subsequent dose" refers to a single dose administered in each course of treatment or the total dose in each course of treatment during the multiple courses of treatment after the first dose is administered. In some embodiments, the method includes the administration of multiple courses, that is, administration of one or more subsequent doses, wherein the first subsequent dose is also called the second course dose, and the second subsequent dose is also called the third course dose, and so on. And, in the series of doses, the previous dose is the dose immediately preceding the subsequent dose. In some embodiments, the subsequent dose is administered using a similar time and manner of administration to the first dose. In some embodiments, the interval between the first dose and the first subsequent dose or the dose of the second course of treatment and the interval between multiple subsequent doses may be the same or different, as described in detail above.

The Amount or Size of the Dose

The dosage of the first dose and/or one or more subsequent doses is usually designed to provide improved efficacy and/or reduced risk of toxicity. In some embodiments, the number of immune effector cells in the first dose or in a single subsequent dose is higher, lower than or equal to about $1 \times 10^6$ cells/kg of subject's body weight to about $3 \times 10^7$ cells/kg of subject's body weight, for example, higher than, lower than or equal to about $1 \times 10^5$, $1.5 \times 10^5$, $2 \times 10^5$, $2.5 \times 10^5$, $3 \times 10^5$, $3.5 \times 10^5$, $4 \times 10^5$, $4.5 \times 10^5$, $5 \times 10^5$, $5.5 \times 10^5$, $6 \times 10^5$, $6.5 \times 10^5$, $7 \times 10^5$, $7.5 \times 10^5$, $8 \times 10^5$, $8.5 \times 10^5$, $9 \times 10^5$, $9.5 \times 10^5$, $1 \times 10^6$, $1.5 \times 10^6$, $2 \times 10^6$, $2.5 \times 10^6$, $3 \times 10^6$, $3.5 \times 10^6$, $4 \times 10^6$, $4.5 \times 10^6$, $5 \times 10^6$, $5.5 \times 10^6$, $6 \times 10^6$, $6.5 \times 10^6$, $7 \times 10^6$, $7.5 \times 10^6$, $8 \times 10^6$, $8.5 \times 10^6$, $9 \times 10^6$, $9.5 \times 10^6$, $1 \times 10^7$, $1.5 \times 10^7$, $2 \times 10^7$, $2.5 \times 10^7$, $3 \times 10^7$, $3.5 \times 10^7$, $4 \times 10^7$, $4.5 \times 10^7$, $5 \times 10^7$, $6 \times 10^7$, $6.5 \times 10^7$, $7 \times 10^7$, $7.5 \times 10^7$, $8 \times 10^7$, $8.5 \times 10^7$, $9 \times 10^7$, $9.5 \times 10^7$, $1 \times 10^8$, $1.5 \times 10^8$, $2 \times 10^8$, $2.5 \times 10^8$, $3 \times 10^8$, $3.5 \times 10^8$, $4 \times 10^8$, $4.5 \times 10^8$, $5 \times 10^8$, $5.5 \times 10^8$, $6 \times 10^8$, $6.5 \times 10^8$, $7 \times 10^8$, $7.5 \times 10^8$, $8 \times 10^8$, $8.5 \times 10^8$, $9 \times 10^8$, $9.5 \times 10^8$, $1 \times 10^9$, $1.5 \times 10^9$, $2 \times 10^9$, $2.5 \times 10^9$, $3 \times 10^9$, $3.5 \times 10^9$, $4 \times 10^9$, $4.5 \times 10^9$, $5 \times 10^9$, $5.5 \times 10^9$, $6 \times 10^9$, $6.5 \times 10^9$, $7 \times 10^9$, $7.5 \times 10^9$, $8 \times 10^9$, $8.5 \times 10^9$, $9 \times 10^9$, $9.5 \times 10^9$, $1 \times 10^{10}$, $1.5 \times 10^{10}$, $2 \times 10^{10}$, $2.5 \times 10^{10}$, $3 \times 10^{10}$, $3.5 \times 10^{10}$, $4 \times 10^{10}$, $4.5 \times 10^{10}$, $5 \times 10^{10}$, $5.5 \times 10^{10}$, $6 \times 10^{10}$, $6.5 \times 10^{10}$, $7 \times 10^{10}$, $7.5 \times 10^{10}$, $8 \times 10^{10}$, $8.5 \times 10^{10}$, $9 \times 10^{10}$, $9.5 \times 10^{10}$, $1 \times 10^{11}$ cells/kg of subject's body weight.

In a specific embodiment, the number and/or concentration of immune effector cells refers to the number of immune effector cells expressing a chimeric antigen receptor (for example, CAR). In other embodiments, the number and/or concentration of immune effector cells refers to the number or concentration of all administered cells, T cells, or peripheral blood mononuclear cells (PBMC).

In some embodiments, the number of immune effector cells, chimeric antigen receptor (for example, CAR)-expressing cells, T cells, or peripheral blood mononuclear cells (PBMC) in the first dose is greater than about $1 \times 10^6$ cells/kg of subject's body weight, such as about or at least about $1 \times 10^6$, $1.1 \times 10^6$, $2 \times 10^6$, $2.9 \times 10^6$, $3 \times 10^6$, $3.3 \times 10^6$, $5 \times 10^6$, $1 \times 10^7$, $1.3 \times 10^7$, $1.6 \times 10^7$, $2.6 \times 10^7$, $2.8 \times 10^7$, $3 \times 10^7$, $5 \times 10^7$, $2.5 \times 10^8$, $1 \times 10^9$, $1 \times 10^{10}$, $5 \times 10^{10}$ cells/kg of body weight, or a range between any two of the foregoing values.

In some embodiments, the number of immune effector cells administered in a subsequent dose(s) is the same as or similar to or greater than the number of immune effector cells administered in the first dose in any of the embodiments herein, such as equal to or about $1\times10^6$, equal to or about $1\times10^7$, equal to or about $1.3\times10^7$, equal to or about $1.6\times10^7$, equal to or about $1.9\times10^7$, equal to or about $2\times10^7$, equal to or about $2.2\times10^7$, equal to or about $3.7\times10^7$, equal to or about $5\times10^7$, or equal to or about $5.1\times10^7$, or equal to or about $1\times10^8$, or equal to or about $2.5\times10^8$, or equal to or about $1\times10^9$, or equal to or about $1\times10^{10}$, or equal to or about $5\times10^{10}$ cells/kg of subject's body weight, or a value in a range between any two of the above values.

Regarding the number of immune effector cells, in some embodiments, these values refer to the number of chimeric antigen receptor-expressing (for example, CAR-expressing) cells; in other embodiments, they refer to the number of administered T cells or PBMC or total cells.

In some aspects, the subsequent dose is greater than or equal to or less than the first dose. For example, in some embodiments, the subsequent dose contains more than about $1\times10^6$ cells, chimeric antigen receptor (e.g., CAR)-expressing cells, T cells, and/or PBMC/kg of subject's body weight, such as about or at least about $1\times10^6$, $1\times10^7$, $1.3\times10^7$, $1.6\times10^7$, $1.9\times10^7$, $2\times10^7$, $2.2\times10^7$, $3.7\times10^7$, $5\times10^7$, $5.1\times10^7$, $1\times10^8$, $2.5\times10^8$, $1\times10^9$, $1\times10^{10}$, $5\times10^{10}$ cells/kg of subject's body weight, or a value in a range between any two of the above values, with end-points being included.

In some embodiments, the amount or size of the subsequent dose is sufficient to reduce tumor burden or indicators thereof, and/or one or more symptoms of a disease or disorder. In some embodiments, the dose is effective to improve the survival of a subject, for example, improve the survival of a subject, for example, to induce survival, recurrence-free survival, or event-free survival of the subject for at least 1 month or at least 1, 2, 3, 4 or 5 years.

In some embodiments, the tumor burden, including tumor size, tumor volume, and/or tumor mass, is reduced by at least equal to or about 1%, 2%, 3% 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90% or more after the subsequent dose is administered, compared with that before the first dose or subsequent dose is administered.

In other embodiments, the number of immune effector cells administered in the subsequent dose is lower than the number of immune effector cells administered in the first dose.

In some aspects, the size of the first and/or subsequent dose is determined based on one or more criteria, such as the subject's response to prior treatments, such as chemotherapy, the subject's tumor burden, such as tumor volume, size, or degree, or type, stage of metastasis and/or common complications of advanced cancer, such as cancerous pleural effusion and/or the likelihood or incidence of toxic results in the subject, such as CRS, macrophage activation syndrome, tumor lysis syndrome, neurotoxicity and/or host immune response against the administered cells and/or chimeric antigen receptor.

Based on the teachings of the present invention, a skilled person should understand that the dose specifically disclosed in the present invention is a safe and effective dose obtained by the inventors through research. A skilled person, such as a clinician, can determine the specific first dose according to various actual conditions, such as the patient's tumor burden and the patient's own physical condition; if a further subsequent dose is required, a skilled person can determine the subsequent dose based on, for example, the change in tumor burden after the immune effector cells are administered.

A skilled person should also understand that the immune effector cells of the present invention, such as CLD18A2-CAR-T cells, can be used in combination with other CAR-Ts. For example, a patient's tumor can express several tumor antigens, then the patient can receive CAR-T cells targeting other tumor antigens in an early stage, and then receive the CLD18A2-CAR-T cell therapy of the present invention; the patient can also receive other CLD18A2-CAR-T cell therapy different from the present invention in an early stage, and in the case of poor antibody specificity or murine rejection, the CLD18A2-CAR-T cell therapy of the present invention is used. Therefore, under the above circumstances, a skilled person, such as a clinician, can determine the number of administrations and dosage of CLD18A2-CAR-T cells of the present invention according to the previous treatment. For example, the safe and effective doses and the number of administrations disclosed herein, that is, not more than about $2\times10^{10}$ cells/kg of the subject's body weight or a total amount of not more than about $1\times10^{12}$ cells; preferably, not more than about $2\times10^9$ cells/kg of the subject's body weight or a total amount of not more than about $2\times10^{11}$ cells; more preferably, not more than about $2.5\times10^8$ cells/kg of the subject's body weight, or $5\times10^7$ cells/kg of the subject's body weight, or $3\times10^7$ cells/kg of the subject's body weight, or a total amount of not more than $5\times10^9$ or about $1\times10^{10}$ cells, can be taken into consideration.

In some aspects, the size of the first dose and/or subsequent dose is determined by the burden of the disease or disorder in a subject. For example, in some aspects, the number of immune effector cells administered in the first dose is determined based on the tumor burden present in the subject before the first dose is administered. In some embodiments, the size of the first dose and/or subsequent dose is inversely proportional to the tumor burden.

In some aspects, the number of immune effector cells to be administered in the subsequent dose is determined based on the tumor burden that is present in a subject before the first dose is administered. In some embodiments, if the first dose results in a reduction or decrease in tumor burden, or the tumor burden lower than a certain threshold amount or level (for example, higher than which indicates an increased risk of toxic results), the subsequent dose is increased, for example, more than about $1\times10^7$ cells (e.g., total cells, receptor-expressing cells, T cells, or PBMC)/kg of body weight, for example, more than about $2.0\times10^7$, $2.5\times10^7$, $3.0\times10^7$, $5.0\times10^7$, $1.0\times10^8$, $2.5\times10^8$ cells/kg, and/or higher than the first dose.

In some cases, even if the subject's tumor burden does not decrease after receiving the first dose, the subsequent dose can be increased, for example, more than about $1\times10^7$ cells (e.g., total cells, receptor-expressing cells, T cells or PBMC)/kg of body weight, such as more than about $2.0\times10^7$, $2.5\times10^7$, $3.0\times10^7$, $5.0\times10^7$, $1\times10^8$, $2.5\times10^8$ cells/kg, and/or more than the first dose.

T cells (such as CAR T cells) can be administered by any route (including intravenous injection (IV)). In some embodiments, IV is used to administer CAR T cells within the following period of time: about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 21 minutes, about 22 minutes, about 23 minutes, About 24 minutes, about 25 minutes, about 26 minutes, about 27 minutes, about 28 minutes, about 29 minutes, about 30 minutes, about 40 minutes, about 50 minutes, about 60 minutes.

In some embodiments, the first dose includes immune effector cells in an amount that does not cause or reduce the likelihood of toxicity or toxic results, such as cytokine release syndrome (CRS), severe CRS (sCRS), macrophage activation syndrome, Tumor lysis syndrome, fever of at least 38° C. or about 38° C. Celsius that lasts for three or more days, CRP plasma levels at least equal to about 20 mg/dL, and/or neurotoxicity. In some aspects, the number of cells administered in the first dose is determined based on the likelihood that the subject will show toxicity or toxic results (e.g., CRS, sCRS, and/or CRS related results) after the cells are administered. For example, in some embodiments, the likelihood of developing a toxic outcome in a subject is predicted based on tumor burden. In some embodiments, the method includes detecting or evaluating toxicity results and/or tumor burden before administering the dose.

In some embodiments, a subject is administered a subsequent dose, when the serum level of the biochemical indicators or other indicators of toxicity results, for example, the CRS indicator does not increase above a given level, such as an acceptable level, for example, higher than or equal to or about 10, 15, 20, 25, 50, 75, or 100 times the serum level of the indicator before the first dose is administered, or has increased above the acceptable level, but has been reduced to an acceptable level or below after the first dose is administered. In some aspects, if the indicator drops below the acceptable level in 10, 11, 12, 13, 14, 15, 16, 17, 18, 19, 20, 21, 22, 23, 24, 25, 26, 27, 28, 29, 30, 31, 32, 33, 34, or 40 days after the first dose is administered, the subsequent dose will be administered, but if the level of the indicator does not drop below the acceptable level within this period of time, the subsequent dose will not be administered.

In some embodiments, if the clinical risk of cytokine release syndrome (CRS), macrophage activation syndrome or tumor lysis syndrome or neurotoxicity does not exist or has passed or has regressed after the first dose is administered, the subsequent dose is administered, for example, after a critical window where such an event has generally regressed and/or is unlikely to occur, for example in about 60%, 70%, 80%, 90% or 95% of subjects with a particular disease or disorder.

In some embodiments, whether to administer the subsequent dose, when to administer the subsequent dose, and/or the number of cells administered in the subsequent dose can be determined according to the presence or degree of the immune response or detectable immune response in a subject against the cells in the first dose or the chimeric antigen receptor expressed by the cells. In some aspects, the subsequent dose containing cells expressing receptors expressed by the cells in the first dose won't be administered to a subject who has a detectable host adaptive immune response or has established or achieved a certain level, stage, or degree of immune response.

Administration Time

In some embodiments, the time for administering the subsequent dose starts from the completion of the first dose (the day, when the infusion of the total dose of the first dose is completed, is set as day 0).

In some embodiments, the subsequent dose is administered, when the serum level of the factor indicative of CRS in a subject does not exceed about 10, 25, 50, or 100 times the serum level of the indicator in the subject before the first dose is administered.

In some embodiments, the subsequent dose is administered when the results related to CRS (for example, serum factors related to CRS or indicative of CRS) or a clinical sign or symptom thereof such as fever, hypoxia, hypotension, or neurological disorders in a subject reach the peak level, and begin to decrease after the first dose is administered. In some embodiments, the subsequent dose is administered when a decrease is observed compared with the highest level of such results after administration, or when a decrease is observed after the maximum value or level of results is reached after administration.

In some embodiments, the subsequent dose is administered, when the level of an indicator of toxicity results (e.g., a serum indicator of CRS) drops below about 25 times the level of the indicator before the first dose. In some aspects, the subsequent dose is administered when the subject does not exhibit CRS or severe CRS.

In some aspects, the subsequent dose is administered when the tumor burden in a patient decreases compared with the tumor burden before the first dose is administered. In some embodiments, the subsequent dose is administered, when the tumor burden or an indicator thereof, such as the volume or number or percentage of a disease (e.g., tumor) cells in a subject's blood, other body fluids, organs or tissues, or tumor size is reduced by about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90% or more after the first dose is administered.

In some embodiments, the subsequent dose is administered when the subject's disease or condition does not relapse after a reduction in response to the first dose or the previous dose. In some embodiments, the reduction in tumor burden is indicated by a decrease in one or more factors, such as the expression level of tumor markers in the subject or the body fluids or organs or tissues thereof, the burden or number of tumor cells, the mass or volume of the tumor, the degree or extent of metastasis. In some embodiments, the recurrence is general or one or more factors, or in tumor burden. In some aspects, the subsequent dose is administered when the subject, disease burden, or factor thereof relapses compared with the lowest point measured or reached after the first or previous dose, but is still lower than those before the first dose. In some embodiments, the subsequent dose is administered to a subject when the tumor burden or an indicator thereof is not changed, for example, when the tumor burden has been prevented from increasing.

In some embodiments, the subsequent dose is administered when the host's adaptive immune response has not been detected, has not yet been established, or has not reached a certain level, degree or stage. In some aspects, the subsequent dose is administered before the subject's memory immune response develops.

In some aspects, the time between administration of the first dose and administration of the subsequent dose is about 21 to about 80 days, about 25 to about 60 days, or 25 to 55 days. In some embodiments, the administration of the subsequent dose does not exceed about 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58, 59 days or 60 days after the first dose is administered. In some embodiments, the administration of the subsequent dose does not exceed about 44 days, 45 days, 46 days, 47 days, or 48 days after the first dose is administered.

In some embodiments, after the subsequent dose (i.e., the first subsequent dose, or named as the second course dose) is administered, an additional or further subsequent dose is administered, for example, the second subsequent dose (the third course dose), the third subsequent dose (the fourth course dose), and so on. In some aspects, the additional subsequent dose is administered at least about 21 days and less than about 80 days after the previous subsequent dose (e.g., the first subsequent dose) is administered. In some embodiments, an exemplary dosage regimen includes a schedule of when or approximately when the chimeric antigen receptor expressing cells (e.g., CAR-expressing cells, such as CAR T cells) are administered. In some embodiments, the additional dose (the second subsequent dose) is administered about 49 days after the first subsequent dose, and so on. In some embodiments, the subsequent dose is administered not exceeding about 21 to about 80 days, about 25 to about 60 days, or 25 to 55 days after the adjacent preceding subsequent dose is administered. In some embodiments, the subsequent dose is administered not exceeding about 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days or 60 days after the adjacent preceding subsequent dose is administered.

In any embodiment, in some cases, the method includes administering a first dose or a preceding dose and subsequent dose, and in other cases, includes administering a subsequent dose to a subject who has previously received the first dose or preceding dose, but does not include the first dose or the previous dose itself. Therefore, in some cases, the method involves administering consolidation therapy, for example, by administering consolidation subsequent dose to a subject who has previously received a dose (e.g., reduced dose) of chimeric antigen receptor-expressing (e.g., CAR-expressing) cells. In some aspects, the previous dose of the receptor-expressing, such as CAR-expressing cells, is already sufficient to reduce the disease or disease burden in a subject, so that the efficacy and/or safety of the cells administered in the subsequent dose is improved compared with the dose administered to the subject given without receiving the first dose.

In some embodiments, after the subsequent dose, the tumor burden, including tumor markers, tumor size, tumor volume, and/or tumor mass, is reduced by at least equal to or about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90% or more, compared with that before the first dose or subsequent dose.

Host Immune Response Against the Reinfused Cells

In some embodiments, one or more doses, such as subsequent doses, are administered, when the immune response (such as adaptive or specific immune response to transgenic receptors or cells) in a subject is absent, undetectable, or can not be detected above a certain level. The presence or extent of a specific immune response to a transgene is usually related to the immunogenicity of the recipient (e.g., CAR or transgenic TCR expressed by the cell) and/or the time the subject is exposed to the cell. For example, in some embodiments, no immune response to the receptor, such as specific humoral and/or cell-mediated immune response is detected within 28 days, 35 days, or 42 days after the subject is firstly exposed to the receptor-expressing cells. Therefore, in some embodiments, the subsequent dose is administered before the subject has developed an immune response, an adaptive or specific immune response, a detectable immune response and/or a memory response against the chimeric antigen receptor or cell. In this regard, the ability of cells in the subsequent dose to proliferate and/or persist in a subject is improved compared with other methods in which the subsequent dose is administered at a later time point relatively to the previous or first dose. The method includes detecting the presence or level of such an immune response or an indicator thereof, for example, after the first or subsequent dose is administered and before the subsequent or next subsequent dose is administered.

In some embodiments, when and/or whether to administer a subsequent dose depends on whether the subject exhibits such an immune response or a detectable reading, such as a detectable specific or adaptive host immune response for a cell or a chimeric antigen receptor, such as CAR expressed by the cells in the first dose, and/or whether such a response is detected at a certain level. In some embodiments, where such a response is detected, no subsequent dose is administered to the subject. When the subject does not exhibit a specific or adaptive (e.g., humoral or cell-mediated) immune response to the receptor (e.g., CAR expressed by the cells in the first dose), or does not exhibit a response or an indicator thereof, which is at a detectable level or higher that an acceptable level, the subsequent dose is adminstered. In some aspects, when the subsequent dose is administered, the subject exhibits a reduced humoral or cell-mediated immune response to the CAR expressed by the cells in the first dose compared with the higher initial dose.

In any of the above embodiments, a detectable immune response refers to an amount which can be detected by any one of many known methods for evaluating specific immune responses to specific antigens and cells. For example, in some embodiments, ELISPOT, ELISA, or cell-based antibody detection methods (eg, by flow cytometry) are performed on the subject's serum to detect the presence of antibodies specifically binding to and/or neutralizing antigens on cells, such as binding to epitopes on chimeric antigen receptors, such as CAR, to detect specific types of immune responses. In some such assays, the isotype of the antibody detected is determined and can indicate the type of response and/or whether the response is a memory response.

In some aspects, for example, after the first dose or subsequent dose is administered, the presence or absence of such host immune response and/or quantity, degree thereof is detected or measured.

In some embodiments, this method reduces the burden of diseases or disorders to a greater extent, such as the number of tumor cells, the size of the tumor, a longer duration of patient survival or event-free survival, and period of time, compared with the observed reduction obtained by methods using alternative dosing regimens, for example, where the subject receives a single dose (e.g., a single large dose of cells), for example, uniformly replacing a single dose with the total number of cells given in the first dose and subsequent dose by the provided method, or administering multiple boluses or multiple doses separated by less than about 21 or more than about 80 days. In some aspects, the subject's survival, survival within a certain period of time, survival range, the presence or duration of event-free or asymptomatic survival, or recurrence-free survival are assessed.

In some aspects, the disease burden is measured or detected before the first dose is administered, after the first dose is administered but before the subsequent dose is administered, and/or after the subsequent dose is administered. In the case of multiple subsequent doses, in some embodiments, the disease burden can be measured before or after any subsequent dose or between the administration of subsequent doses.

In some embodiments, after the first dose is administered, the burden is reduced by at least or about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90% or 100%. In some aspects, administration of subsequent doses will further reduce disease burden, tumor burden, for example, compared with the burden before the subsequent dose is administered or before the first dose, the burden reduction is equal to or about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90% or 100%.

In some embodiments, this method improves the event-free survival rate or overall survival rate of a subject compared with other methods. For example, in some embodiments, the progression-free event survival rate or probability of a subject treated by this method 1 month after the first dose is greater than about 10%, greater than about 20%, greater than about 30%, greater than about 40%, greater than about 50%, greater than about 60%, greater than about 70%, greater than about 80%, greater than about 90%, or greater than about 95%. In some aspects, the overall survival rate is greater than about 10%, greater than about 20%, greater than about 30%, greater than about 40%, greater than about 50%, greater than about 60%, greater than about 70%, greater than about 80%, greater than about 90% % or greater than about 95%. In some embodiments, the subject treated by the method exhibits progression-free survival, recurrence-free survival, or survival for at least about 1 month, or at least about 2, 3, 4, 5, 6, 7, 8, 9, 10, 11 months, or 1, 2, 3, 4, 5, 6, 7, 8, 9 or 10 years. In some embodiments, the time of is improved, for example, greater than or about 1 month, or at least about 2, 3, 4, 5, 6, 7, 8, 9, 10, 11 months, or 1, 2, 3, 4, 5, 6, 7, 8, 9 or 10 years of progress.

In some embodiments, the probability of recurrence is reduced by this treatment method compared with other methods. For example, in some embodiments, the probability of recurrence or progression 1 month after the first dose is less than about 80%, less than about 70%, less than about 60%, less than about 50%, less than about 40%, less than about 30%, less than About 20%, less than about 10%, less than about 9%, less than about 8%, less than about 7%, less than about 6%.

Cell Exposure and Persistence

In some embodiments, the dosage and/or duration is designed to promote exposure of a subject to the cells, for example by increasing cell proliferation and/or persistence over time.

In some embodiments, the provided methods increase the subject's exposure to the administered cells (e.g., increase in the number or duration of cells over time) and/or improve the efficacy and treatment outcome in immune cell therapy. In some aspects, the advantage of this method is that, compared with other methods, the exposure of chimeric antigen receptor-expressing cells (such as CAR-expressing cells) to a greater degree and/or longer improves the treatment outcome. These results can include patient survival and remission, even in individuals with severe tumor burden.

In some embodiments, the presence and/or amount of cells expressing chimeric antigen receptors (e.g., CAR-expressing cells) in a subject after the first dose and/or subsequent doses are detected. In some aspects, quantitative PCR (qPCR) is used to assess the amount of cells (e.g., CAR-T) expressing chimeric antigen receptors in the subject's blood or serum or organs or tissues (e.g., disease sites). In some aspects, persistence is quantified as a copy of DNA or plasmid encoding a receptor, such as CAR per microgram of DNA, or as the number of cells expressing receptor, such as CAR per microliter of sample, such as blood or serum, or the total number of peripheral blood mononuclear cells (PBMC) or white blood cells or T cells per microliter sample.

In some embodiments, after the first dose is administered or at least on the day 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, cells were detected in the subject. In some aspects, cells were detected at or at least 2, 4, or 6 weeks or 3, 6 or 12, 18 or 24, or 30 or 36 months, or 1, 2, 3, 4, 5, or more years after the first or subsequent dose is administered.

In some embodiments, alternative methods, such as methods involving administering a single dose, for example, methods that contain more cells than the first dose, the total dose of cells is administered as a single dose, a subsequent dose of cells is administered to a subject who have not received the first dose, and/or a subsequent dose is administered at a time outside the designated time window, for example, later than or after a prescribed time when the subject's immune response to the receptor (e.g., CAR) appears.

The maximum number of cells exposed to the subject, the duration of detectable cells higher than a specific number or percentage, the area under the cell number curve over time and/or a combination thereof and its indicators can be used to indicate, for example, indicating cell number, proliferation and/or continuous contact. Compared with the total amount of nucleic acid or DNA in a specific sample, such as blood or serum, known methods such as qPCR can be used to evaluate such results to detect the copy number of the nucleic acid encoding the chimeric antigen receptor, and/or flow cytometry assays that usually use antibodies specific for the receptor to detect cells expressing the receptor. Cell-based assays can also be used to detect the number or percentage of functional cells, such as those capable of binding and/or neutralizing and/or inducing responses to diseases or disorders or cells expressing antigens recognized by the receptor (e.g, cytotoxic response).

In some aspects, the increased exposure of a subject to cells includes increased cell proliferation. In some embodiments, the receptor- (e.g., CAR-) expressing cells proliferate in the subject after the first dose is given and/or the subsequent doses are given. In some aspects, compared with other methods, such as those involving administering cells in a single dose, giving a larger first dose, giving subsequent doses without giving the first dose, and/or giving subsequent doses before or after a specified time window or time point, so as to for example, generate an immune response before the subsequent doses are administered, this method results in a greater cell proliferation.

In some aspects, the method results in a high in vivo proliferation of the administered cells, as measured by, for example flow cytometry. In some aspects, a peak proportion of cells is detected. For example, in some embodiments, after the first or subsequent dose is administered, at least about 10%, at least about 20%, at least about 30%, at least about 40%, at least about 50%, at least about 60%, at least about 70%, at least about 80%, or at least about 90% of cells express chimeric antigen receptors, for example, CAR, when a peak or maximum level in the subject's blood or disease site or white blood cell fraction thereof (e.g, PBMC fraction or T cell fraction).

In some embodiments, the method results in at least 10, 20, 30, 40, 50, 60, 70, 80, 90, 100, 500, 1000, 1500, 2000, 5000, 10000, or 15000 copies or maximum concentration of nucleic acid encoding the receptor, per microgram of DNA, or at least 0.1, 0.2, 0.3, 0.4, 0.5, 0.6, 0.7, 0.8, or 0.9 of the total number of receptor-expressing, such as CAR-expressing cells/peripheral blood mononuclear cells (PBMC), the total number of monocytes, the total number of T cells or the total number of microliters in the blood or serum or other body fluids or organs or tissues of the subject. In some embodiments, the receptor-expressing cells are detected as at least 10%, 20%, 30%, 40%, 50%, or 60% of the total PBMC in the blood of the subject, and/or maintain at this level after the first administration or subsequent administration for at least 1, 2, 3, 4, 5, 6, 7, 8, 9, 10, 11, 12, 24, 36, 48, or 52 weeks, or after such administration for 1, 2, 3, 4, or 5 years or more.

In some aspects, the method results in, for example, an at least 2-fold, at least 4-fold, at least 10-fold, or at least 20-fold increase in copies of a nucleic acid encoding a chimeric antigen receptor, such as a CAR, per microgram of DNA in the serum of the subject.

In some embodiments, the receptor-expressing cells can be detected in the blood or serum of a subject, for example, by a designated method, such as qPCR or flow cytometry-based detection methods, and maintain at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 or more days after the first dose or subsequent dose is administered, or at least or about 2, 3, 4, 5, 6, 7, 8, 9, 10, 11, 12, 13, 14, 15, 16, 17, 18, 19, 20, 21, 22, 23, or 24 or more weeks after the first dose or subsequent dose is administered.

In some aspects, at least about $1 \times 10^2$, at least about $1 \times 10^3$, at least about $1 \times 10^4$, at least about $1 \times 10^5$, at least about $1 \times 10^6$ or at least about $5 \times 10^6$ or at least about $1 \times 10^7$ or at least about $5 \times 10^7$ or at least about $1 \times 10^8$ or at least about $2.5 \times 10^8$ chimeric antigen receptor-expressing, such as CAR-expressing cells, and/or at least 10, 25, 50, 100, 200, 300, 400, or 500, or 1000 receptor expression-cells per microliter, such as at least 10 per microliter, can be detected or present in the subject or its fluid, tissues or compartments, such as in the blood, such as peripheral blood or its diseased location. In some embodiments, after the first dose or subsequent dose is administered, the number or concentration of cells is detectable in the subject for at least about 1 day, at least about 2 days, at least about 3 days, at least about 4 days, or at least About 5 days, at least about 6 days, at least about 7 days, at least about 8 days, at least about 9 days, at least about 10 days, at least about 11 days, at least about 12 days, at least about 13 days, at least about 14 days, at least About 15 days, at least about 16 days, at least about 17 days, at least about 18 days, at least about 19 days, at least about 20 days, at least about 40 days, or at least about 60 days, or at least about 3, 4, 5, 6, 7, 8, 9, 10, 11, or 12 months, or at least 2 or 3 years. Such cell number can be detected by a method based on flow cytometry or quantitative PCR, and extrapolated to the total cell number using known methods.

In some aspects, the number of copies of the nucleic acid encoding the chimeric antigen receptor, such as the number of vector copies per 100 cells, for example, in peripheral blood or bone marrow or other chambers can be measured by immunohistochemistry, PCR and/or flow cytometry as at least 0.01, at least 0.1, at least 1, or at least 10, when the cells are administered, for example after the first dose or subsequent dose is administered, about 1 week, about 2 weeks, about 3 weeks, about 4 weeks, about 5 weeks, or at least about 6 weeks, or at least about 2, 3, 4, 5, 6, 7, 8, 9, 10, 11, or 12 months, or at least 2 or 3 years. In some embodiments, the number of copies of the vector expressing the receptor, for example, the CAR per microgram of genomic DNA, is at least 10, 20, 30, 40, 50, 60, 70, 80, 90, 100, at least 1,000, at least 5,000, or at least 10,000, or at least 15,000, or at least 20,000, at about 1 week, about 2 weeks, about 3 weeks or at least about 4 weeks after the first dose or subsequent dose of cells expressing the receptor, for example CAR, are administered, or at least 2, 3, 4, 5, 6, 7, 8, 9, 10, 11, or 12 months, or at least 2 or 3 years after such administration.

In some aspects, receptors expressed by cells, such as CARs, can be detected in the subject, their blood and/or their diseased sites by quantitative PCR (qPCR) or by flow cytometry after the cells are administered, for example, at least about 3 days, at least about 6 days, at least about 10 days, at least about 15 days, at least about 20 days, at least about 30 days, at least about 40 days, at least about 50 days, at least about 60 days, at least about 80 days, 3 months, at least about 6 months, at least about 12 months, at least about 1 year, at least about 2 years, at least about 3 years, or more than 3 years after the first dose or subsequent dose or sub-subsequent dose is administered.

Chimeric Antigen Receptor Expressed by Cells

Cells usually express chimeric antigen receptors, including antigen receptors, such as functional non-TCR antigen receptors, such as chimeric antigen receptors (CAR) and other antigen-binding receptors such as transgenic T cell receptors (TCR), T cells Fusion protein (TFP) and T cell antigen coupler (TAC).

Exemplary antigen receptors, including CARs, and methods for engineering and introducing receptors into cells, include, for example, Chinese Patent Application Publication Nos. CN107058354A, CN107460201A, CN105194661A, CN105315375A, CN105713881A, CN106146666A, CN106519037A, CN106554414A, CN105331585A, CN106397593A, CN106467573A, those described in International Patent Application Publication Nos. WO2018006882A1, WO2015172339A8.

The chimeric receptor includes a chimeric antigen receptor (CAR). Chimeric receptors, such as CARs, usually include an extracellular antigen binding domain, such as a part of an antibody molecule, usually the variable heavy (VH) chain region and/or variable light (VL) chain region of an antibody, for example, scFv antibody Fragment. In some embodiments, the chimeric receptor can recognize the splice variant 1 of claudin 18 (Claudin 18, CLD18) (CLD18A1, CLD18.1) (accession numbers NP_057453, NM016369) or variants thereof, for example comprising the amino acid sequence as shown in SEQ ID NO: 34, or an amino acid sequence having at least 85%, 86%, 87%, 88%, 89%, 90%, 91%, 92%, 93%, 94%, 95%, 96%, 97%, 98%, 99% or more sequence identity with SEQ ID NO: 34, and can recognize splice variant 2 (CLD18A2, CLD18.2) (registration number NM_001002026, NP_001002026) or variants thereof, for example comprising the amino acid sequence as shown in SEQ ID NO: 33, or an amino acid sequence having at least 85%, 86%, 87%, 88%, 89%, 90%, 91%, 92%, 93%, 94%, 95%, 96%, 97%, 98%, 99% or more sequence identity with SEQ ID NO: 33. In some embodiments, the chimeric receptor specifically recognizes CLD18A2, but not CLD18A1.

In some embodiments, the antibody portion of the chimeric antigen receptor (e.g., CAR) includes scFv antibody fragments, for example, comprising the HCDR or LCDR amino acid sequence shown in SEQ ID NO: 1 or 2 or 3 or 4 or 5 or 6 or 7 or a variant thereof, or an amino acid sequences having at least 85%, 86%, 87%, 88%, 89%, 90%, 91%, 92%, 93%, 94%, 95%, 96%, 97%, 98%, 99% or more sequence identity with SEQ ID NO: 1 or 2 or 3 or 4 or 5 or 6 or 7.

In some embodiments, the antibody portion of the chimeric antigen receptor (e.g., CAR) includes scFv antibody fragments, for example, comprising the HCDR or LCDR amino acid sequence shown in SEQ ID NO: 8 or 9 or 10 or 11 or 12 or 13 or a variant thereof, or an amino acid sequences having at least 85%, 86%, 87%, 88%, 89%, 90%, 91%, 92%, 93%, 94%, 95%, 96%, 97%, 98%, 99% or more sequence identity with SEQ ID NO: 8 or 9 or 10 or 11 or 12 or 13.

In some embodiments, the antibody portion of the chimeric antigen receptor (e.g., CAR) includes scFv antibody fragments, for example, comprising the HCDR or LCDR amino acid sequence shown in SEQ ID NO: 8 or 9 or 10 or 11 or 12 or 13 or a variant thereof, or an amino acid sequences having at least 85%, 86%, 87%, 88%, 89%, 90%, 91%, 92%, 93%, 94%, 95%, 96%, 97%, 98%, 99% or more sequence identity with SEQ ID NO: 8 or 9 or 10 or 11 or 12 or 13.

In some embodiments, the antibody portion of the chimeric antigen receptor (e.g., CAR) includes scFv antibody fragments, for example, comprising the HCDR or LCDR amino acid sequence shown in SEQ ID NO: 14 or 15 or 16 or 17 or 18 or 19 or a variant thereof, or an amino acid sequences having at least 85%, 86%, 87%, 88%, 89%, 90%, 91%, 92%, 93%, 94%, 95%, 96%, 97%, 98%, 99% or more sequence identity with SEQ ID NO: 14 or 15 or 16 or 17 or 18 or 19.

In some embodiments, the antibody portion of the chimeric antigen receptor (e.g., CAR) includes scFv antibody fragments, for example, comprising an amino acid sequence of heavy or light chain variable region as shown in SEQ ID NO: 20 or 21 or 22 or 23 or a variant thereof, or an amino acid sequences having at least 85%, 86%, 87%, 88%, 89%, 90%, 91%, 92%, 93%, 94%, 95%, 96%, 97%, 98%, 99% or more sequence identity with SEQ ID NO: 20 or 21 or 22 or 23.

In some embodiments, the antibody portion of the chimeric antigen receptor (e.g., CAR) includes scFv antibody fragments, for example, comprising an amino acid sequence of heavy or light chain variable region as shown in SEQ ID NO: 20 or 21 or 22 or 23 or a variant thereof, or an amino acid sequences having at least 85%, 86%, 87%, 88%, 89%, 90%, 91%, 92%, 93%, 94%, 95%, 96%, 97%, 98%, 99% or more sequence identity with SEQ ID NO: 20 or 21 or 22 or 23.

In some embodiments, the antibody portion of the chimeric antigen receptor (e.g., CAR), for example, comprises an amino acid sequence as shown in SEQ ID NO: 24 or 25 or 26 or 27 or 28 or 29 or 30 or 31 or 32 or a variant thereof, or an amino acid sequences having at least 85%, 86%, 87%, 88%, 89%, 90%, 91%, 92%, 93%, 94%, 95%, 96%, 97%, 98%, 99% or more sequence identity with SEQ ID NO: 24 or 25 or 26 or 27 or 28 or 29 or 30 or 31 or 32.

In some embodiments, the antibody portion of the chimeric antigen receptor (e.g., CAR) further includes a linking sequence, which may be or include at least a portion of an immunoglobulin constant region or a variant or modified form thereof, such as a hinge region, such as IgG4 hinge region and/or CH1/CL and/or Fc region. In some embodiments, the constant region or portion is of human IgG, such as IgG4 or IgG1. In some aspects, the portion of the constant region serve as the linking sequence between antigen-recognition portion, for example, scFv, and the transmembrane domain. The linking sequence may have a length that increases cell response after binding to antigen, compared with the situation in the absence of the linking sequence. In some examples, the linking sequence is 12 or about 12 amino acids in length or not more than 12 amino acids in length. Exemplary linking sequences include those having the following lengths: at least about 10-229 amino acids, about 10-200 amino acids, about 10-175 amino acids, about 10-150 amino acids, about 10-125 amino acids, about 10-100 amino acids, about 10-75 amino acids, about 10-50 amino acids, about 10-40 amino acids, about 10-30 amino acids, about 10-20 amino acids, or about 10-15 amino acids, including an integer between any endpoints of the above listed range. In some embodiments, the linker region has about 12 amino acids or shorter, about 119 amino acids or shorter, or about 229 amino acids or shorter. Exemplary linking sequences include IgG4 hinges alone, IgG4 hinges binding to CH2 and CH3 domains, or IgG4 hinges binding to CH3 domains.

The antigen recognition domain is generally connected to one or more intracellular signal transduction moieties, for example, in the case of CAR, a signal transduction moiety mimicking the activation through the antigen receptor complex (such as TCR complex), and/or signal through another cell surface receptor. Therefore, in some embodiments, the antigen binding component (e.g., antibody) is linked to one or more transmembrane and intracellular signal transduction domains. In some embodiments, the transmembrane domain is fused to the extracellular domain. In one embodiment, the transmembrane domain of one of the domains in the naturally associated receptor (e.g., CAR) is used. In some cases, the transmembrane domain is selected or modified by amino acid substitutions to prevent the domain from binding to the transmembrane domain of the same or different surface membrane protein, so that the interaction with other members of the receptor complex is minimized.

In some embodiments, the transmembrane domain is derived from natural or synthetic sources. When the source is a natural source, in some aspects, the domain is derived from any membrane-bound or transmembrane protein. The transmembrane region includes α, β or ζ chains derived from T-cell receptors, CD28, CD38, CD45, CD4, CD5, CD8, CD9, CD 16, CD22, CD33, CD37, CD64, CD80, CD86, CD 134, CD137, CD 154, and/or transmembrane regions include functional variants (e.g., those that substantially retain their structural parts (e.g., transmembrane structural parts), properties) (i.e., include at least their transmembrane regions). In some embodiments, the transmembrane domain is a transmembrane domain derived from CD4, CD28, or CD8, for example, CD8α or a functional variant thereof. Alternatively, in some embodiments, the transmembrane domain is synthetic. In some aspects, the synthetic transmembrane domain mainly contains hydrophobic residues such as leucine and valine. In some aspects, trimers of phenylalanine, tryptophan and valine will appear at each end of the synthetic transmembrane domain. In some embodiments, the connection occurs through linkers, spacers, and/or transmembrane domains.

The intracellular signal transduction domains include those that mimic or approximate signals through natural antigen receptors, signals through such receptors in combination with co-stimulatory receptors, and/or signals through individual co-stimulatory receptors. In some embodiments, there is a short oligopeptide or polypeptide linker, for example, a linker of 2-10 amino acids in length, for example, a linker containing glycine and serine, for example, a glycine-serine doublet, and forming a connection between the cytoplasm signal transduction domain and the transmembrane domain of a CAR.

The receptor, for example, CAR, generally includes at least one of one or more intracellular signal transduction moieties. In some embodiments, the receptor includes the intracellular component of the TCR complex, such as the TCRCD3+ chain that mediates T-cell activation and cytotoxicity, for example, the CD3ζ chain. Therefore, in some aspects, the antigen binding moiety is connected to one or more cell signal transduction modules. In some embodiments, the cell signal transduction module includes a CD3 transmembrane domain, a CD3 intracellular signal transduction domain, and/or other CD transmembrane domains. In some embodiments, the receptor, for example, CAR, also includes portions of one or more other molecules, such as Fc receptor γ, CD8, CD4, CD25, or CD16. For example, in some aspects, CAR or other chimeric receptors include chimeric molecules between CD3ζ (CD3-ζ) or Fc receptor γ and CD8, CD4, CD25, or CD16.

In some embodiments, when the CAR or other chimeric receptor is bound, the cytoplasmic domain or intracellular signal transduction domain of the receptor activates at least one of the normal effector function or response of immune cells, such as T cells which are engineered to express a CAR. For example, in some cases, CAR induces T cell functions, such as cytolytic activity or helper T cell activity, such as secretion of cytokines or other factors. In some embodiments, an antigen receptor portion or a truncated portion of the intracellular signal transduction domain of a costimulatory molecule is used to replace the complete immunostimulatory chain, for example, if it transduces effector function signals. In some embodiments, the intracellular signal transduction domain includes the cytoplasmic sequence of the T cell receptor (TCR), and in some aspects, it also includes those co-receptors that exist in nature in concert with these receptors, so that the signal transduction is initiated after antigen receptor engagement.

In the case of natural TCR, complete activation generally requires not only signal transduction through TCR, but also costimulatory signals. Therefore, in some embodiments, in order to promote complete activation, components used to generate a second or costimulatory signal are also included in the CAR. In other embodiments, the CAR does not include components used to generate costimulatory signals. In some aspects, other CARS are expressed in the same cell and provide components for generating a second or costimulatory signal.

In some aspects, T cell activation is mediated by two types of cytoplasmic signal transduction sequences: those that initiate antigen-dependent first activation via TCR (the first cytoplasmic signal transduction sequence), and those that acts in an antigen-independent manner to provide a second or costimulatory signal (second cytoplasmic signal transduction sequence). In some aspects, the CAR includes one or both of such signal transduction components.

In some embodiments, the antibody portion of the chimeric antigen receptor (e.g., CAR) also includes a signal peptide, such as a signal peptide including CD8 or a variant thereof, for example, including the amino acid sequence as shown in SEQ ID NO: 35, or an amino acid sequences having at least 85%, 86%, 87%, 88%, 89%, 90%, 91%, 92%, 93%, 94%, 95%, 96%, 97%, 98%, 99% or more of sequence identity with SEQ ID NO: 35.

In some aspects, the CAR includes a major cytoplasmic signal transduction sequence that regulates the initial activation of the TCR complex. The first cytoplasmic signal transduction sequence that acts in a stimulating manner may contain a signal transduction motif, which is known as an immune receptor tyrosine-based activation motif or ITAM. Examples of ITAM include first cytoplasmic signal transduction sequences, which include those derived from: TCRζ, FcRγ, FcRβ, CD3γ, CD3δ, CD3ε, CDS, CD22, CD79a, CD79b, and CD66d. In some embodiments, the cytoplasmic signal transduction molecule in the CAR comprises a cytoplasmic signal transduction domain, part of which is derived from a sequence of CD3ζ.

In some embodiments, the CAR includes the transmembrane portion of a costimulatory receptor and/or signal transduction domain, such as CD28, CD137, OX40, DAP10, and ICOS. In some aspects, the same CAR includes both activation and costimulatory components.

In some embodiments, the activation domain is included in one CAR, and the costimulatory component is provided by another CAR that recognizes another antigen.

In some embodiments, the CAR includes an activating or stimulating CAR and co-stimulating CAR, all of which are expressed on the same cell (see WO2014/055668). In some aspects, the cell includes one or more stimulating or activating CAR and/or costimulating CAR. In some embodiments, the cell also includes an inhibitory CAR (iCAR, see Fedorov et al., Sci. Transl. Medicine, 5 (215) (December 2013)), for example, a CAR recognizing antigens in addition to disease or disorder related and/or specific antigen, thereby reducing or inhibiting the activation signal delivered by the disease-targeted CAR by the binding of the inhibitory CAR to its ligand, for example, to reduce off-target effects.

In some embodiments, the intracellular signal transduction portion of the chimeric antigen receptor, such as a CAR, comprises a CD3ζ intracellular domain and a costimulatory signal transduction region. In certain embodiments, the intracellular signal transduction domain comprises a CD28 transmembrane and signal transduction domain, which is connected to the CD3 (e.g., CD3-ζ) intracellular domain. In some embodiments, the intracellular signal transduction domain comprises a chimeric CD28 and/or CD137 (4-1BB, TNFRSF9) costimulatory domain, which is linked to the CD3ζ intracellular domain.

In some embodiments, the CAR encompasses one or more, for example, two or more, costimulatory domains and activation domains, for example, the initial activation domain in the cytoplasmic portion. Exemplary CARs include the intracellular portions of CD3-ζ, CD28, and CD137.

In some cases, CARs are referred to as the first, second and/or third generation of CARs. In some aspects, the first-generation of CAR is a CAR that only provides CD3 chain induction signals upon binding to an antigen; in some aspects, the second-generation of CAR is a CAR that provides such signals and co-stimulatory signals, for example, a CAR including the intracellular signal transduction domain derived from co-stimulatory receptors (for example, CD28 or CD137); in some aspects, the third-generation of CAR is a CAR that includes multiple costimulatory domains of multiple costimulatory receptors.

In some embodiments, the chimeric antigen receptor includes an extracellular portion containing an antibody or antibody fragment. In some aspects, the chimeric antigen receptor includes an extracellular portion containing an antibody or fragment and an intracellular signal transduction domain. In some embodiments, the antibody or a fragment thereof includes scFv, and the intracellular domain includes ITAM. In some aspects, the intracellular signal transduction domain includes the signal transduction domain of the ζ chain of the CD3-ζ chain. In some embodiments, the chimeric antigen receptor includes a transmembrane domain that connects the extracellular domain and the intracellular signal transduction domain. In some aspects, the transmembrane domain comprises the transmembrane portion of CD28. In some embodiments, the chimeric antigen receptor contains the intracellular domain of a T cell costimulatory molecule. The extracellular domain and the transmembrane domain can be directly or indirectly connected. In some embodiments, the extracellular domain and transmembrane is connected through a linking sequence. In some embodiments, the receptor comprises the extracellular portion of the molecule from which the transmembrane domain is derived, such as CD28 extracellular portion. In some embodiments, the chimeric antigen receptor comprises an intracellular domain derived from a T cell costimulatory molecule or a functional variant thereof, for example, between the transmembrane domain and intracellular signal transduction domain. In some aspects, the T cell costimulatory molecule is CD28 or 41BB. For example, in some embodiments, the CAR contains an antibody, such as an antibody fragment, is or contains the transmembrane portion of CD28 or the transmembrane domain of a functional variant thereof, and contains the signal transduction portion of CD28 or internal signal transduction domain of a functional variant thereof, and the signal transduction portion of CD3ζ or a functional variant thereof. In some embodiments, the CAR contains an antibody, such as an antibody fragment, which contains or comprises the transmembrane portion of CD28 or the transmembrane domain of a functional variant thereof, and contains the signal transduction portion of CD137 or internal signal transduction domain of a functional variant thereof, and the signal transduction portion of CD3ζ or a functional variant thereof. In some such embodiments, the receptor further includes a linking sequence that includes a portion of an Ig molecule (e.g., a human Ig molecule), such as an Ig hinge, such as an IgG4 hinge, such as only the hinge linking sequence. In some embodiments, the chimeric antigen receptor has: (i) an antibody specifically recognizing a tumor antigen, the transmembrane region of CD28 or CD8, costimulatory signal domain of CD28, and CD3ζ; or (ii) an antibody specifically recognizing a tumor antigen, the transmembrane region of CD28 or CD8, the costimulatory signal domain of CD137, and CD3ζ; or (iii) an antibody specifically recognizing a tumor antigen, the transmembrane region of CD28 or CD8, and the costimulatory signal of CD28, the costimulatory signal domain of CD137 and CD3ζ.

In some embodiments, the transmembrane domain of the chimeric antigen receptor (e.g., CAR) is or includes the transmembrane domain of human CD28 (for example, accession number P01747.1) or the transmembrane domain of a variant thereof, such as the transmembrane domain comprising the amino acid sequence as shown in SEQ ID NO: 39, or comprising the amino acid sequence having at least 85%, 86%, 87%, 88%, 89%, 90%, 91%, 92%, 93%, 94%, 95%, 96%, 97%, 98%, 99% or more sequence identity with the amino acid sequences as shown in SEQ ID NO: 39.

In some embodiments, the transmembrane domain of the chimeric antigen receptor (e.g., CAR) is or includes the transmembrane domain of human CD8 or a variant thereof, such as the transmembrane domain comprising the amino acid sequence as shown in SEQ ID NO: 45, or comprising the amino acid sequence having at least 85%, 86%, 87%, 88%, 89%, 90%, 91%, 92%, 93%, 94%, 95%, 96%, 97%, 98%, 99% or more sequence identity with the amino acid sequences as shown in SEQ ID NO: 45.

In some embodiments, the intracellular signal transduction portion of the chimeric antigen receptor (e.g., CAR) includes the intracellular costimulatory signal transduction domain of human CD28 or a functional variant or portion thereof. For example, the intracellular signal transduction portion comprises the amino acid sequence as shown in SEQ ID NO: 41, or the amino acid sequence having at least 85%, 86%, 87%, 88%, 89%, 90%, 91%, 92%, 93%, 94%, 95%, 96%, 97%, 98%, 99% or more sequence identity with the amino acid sequences as shown in SEQ ID NO: 41.

In some embodiments, the intracellular domain comprises the intracellular costimulatory signal transduction domain of CD137 (e.g., Accession No. Q07011.1) or a functional variant or portion thereof, such as the amino acid sequence as shown in SEQ ID NO: 47, or the amino acid sequence having at least 85%, 86%, 87%, 88%, 89%, 90%, 91%, 92%, 93%, 94%, 95%, 96%, 97%, 98%, 99% or more amino acid sequence identity with SEQ ID NO: 47.

In some embodiments, the intracellular signal transduction domain of the chimeric antigen receptor (e.g., CAR) comprises a human CD3 stimulation signal transduction domain or a functional variant thereof. For example, in some embodiments, the intracellular signal transduction domain comprises the amino acid sequence as shown in SEQ ID NO: 43 or the amino acid sequence having at least 85%, 86%, 87%, 88%, 89%, 90%, 91%, 92%, 93%, 94%, 95%, 96%, 97%, 98%, 99% or more sequence identity with SEQ ID NO: 43.

In some aspects, the chimeric antigen receptor comprises a hinge, such as a CD8 hinge. For example, in some embodiments, the CD8 hinge comprises the amino acid sequence as shown in SEQ ID NO: 37 or the amino acid sequence having at least 85%, 86%, 87%, 88%, 89%, 90%, 91%, 92%, 93%, 94%, 95%, 96%, 97%, 98%, 99% or higher sequence identity with SEQ ID NO: 37.

For example, in some embodiments, the CAR includes antibodies, such as antibody fragments, including scFv, linking sequences, such as linking sequences containing a portion of an immunoglobulin molecule, such as a hinge region and/or one or more heavy chain constant regions, for example, a linking sequence containing an Ig-hinge, a transmembrane domain containing all or part of a CD28-derived transmembrane domain, a CD28-derived intracellular signal domain and a CD3ζ signal transduction domain. In some embodiments, the CAR includes antibodies or fragments, such as scFv, linking sequences, such as any linking sequence containing Ig-hinge, CD28-derived transmembrane domain, CD137-derived intracellular signal transduction domain and CD3ζ-derived signal transduction domain.

The terms "polypeptide" and "protein" are used interchangeably to refer to a polymer of amino acid residues and are not limited to a minimum length. Polypeptides including provided receptors and other polypeptides (e.g., linkers or peptides) can include amino acid residues, including natural and/or unnatural amino acid residues. The term also includes post-expression modifications of the polypeptide, such as glycosylation, sialylation, acetylation, and phosphorylation. In some aspects, the polypeptide may include modifications to the original or native sequence, as long as the protein retains the desired activity. These modifications may be intentional, such as by site-directed mutagenesis or may be accidental, such as by mutation of the host producing the protein or errors caused by PCR amplification.

In some embodiments, the methods described herein include administering an adoptive cell or immune effector cell to a subject. In some embodiments, the methods described herein include administering to the subject two or more adoptive cells or immune effector cells directed against the same tumor antigen in different courses of treatment. In some embodiments, the methods described herein include administering to the subject two or more adoptive cells or immune effector cells directed against different tumor antigens in different courses of treatment. In some embodiments, the methods described herein include administering two or more adoptive cells or immune effector cells to the same epitope of the same tumor antigen to the subject in different courses of treatment. In some embodiments, the methods described herein include administering two or more adoptive cells or immune effector cells to different epitopes of the same tumor antigen to the subject in different courses of treatment. In some embodiments, the methods described herein include administering two or more adoptive cells or immune effector cells to the subject in different courses of treatment to treat tumors at the same site. In some embodiments, the methods described herein include administering two or more adoptive cells or immune effector cells to the subject in different courses of treatment to treat tumors at different locations. In some embodiments, at least one of the adoptive cells or immune effector cells used in the methods described herein is a CAR-T cell targeting CLD18A2. In some embodiments, at least one of the adoptive cells or immune effector cells used in the methods described herein is the CAR-T cells targeting CLD18A2 described herein.

Chimeric antigen receptors (e.g., CAR) expressed by cells administered to a subject in various doses generally recognize or specifically bind to a molecule which is expressed by the treated disease or condition or cell, relevant to the disease or condition or cell and/or specific for the disease or condition or cell. When specifically binding a molecule such as an antigen, the receptor usually delivers an immunostimulatory signal (such as an ITAM-transduced signal) to the cell, thereby promoting an immune response targeting to a disease or disorder. For example, in some embodiments, the cells in the first dose express a CAR that specifically binds to an antigen expressed by the cells or tissues of the disease or disorder or an antigen associated with the disease or disorder.

The receptor expressed by the cell in the subsequent dose (e.g., CAR) usually specifically binds to the same antigen as the CAR in the first dose, and is usually the same or extremely similar receptor as the receptor of the cells of the first dose. In some embodiments, the receptors on the cells in the subsequent dose are the same as the receptors on the cells in the first dose or are substantially identical to the receptors.

In some embodiments, the CAR expressed by the cells in the subsequent dose contains the same scFv, the same signal transduction domain and/or the same linkage as the CAR expressed by the cells in the first dose. In some embodiments, it also contains the same co-stimulatory, stimulatory, transmembrane and/or other domains as the first dose. In some embodiments, one or more components of the CAR in the subsequent dose are different from those of the CAR in the first dose.

Immune Effector Cells

In the present invention, the cells expressing the chimeric receptor and provided by the methods described herein are immune effector cells. The cells are generally eukaryotic cells, such as mammalian cells, and usually human cells. In some embodiments, the cells are derived from blood, bone marrow, lymph, or lymphoid organs, and are cells of the immune system, such as cells of innate or adaptive immunity, for example, bone marrow or lymphoid cells, including lymphocytes, generally T cells and/or NK cells. Other exemplary cells include stem cells, such as multipotent and pluripotent stem cells, including induced pluripotent stem cells (iPSC). The cells are generally primary cells, such as those cells isolated directly from the subject and/or isolated and frozen from the subject. In some embodiments, the cells include one or more subgroups of T cells or other cell types, such as whole T cell populations, CD4+ cells, CD8+ cells and subgroups thereof, such as those defined by function, activation state, maturation, differentiation potential, expansion, recycling, localization, and/or persistence, antigen specificity, antigen receptor type, presence in a specific organ or compartment, marker or cytokine secretion profile, and/or degree of differentiation. Regarding the subject to be treated, the cells may be allogeneic and/or autologous. Methods include existing methods. In some aspects, for the existing technologies, the cells are pluripotent and/or multipotent, such as stem cells, such as induced pluripotent stem cells (iPSC). In some embodiments, the method includes isolating cells from the subject, preparing, processing, culturing, and/or engineering the same, and reintroducing them into the same patient before or after cryopreservation.

The subtypes and subgroups of T cells and/or CD4+ and/or CD8+ T cells include: naive T (TN) cells, effector T cells (TEFF), memory T cells and their subtypes, such as stem cell memory T (TSCM), Central memory T (TCM), effector memory T (TEM), or terminally differentiated effector memory T cells, tumor-infiltrating lymphocytes (TIL), immature T cells, mature T cells, helper T cells, cytotoxicity T cells, mucosal-associated non-variant T (MAIT) cells, naturally occurring and adoptive regulatory T (Treg) cells, helper T cells, such as TH1 cells, TH2 cells, TH3 cells, TH17 cells, TH9 cells, TH22 cells, follicular helper T cells, α/β T cells, and ε/γ T cells.

In some embodiments, the cell is a natural killer (NK) cell. In some embodiments, the cells are monocytes or granulocytes, for example, bone marrow cells, macrophages, neutrophils, dendritic cells, mast cells, eosinophils, and/or basophils granulocyte. In some embodiments, the cell includes one or more nucleic acids introduced by genetic engineering, thereby expressing a recombinant or genetically engineered product of the nucleic acid. In some embodiments, the nucleic acid is heterologous, that is, it is not normally present in a cell or a sample obtained from the cell, such as a sample obtained from another organism or cell, that is not normally found in the engineering cells and/or organisms from which such cells are derived. In some embodiments, the nucleic acid is not naturally occurring, for example, the nucleic acid is not found in nature, including chimeric combinations comprising nucleic acids encoding various domains from multiple different cell types.

Methods and Vectors for Genetic Engineering

The invention also provides methods, compositions and kits for producing genetically engineered cells expressing chimeric antigen receptors. The genetic engineering generally involves introducing the nucleic acid encoding the recombinant or engineered part into a cell, for example, by retroviral transduction, transfection, or transformation.

In some embodiments, gene transfer is performed: firstly, a cell is stimulated, for example, by combining it with a stimulus that induces a response, such as proliferation, survival, and/or activation, for example, detected by the expression of cytokine or activation markers, and then the activated cell is transduced and expanded in culture to a sufficient number for clinical application.

In some cases, overexpression of stimulating factors (e.g., lymphokines or cytokines) may be toxic to the subject. Therefore, in some cases, engineered cells include, for example, gene segments that make the cells susceptible to negative selection in vivo after administration in immune effect therapy. For example, in some aspects, the cells are engineered so that they can be eliminated due to changes in the in vivo condition of the subject to which they are administered. The negatively selectable phenotype can be produced by applying genes that provide sensitivity to administered agents (e.g., compounds). Genes that can be negatively selected include: herpes simplex virus type I thymidine kinase (HSV-I TK) gene (Wigler et al., Cell II: 223, 1977), which provides sensitivity to ganciclovir; cellular hypoxanthine phosphoribosyl Transferase (HPRT) gene, cellular adenine phosphoribosyl transferase (APRT) gene, bacterial cytosine deaminase (Mullen et al., Proc. Natl. Acad. Sci. USA. 89:33 (1992)).

In some aspects, the cells are also engineered to promote the expression of cytokines or other factors. Various methods for introducing genetically engineered components, for example, antigen receptors (e.g., CARs) are well known, and the methods and compositions provided herein can be used. Exemplary methods include those used to transfer the nucleic acid encoding the receptor, including via virus, for example, retrovirus or lentivirus, transduction, transposon, and electroporation.

In some embodiments, recombinant infectious virus particles are used to transfer recombinant nucleic acid into cells, for example, vectors derived from simian virus 40 (SV40), adenovirus, adeno-associated virus (AAV). In some embodiments, recombinant lentiviral vectors or retroviral vectors, such as γ-retroviral vectors, are used to transfer recombinant nucleic acids into T cells (see, for example, Koste et al., (2014) Gene Therapy Apr. 3, 2014. doi: 10.1038/gt.2014.25; Carlens et al., (2000) Exp Hematol 28 (10): 1137-46; Alonso-Camino et al., (2013) Mol Ther Nucl Acids 2, e93; Park et al., Trends Biotechnol. 2011 November; 29 (11): 550-557).

In some embodiments, the retroviral vector has a long terminal repeat (LTR), for example, retroviral vector derived from Moloney murine leukemia virus (MoMLV), myeloproliferative sarcoma virus (MPSV), murine embryonic stem cell virus (MESV)), murine stem cell virus (MSCV), spleen foci forming virus (SFFV) or adeno-associated virus (AAV). Most retroviral vectors are derived from murine retroviruses. In some embodiments, the retroviruses include those derived from any avian or mammalian cell source. Retroviruses are usually amphiphilic, which means that they can infect host cells of several species, including humans. Lentiviral transduction methods are known. Exemplary methods are described in, for example, Wang et al., (2012) J. Immunother. 35 (9): 689-701; Cooper et al., (2003) Blood. 101: 1637-1644; Verhoeyen et al., (2009) Methods Mol Biol 506:97-114; and Cavalieri et al. (2003) Blood. 102 (2): 497-505.

In some embodiments, the recombinant nucleic acid is transferred into T cells by electroporation (see, e.g., Chicaybam et al., (2013) PLOS ONE 8 (3): e60298 and Van Tedeloo et al., (2000) Gene Therapy 7 (16): 1431-1437). In some embodiments, the recombinant nucleic acid is transferred into T cells by translocation (see, for example, Manuri et al., (2010) Hum Gene Ther 21 (4): 427-437; Sharma et al., (2013) Molec Ther Nucl Acids 2, e74; and Huang et al., (2009) Methods Mol Biol 506:115-126). Other methods for introducing and expressing genetic material in immune cells include calcium phosphate transfection (e.g., described in "Current Protocols in Molecular Biology", John Wiley & Sons, New York, NY), protoplast fusion, cationic liposome-mediated transfection; particle bombardment promoted by tungsten particles (Johnston, Nature, 346:776-777 (1990)); and strontium phosphate DNA co-precipitation (Brash et al., Mol. Cell Biol., 7:2031-2034 (1987)).

Other methods and vectors for transferring nucleic acids encoding recombinant products are those described in, for example, WO2014055668 and U.S. Pat. No. 7,446,190.

Other nucleic acids (such as genes) used for introduction include those used to improve the efficacy of treatment, such as by promoting the viability and/or function of transferred cells; genes used to provide genetic markers for selection and/or evaluation of cells, such as assessing survival or localization in vivo; genes to improve safety, for example, by making cells susceptible to negative selection in vivo, such as Lupton S. D. et al., Mol. and Cell Biol., 11:6 (1991); and Riddell Et al., Human Gene Therapy 3:319-338 (1992); see also Lupton's publication numbers PCT/US91/08442 and PCT/US94/05601, etc., which describe applications of dominant positive selectable markers and negative selectable markers, bifunctional selectable fusion genes derived from the fusion of markers. See, for example, Riddell et al., U.S. Pat. No. 6,040,177, columns 14-17.

Preparation of Immune Effector Cells

In some embodiments, the preparation of engineered cells includes one or more culture and/or one or more preparation steps. Cells used to introduce nucleic acid encoding a transgenic receptor (e.g., CAR) can be isolated from a sample (e.g., a biological sample, such as a sample obtained or derived from a subject). In some embodiments, the subject from which the cells are isolated is a subject suffering from a certain disease or condition or in need of cell therapy or to be given cell therapy. In some embodiments, the subject is a person in need of specific therapeutic intervention, for example, a person in need of adoptive cell therapy or effector cell therapy, and the cells used for the therapy are isolated, processed, and/or engineered. In some embodiments, the cell is a primary cell, for example, a primary human cell. The sample includes tissues, body fluids and other samples taken directly from the subject, as well as obtained from one or more processing steps, such as separation, centrifugation, genetic engineering (such as transduction with viral vectors), washing and/or Incubate the sample. The biological sample may be a sample obtained directly from a biological source or a processed sample. Biological samples include, but are not limited to, body fluids such as blood, plasma, serum, cerebrospinal fluid, synovial fluid, urine and sweat, tissue and organ samples, including processed samples derived from them.

In some aspects, the sample from which the cells are derived or isolated is a blood or blood-derived sample or is or is derived from apheresis or leukopenia products. Exemplary samples include whole blood, peripheral blood mononuclear cells (PBMC), white blood cells, bone marrow, thymus, tissue biopsy, tumor, leukemia, lymphoma, lymph nodes, intestinal-associated lymphoid tissue, mucosal-associated lymphoid tissue, spleen, other lymphoid tissues, liver, lung, stomach, intestine, colon, kidney, pancreas, breast, bone, prostate, cervix, testis, ovary, tonsil or other organs, and/or cells derived therefrom. In the case of cell therapy (e.g., adoptive cell therapy or immune effector cell therapy), samples include samples from autologous and allogeneic sources.

In some embodiments, the cell is derived from a cell line, for example, a T cell line. In some embodiments, the cells are obtained from xenogeneic sources, for example, from mice, rats, non-human primates, and pigs.

In some embodiments, the separation of cells includes one or more preparation and/or non-affinity-based cell separation steps. In some instances, the cells are washed, centrifuged, and/or incubated in the presence of one or more substances, for example, to remove unwanted components, enrich required components, lyse or remove cells sensitive to specific substances. In some instances, cells are separated based on one or more properties, such as density, adhesion properties, size, sensitivity and/or resistance to specific components. In some examples, cells from the circulating blood of the subject are obtained, for example, by apheresis or leukopenia. In some aspects, the sample includes lymphocytes, including T cells, monocytes, granulocytes, B cells, other nucleated blood leukocytes, red blood cells, and/or platelets, and, in some aspects, cells different from red blood cells and platelets.

In some embodiments, the blood cells collected from the subject are washed, for example, to remove the plasma fraction, and the cells are placed in a suitable buffer or medium for subsequent processing steps. In some embodiments, the cells are washed with phosphate buffered saline (PBS). In some embodiments, the cleaning solution lacks calcium and/or magnesium and/or many or all divalent cations. In some aspects, the washing step is performed by a semi-automated "flow-through" centrifugation method (eg, COBE 2991 cell processor, BaXter) according to the manufacturer's instructions. In some aspects, the cleaning step is accomplished by intangential flow filtration (TFF) according to the manufacturer's instructions. In some embodiments, after washing, the cells are resuspended in a variety of biocompatible buffers, for example, Ca++/Mg++-free PBS. In some embodiments, blood cell sample components are removed and the cells are directly resuspended in the culture medium.

In some embodiments, the method includes a density-based cell separation method, for example, by lysing red blood cells or not lysing red blood cells and centrifuging the peripheral blood by Percoll or Ficoll gradient or single sampling or leukocyte ablation sample preparation to obtain a single peripheral blood Nuclear cells (PBMC).

In some embodiments, the separation method includes separating different cell types based on the expression or presence of one or more specific molecules in the cell, such as surface markers, for example, surface proteins, intracellular markers or nucleic acids. In some embodiments, any known method of separation based on such markers can be used. In some embodiments, the separation is based on affinity or based on immunoaffinity. For example, in some aspects, the separation includes separating cells and cell populations based on the expression or expression levels of one or more markers (usually cell surface markers) of the cells, for example, by incubating with an antibody or binding partner specifically binding to such markers, usually followed by a washing step, and separating cells binding to the antibody or binding partner from those cells not binding to the antibody or binding partner.

Such separation steps may be based on positive selection, where cells binding to the agent are retained for further use, and/or, negative selection, where cells not binding to the antibody or binding partner are retained. In some instances, both parts are reserved for further applications. In some aspects, negative selection may be particularly useful when there are no antibodies that can be used to specifically identify cell types in a heterogeneous population, so that separation is performed based on markers expressed by cells different from the desired population.

It is not necessary for the separation to result in 100% enrichment or removal of specific cell populations or cells expressing specific markers. For example, the positive selection or enrichment of specific types of cells, such as those expressing markers, refers to increasing the number or percentage of said cells, but does not need to result in the complete absence of cells that do not express the marker. Likewise, the negative selection, removal or consumption of specific types of cells, such as those expressing markers, refers to reducing the number or percentage of said cells, but need not result in the complete removal of all such cells.

In some instances, multiple rounds of separation steps are performed, where the positive or negative selection from one step is subjected to another separation step, such as subsequent positive or negative selection. In some examples, a single isolation step simultaneously consumes cells expressing multiple markers, such as by incubating the cells with multiple antibodies or binding partners that are specific for the marker targeted by negative selection respectively. Likewise, multiple cell types can be positively selected simultaneously by incubating the cells with multiple antibodies or binding partners to antigens expressed on various cell types.

For example, in some aspects, a specific subset of T cells, such as one or more surface marker positive cells or cells expressing high levels of one or more surface markers, for example, CD3+, CD28+, CD62L+, CCR7+, CD27+, CD127+, CD4+, CD8+, CD45RA+ and/or CD45RO+ T cells, is separated by positive or negative selection techniques.

For example, CD3+ and CD28+ T cells can be positively selected using CD3/CD28-connected magnetic beads (for example, DYNA bead M-450 CD3/CD28 T cell expander).

In some embodiments, separation is performed by enriching specific cell populations by positive selection or depleting specific cell populations by negative selection. In some embodiments, the positive or negative selection is accomplished by incubating the cells with one or more antibodies or other binding reagents that specifically bind to one or more surface markers, which are expressed on positively or negatively selected cells (marker+) or at relatively high levels (marker high).

In some embodiments, T cells are isolated from PBMC samples by negative selection of markers (e.g., CD14) expressed on non-T cells (eg, B cells, monocytes, or other blood leukocytes). In some aspects, a CD4+ or CD8+ selection step is used to isolate helper CD4+ and CD8+ cytotoxic T cells. By positively or negatively selecting markers expressed on one or more primary, memory and/or effector T cell subpopulations or at a relatively high degree, such CD4+ and CD8+ populations can be further sorted into subpopulations.

In some embodiments, CD8+ cells are further enriched or depleted against naive, central memory, effector memory, and/or central memory stem cells, for example, by positive or negative selection based on surface antigens associated with the corresponding subpopulation. In some embodiments, enrichment for central memory T (TCM) cells is performed to increase efficacy, for example, to improve long-term survival, expansion, and/or implantation after administration. In some aspects, it is particularly strong in such subpopulations. See Terakura et al. (2012) Blood. 1:72-82; Wang et al. (2012) J Immunother. 35 (9): 689-701. In some embodiments, TCM-enriched CD8+ T cells are combined with CD4+ T cells to further enhance efficacy.

In an embodiment, memory T cells are present in the CD62L+ and CD62L− subgroups of CD8+ peripheral blood lymphocytes. PBMC can be enriched or consumed against the CD62L−CD8+ and/or CD62L+CD8+ part, for example, using anti-CD8 and anti-CD62L antibodies.

In some embodiments, the enrichment for central memory T (TCM) cells is based on CD45RO, CD62L, CCR7, CD28, CD3, and/or CD127 positive or high surface expression; in some aspects, it is based on negative selection for cells expressing or highly expressing CD45RA and/or granzyme B. In some aspects, the isolation of the CD8+ population enriched for TCM cells is performed by consuming cells expressing CD4, CD14, CD45RA, and positive selecting or enriching cells expressing CD62L. On the one hand, the enrichment for central memory T (TCM) cells is performed by starting from the negative part of cells selected based on CD4 expression, negative selection based on the expression of CD14 and CD45RA, and positive selection based on CD62L. In some aspects, such selections are performed simultaneously, and in other aspects, such selections are performed sequentially in a certain order. In some aspects, the same CD4 expression-based selection step is used to prepare CD8+ cell populations or subpopulations, and is also used to generate CD4+ cell populations or subpopulations, thereby retaining the positive and negative portions from the CD4-based separation, and optionally used in the subsequent steps of the method, after one or more further positive or negative selection steps.

In a specific example, CD4+ cell selection is performed on PBMC samples or other blood leukocyte samples, wherein negative and positive parts are retained. Then, negative selection is performed on the negative part based on the expression of CD14 and CD45RA or CD19, and positive selection is performed based on central memory T cell characteristic markers, such as CD62L or CCR7, wherein the positive and negative selections are performed in a certain order.

By identifying cell populations with cell surface antigens, helper CD4+ T cells are sorted into primary, central memory and effector cells. CD4+ lymphocytes can be obtained by standard methods. In some embodiments, the naive CD4+ T lymphocytes are CD45RO−, CD45RA+, CD62L+, CD4+ T cells. In some embodiments, the central memory CD4+ cells are CD62L+ and CD45RO+. In some embodiments, the effector CD4+ cells are CD62L− and CD45RO−.

In one example, in order to enrich CD4+ cells by negative selection, the monoclonal antibody mixture usually includes antibodies against CD14, CD20, CD11b, CD16, HLA-DR, and CD8. In some embodiments, the antibody or binding partner is bound to a solid support or matrix, such as magnetic beads or paramagnetic beads, to allow separation of cells for positive and/or negative selection.

In some embodiments, the preparation method includes a freezing step, for example, freezing the cells before or after isolation, incubation, and/or engineering. In some embodiments, granulocytes are removed by the freezing and subsequent thawing steps, and, to some extent, monocytes are removed in the cell population. In some embodiments, for example, after a washing step to remove plasma and platelets, the cells are suspended in a freezing solution. In some aspects, any of a variety of known freezing solutions and parameters can be used. One example involves the use of PBS containing 20% DMSO and 8% human serum albumin (HAS) or other suitable cell freezing medium. Then, it is diluted at 1:1 with medium so that the final concentrations of DMSO and HSA are 10% and 4%, respectively. Then, the cells are generally frozen to −80° C. or −90° C. according to a predetermined procedure or principle, such as a rate of 1°/min, with a programmable cooling device, and stored in the vapor phase of a liquid nitrogen storage tank.

In some embodiments, the provided methods include cultivation, incubation, cultivation, and/or genetic engineering steps. For example, in some embodiments, methods are provided for incubating and/or engineering the depleted cell population and the culture starting composition.

In some embodiments, the cell population is incubated in the culture starting composition. Incubation and/or engineering can be performed in culture vessels, such as cells, chambers, wells, columns, tubes, tube sets, valves, vials, petri dishes, bags, or other containers used to culture or grow cells.

In some embodiments, the cells are incubated and/or cultured before or with genetic engineering. The incubation step may include culture, incubation, stimulation, activation, and/or propagation. In some embodiments, the cells or compositions are incubated in the presence of stimulating conditions or stimulating agents. Such conditions include those designed to induce cell proliferation, reproduction, activation, and/or survival in a population to mimic antigen contact, and/or trigger cells for genetic engineering, such as those used to introduce recombinant antigen receptors.

The conditions may include one or more of the following: specific medium, temperature, oxygen content, carbon dioxide content, time, reagents, such as nutrients, amino acids, antibiotics, ions, and/or stimulating factors, such as cytokines, chemokines, antigens, binding partners, fusion proteins, recombinant soluble receptors, and any other substances designed to maintain an activated cell state.

In some embodiments, the stimulating condition or agent includes one or more substances, for example, a ligand, which can activate the intracellular signal transduction domain of the TCR complex. In some aspects, the substance turns on or initiates the TCR/CD3 intracellular signal transduction cascade in T cells. Such substances may include antibodies, such as those specific for TCR components and/or costimulatory receptors, for example, anti-CD3, anti-CD28, for example, which are bound to a solid support, such as beads, and/or one or multiple cytokines. Optionally, the amplification method may further include the step of adding anti-CD3 and/or anti-CD28 antibodies to the culture medium (for example, at a concentration of at least about 0.5 ng/ml). In some embodiments, the stimulant includes 1L-2 and/or IL-15 and/or IL-7 and/or IL-21, for example, IL-2 at a concentration of at least about 10 units/mL.

In some aspects, the incubation is performed in accordance with some techniques, such as those described in U.S. Pat. No. 6,040,177 to Riddell et al., Klebanoff et al. (2012) J Immunother. 35 (9): 651-660, Terakura et al., (2012) Blood. 1:72-82 and/or Wang et al. (2012) J Immunother. 35 (9): 689-701.

In some embodiments, the T cell population is expanded by adding to the culture starting composition feeder cells, such as non-dividing peripheral blood mononuclear cells (PBMC), (for example, for each T lymphocyte in the initial population to be expanded, the resulting cell population contains at least about 5, 10, 20, or 40 or more PBMC feeder cells); and incubating the culture (e.g., for a time sufficient to expand the number of T cells). In some aspects, the non-dividing feeder cells may include γ-ray irradiated PBMC feeder cells. In some embodiments, the PBMC is irradiated with γ ray in the range of about 3000-3600 rads to prevent cell division. In some aspects, the feeder cells are added to the culture medium before the population of T cells is added.

In some embodiments, the stimulation conditions include a temperature suitable for the growth of human T lymphocytes, for example, at least about 25 degrees Celsius, generally at least about 30 degrees Celsius, and generally at or about 37 degrees Celsius. Optionally, the incubation may also include the addition of non-dividing EBV-transformed lymphoblastoid cells (LCL) as feeder cells. LCL can be irradiated with γ ray in the range of about 6000-10000 rads.

In some aspects, the LCL feeder cells are provided in any suitable amount, for example, the ratio of LCL feeder cells to naive T lymphocytes is at least about 10:1.

In a certain embodiment, antigen-specific T cells, such as antigen-specific CD4+ and/or CD8+ T cells, are obtained by stimulating natural or antigen-specific T lymphocytes with an antigen. For example, antigen-specific T cell lines or clones can be generated against cytomegalovirus antigens by isolating T cells from an infected subject and stimulating the cells in vitro with the same antigen.

Composition and Formulation

The invention also provides pharmaceutical compositions and formulations used in the methods of the invention. In some embodiments, the pharmaceutical compositions and formulations of the present invention include compositions of cells for administration, including pharmaceutical compositions and preparations, such as unit dosage form composition comprising the number of cells used for administration in a given dose or part thereof. The pharmaceutical compositions and formulations generally include one or more optional pharmaceutically acceptable carriers or excipients. In some embodiments, the composition includes at least one other therapeutic agent.

The term "pharmaceutical formulation" refers to a formulation in a form that allows the biological activity of the active ingredient contained therein to be effective, and does not contain additional ingredients with unacceptable toxicity to the subject to which the formulation is to be administered.

"Pharmaceutically acceptable carrier" refers to an ingredient in a pharmaceutical formulation that is not an active ingredient and is not toxic to a subject. Pharmaceutically acceptable carriers include, but are not limited to, buffers, excipients, stabilizers or preservatives.

In some aspects, the selection of carrier is determined in part by the particular cell and/or method of administration. Therefore, there are many suitable formulations. For example, the pharmaceutical composition may include a preservative. Suitable preservatives may include, for example, methyl paraben, propyl paraben, sodium benzoate, and benzalkonium chloride. In some aspects, a mixture of two or more preservatives is used. The preservative or mixture thereof is usually present in an amount of from about 0.0001% to about 2% (based on the total weight of the composition). The carrier is described in, for example, "Remington's Pharmaceutical Sciences" (Remington's Pharmaceutical Sciences), 16th edition, Osol, A. Ed. (1980). At the used dosage and concentration, pharmaceutically acceptable carriers are usually non-toxic to the recipient, including but not limited to: buffers such as phosphate, citrate and other organic acid buffers; antioxidants, including ascorbic acid and Methionine; preservatives (such as octadecyl dimethyl benzyl ammonium chloride; hexaalkyl quaternary ammonium chloride; benzalkonium chloride, benzethonium chloride; phenol, butyl or benzyl alcohol; p-hydroxy Alkyl benzoate, such as methyl or propyl p-hydroxybenzoate; catechol; resorcinol; cyclohexanol; 3-pentanol; and m-cresol); polypeptides of low molecular weight (less than about 10 residues); protein, such as serum albumin, gelatin or immunoglobulin; hydrophilic polymer, such as polyvinylpyrrolidone; amino acid, such as glycine, glutamine, asparagine, histidine, arginine or lysine; monosaccharides, disaccharides, and other sugars, including glucose, mannose, or dextrin; chelating agents, such as EDTA; sugars, such as sucrose, mannitol, trehalose, or sorbitol; salt-forming counterions, such as sodium; metal complexes (such as Zn-protein complexes); and/or non-ionic surfactants, such as polyethylene glycol (PEG).

In some aspects, the composition includes a buffer. Suitable buffers include, for example, citric acid, sodium citrate, phosphoric acid, potassium phosphate, and various other acids and salts. In some aspects, a mixture of two or more buffers is used. The buffering agent or mixture thereof is usually present in an amount of about 0.001% to about 4% (based on the total weight of the composition). Methods for preparing administrable pharmaceutical compositions are known. Exemplary methods are described in detail in, for example, "Remington: The Science and Practice of Pharmacy" (Lippincott Williams & Wilkins); 21st edition (May 1, 2005).

The formulation may comprise an aqueous solution. The formulation or composition may also contain more than one active ingredients, which can be used for the specific indication, disease or condition to be treated with the cell, preferably those with complementary activity to the cell, wherein the corresponding activity agents do not negatively affect each other. Such active ingredients are suitably present in combination in an amount effective for the desired purpose. Therefore, in some embodiments, the pharmaceutical composition further comprises other pharmaceutically active substances or drugs, such as chemotherapeutics, for example, asparaginase, busulfan, carboplatin, cisplatin, daunorubicin, doxorubicin, fluorouracil, hydroxyurea, methotrexate, paclitaxel, rituximab, vinblastine, and/or vincristine.

In some embodiments, the pharmaceutical composition includes an amount effective to treat or prevent a disease or condition, such as a therapeutically effective or preventive effective amount of cells. In some embodiments, the efficacy of treatment or prophylaxis is monitored by regularly evaluating the treated subjects. The required dose can be delivered by administering the cells by a single bolus, by administering the cells by multiple boluses, or by administering the cells by continuous infusion.

In some embodiments, the composition comprises an amount of cells effective to reduce the burden of a disease or condition, and/or an amount that does not cause CRS or severe CRS in a subject and/or an amount that achieves any other results of the methods described herein.

The cells and compositions can be administered using standard administration techniques, formulations and/or devices. The administration of the cells can be autologous or heterologous. For example, immunosuppressive cells or progenitor cells can be obtained from one subject and administered to the same subject or different compatible subjects. Peripheral blood-derived immunosuppressive cells or progenies thereof (e.g., in vivo, ex vivo, or in vitro derived) can be administered by local injection, including catheter administration, systemic injection, local injection, intravenous injection, or parenteral administration. When a therapeutic composition (for example, a pharmaceutical composition containing genetically modified immunosuppressive cells) is administered, it is usually formulated in a unit-dose injectable form (solution, suspension, emulsion).

Formulations include those for oral, intravenous, intraperitoneal, subcutaneous, pulmonary, transdermal, intramuscular, intranasal, mucosal, sublingual or suppository administration. In some embodiments, the cell population is administered parenterally. The term "parenteral" as used herein includes intravenous, intramuscular, subcutaneous, rectal, vaginal and intraperitoneal administration. In some embodiments, the cells are administered to a subject by intravenous, intraperitoneal or subcutaneous injection using peripheral systemic delivery.

In some embodiments, the composition is provided in the form of a sterile liquid formulation, for example, an isotonic aqueous solution, suspension, emulsion, dispersion, or viscous composition, which in some aspects can be buffered to a selected pH. Liquid formulations are generally easily prepared, compared with gels, other viscous compositions, and solid compositions. In addition, liquid compositions are somewhat easier to be administered, especially by injection. In another aspect, the viscous composition can be formulated in a suitable viscosity range to provide a longer contact time with a specific tissue. The liquid or viscous composition may include a carrier, which may be a solvent or dispersion medium, which contains, for example, water, saline, phosphate buffered saline, polyhydroxy compounds (for example, glycerol, propylene glycol, liquid polyethylene glycol) and a suitable mixture thereof. Sterile injectable solutions can be prepared by incorporating the cells into a solvent, such as a suitable carrier, diluent, or excipient such as sterile water, physiological saline, glucose, dextrose, and the like. The composition may contain auxiliary substances such as wetting, dispersing, or emulsifying agents (for example, methyl cellulose), pH buffering agents, gelling or viscosity enhancing additives, preservatives, flavoring agents, and/or pigments, depending on the desired route of administration and preparation. In some aspects, textbooks can be consulted to prepare suitable preparations.

Various additives can be added to enhance the stability and sterility of the composition, including antimicrobial preservatives, antioxidants, chelating agents, and buffers. Various antibacterial and antifungal agents, such as parabens, chlorobutanol, phenol, and sorbic acid, can also be used to prevent microorganisms. The absorption of the injectable drug form can be delayed by using substances that delay absorption, such as aluminum monostearate and gelatin.

The formulations for in vivo administration are generally sterile. Sterility can be easily achieved, for example, by filtration through a sterile filter membrane.

Article

The present invention also provides articles, such as kits and devices, for administering cells to a subjects according to the provided methods for adoptive cell therapy or immune effector cell therapy, and for storing and administering the cells and compositions.

The article includes one or more containers, generally multiple containers, packaging materials, and a label or package insert combined with or on one or more containers and/or packaging, and generally includes instructions for administering cells to a subject.

The container generally contains the cells to be administered, for example, one or more unit doses thereof. The article generally includes multiple containers, each containing a single unit dose of cells. The unit dose may be the amount or number of cells to be administered to the subject in the first dose or twice (or more) the number of cells to be administered in the first or subsequent doses. It may be the lowest dose or lowest possible dose of cells administered to a subject in relation to the method of administration. In some embodiments, the unit dose is the number of cells or the minimum number of cells that will be administered to any subject with a specific disease or condition in a unit dose according to the method of the present invention. For example, in some aspects, a unit dose may include the minimum amount of cells to be administered to a subject with a lower body weight and/or a lower disease burden, for example administering one or in some cases more unit doses to a given subject in the first dose, and administering one or more unit doses to a given subject in one or more subsequent doses, for example, according to the methods provided. In some embodiments, the number of cells in a unit dose is the number of cells expressing a chimeric antigen receptor or CAR to be administered to a specific subject, from whom the cells are derived, in the first dose. In some embodiments, the cells are derived from a subject to be treated by the methods provided herein or in need thereof.

In some embodiments, each container individually contains a unit dose of cells, for example, including the same or substantially the same number of cells. Therefore, in some embodiments, each container contains the same or approximately or substantially the same number of cells or chimeric antigen receptor-expressing cells. In some embodiments, the unit dose includes less than about $1\times10^{10}$, less than about $1\times10^9$, less than about $1\times10^8$, or less than about $1\times10^7$ engineered cells, total cells, T cells or PBMC per kilogram of the subject to be treated and/or from whom the cells are derived.

Suitable containers include, for example, bottles, vials, syringes, and flexible bags such as freezer bags. In certain embodiments, the container is a bag, for example, a flexible bag, such as those suitable for infusion of cells into a subject, for example, a flexible plastic or PVC bag or EVA or ULPDE, and/or an IV solution bag. In some embodiments, the bag is sealable and/or sterilizable to provide delivery of sterile solutions and cells and compositions. In some embodiments, the volume of the container, for example, the bag is equal to or about or at least or about 10, 20, 30, 40, 50, 60, 70, 80, 90, 100, 200, 300, 400, 500, or 1000 ml, such as a volume of equal to or about 10 to equal to or about 100 mL or equal to or about 10 to equal to or about 500 mL. In some embodiments, the container, for example, the bag is of and/or is made of a material that is stable and/or provides stable storage and/or maintenance of cells at one or more different temperatures, such as at low temperatures, for example, lower than or about or equal to or about −20° C., −80° C., −120° C., 135° C., −196° C. and/or a temperature suitable for cryopreservation, and/or other temperatures, such as a temperature suitable for freezing and thawing cells and body temperature, such as at or about 37° C. or −38° C., or −39° C., or −40° C., to allow immediate freezing and thawing prior to treatment, for example, at the site of a subject or treatment site, for example, at the bedside.

The container can be made of various materials such as glass or plastic. In some embodiments, the container has one or more ports, for example, a sterile immersion port, for example, for connecting to one or more tubes through a tube or catheter, for example, for intravenous or other infusion and/or used for connection for the purpose of transferring from and to other containers, such as cell culture and/or storage bags or other containers. Exemplary containers include freezer bags, intravenous solution bags, vials, including those with stoppers that can be pierced by an injection needle.

The article may also include a package insert or label, one or more pieces of which display usage information and/or instructions. In some embodiments, the information or instructions show contents regarding what can or should be used to treat a particular disease or condition, and/or provide instructions for it. The label or package insert may show the contents of the article to be used to treat the disease or condition. In some embodiments, the label or package insert provides instructions for treating a subject, for example, a subject whose cells have been derived, by including the first and one or more subsequent doses of cells, for example, according to the provided method of any one of the embodiments. In some embodiments, the instructions specify that in the first dose, a unit dose, for example, the contents of a single container of an article, is administered, and then, at a specified time point or within a specified time window and/or after the presence or absence or amount or extent of one or more factors or results are detected in a subject, one or more subsequent doses are administered.

In some embodiments, the instructions specify that multiple unit doses are administered to a subject by performing the first administration and continuous administration. In some embodiments, the first administration includes delivering one of the unit doses to a subject and subsequent administration includes administering one or more of the unit doses to the subject.

In some embodiments, the instructions specify that the subsequent dose(s) is administered after the first administration, for example, about 21 days to about 80 days or about 25 days to about 60 days after the first administration or the start of the preceeding administration, for example, equal to or about 50 days. In some embodiments, it is stated that specifying the subsequent dose will be administered after the serum level of a factor indicative of cytokine release syndrome (CRS) in a subject is determined about 10 times lower, about 25 times, and/or about 50 times lower than the serum level of the indicator in the subject before the first administration, and/or the index of CRS has reached a peak and is declining, and/or the subject does not show a detectable adaptable host immune response specific to the receptor (e.g., CAR) expressed by the cells.

In some embodiments, the label or package insert or package contains an identifier to indicate the identity of a subject from which the cells are derived and/or the subject to be administered. In the case of autologous transplantation, the identity of the subject from which the cells are derived is the same as the identity of the subject to whom the cells are to be administered. Therefore, the identification information can specify that the cells are administered to a specific patient, such as the cells from which the cells are originally derived. Such information may be present in the packaging material and/or label in the form of a barcode or other coded identifier, or may indicate the subject's name and/or other identifying characteristics.

In some embodiments, the article includes one or more, usually multiple containers containing a cell-containing composition, such as a separate unit dosage form thereof, and also includes one or more other containers containing the composition therein, wherein the composition includes other agents, such as cytotoxic or other therapeutic agents, which, for example, will be combined with the cells, and for example, administered simultaneously or at once in any order. Alternatively or in addition, the article may also include another or the same container containing a pharmaceutically acceptable buffer. It may also include other materials, such as other buffers, diluents, filters, tubes, needles, and/or syringes.

The term "package insert" refers to the instructions often included in the commercial packaging of therapeutic products, and the instructions contain information about the instructions, usage, dosage, administration, combination therapy, contraindications and/or warnings of such therapeutic products.

Treatment of Cancer Patients with the First and Subsequent Dose(s) of Autologous CAR-Expressing T Cells The method of the present invention can be summarized as:

Peripheral blood mononuclear cells (PBMC) or T cells are isolated from human subjects with cancer based on "Demononuclear Cell Separation", cultured and transduced with viral vectors encoding chimeric antigen receptors (CAR). The chimeric antigen receptor (CAR) specifically binds to an antigen expressed by cancer in the subject, which is a tumor-related or tumor-specific antigen. The cells are cryopreserved in an infusion medium in a separate flexible freezing bag, each containing a single unit dose of cells, which is about $1\times10^6$ cells to $5\times10^7$ cells. The first dose per subject to be infused is not higher than about $1\times10^{12}$ cells, preferably, not higher than about $1\times10^{11}$ cells, more preferably, not higher than about $1\times10^{10}$ cells or about $5\times10^9$ or approximately $2\times10^9$ cells. Prior to infusion, the cells are maintained at a temperature of about below $-130°$ C. or about below $-175°$ C.

Before the cell therapy, blood is obtained from the subject, and the serum levels of one or more serum factors indicative of cytokine release syndrome (CRS) are optionally evaluated by ELISA and/or MSD and/or CBA, such as tumor necrosis factor alpha (TNFα), interferon γ (IFNγ), IL-10 and IL-6. Before the treatment, tumor burden can optionally be assessed by measuring the size or quality of the solid tumor, for example by PET or CT scan.

The resuscitation was performed by warming to about 38° C., and the subject was administered the first dose of cells by multiple infusions. Each infusion is a continuous intravenous (IV) infusion over a period of about 3-30 minutes.

After the first dose is administered, the subject is subjected to a physical examination and monitored for any symptoms of toxicity or toxicity results, such as fever, hypotension, hypoxia, neurological disorders, or increased serum levels of inflammatory cytokines or C-reactive protein (CRP). Optionally, after the first dose is administered, in one or more cases, blood is obtained from the patient, and the level of serum factors indicative of CRS is evaluated by ELISA and/or MSD and/or CBA methods. The serum factor level is compared with the serum factor level obtained just before the first dose. If necessary, anti-IL6 or other CRS treatments are administered to reduce the symptoms of CRS.

After the first dose is administered, for example, 1, 2, 3, and/or 4 weeks after the administration, the subject is optionally tested for the presence of an anti-CAR immune response, for example, by qPCR, ELISA, ELISPOT, cell-based antibody assay and/or mixed lymphocyte reaction.

The percentage reduction in tumor burden achieved by the first dose can optionally be measured by scanning one or more times after the first dose is administered in the patient with solid tumors (e.g., PET and CT scans), and/or by quantifying the disease-positive cells in the blood or at the tumor site.

The subsequent dose(s) is administered. In some subjects, the subsequent dose(s) is administered within about 80 days, preferably about 60 days, and more preferably about 50 days after the first dose. In some cases, the subsequent dose(s) is administered only when the tested CRS-related results or serum factor levels are lower than the acceptable level and no anti-CAR immune response is detected in the subject about 60 days after the first dose. In other subjects, the subsequent dose(s) is administered more than 30 days after the first dose is administered, and the subject is deemed as having no CRS or severe CRS, or levels of all tested serum factors indicative of CRS are lower than 20% of the CRS observed at the peak after the first dose and the subject is deemed as having no detectable anti-CAR immune response. In some embodiments, one or more subsequent doses of cells are administered. The time interval between each dose is 21-80 days, preferably 25-60 days, more preferably 25-55 days.

The size of subsequent dose is patient-specific and is based on tumor burden, the presence of an anti-CAR immune response, and the level of CRS-related results. Some subjects are administered with subsequent doses containing 1, 2, 3 or even more unit doses of cells. The infused subsequent dose per subject is not higher than about $1\times10^{12}$ cells, or not higher than about $1\times10^{11}$ cells, or not higher than about $1\times10^{10}$ cells, or not higher than about $5\times10^{9}$, or not higher than about $2\times10^{9}$. The subsequent dose(s) is administered in about 3 to 30 minutes by continuous intravenous infusion.

The subjects are regularly monitored from the first dose and continued for several years. During the follow-up period, the tumor burden is measured, and/or CAR-expressing cells are detected by flow cytometry and quantitative polymerase chain reaction (qPCR) to measure the in vivo proliferation and persistence of the administered cells, and/or evaluate the development of the anti-CAR immune response.

Advantages of the Invention

1. The present invention significantly improves the efficacy of using immune effector cells expressing chimeric antigen receptors for tumor treatment: the number or size of tumors is reduced, and/or the number and/or degree of metastasis is reduced, and/or tumor markers are reduced, and/or the common complications of advanced cancer disappear or weaken.
2. It exhibits significant anti-tumor effects on solid tumors, and provides a safe and effective treatment method that can stabilize or even cure CLA18A2 positive adenocarcinoma of the digestive tract.
3. A pretreatment composition for improving anti-tumor therapy of immune effector cells is provided. Before the immune effector cell is administered, a composition of fludarabine, cyclophosphamide and albumin-bound paclitaxel can be administered, which can significantly promote the anti-tumor efficacy of immune effector cells, greatly reduce the tumor burden of patient, and improve the quality of life, and prolong survival of patients.

The present invention will be further described below in conjunction with specific embodiments. It should be understood that these examples are only used to illustrate the present invention and not to limit the scope of the present invention. The experimental methods without specific conditions in the following examples usually follow the conventional conditions such as those described in J. Sambrook et al., Molecular Cloning Experiment Guide, Third Edition, Science Press, 2002, or according to the conditions suggested by the manufacturer.

Materials and Methods

Material

Various materials used in the present invention, including reagents, can be purchased from commercial channels.

Exemplary antigen receptors of the present invention, including CAR, and methods for engineering and introducing receptors into cells, can be found in, for example, full contents disclosed in Chinese Patent Application Publication Nos. CN107058354A, CN107460201A, CN105194661A, CN105315375A, CN105713881A, CN106146666A, CN106519037A, CN106554414A, CN105331585A, CN106397593A, CN106467573A, International Patent Application Publication Nos. WO2018006882A1, and WO2015172339A8.

In the following examples of the present invention, the scFv portion of the chimeric antigen receptor has the heavy chain variable region as shown in SEQ ID NO: 14 and the light chain variable region as shown in SEQ ID NO: 16, the chimeric antigen receptor has the sequence as shown in SEQ ID NO: 24, the amino acid sequence of scFv is shown in SEQ ID NO: 54, the nucleic acid sequence thereof is shown in SEQ ID NO: 55, and the CDR region is HCDR1 as shown in SEQ ID NO: 1, HCDR2 as shown in SEQ ID NO: 7, HCDR3 as shown in SEQ ID NO: 3, LCDR1 as shown in SEQ ID NO: 4, LCDR2 as shown in SEQ ID NO: 5, and LCDR3 as shown in SEQ ID NO: 6.

The method for constructing CAR-T cells: firstly, the CAR gene is constructed, such as the construction of hu8E5-2I-BBZ, from the 5'end to 3'end including: CD8a signal peptide (nucleotide sequence is shown in SEQ ID NO: 36), hu8E5-21 scFV (nucleotide sequence is shown in SEQ ID NO: 55), CD8 hinge (nucleotide sequence is shown in SEQ ID NO: 38), CD8 transmembrane region (nucleotide sequence is shown in SEQ ID NO: 46) and the intracellular signaling domain of CD137 (nucleotide sequence is shown in SEQ ID NO: 48) and the intracellular signaling domain of CD3ζ (nucleotide sequence is shown in SEQ ID NO: 44). Then the CAR gene is cloned into a shuttle plasmid to obtain the target plasmid containing the CAR gene. The constructed target plasmid and packaging plasmid are co-transfected into 293T cells to prepare a lentiviral vector, and the lentiviral vector is transduced into T cells obtained from the patient's peripheral blood to obtain CAR-T cells. As an example, hu8E5-2I-BBZ is used in the following embodiments.

Example 1: Treatment of Cancer Patients with the First and Subsequent Dose(s) of CAR-Expressing Autologous T Cells Patients with CLD18A2 positive gastrointestinal tumors (such as gastric adenocarcinoma, pancreatic cancer) were administered with autologous T cells expressing anti-CLD18A2 chimeric antigen receptor (CAR). Before administering the cells, the patients were subjected to apheresis separation technique of "mononuclear cell separation" and the pretreatment. For obtaining autologous T cells expressing CAR, PBMCs were obtained by isolation based on a single sample from individual subjects, transduced with a viral vector encoding anti-CLD18A2CAR, then subjected to a large number of amplifications, and the prepared autologous T cells expressing CAR were cryopreserved in the infusion medium in a separate flexible freezer bag. The infused first dose per subject was not higher than about $1\times10^{12}$ cells, preferably, not higher than about $1\times10^{11}$ cells, preferably, not higher than about $1\times10^{10}$ cells, or not higher than about $5\times10^{9}$ cells, or not higher than about $2\times10^{9}$ cells. Before the infusion, the cells were kept at a temperature below $-175°$ C.

Before the cell therapy, blood was obtained from the subject, and optionally evaluated for the level of one or more factors indicative of cytokine release syndrome (CRS) in the serum by ELISA and/or MSD and/or CBA methods, such as tumor necrosis factor α (TNFα), interferon γ (IFNγ), IL-10 and IL-6. Before treatment, the tumor burden can be optionally assessed by measuring the size or characteristics of solid tumors, for example, by PET or CT scanning, and the tumor burden can also be assessed by detecting tumor markers and/or observing the occurrence and severity of tumor complications.

Resuscitation was performed by warming to around 38° C., and the subject was administered with the first dose of cells by multiple infusions. The first dose was divided into multiple times within a period of not more than 20 days, for example 1-6 times, preferably 1-5 times, preferably 1-4 times, preferably 1-3 times, more preferably 2-3 times. Each infusion was about 3-30 minutes, preferably intravenous (IV) infusion within 5-25 minutes.

After the first dose is administered, the subject was subjected to a physical examination and monitored for any symptoms of toxicity or toxicity results, such as fever, hypotension, hypoxia, neurological disorders, or increased serum levels of inflammatory cytokines or C-reactive protein (CRP). Optionally, after the first dose is administered, blood was obtained from the patient, and the level of serum factors indicative of CRS was evaluated by ELISA and/or MSD and/or CBA methods for one or more times. The serum factor level was compared with the serum factor level obtained just before the first dose. If necessary, anti-IL6 or other CRS treatments were administered to reduce the symptoms of CRS.

After the first dose was administered, for example, 1, 2, 3, and/or 4 weeks after the administration, the subject was optionally tested for the presence of an anti-CAR immune response, for example, by qPCR, ELISA, ELISPOT, Cell-based antibody assay and/or mixed lymphocyte reaction.

The reduction percentage in tumor burden achieved by the first dose can optionally be measured one or more times after the first dose was administered to the patient with a solid tumor by scanning (e.g., PET and CT scans), and/or by quantifying the disease-positive cells in the blood or at the tumor site.

The subsequent dose(s) was administered. In some subjects, the subsequent dose(s) was administered within about 80 days, preferably about 60 days, and more preferably about 50 days after the first dose was administered. In some cases, the subsequent dose(s) was administered only when the tested CRS-related results or serum factor levels were lower than the acceptable level and no anti-CAR immune response was detected in the subject about 60 days after the first dose. In other subjects, the subsequent dose(s) was administered more than 30 days after the first dose was administered, and the subject is deemed as having no CRS or severe CRS, or the levels of all tested serum factors indicative of CRS were lower than 20% of the CRS observed at the peak after the first dose and the subject was deemed as having no detectable anti-CAR immune response. In some embodiments, one or more subsequent doses of cells were administered. The time interval between each dose is 21-80 days, preferably 25-60 days, more preferably 25-55 days.

The size of subsequent dose was patient-specific and based on tumor burden, the presence of an anti-CAR immune response, and the level of CRS-related results. Some subjects were administered with subsequent doses containing 1, 2, 3 or even more unit doses of cells. The infused subsequent dose per subject was not higher than about $1 \times 10^{12}$ cells, or not higher than about $1 \times 10^{11}$ cells, or not higher than about $1 \times 10^{10}$ cells, or not higher than about $5 \times 10^9$, or not higher than about $2 \times 10^9$. The subsequent dose(s) was administered in about 3 to 30 minutes, preferably 5-25 minutes by continuous intravenous infusion (IV).

The subjects were regularly monitored from the first dose and continued for several years. During the follow-up period, the tumor burden is measured, and/or CAR-expressing cells were detected by flow cytometry and quantitative polymerase chain reaction (qPCR) to measure the in vivo proliferation and persistence of the administered cells, and/or evaluate the development of the anti-CAR immune response.

Example 2: Evaluation of the Neurotoxicity of CAR-T Cell Therapy in Subjects with Morphological Diseases Before Treatment The target lesions were detected by imaging to evaluate the tumor burden before treatment, and the number and size of the target lesions were determined. The efficacy evaluation criteria are shown in Table 1.

TABLE 1

Efficacy evaluation criteria for target lesions

| Efficac | Criteria |
|---|---|
| Complete relief (CR) | All target lesions disappear, and the short diameter value of all pathological lymph nodes (whether target disease or not) must be <10 mm |
| Partial relief (PR) | The total diameter of the target lesion is reduced by ≥30% |
| Stable disease (SD) | The reduction of the total diameter of the target lesion does not meet the PR standard or the increase of the total diameter of the target lesion does not meet the PD standard |
| Progressive disease (PD) | The total diameter of the target lesions increases by ≥20%, and the absolute value increases by ≥5 mm and/or one or more new lesions appear. |

In about 3-30 minutes, T cells expressing CAR were administered to the subject through single, two or three intravenous (IV) continuous infusions in a total amount of about $1.1 \times 10^6$ CAR-T cells/KG to about $2.8 \times 10^7$ CAR-T/KG. Fludarabine, or cyclophosphamide, or albumin-bound paclitaxel, or fludarabine in combination with albumin-bound paclitaxel, or cyclophosphamide in combination with albumin-bound paclitaxel, or fludarabine in combination with cyclophosphamide, or fludarabine in combination with cyclophosphamide and albumin-bound paclitaxel as a pre-treatment chemotherapy were administered to the subject 1-30 days, preferably 1-20 days, more preferably 4-12 days before CAR-T cell infusion.

After CAR-T cells were administered, the disease state of the subject was evaluated to evaluate the response to treatment. After treatment, the subjects were evaluated and monitored for neurotoxicity (neurological complications, including confusion symptoms, aphasia, seizures, convulsions, lethargy and/or altered mental state), and graded according to severity (1-5 scales was used, for example, Guido Cavaletti and Paola Marmiroli Nature Reviews Neurology 6, 657-666 (December 2010), where grade 3 (severe symptoms), 4 (life-threatening symptoms) or 5 (death) are considered as serious neurotoxicity.

(1) Determining and Monitoring Cytokine Release Syndrome (CRS):

Grade 1 (mild)—not life-threatening, only systemic treatments such as antipyretics and antiemetics are required (for example, fever, nausea, fatigue, headache, myalgia, malaise);

Grade 2 (Medium)—moderate intervention is needed and responds:

Oxygen demand <40%, or

Hypotension, for which corresponding body fluid or low-dose of single vasopressor drug is needed, or Grade 2 organ toxicity (passed CTCAE v4.0);
Grade 3 (serious)—active intervention is needed and responds:
  Oxygen demand ≥40%, or
  Hypotension, for which a high dose of a single vasopressor drug (for example, norepinephrine ≥20 ug/kg/min, dopamine ≥10 ug/kg/min, phenylephrine ≥200 ug/kg/min, or epinephrine ≥10 ug/kg/min) is needed, or
  Hypotension, for which multiple vasopressor drugs (for example, antidiuretic+one of the above agents, or a combination of vasopressor drugs equal to ≥20 ug/kg/min norepinephrine) are needed, or
  Grade 3 organ toxicity or Grade 4 transaminase inflammation (through CTCAE v4.0);
Grade 4 (life-threatening)—ventilator support is needed, or
  Grade 4 organ toxicity (excluding transaminase inflammation);
Grade 5 (Fatal)—death.

(2) Exemplary Classification Standards for Neurotoxicity:
  Grade 1 (no or mild clinical symptoms)—mild or no clinical symptoms;
  Grade 2 (moderate)—there are symptoms that restrict active daily activities (ADL), such as cooking, buying vegetables or clothes, using the phone, and managing money;
  Grade 3 (Severe)—There is restrictive self-management ADL, such as symptoms in bathing, dressing or undressing, eating, using the toilet, and taking medication;
  Grade 4 (life-threatening)—life-threatening symptoms, for which urgent intervention is needed;
  Grade 5 (Fatal)—death.

In a group of subjects separated based on disease burden before treatment, the response, the presence of severe CRS, and the presence of severe neurotoxicity after treatment with a single infusion of different doses of CAR-T cells compared with the dose were evaluated. The results are shown in Table 2. Table 2 lists the specific doses of the cells administered in various multiple doses, the first dose and the subsequent dose, and the interval time between the adjacent previous subsequent dose and the adjacent subsequent dose. Table 2 also lists the response after each round of CAR T cell treatment evaluated according to the criteria described in Example 2 as the baseline tumor burden before the first dose was administered. Table 2 also lists the results of the response from 6 patients to each administration (the tumor burden after administration is listed in the "response" column, which indicates the response to treatment compared with the baseline tumor burden), and the presence of (Y/N) severe CRS and severe neurotoxicity. As shown in Table 2, regardless of the disease burden before treatment, SD was observed in subjects treated with CAR-T cells at all tested doses. It was observed that none of the subjects who received CAR-T cells at various dose levels developed severe CRS or severe neurotoxicity.

These results suggest that, for minimizing toxicity and maximizing efficacy, a dosage regimen is used, which includes administering a first low-dose CAR-T cells to subjects with morphological diseases to reduce disease burden, and then after tumor burden is stable or has decreased or progressed, the subsequent dose(s) of cells can be administered, and higher subsequent dose(s) can be administered, without severe CRS or risk of severe neurotoxicity. For the first dose, a higher dose of CAR-T cells can be administered to reduce the disease burden, and the subsequent dose(s) of cells can be administered after the tumor burden is stable or reduced, and a lower subsequent dose(s) can be administered, without severe CRS or severe neurotoxicity risk.

TABLE 2

Safety and efficacy of the first dose and subsequent dose(s) of CAR-T cells

| | | | | the first dose | | | | |
|---|---|---|---|---|---|---|---|---|
| ID | disease | expression of CLDN18.2 | disease burden | dose × $10^7$/kg | severe CRS | severe neurotoxicity | response | disease burden |
| 1 | Pancreatic cancer | +++ (90%) | The longest diameter of the lesion in the left abdomen spleen area was 5.4 cm | 0.111 | N | N | SD | 6 weeks after the injection the first dose of CAR-T cell: the longest diameter of the lesion in the left abdominal spleen area increased by <20% compared with the baseline. |
| 2 | Gastric adenocarcinoma | ++ (40%) | Multiple pelvic metastases with metastatic lymph nodes | 0.288 | N | N | PD | 5 weeks after the injection of the first dose of CAR-T cells: 1) The sum of the longest diameter of the pelvic appendage target lesion and the inguinal lymph node lesion increased = 20%, and the increase was >5 mm 3) After thoracic drainage to the $6^{th}$ week (subject withdrew) |
| 3 | Pancreatic cancer | +++ (100%) | Multiple pelvic metastases with metastatic lymph nodes | 1.0 | N | N | SD | The subjects withdrew from the trial 2 weeks after the injection of the first dose of CAR-T cells: 1) The swollen lymph nodes around the superior mesenteric artery and the fusion area were significantly smaller than before; 2) More pleural fluid and ascites than before; |

TABLE 2-continued

Safety and efficacy of the first dose and subsequent dose(s) of CAR-T cells

| | | | | | | | |
|---|---|---|---|---|---|---|---|
| 4 | Gastric adenocarcinoma | ++~+++ (85%) | The longest diameter of the largest lesion in the right pelvic cavity was 6.5 cm; and the longest diameter of the largest lesion in the left pelvic cavity was 5.2 cm | 0.333 | N | N | PD | 3) CEA decreased from 28.47 U/ml (before injection) to 5.55 U/ml, CA125 decreased from 241 to 179.5 U/ml, and CYFRA21-1 decreased from 3.02 U/ml to 1.61 U/ml<br>6 weeks after the injection of the first dose of CAR-T cells:<br>1) No significant changes in the two target lesions in the pelvis;<br>2) New lesions in the pelvis, 1.9 cm;<br>3) The pleural and ascites fluid was significantly reduced and the color changed from bloody to light yellow;<br>4) CA125 decreased from 106.7 U/ml to 16.7 U/ml, CA199 decreased from 99.41 U/ml to 56.33 U/ml |
| 5 | Gastric adenocarcinoma | +++ (95%) | Multiple liver metastases with metastatic lymph nodes | 1.6 | N | N | SD | 6 weeks after the injection of the first dose of CAR-T cells:<br>1) For intrahepatic target lesions, the sum of the longest diameters did not change significantly compared with baseline;<br>2) AFP decreased from 1302 U/ml to 785 and then increased again >1500; and CA199 decreased from >1200 U/ml to 655.8 U/ml; |
| 6 | Gastric adenocarcinoma | +++ (90%) | Multiple pelvic metastases with metastatic lymph nodes | 1.25 | N | N | SD | 6 weeks after the injection the first dose of CAR-T cell:<br>1) The sum of the longest diameter of the target pelvic lesions increased by <20% from the baseline;<br>2) CA 125 increased from 76.3 U/ml to 249.8 U/ml; |

| | No of | the second dose | | | | |
|---|---|---|---|---|---|---|
| ID | days between doses | dose × $10^7$/kg | severe CRS | severe neurotoxicity | response | disease burden |
| 1 | 45 | 1.11 | N | N | PD | 5 weeks after the injection of the second dose of CAR-T cell (the subject withdrew): new lesions appeared in the liver |
| 2 | | | | | / | |
| 3 | | | | | / | |
| 4 | 46 | 2.22 | N | N | PD | 6 weeks after the injection of the second dose of CAR-T cells:<br>1) Two target lesions in the pelvis were reduced, and the sum of the longest diameters decreased by <30% compared with the baseline;<br>2) New pelvic lesions decreased to 1.6 cm;<br>3) Pleural and ascites continuously decreased and CAR copies can be detected in the ascites;<br>4) CA125 is 19.8 U/ml, CA199 decreased to 22.83 U/ml; |
| 5 | 46 | 1.6 | N | N | PD | 6 weeks after the injection of the second dose of CAR-T cells:<br>1) The sum of the longest diameters of the target liver lesions did not significantly change;<br>2) New tumor lesions appeared on the outer wall of the left orbit;<br>3) AFP was still >1500; and CA199 increased >1200 U/ml; |

TABLE 2-continued

Safety and efficacy of the first dose and subsequent dose(s) of CAR-T cells

| | | | | | | |
|---|---|---|---|---|---|---|
| 6 | 48 | 1.25 | N | N | SD | 6 weeks after the injection of the second dose of CAR-T cells: 1) The sum of the longest diameters of the target pelvic lesions did not significantly change; 2) CA 125 decreased to 181.2 U/ml |

ID: Number of the subject
SD: Stable disease
PD: Progressive disease
N/A: not available
N: None The results in Table 2 indicate that severe CRS and severe neurotoxicity did not occur during the first dose of treatment, so the first dose of cells is safe for all subjects.

It was observed that some subjects were in stable disease (SD). After the first dose or subsequent dose(s) of cells were administered, it was observed by imaging methods that the tumor was not changed or slightly reduced (see the course of treatment for the first dose of patient number: No. 1, 2, 3, 5, 6 subjects, the course of treatment for the subsequent (the second) dose of patient number: 4, 5, 6, and the course of treatment for the subsequent (the third and fourth) dose of patient number: 4. None of the subjects showed severe CRS or severe neurotoxicity at any dose.

In some cases, Table 2 shows that some subjects are non-responsive (NR) to the first dose (see the course of treatment for the first dose of patient number: 2 and 4), thus failing to achieve stable or decreased disease or tumor burden level. In addition, the results showed that when clinical remission could not be achieved and the risk or frequency of severe CRS and neurotoxicity in subjects was not increased after the first dose infusion, severe CRS or severe neurotoxicity was not detected in these subjects after receiving higher subsequent dose(s).

In some embodiments, lacking (or relatively low) degree of reactivity or toxicity in a subject indicates that the subject may not be able to respond well to CAR-T cell therapy, but also does not have the risk of some toxic adverse events in another infusion, otherwise, it may indicate that it is necessary to avoid higher doses in the subsequent administration. Therefore, compared with the first dose, these results support the dosage regimen (e.g., if it is necessary or to maximize or improve efficacy), that is, using a higher dose in the subsequent administration after the low dose of the first administration. Even if some subjects did not respond to the first dose, the risk of severe neurotoxicity after the subsequent dose(s) was low.

Figure 2A:
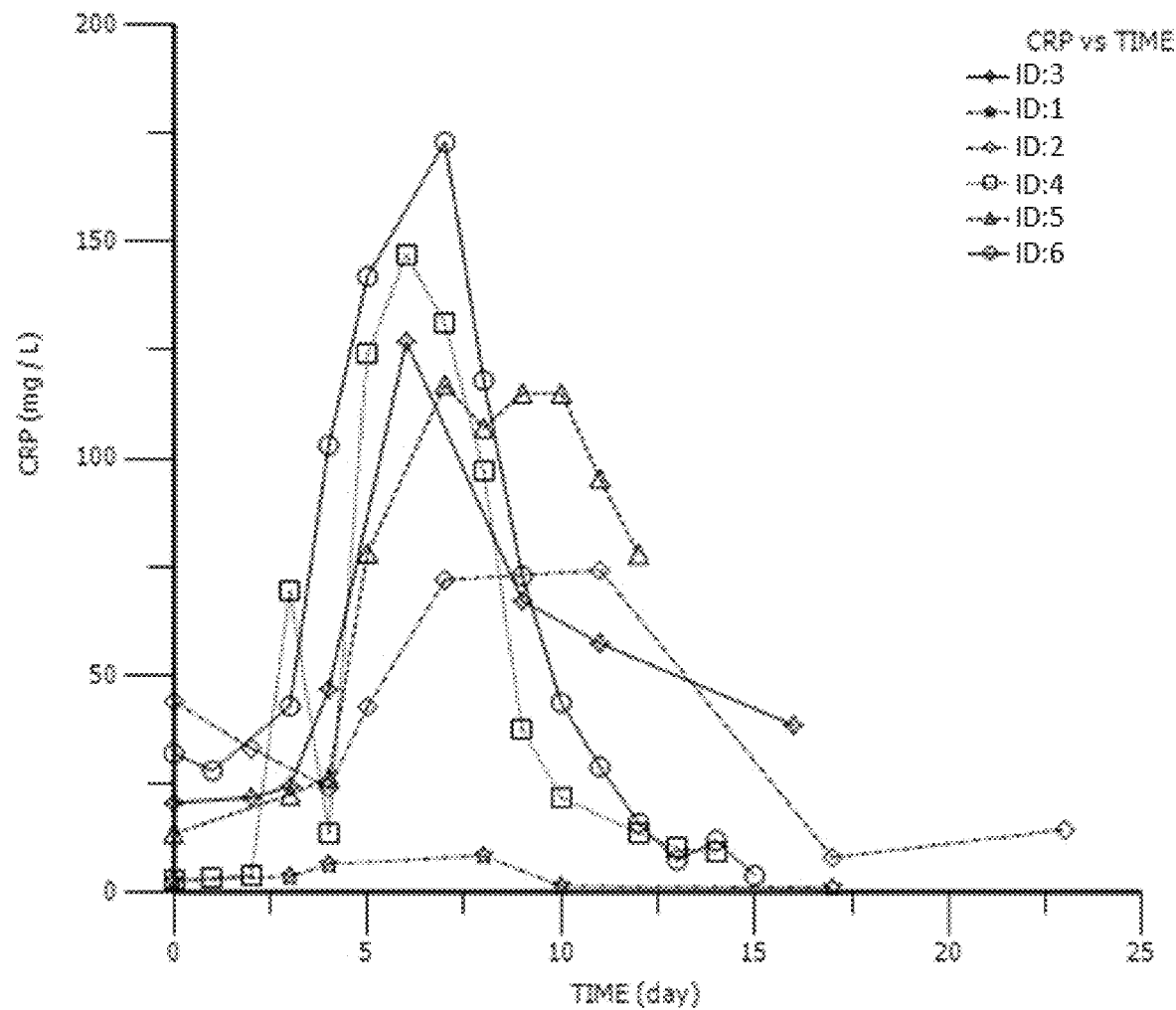
FIG. 2A shows the change of C-reactive protein (CRP) in a subject after the first dose of CAR-T injection (the first course of treatment)
Figure 2B:
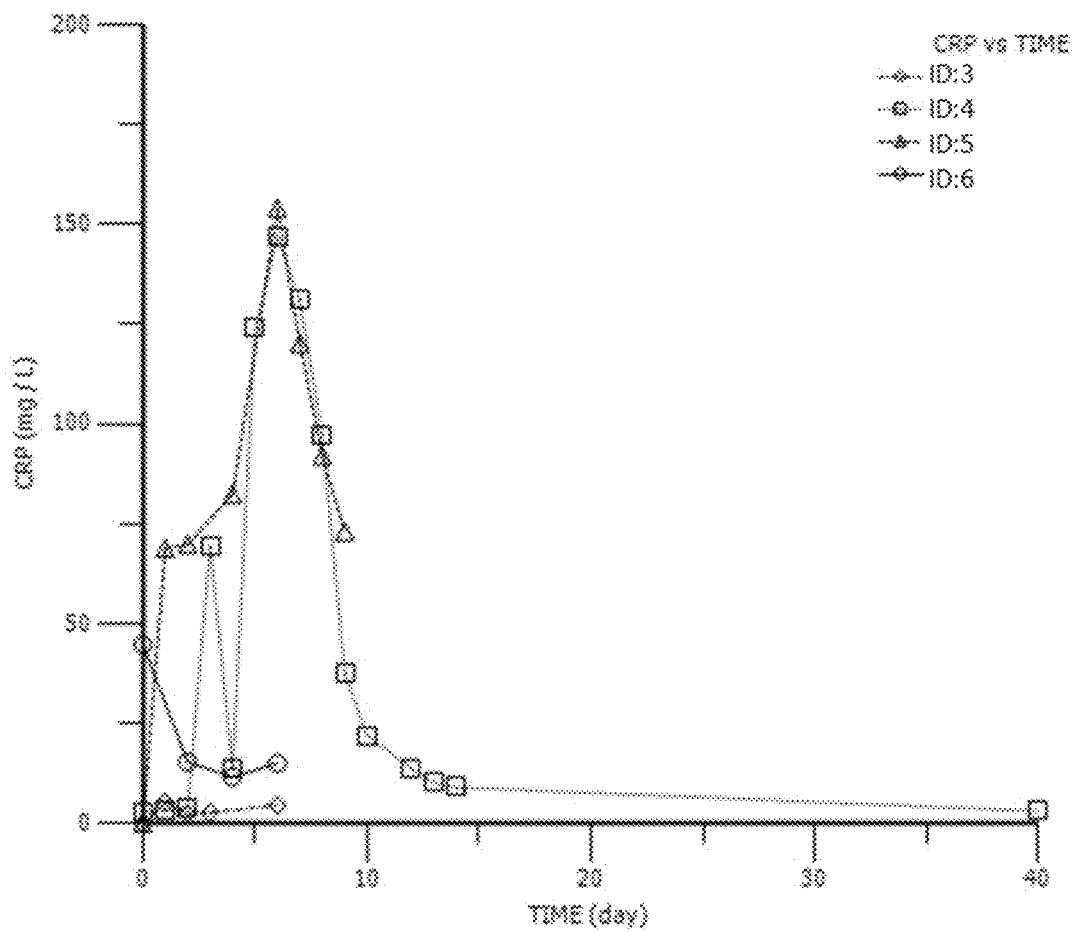
FIG. 2B shows the change of CRP in a subject after the subsequent dose of CAR-T injection (the second course of treatment).

For further evaluating the efficacy of cells administered in the first dose and subsequent dose(s), the continuous survival period of CAR-T cells in the body, that is, the continuous survival period of CAR-T cells "implanted" in the body, was tested. From the end of the initial infusion (day 0), Q-PCR was used at each visit point (the used probe: FAM-5'-CTGAGCAGCGTGACCGCCGC-3'TAMRA (SEQ ID NO: 49); upstream primer sequence: 5'-TGGAGTGGATCGGCTACATC-3' (SEQ ID NO: 50); the downstream primer sequence is: 5'-AGTAGTAGATGGCGGTGTCG-3' (SEQ ID NO: 51)) to detect the copy number of CAR-CLD18 DNA in peripheral blood, until any 2 consecutive tests were negative, recorded as the continuous survival period of CAR-CLD18 T cells. The results are shown in FIG. 1. CAR-T cells proliferated in all subjects. The biological activities of the administered CAR-T cells were compared based on the peak level measured using the serum level of C-reactive protein (CRP). The elevated peak level of CRP in serum also served as an evidence of T cell proliferation after infusion. The results are shown in FIGS. 2A and 2B. After the first dose and subsequent dose(s) of T cells were infused, the cells proliferated in all subjects.

Example 3. Multiple Dose Regimen of CAR-T Cell for Pancreatic Cancer Treatment

CAR-T cells were prepared according to the materials and methods as said above.

In an exemplary dosage regimen, repeated doses of CAR-T cells were used to treat subjects with relapsed or refractory pancreatic cancer, and the interval between each dose is about 21-80 days, preferably about 25-60 days, more preferably, about 25-55 days. Optionally, the subject received fludarabine in combination with cyclophosphamide or fludarabine in combination with cyclophosphamide and albumin-bound paclitaxel or albumin-bound paclitaxel alone for chemotherapy, which was administered at least two days before the first dose and subsequent dose of CAR-T cells were administered and generally not more than about 15 days or not more than about 12 days before the cells were administered.

The subject received the first dose of CAR-T cells of less than or equal to about $2.5 \times 10^8$ cells/kg of the patient's body weight, for example, about $1.1 \times 10^6$ cells/kg to about $2.83 \times 10^7$ cells/kg, with the ends being included. A lower, equal or higher dose of cells were infused to the subject within 80 days after the first dose was administered and/or before the subject developed an immune response to the CAR. In some embodiments, a subsequent dose of CAR-T cells was administered about 44 days after the first dose at a dose higher or lower than the first dose, for example, about $1.1 \times 10^7$ cells/kg (total dose was about $5 \times 10^8$) to about $1.9 \times 10^7$ cells/kg (total dose was about $1 \times 10^9$), and one or more subsequent doses of cells were administered. The time interval of each administration is about 21-80 days, preferably, about 25-60 days, and more preferably, about 25-55 days. Optionally, the subject received fludarabine in combination with cyclophosphamide or fludarabine in combination with cyclophosphamide and albumin-bound paclitaxel or albumin-bound paclitaxel alone for chemotherapy, which was administered at least two days before each dose of CAR-T cells and generally not more than about 15 days or not more than about 20 days before the cells were administered.

In an exemplary dosage regimen, two doses of CAR-T cells were used to treat CLD18A2-positive relapsed, refractory pancreatic cancer subject No. 1, including the first low dose of cells and the subsequent higher doses of cells. Before treatment, autologous CAR-T cells were generated substantially as described in Example 2. The subjects received chemotherapy pretreatment before the first administration of CAR-T cells (the day when the patient was administered with CAR T cell therapy for each round was designated as day 0), including fludarabine about 20 mg/m$^2$/day×4 days (day −6, day −5, day −4, day −3), cyclophosphamide about 500 mg/m$^2$/day×2 days (day −6, day −5). The first dose included approximately $1.1×10^6$ CAR-T cells/kg of the patient's body weight (total dose is $5×10^7$), and it was injected every other day, according to 10%: 30%: 60% of the total dose of the treatment course, divided into 3 infusions. After the first dose was administered, the serum levels of factors indicative of cytokine-release syndrome (CRS) in the subject reached a peak level and began to decrease to around the level before the infusion of the first dose, and subsequent doses were administered (the second course of treatment). In the second course of treatment, fludarabine was administered at about 20 mg/m$^2$/day×4 days (day −6, day −5, day −4, day −3), and cyclophosphamide about 500 mg/m$^2$/day×2 days (day −6, day −5); and about $1.11×10^7$ CAR-T cells/kg of the patient's body weight (total dose is about $5×10^8$) were infused, according to 10%: 30%: 60% of the total dose of the treatment course, divided into 3 infusions for the consecutive days.

The therapeutic efficacy of the subject was monitored, including assessing and monitoring the disease burden, evidence of adverse events, including CRS and neurotoxicity, and survival by imaging (including nuclear magnetic, CT, etc.) the abdomen or other parts (such as metastasis) and tumor marker examinations, using the results of imaging (including MRI, CT, etc.) the abdomen or other parts (such as metastasis) and tumor marker examinations after chemotherapy pretreatment and before the first dose of CAR-T cell infusion as the baseline.

Figure 3A:
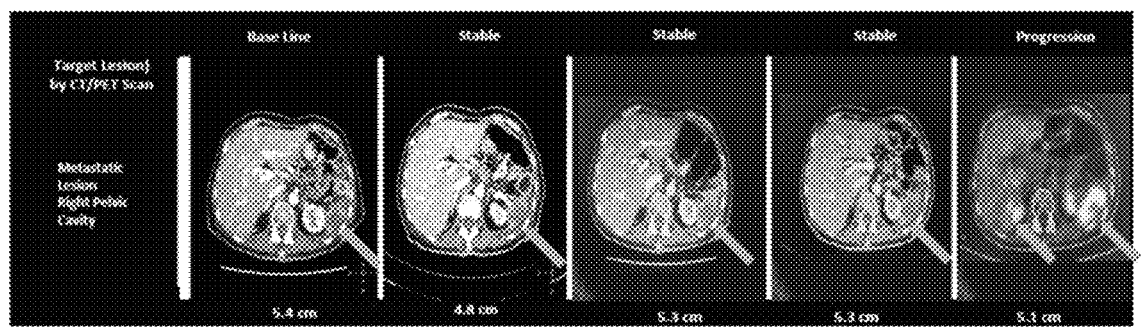
FIG. 3A shows the change of tumor lesions during CAR-T treatment in a pancreatic cancer subject.
Figure 3A:
Figure 3B:
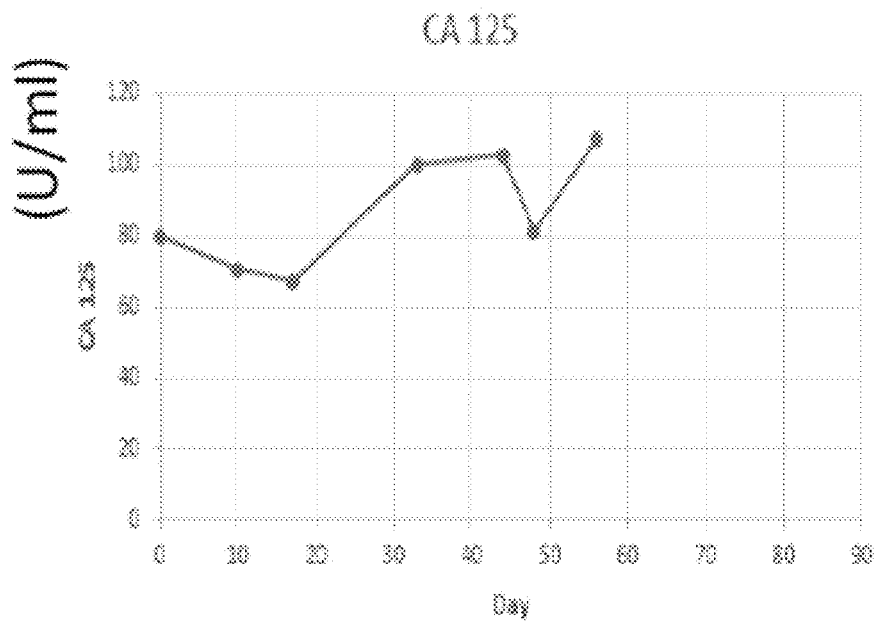
FIG. 3B shows the change of tumor markers during CAR-T treatment in a pancreatic cancer subject.

FIG. 3A shows that subject No. 1 received a total dose of approximately $5×10^7$ CAR-T cells, and 2 weeks after the last infusion in the first course of treatment: the lesions in the left abdominal spleen area were stable and the short diameter was slightly reduced; 6 weeks after the last infusion in the first course of treatment: the lesions in the left abdominal spleen area were stable; 2 weeks after the second course of infusion (a total dose of approximately $5×10^8$ CAR T cells): the lesions in the left abdominal spleen area were stable; 5 weeks after the second course of infusion: the lesions in the spleen area of the left abdomen were stable, and the new liver lesions were progressing. FIG. 3B shows the detection of the tumor marker CA125 in Subject No. 1, and the first infusion day of the first dose was day 0. After the infusion of the first course of treatment and before the second course of treatment, the lesions at the subject's left abdominal spleen were in a stable state, and the expression of CA125 in vivo also slightly decreased, therefore the subject was in stable disease (SD). After the second course of infusion, the lesions at the subject's left abdominal spleen were in a stable state, however the treatment was withdrawn due to new lesions in the liver. There was no severe CRP and severe neurotoxicity during these two courses. The patient continuously used analgesics, the pain was scored as 3-4 points without the analgesics, and the pain was scored as 1 point after using the analgesics. After the first infusion of the continuous dose, the analgesics was no longer used and there was no pain.

Example 4. Repeated Dosing Regimen and Multiple Dosing Regimen of CAR-T Cells for Treating Gastric Adenocarcinoma In an exemplary dosage regimen, repeated doses of CAR-T cells were used to treat subjects with relapsed, refractory gastric adenocarcinoma, and the interval between each dose was about 21-80 days, preferably about 25-60 days, more preferably, about 25-55 days. Before treatment, autologous CAR-T cells were generated substantially as described in Example 2. Optionally, the subject received fludarabine in combination with cyclophosphamide or fludarabine in combination with cyclophosphamide and albumin-bound paclitaxel or albumin-bound paclitaxel alone for chemotherapy, which was administered at least two days before the first and subsequent doses of CAR-T cells and generally not more than about 15 days or not more than about 12 days before the cells were administered.

Subjects with relapsed or refractory gastric adenocarcinoma received the first dose of CAR-T cells of less than or equal to about $2.5×10^8$ cells/kg of the patient's body weight, for example, about $2.9×10^6$ cells/kg to about $2.6×10^7$ cells/kg, with ends being included. A lower, equal or higher dose of cells were infused to the subject within 80 days after the first dose was administered and/or before the subject developed an immune response to the CAR. In some embodiments, a subsequent dose of CAR-T cells was administered about 50 days after the first dose at a dose higher or lower than the first dose, for example, about $1.3×10^7$ cells/kg to about $5.1×10^7$ cells/kg (total dose was about $2×10^9$), for example a dose of about $2.2×10^7$ cells/kg of the patient's body weight.

In some embodiments, one or more subsequent doses of cells were administered. The time interval of each administration was about 21-80 days, preferably, about 25-60 days, and more preferably, about 25-55 days. Optionally, the subject received fludarabine in combination with cyclophosphamide or fludarabine in combination with cyclophosphamide and albumin-bound paclitaxel or albumin-bound paclitaxel alone for chemotherapy, which was administered at least two days before each dose of CAR-T cells and generally not more than about 15 days or not more than about 12 days before the cells were administered.

The relapsed and refractory gastric adenocarcinoma subject No. 4, who was a patient with gastric cancer with ovarian metastasis and malignant pleural and ascites, firstly received pretreatment, including fludarabine about 30 mg/day×4 days (i.e., about 20 mg/m$^2$/day×4 days (day −7, day −6, day −5, day −4)), cyclophosphamide 0.75 g/day×2 days (i.e., about 514 mg/m$^2$/day×2 days (day −7, day −6)), and then received the first course of treatment with the first injection dose of about $3.3×10^6$ CAR-T cells/kg (a total dose was about $1.5×10^8$ CAR-T cells). The first dose was divided into 3 consecutive days, and administered once a day at 10%: 30%: 60% of the total dose of the course of treatment. After the first dose was administered, when the serum level of the factor indicative of CRS in the subject did not exceed 20 times (and at an acceptable level) the subject's serum level before the first dose, where IL-10, TNFα begun to decline, and IL-6 fell below the level before the first dose of infusion, the subsequent dose (the second course of treatment) was administered. In the second course of treatment, the pretreatment included fludarabine about 37 mg/day×2 days (i.e., about 25 mg/m$^2$/day×2 days (day −5, day −4)), and cyclophosphamide about 0.75 g/day×3 days (i.e., about 514 mg/m$^2$/day×3 days (day −5, day −4, day −2)); then the infusion of about $2.2×10^7$ CAR-T cells/kg (a total dose about 1.0×10⁹ CAR-T cells), which was divided into 2 injections, once every other day at 50%: 50% of the total dose of the course of treatment. After the second course of treatment, the subsequent dose was administered (the third course of treatment), when the serum level of the factor indicative of CRS in the subject reached the peak level and began to drop to about or lower than the level before the infusion of the second course of treatment. In the third course of treatment, the pretreatment included the administration of albumin-bound paclitaxel about 137 mg/m²/day×1 days (i.e., −4); then the infusion of about 2.2×10⁷ CAR-T cells/kg (a total dose about 1.0×10⁹ CAR-T cells), which was divided into 2 injections, once every other day at 50%: 50% of the total dose of the course of treatment. At 6 weeks after the third course of treatment, the sum of the longest diameters of the pelvic target lesions did not significantly change compared with 6 weeks after the second injection, and the new pelvic lesions were larger than before; there was a small amount of ascites, and there was a little liquid in the pelvic cavity; and CA125 was 11.3 U/ml. After the third course of treatment, the subsequent dose was administered (the fourth course of treatment), when the serum level of the factor indicative of CRS in the subject was not more than 10 times the serum level in the subject before the dose of the third course of treatment was administered (and at an acceptable level) and the factor indicative of CRS reached the peak level and began to drop to approximately or below the level before the infusion of the third course of treatment. In the fourth course of treatment, the pretreatment included fludarabine about 20 mg/m²/day×2 days (day −6, day −5), and cyclophosphamide about 514 mg/m²/day×4 days (day −6, day −5, day −4, day −3); then the infusion of about 3.7×10⁷ CAR-T cells/kg (a total dose about 1.65×10⁹ CAR-T cells), which was divided into 3 injections (day 0, day 1, day 13) at 46%: 18%: 36% of the total dose of the course of treatment. Six weeks after the fourth course of treatment, the sum of the longest diameters of the target pelvic lesions did not significantly change compared with the previous period; new pelvic lesions did not significantly change compared with the previous period; the pleural and ascites continued to decrease, suggesting that CAR-CLD18 T cell therapy was also effective in controlling malignant pleural and ascites.

Figure 4A:
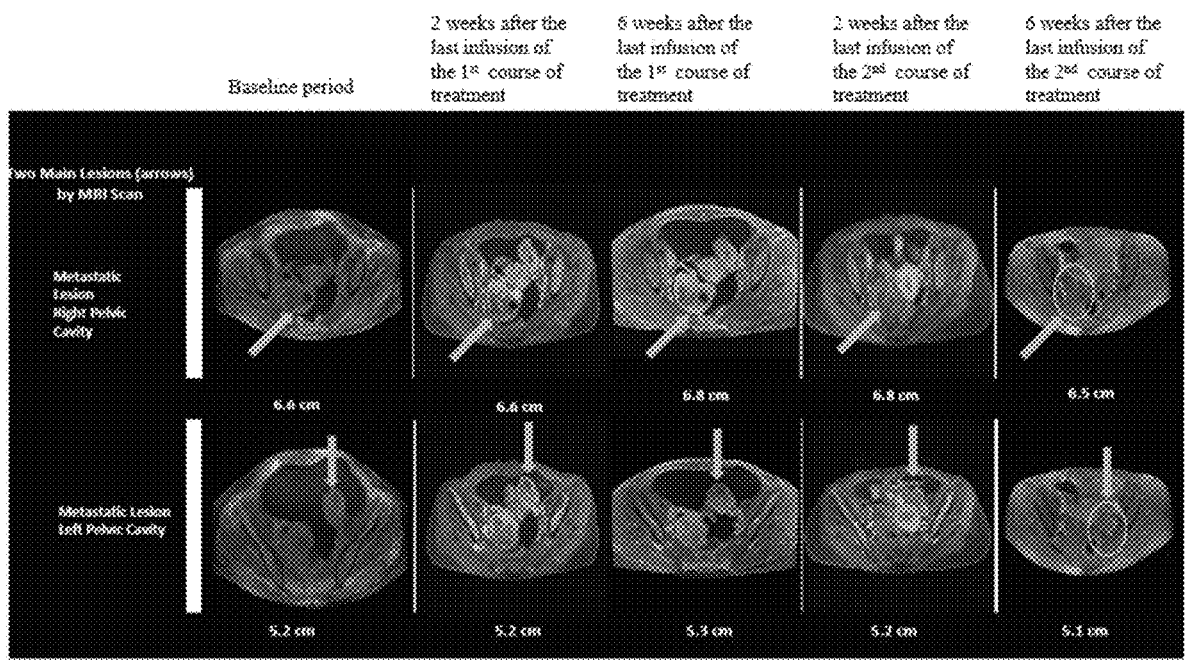
FIG. 4A shows the change of tumor lesions during CAR-T treatment in a gastric adenocarcinoma subject.
Figure 4B:
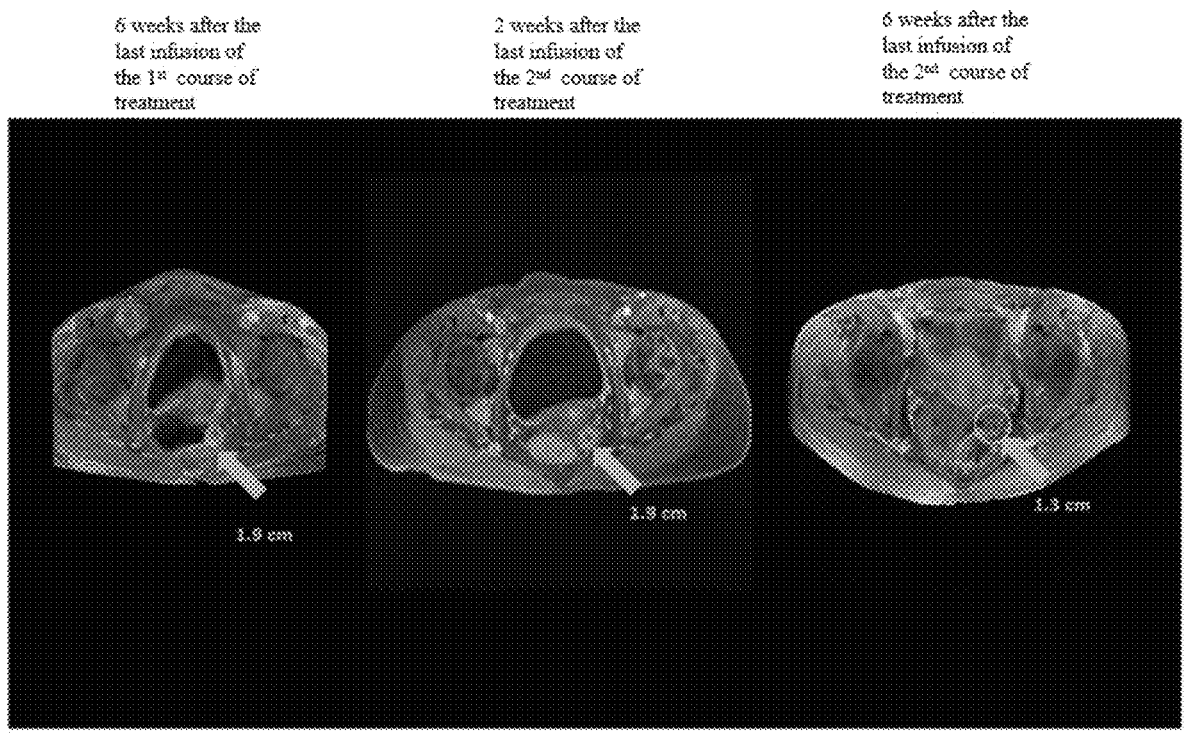
FIG. 4B shows the change of new lesions during CAR-T treatment in a gastric adenocarcinoma subject.

FIG. 4A shows that 2 weeks after the subject No. 4 received the last infusion of the first dose of the first course of treatment: the longest diameter of the largest lesion in the right pelvis was 6.5 cm, and the longest diameter of the largest lesion in the left pelvis was 5.2 cm; 6 weeks after the last infusion of the first course of treatment: the longest diameter of the largest pelvic lesion on the right was 6.8 cm, the longest diameter of the largest pelvic lesion on the left was 5.3 cm, and the new pelvic lesion was 1.9 cm (FIG. 4B), and such results were also used as the baseline for the second course of treatment. 2 weeks after the infusion of the subsequent dose during the second course of treatment: the longest diameter of the largest lesion in the right pelvis was 6.8 cm, the longest diameter of the largest lesion in the left pelvis was 5.2 cm, and the new lesion was 1.9 cm; 6 weeks after the last infusion of the second course of treatment: the longest diameter of the largest lesion in the right pelvic cavity was 6.5 cm; the longest diameter of the largest lesion in the left pelvic cavity was 5.1 cm; and the new pelvic lesion was 1.3 cm.

Figure 4C:
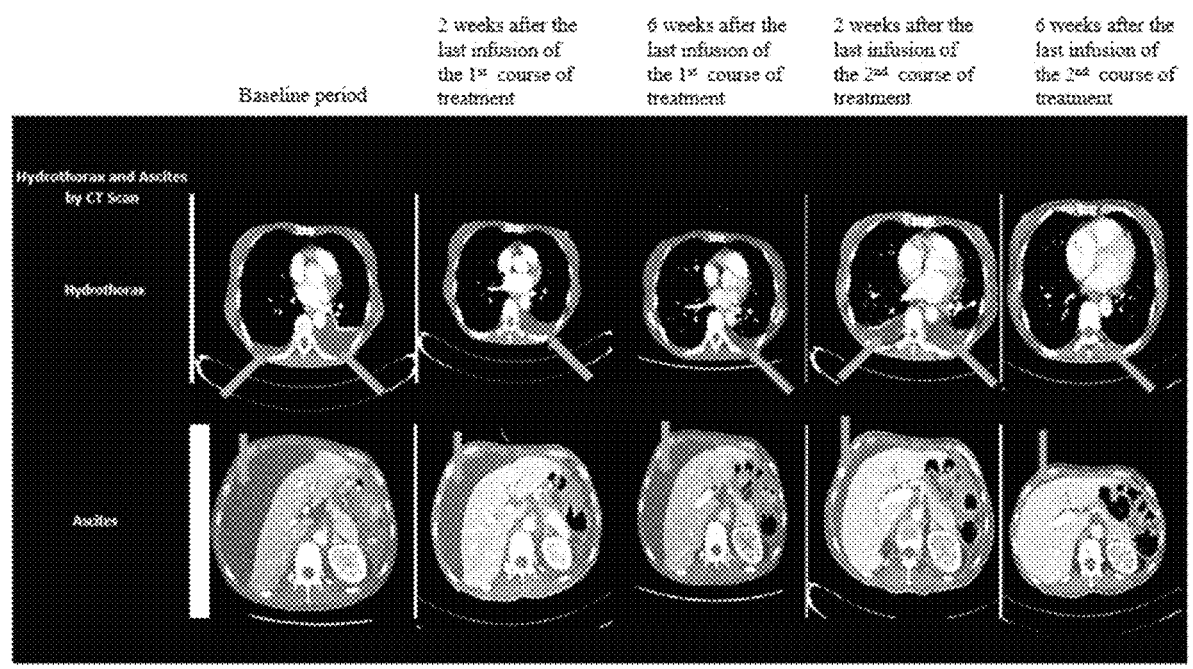
FIG. 4C shows the change of pleural and ascites during CAR-T treatment in a gastric adenocarcinoma subject.
Figure 4D:
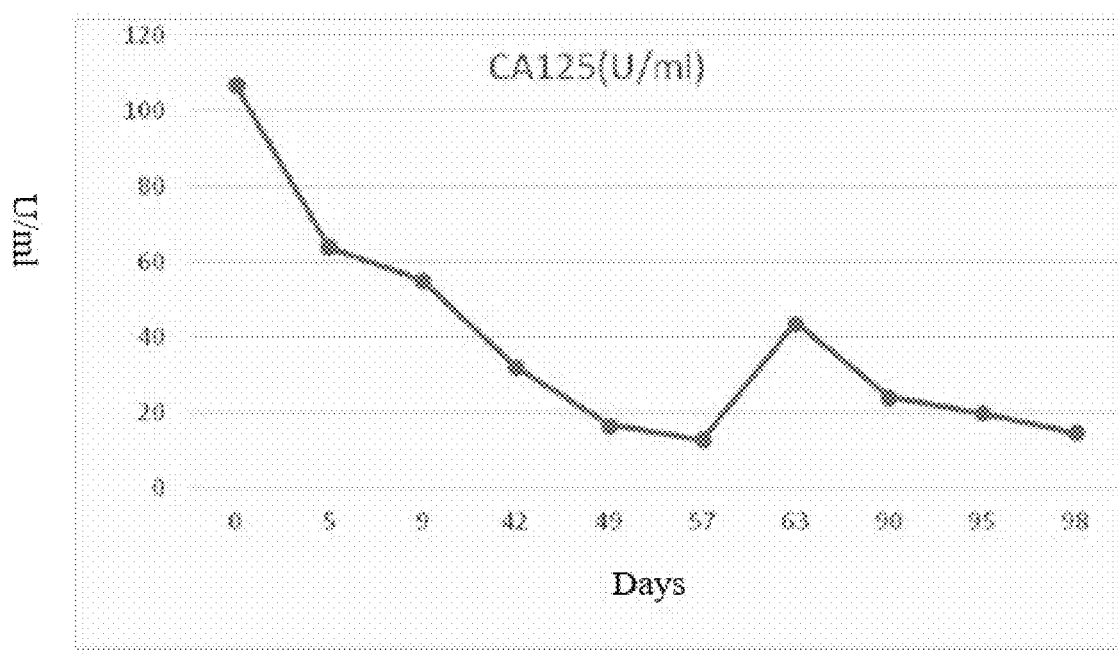
FIG. 4D shows the change of CA125 level during CAR-T treatment in a gastric adenocarcinoma subject.
Figure 4E:
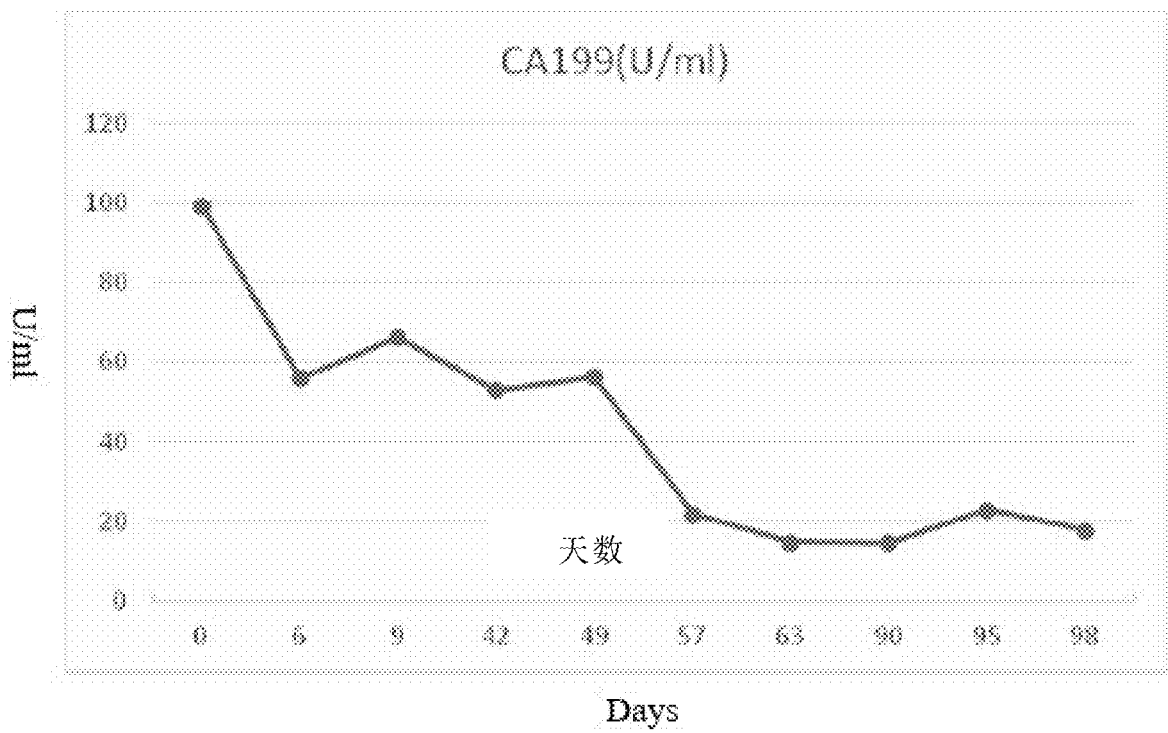
FIG. 4E shows the change of CA199 level during CAR-T treatment in a gastric adenocarcinoma subject.

FIG. 4C shows that the cancerous pleural and ascites fluid of the subjects was significantly reduced during the CAR-T treatment. In FIGS. 4D and 4E, the tumor markers CA125 and CA199 were detected, respectively, and the first infusion day of the first dose was day 0. The tumor markers CA125 and CA199 decreased significantly, wherein, in the first course of treatment, CA125 decreased from 106.7 U/ml before CAR-T injection to 32.1 U/ml before the injection the second course of treatment (normal range <35 U/ml). CA125 remained at a low level during the course of treatment. In the first course of treatment, CA199 decreased from 99.41 U/ml before CAR-T injection to 52.98 U/ml before the injection the second course of treatment (normal range <37 U/ml), and CA199 remained within the normal range during the second course of treatment.

The above results indicate that the original lesions of Subject No. 4 were in a stable state during the first course of treatment, but new lesions emerged. In the second course of treatment, the original lesions were in a stable state, while the new lesions were significantly reduced, with a reduction ratio of 31.6%. At the same time, the tumor marker CA125 in the subjects remained at a low level, and CA199 remained at a normal level. There was no severe CRS or severe neurotoxicity during these two courses.

Subject No. 5 with recurrent and refractory gastric adenocarcinoma received chemotherapy pretreatment before the first administration of CAR-T cells, including fludarabine at about 20 mg/m²/day×2 days (day −6, day −5), cyclophosphamide at about 500 mg/m²/day×4 days (day −6, day −5, day −4, day −3). The first dose included about 1.6×10⁷ CAR-T cells/kg of the patient's body weight (the total dose was about 1×10⁹), injected once every other day, according to 50%: 50% of the total dose of the course of treatment, divided into 2 infusions. After the first dose was administered, the serum level of the factor indicative of CRS in the subject reached the peak level and began to decrease, or decrease to about or below the level before the infusion of the first dose, and the subsequent dose was administered (the second course of treatment). In the second course of treatment, the pretreatment included infusion of fludarabine at about 20 mg/m²/day×1 day (day −5), and cyclophosphamide at about 500 mg/m²/day×3 days (day −5, day −4, day −3), and albumin-bound paclitaxel at about 100 mg/m²/day×1 day (day −4) chemotherapy; then about 1.6×10⁷ CAR-T cells/kg of the patient's body weight (the total dose was about 1×10⁹) were infused, injected once every other day, according to 50%: 50% of the total dose of the course of treatment, divided into 2 infusions.

Subject No. 6 with recurrent and refractory gastric adenocarcinoma received chemotherapy pretreatment before the first administration of CAR-T cells, including fludarabine at about 20 mg/m²/day×2 days (day −6, day −5), cyclophosphamide at about 500 mg/m²/day×4 days (day −6, day −5, day −4, day −3). The first dose included about 1.25×10⁷ CAR-T cells/kg of the patient's body weight (the total dose was about 1×10⁹), injected once every other day, according to 50%: 50% of the total dose of the course of treatment, divided into 2 infusions. After the first dose was administered, the serum level of the factor indicative of CRS in the subject reached the peak level and began to decrease to about or below the level before the infusion of the first dose, and the subsequent dose was administered (the second course of treatment). The pretreatment in the second course of treatment included the administration of fludarabine at about 20 mg/m²/day×1 day (day −5), cyclophosphamide at about 500 mg/m²/day×3 days (day −5, day −4, day −3), and albumin-bound paclitaxel at about 100 mg/m²/day×1 day (day −4); the about 1.25×10⁷ CAR-T cells/kg of the patient's body weight (total dose is about 1×10⁹) were infused, injected once every other day, according to 50%: 50% of the total dose of the course of treatment, divided into 2 infusions.

Example 5 Treatment of Subjects with Relapsed and Refractory Gastric Adenocarcinoma The subject No. 7 with relapsed and refractory gastric adenocarcinoma had gastric cardia adenocarcinoma for 1.3 years. The disease progressed with multiple liver metastases after gastrectomy. And then the subject received treatments such as tigeo, docetaxel, oxaliplatin, capecitabine, and were still in a state of disease progression. In this case, the patient received the CAR-T cell therapy of the present invention.

Before the first administration of CAR-T cells, the subject received a chemotherapy pretreatment, including fludarabine at about 20 mg/m$^2$/day×1 day (day −12), and cyclophosphamide at about 500 mg/m$^2$/day×3 days (day −12, day −11, day −10). The first dose included about 2.6×10$^7$ CAR-T cells/kg of the patient's body weight (the total dose was about 1×10$^9$), injected once every other day, according to 50%: 50% of the total dose of the course of treatment, divided into 2 infusions. After the infusion, the patient had a fever, up to 39.3°, which can be controlled by physical cooling. Two weeks after the first dose was administered, the carcinoembryonic antigen decreased from 12.49 U/ml to less than 5 U/ml, and the carbohydrate antigen CA199 decreased from 12.17 U/ml to less than 4 U/ml. 6 weeks after the first dose was administered, the MR scan showed that the tumor in the upper right posterior lobe was reduced by 41%.

After the first dose was administered, the serum level of the factor indicative of CRS in the subject reached the peak level and began to decrease to about or below the level before the infusion of the first dose, and the subsequent dose was administered (the second course of treatment, 47 days after the first dose was administered). The pretreatment in the second course of treatment included the administration of fludarabine at about 21 mg/m$^2$/day×1 day (day −6), cyclophosphamide at about 540 mg/m$^2$/day×3 days (day −6, day −5, day −4), and albumin-bound paclitaxel at about 71 mg/m$^2$/day×1 day (day −5); and then about 5.1×10$^7$ CAR-T cells/kg of the patient's body weight (the total dose was about 2×10$^9$), according to 25%: 25%: 25%: 25% of the total dose of the course of treatment, divided into 4 infusions (day 0, day 2, day 9, day 13). Two weeks after the subsequent dose of the second course of treatment was administered, the tumor in the upper right posterior lobe was reduced by 63%.

The subject No. 9 with relapsed and refractory gastric adenocarcinoma received 8 weeks of SOX chemotherapy after bilateral ovarian metastasis of gastric cancer, and 2 weeks of oral TS chemotherapy for 5 cycles (docetaxel, Tiggio), and was still in a state of disease progression. In this case, the patient received the CAR-T cell therapy of the present invention.

Before the first administration of CAR-T cells, the subject received a chemotherapy pretreatment, including fludarabine at about 20 mg/m$^2$/day×1 day (day −6), cyclophosphamide at about 500 mg/m$^2$/day×4 days (day −6, day −5, day −4, day −3), albumin-bound paclitaxel at about 64 mg/m$^2$/day×1 day (day −5). The first dose included about 1.82×10$^7$ CAR-T cells/kg of the patient's body weight (the total dose was about 1×10$^9$ CAR-T cells), divided into multiple infusions according to 50%: 50% of the total dose of the course of treatment, injected for two consecutive days, once a day. After the first infusion, the patient developed a fever of grade 2 and was treated with indomethacin suppository to reduce the fever.

After the first dose was administered, IL-2 increased significantly from the 3rd day after infusion, reached the peak level about 10 days and began to decrease to about or lower than the level before the infusion of the first dose, and the remaining cytokines did not change significantly. The subsequent dose was administered (the second course of treatment, the 40$^{th}$ day after the first dose was administered). After the pretreatment in the second course of treatment (the same as the pretreatment of the first course of treatment), about 2.73×10$^7$ CAR-T cells/kg of the patient's body weight (the total dose was about 1.5×10$^9$ CAR-T cells), according to ⅓:⅓:⅓ of the total dose of the course of treatment, divided into 3 consecutive infusions, once a day. During the period, III lymphopenia and leukopenia related to the treatment, and II hypocalcemia, hypokalemia, and nausea occurred, all of which recovered after symptomatic and supportive treatment. No SAE occurred.

The subsequent dose was administered (the third course of treatment, the 25$^{th}$ day after the dose of the second course of treatment was administered). After the pretreatment of the third course of treatment (the same as the pretreatment of the first course of treatment), about 1.82×10$^7$ CAR-T cells/kg (the total dose of about 1.0×10$^9$ CAR-T cells) was infused, according to 50%: 50% of the total dose of the course of treatment, infused in divided doses, injected for two consecutive days, once a day. The imaging examination showed that the patient's lesion disappeared and was evaluated by an imaging specialist as complete remission (CR).

Example 6 Treatment of Subjects with Relapsed and Refractory Pancreatic Cancer Before receiving CAR-T cell therapy, Subject No. 8 with relapsed and refractory pancreatic cancer received a resection of the pancreatic body and tail of the pancreas, and developed PD after the operation with metastases in the mesenteric lymph nodes and liver. After received a local radiotherapy, the subject was still in disease progression, and 4 new lesions developed in the liver.

Before the first administration of CAR-T cells, the subject received a chemotherapy pretreatment, including fludarabine at about 20 mg/m$^2$/day×1 day (day −6), cyclophosphamide at about 507 mg/m$^2$/day×4 days (day −6, day −5, day −4, day −3), and albumin-bound paclitaxel at about 68 mg/m$^2$/day×1 day (day −5). The first dose included about 2.83×10$^7$ CAR-T cells/kg of the patient's body weight (the total dose was about 1.5×10$^9$), according to ⅓:⅓:⅓ of the total dose of the course of treatment, divided into 3 infusions (day 0, 11, 14). Six weeks after the first dose of CAR-T cells was injected, the longest diameters of 2 target lesions in the liver and 1 target lesion in the pelvis were reduced by 90% compared with the baseline, and CA 199 decreased from 899.6 U/ml to 56.79 U/ml, which was evaluated as reaching PR (Partial Relief).

The subsequent dose (the second course of treatment) was administered on the 44th day after the first dose was administered, wherein fludarabine was administered at about 20 mg/m$^2$/day×1 day (day −6), cyclophosphamide was administered at about 507 mg/m$^2$/day×4 days (day −6, day −5, day −4, day −3), and albumin-bound paclitaxel was administered at about 68 mg/m$^2$/day×1 day (day −5); and CAR-T cells were infused at about 1.887×10$^7$ CAR-T cells/kg of the patient's body weight (the total dose was about 1×10$^9$), injected once every other day, according to 50%: 50% of the total dose of the course of treatment, divided into 2 infusions. 9 days after the continuous doses of the second course of treatment were administered, the liver MR scan showed no clear active lesions in the liver. The pelvic CT scan revealed that the pelvic soft tissue nodules were significantly reduced compared with the results during the 6 weeks of the first course of treatment.

Example 7 Statistics of Adverse Reactions of Patients

The 9 patients in the foregoing examples were subjected to physical examinations, and symptoms of adverse events (AE) were detected, including the symptoms listed in Table 3. The treatment acute AE (TEAE) after the first dose was infused is defined as any AE that occurs after receiving the first dose. The results are shown in Table 3:

TABLE 3

Statistics of adverse events

| adverse events | TEAE(n = 9) |
|---|---|
| All | 9 |
| Hypoalbuminemia | 4 |
| Hypokalemia | 3 |
| Hypocalcemia | 4 |
| fever | 9 |
| Chills | 2 |
| Joint pain | 1 |
| stomach ache | 1 |
| Skin cyanosis | 1 |
| Itchy skin | 1 |
| Tachycardia | 1 |
| CRS | 0 |

Example 8 Establishment of Panc02/Luc-GFP-Claudin 18.2, 8E5-2I-mBBZ CAR T Cell

1. Construction of Panc02/Luc-GFP-Claudin 18.2 Cells

A model of Panc02 pancreatic cancer cells overexpressing mouse Claudin 18.2 (SEQ ID NO: 67) was established by conventional methods of molecular biology. Mouse Claudin 18.2 (SEQ ID NO: 67) was inserted to construct plasmid pWPT-mClaudin 18.2 by using pWPT as a vector. Afterwards, the pancreatic cancer cell Panc02/Luc-GFP-Claudin 18.2 overexpressing mouse Claudin 18.2 was established by lentivirus packaging infection method.

2. Construction of T Cells Expressing Chimeric Antigen Receptors (1) Construction of plasmid Using conventional methods in molecular biology, the amino acid sequence of scFv used in this example is shown in SEQ ID NO: 54, the nucleic acid sequence is shown in SEQ ID NO: 55, and the CDR regions are: HCDR1 as shown in SEQ ID NO: 1, HCDR2 as shown in SEQ ID NO: 7, HCDR3 as shown in SEQ ID NO: 3, LCDR1 as shown in SEQ ID NO: 4, LCDR2 as shown in SEQ ID NO: 5, and LCDR3 as shown in SEQ ID NO: 6.

Figure 5:
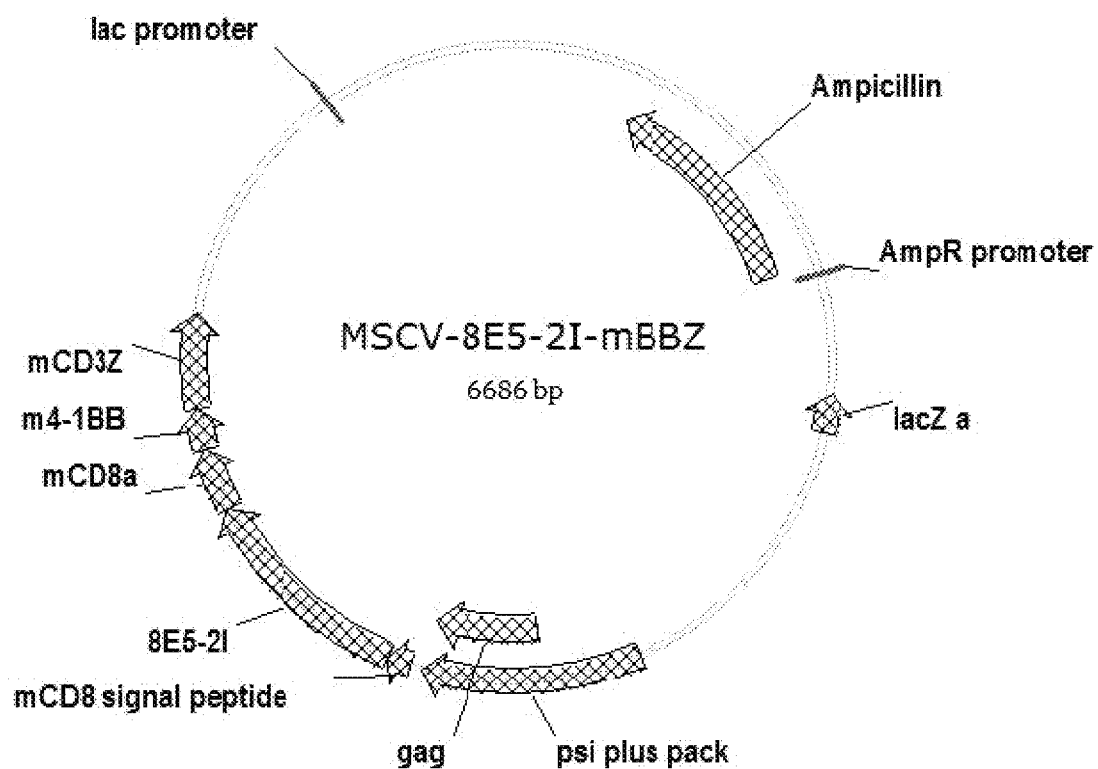
FIG. 5 shows a plasmid map of the recombinant vector MSCV-8E5-2I-mBBZ.

The used chimeric antigen receptor is a second generation of chimeric antigen receptor, including a transmembrane domain of CD8, intracellular domain of 4-1BB, and CD3ζ. According to the plasmid map as shown in FIG. 5, the plasmid MSCV-8E5-21-mBBZ was constructed.

A retroviral plasmid MSCV-8E5-2I-mBBZ expressing the second generation of chimeric antigen receptor was constructed by using MSCV.pBABE 5 as a vector. The 8E5-2I-mBBZ sequence is composed of mouse CD8α signal peptide (the amino acid sequence is shown in SEQ ID NO: 59, the nucleotide sequence is shown in SEQ ID NO: 60), scFv targeting claudin 18.2 (SEQ ID NO: 55), mouse CD8 hinge and transmembrane region (the amino acid sequence shown in SEQ ID NO: 61, the nucleotide sequence shown in SEQ ID NO: 62) and mouse 4-1BB intracellular signaling domain (the amino acid sequence is shown in SEQ ID NO: 63, the nucleotide sequence is shown in SEQ ID NO: 64) as well as intracellular segment CD3ζ of mouse CD3 (the amino acid sequence is shown in SEQ ID NO: 65, the nucleotide sequence is shown in SEQ ID NO: 66).

293T cells were transfected by MSCV-8E5-2I-mBBZ for packaging retrovirus, so as to obtain retrovirus. The infection method is a conventional infection method for preparing T cells expressing chimeric antigen receptors in the art.

(2) Construction of CAR T cells: spleen T lymphocytes from C57BL/6 mice were taken, and purified mouse CD3 T lymphocytes were added into Dynabeads Mouse T-activator CD3/CD28 at a volume ratio of 1:1, washed once with PBS, activated, and placed into an incubator for culture. The medium is RPMI 1640 complete medium supplemented with 10% FBS serum.

The mouse spleen T lymphocytes activated for 24 hours were inoculated into a 12-well plate coated with recombinant human fibrin fragments, and retroviruses were added for infection for 12 hours, and then cultured and amplified to the required number to obtain mouse 8E5-21-mBBZ CAR T cells.

Example 9 CCK8 Experiment to Detect the Toxicity of Abraxane on Pancreatic Cancer Cells and CAR-T Cells The Panc02/Luc-GFP-Claudin 18.2 cells and the 8E5-21-mBBZ CAR T cells prepared in Example 8 were plated in a 96-well plate at 10,000 cells per well (Panc02/Luc-GFP-Claudin 18.2) or 100,000 cells per well (hu8E5-21-mBBZ CAR T) in 100 ul of medium. Abraxane with different concentrations were taken and added into the cells to prepare ten gradients (maximum concentration 500 μg/ml, 2-fold gradient dilution). In addition, a group of wells only containing the medium was set as the blank group. After 24 hours, 10 ul of CCK8 reagent (Dojindo) was added to each well and incubated for 2 hours at 37° C., and then the absorbance at 450 nm was measured with a microplate reader to calculate cell viability.

The calculation formula is: cell viability (%)=[A (Administration)-A (blank)]/[A (0 Administration)-A (blank)]

The results are shown in FIGS. 6A and 6B. The IC50 value of Abraxane on Panc02/Luc-GFP-Claudin 18.2 cells was 174.45±20.98 ug/ml. The results of Abraxane for killing 8E5-21-mBBZ CAR-T cells showed that the survival rate of 8E5-21-mBBZ CAR-T cells was still higher than 50%, even under the treatment of 500 μg/ml of Abraxane. Therefore, it is demonstrated that Abraxane is less toxic to 8E5-21-mBBZ CAR-T cells.

Example 10 Inhibitory Effects of Simultaneous Administration of Abraxane and CAR T Cells on Pancreatic Cancer in Mice The pancreas of 6-week-old C57BL/6 mice were inoculated with $2\times10^5$ Panc02/Luc-GFP-Claudin 18.2 cells in situ, and the day of the tumor cell inoculation was recorded as Day 0 (Day 0).

On the second day (Day 2) after tumor inoculation, mouse T cells were taken to construct 8E5-21-mBBZ CAR T cells.

On the $7^{th}$ day after tumor inoculation (Day 7), mice were administered with $1\times10^6$ 8E5-21-mBBZ CAR-T cell through tail vein injection or Abraxane (60 mg/kg) through intraperitoneal injection or a combination of both, and on the 14$^{th}$ day, the same dose of CART and Abraxane was repeatedly injected once, and the therapeutic effects were observed by intravital imaging every week.

The results are shown in FIG. 7A: 19 days after CAR T cell injection (i.e., Day 26), it can be observed that the luciferase activity of the combination group was significantly lower than that of the single CAR-T treatment group or the single Abraxane treatment group (P<0.05, Two way ANOVA). It is demonstrated that, compared with 8E5-21-mBBZ CAR-T group and Abraxane treatment group, the tumor growth rate in the group of 8E5-21-mBBZ CAR-T in combination with Abraxane is the slowest, and there are good inhibitory effects on pancreatic orthotopic tumors. The above results indicate that the combination with Abraxane can increase the inhibitory effects of CAR-T cells on tumor cell growth.

The body weight of the mice was monitored 1 to 2 times every week. The results are shown in FIG. 7B. Compared with the UT control group, the weight of the mice was not reduced during the combined treatment of CAR-T cells with Abraxane and 2 weeks after the treatment. There were no other abnormalities in the mice, indicating that the combination of CAR-T cells with Abraxane exert no serious side effects on the mice.

Example 11 Inhibitory Effects on Mouse Pancreatic Cancer from the Administration of Abraxane and CAR T Cells in Sequence The pancreas of 6-week-old C57BL/6 mice were inoculated with 2×10$^5$ Panc02/Luc-GFP-Claudin 18.2 cells in situ, and the day of the tumor cell inoculation was recorded as Day 0 (Day 0).

On the 7$^{th}$ day after tumor inoculation (Day 7), mouse spleen T cells were taken to construct hu8E5-21-mBBZ CAR T cells.

On the 7$^{th}$ day after tumor inoculation (i.e., Day 7), mice were intraperitoneally administered with Abraxane at 60 mg/kg (Abraxane group), and on the 10$^{th}$ day after tumor inoculation (i.e., Day 10), mice were administered with 3×10$^6$ 8E5-21-mBBZ CAR-T Cells through tail vein injection (8E5-2I-BBZ CAR-T group) or 3×10$^6$ control UT cell through tail vein injection (UT group), or a combination of the both (Abraxane at 60 mg/kg was administered to the mice on the 7$^{th}$ day after tumor inoculation through intraperitoneal injection, and then 3×10$^6$ 8E5-21-mBBZ CAR-T cells were administered to the mice on the 10$^{th}$ day after tumor inoculation through tail vein injection, Abraxane+ 8E5-2I-BBZ CAR-T group), and the survival period of the mice was recorded. The results are shown in FIGS. 8A, 8B and 8C. In the combination group (Abraxane+8E5-2I-BBZ), the survival time of mice was significantly prolonged, compared with the control UT group (P<0.05), and in the combination group, the survival time of mice was significantly prolonged compared with the single Abraxane group (P<0.05).

The body weight of the mice was monitored 1 to 2 times a week. The results are shown in FIG. 9. Compared with the UT control group, the weight of the mice was not reduced during the combined treatment of CAR-T cells with Abraxane and 2 weeks after the treatment. There were no other abnormalities in the mice, indicating that the combination of CAR-T cells with Abraxane exert no serious side effects on the mice.

All documents mentioned in the present invention are cited as references in this application, as if each document was individually cited as a reference. In addition, it should be understood that after reading the above teaching content of the present invention, a skilled person can make various changes or modifications to the present invention, and these equivalent forms also fall within the scope defined by the appended claims of the present application.

The invention claimed is:

1. A method for treating a CLD18A2-positive tumor, comprising administering a first dose of immune effector cells to a subject in need thereof, wherein the immune effector cells express a chimeric antigen receptor (CAR) that specifically recognizes CLD18A2, wherein the method further comprises a pretreatment performed before administering the first dose of the immune effector cells, and the pretreatment comprises administering a chemotherapeutic agent to the subject, and wherein the chemotherapeutic agent comprises cyclophosphamide, fludarabine, and albumin-bound paclitaxel, and wherein the pretreatment is performed 1, 2, 3, 4, 5, 6, 7, 8, 9, 10, 11, or 12 days before the first dose of the immune effector cells is administered.

2. The method of claim 1, wherein the first dose contains a total amount of the immune effector cells not more than $2 \times 10^9$ cells.

3. The method of claim 1, wherein after the first dose of the immune effector cells is administered, at least one subsequent dose of immune effector cells expressing a chimeric antigen receptor (CAR) that specifically recognizing CLD18A2 is administered.

4. The method of claim 3, wherein the at least one subsequent dose contains a total amount of the immune effector cells not more than $2 \times 10^9$ cells.

5. The method of claim 1, wherein the pretreatment is performed days before the first dose of the immune effector cells is administered.

6. The method of claim 1, wherein the tumor is breast cancer, colon cancer, rectal cancer, renal cell carcinoma, liver cancer, lung cancer, gastric cancer, small bowel cancer, esophageal cancer, melanoma, bone cancer, pancreatic cancer, skin cancer, head and neck cancer, ovarian cancer, anal cancer, testicular cancer, uterine cancer, fallopian tube cancer, endometrial cancer, cervical cancer, vaginal cancer, Hodgkin's lymphoma, non-Hodgkin's lymphoma, endocrine system cancer, thyroid cancer, parathyroid cancer, adrenal cancer, soft tissue sarcoma, urethral cancer, penile cancer, bladder cancer, kidney cancer, ureter cancer, renal pelvis cancer, central nervous system (CNS) tumor, primary CNS lymphoma, spinal tumor, brain stem glioma, pituitary adenoma, Kaposi's sarcoma, epidermoid carcinoma, or squamous cell carcinoma.

7. The method of claim 1, wherein the chimeric antigen receptor comprises an scFv antibody fragment specifically binding to CLD18A2, a transmembrane domain, and an intracellular domain, and wherein the scFv antibody fragment comprises:

HCDR1 as shown in SEQ ID NO:1; HCDR2 as shown in SEQ ID NO:2; HCDR3 as shown in SEQ ID NO:3; LCDR1 as shown in SEQ ID NO:4; LCDR2 as shown in SEQ ID NO: 5; and LCDR3 as shown in SEQ ID NO: 6; or HCDR1 as shown in SEQ ID NO:1; HCDR2 as shown in SEQ ID NO:7; HCDR3 as shown in SEQ ID NO:3; LCDR1 as shown in SEQ ID NO:4; LCDR2 as shown in SEQ ID NO: 5; and LCDR3 as shown in SEQ ID NO: 6; or HCDR1 as shown in SEQ ID NO: 8; HCDR2 as shown in SEQ ID NO:9 or 68; HCDR3 as shown in SEQ ID NO: 10; LCDR1 as shown in SEQ ID NO:11; LCDR2 as shown in SEQ ID NO: 12; and LCDR3 as shown in SEQ ID NO: 13.

8. The method of claim 7, wherein the scFv antibody fragment comprises a heavy chain variable region as shown in SEQ ID NO: 14 and a light chain variable region as shown in SEQ ID NO: 16; or a heavy chain variable region as shown in SEQ ID NO: 18 and a light chain variable region as shown in SEQ ID NO: 16; or a heavy chain variable region as shown in SEQ ID NO: 22 and a light chain variable region as shown in SEQ ID NO: 20; or a heavy chain variable region as shown in SEQ ID NO:53 and a light chain variable region as shown in SEQ ID NO:52.

9. The method of claim 7, wherein the scFv antibody fragment comprises an amino acid sequence selected from the group consisting of SEQ ID NO: 54, 56, 57 and 58.

10. The method of claim 7, wherein the chimeric antigen receptor comprises an amino acid sequence selected from the group consisting of SEQ ID NOs: 24, 25, 26, 27, 28, 29, 30, 31, and 32.

11. The method of claim 1, wherein the immune effector cells are T lymphocytes, NK cells, or NKT lymphocytes.

12. The method of claim 1, wherein the chemotherapeutic agent is administered daily for 2, 3, 4, 5, 6, or 7 days.

13. The method of claim 12, wherein the cyclophosphamide and the fludarabine are administered daily for 2, 3, or 4 days, and the albumin-bound paclitaxel is administered once; or the cyclophosphamide, the fludarabine, and the albumin-bound paclitaxel are administered daily for 2, 3, or 4 days.

14. The method of claim 1, wherein the tumor is a digestive tract tumor.

15. The method of claim 14, wherein the digestive tract tumor is adenocarcinoma.

16. The method of claim 1, wherein the tumor is pancreatic cancer, gastric cancer, gastric adenocarcinoma, esophageal cancer, rectal cancer, anal cancer, or small bowel cancer.

17. The method of claim 1, wherein the fludarabine is administered at about 10-50 mg/m²/day, or about 15-40 mg/m²/day, or about 15-30 mg/m²/day, or about 20-30 mg/m²/day, or about 25 mg/m²/day; and the cyclophosphamide is administered at about 300-700 mg/m²/day, or about 400-650 mg/m²/day, or about 450-600 mg/m²/day, or about 450-550 mg/m²/day, or about 490-550 mg/m²/day, or about 250 mg/m²/day; and the albumin-bound paclitaxel is administered at not higher than about 300 mg/m²/day, or not higher than about 200 mg/m²/day, or not higher than about 150 mg/m²/day, or not higher than about 100 mg/m²/day, or not higher than about 80 mg/m²/day, or not higher than about 70, 69, 68, 67, 66, 65, 64, 63, 62, or 61 mg/m²/day, or the albumin-bound paclitaxel is administered at 100 mg/m²/day.

18. The method of claim 17, wherein the fludarabine is administered at about 25 mg/m²/day for 2 days, the cyclophosphamide is administered at about 250 mg/m²/day for 3 days, and the albumin-bound paclitaxel is administered at 100 mg/m²/day or for one day.

19. The method of claim 1, wherein the chimeric antigen receptor comprises at least two or three intracellular signaling domains.

20. The method of claim 19, wherein the at least two or three intracellular signaling domains are selected from the group consisting of a signaling domain of TCRζ, FcRγ, FcRβ, CD3γ, CD3δ, CD3ε, CD3ζ, CDS, CD22, CD79a, CD79b, CD66d, CD28, CD137, OX40, DAP10, and ICOS.

\* \* \* \* \*

SEQUENCE LISTING

```
<160> NUMBER OF SEQ ID NOS: 68

<210> SEQ ID NO 1
<211> LENGTH: 6
<212> TYPE: PRT
<213> ORGANISM: Artificial sequence
<220> FEATURE:
<223> OTHER INFORMATION: Synthesized polypeptide

<400> SEQUENCE: 1

Ser Gly Tyr Asn Trp His
1               5

<210> SEQ ID NO 2
<211> LENGTH: 16
<212> TYPE: PRT
<213> ORGANISM: Artificial sequence
<220> FEATURE:
<223> OTHER INFORMATION: Synthesized polypeptide

<400> SEQUENCE: 2

Tyr Ile His Tyr Thr Gly Ser Thr Asn Tyr Asn Pro Ser Leu Arg Ser
1               5                   10                  15

<210> SEQ ID NO 3
<211> LENGTH: 9
<212> TYPE: PRT
```

```
<213> ORGANISM: Artificial sequence
<220> FEATURE:
<223> OTHER INFORMATION: Synthesized polypeptide

<400> SEQUENCE: 3

Ile Tyr Asn Gly Asn Ser Phe Pro Tyr
1               5

<210> SEQ ID NO 4
<211> LENGTH: 17
<212> TYPE: PRT
<213> ORGANISM: Artificial sequence
<220> FEATURE:
<223> OTHER INFORMATION: Synthesized polypeptide

<400> SEQUENCE: 4

Lys Ser Ser Gln Ser Leu Phe Asn Ser Gly Asn Gln Lys Asn Tyr Leu
1               5                   10                  15

Thr

<210> SEQ ID NO 5
<211> LENGTH: 7
<212> TYPE: PRT
<213> ORGANISM: Artificial sequence
<220> FEATURE:
<223> OTHER INFORMATION: Synthesized polypeptide

<400> SEQUENCE: 5

Trp Ala Ser Thr Arg Glu Ser
1               5

<210> SEQ ID NO 6
<211> LENGTH: 9
<212> TYPE: PRT
<213> ORGANISM: Artificial sequence
<220> FEATURE:
<223> OTHER INFORMATION: Synthesized polypeptide

<400> SEQUENCE: 6

Gln Asn Ala Tyr Ser Phe Pro Tyr Thr
1               5

<210> SEQ ID NO 7
<211> LENGTH: 16
<212> TYPE: PRT
<213> ORGANISM: Artificial sequence
<220> FEATURE:
<223> OTHER INFORMATION: Synthesized polypeptide

<400> SEQUENCE: 7

Tyr Ile His Tyr Thr Gly Ser Thr Asn Tyr Asn Pro Ala Leu Arg Ser
1               5                   10                  15

<210> SEQ ID NO 8
<211> LENGTH: 5
<212> TYPE: PRT
<213> ORGANISM: Artificial sequence
<220> FEATURE:
<223> OTHER INFORMATION: Synthesized polypeptide

<400> SEQUENCE: 8

Ser Tyr Thr Met His
1               5

<210> SEQ ID NO 9
<211> LENGTH: 17
```

```
<212> TYPE: PRT
<213> ORGANISM: Artificial sequence
<220> FEATURE:
<223> OTHER INFORMATION: Synthesized polypeptide

<400> SEQUENCE: 9

Tyr Ile Asn Pro Ser Ser Gly Tyr Thr Asn Tyr Asn Gln Lys Phe Lys
1               5                   10                  15

Asp

<210> SEQ ID NO 10
<211> LENGTH: 9
<212> TYPE: PRT
<213> ORGANISM: Artificial sequence
<220> FEATURE:
<223> OTHER INFORMATION: Synthesized polypeptide

<400> SEQUENCE: 10

Ile Tyr Tyr Gly Asn Ser Phe Ala Tyr
1               5

<210> SEQ ID NO 11
<211> LENGTH: 17
<212> TYPE: PRT
<213> ORGANISM: Artificial sequence
<220> FEATURE:
<223> OTHER INFORMATION: Synthesized polypeptide

<400> SEQUENCE: 11

Lys Ser Ser Gln Ser Leu Leu Asn Ser Gly Asn Gln Lys Asn Tyr Leu
1               5                   10                  15

Thr

<210> SEQ ID NO 12
<211> LENGTH: 7
<212> TYPE: PRT
<213> ORGANISM: Artificial sequence
<220> FEATURE:
<223> OTHER INFORMATION: Synthesized polypeptide

<400> SEQUENCE: 12

Trp Ala Ser Thr Arg Glu Ser
1               5

<210> SEQ ID NO 13
<211> LENGTH: 9
<212> TYPE: PRT
<213> ORGANISM: Artificial sequence
<220> FEATURE:
<223> OTHER INFORMATION: Synthesized polypeptide

<400> SEQUENCE: 13

Gln Asn Asp Tyr Ser Tyr Pro Leu Thr
1               5

<210> SEQ ID NO 14
<211> LENGTH: 118
<212> TYPE: PRT
<213> ORGANISM: Artificial sequence
<220> FEATURE:
<223> OTHER INFORMATION: Synthesized polypeptide

<400> SEQUENCE: 14

Gln Val Gln Leu Gln Glu Ser Gly Pro Gly Leu Ile Lys Pro Ser Gln
1               5                   10                  15
```

```
Thr Leu Ser Leu Thr Cys Thr Val Ser Gly Gly Ser Ile Ser Ser Gly
            20                  25                  30

Tyr Asn Trp His Trp Ile Arg Gln Pro Pro Gly Lys Gly Leu Glu Trp
        35                  40                  45

Ile Gly Tyr Ile His Tyr Thr Gly Ser Thr Asn Tyr Asn Pro Ala Leu
    50                  55                  60

Arg Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Ile Tyr Tyr Cys
                85                  90                  95

Ala Arg Ile Tyr Asn Gly Asn Ser Phe Pro Tyr Trp Gly Gln Gly Thr
            100                 105                 110

Thr Val Thr Val Ser Ser
            115
```

<210> SEQ ID NO 15
<211> LENGTH: 354
<212> TYPE: DNA
<213> ORGANISM: Artificial sequence
<220> FEATURE:
<223> OTHER INFORMATION: Synthesized polynucleotide

<400> SEQUENCE: 15

```
caggtgcagc tgcaggagag cggccccggc ctgatcaagc ccagccagac cctgagcctg      60
acctgcaccg tgagcggcgg cagcatcagc agcggctaca actggcactg gatccggcag     120
ccccccggca agggcctgga gtggatcggc tacatccact acaccggcag caccaactac     180
aaccccgccc tgcggagccg ggtgaccatc agcgtggaca ccagcaagaa ccagttcagc     240
ctgaagctga gcagcgtgac cgccgccgac accgccatct actactgcgc ccggatctac     300
aacggcaaca gcttccccta ctggggccag ggcaccaccg tgaccgtgag cagc           354
```

<210> SEQ ID NO 16
<211> LENGTH: 114
<212> TYPE: PRT
<213> ORGANISM: Artificial sequence
<220> FEATURE:
<223> OTHER INFORMATION: Synthesized polypeptide

<400> SEQUENCE: 16

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Ala Tyr Ser Phe Pro Tyr Thr Phe Gly Gly Gly Thr Lys Leu Glu Ile
            100                 105                 110

Lys Arg
```

<210> SEQ ID NO 17
<211> LENGTH: 342

<212> TYPE: DNA
<213> ORGANISM: Artificial sequence
<220> FEATURE:
<223> OTHER INFORMATION: Synthesized polynucleotide

<400> SEQUENCE: 17

```
gacatcgtga tgacccagag ccccgacagc ctggccgtga gcctgggcga gcgggccacc    60
atcaactgca agagcagcca gagcctgttc aacagcggca accagaagaa ctacctgacc   120
tggtaccagc agaagcccgg ccagcccccc aagctgctga tctactgggc cagcacccgg   180
gagagcggcg tgcccgaccg gttcagcggc agcggcagcg gcaccgactt caccctgacc   240
atcagcagcc tgcaggccga ggacgtggcc gtgtactact gccagaacgc ctacagcttc   300
ccctacacct tcggcggcgg caccaagctg gagatcaagc gg                      342
```

<210> SEQ ID NO 18
<211> LENGTH: 118
<212> TYPE: PRT
<213> ORGANISM: Artificial sequence
<220> FEATURE:
<223> OTHER INFORMATION: Synthesized polypeptide

<400> SEQUENCE: 18

```
Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
            20                  25                  30

Tyr Asn Trp His Trp Ile Arg Gln Pro Pro Gly Lys Gly Leu Glu Trp
        35                  40                  45

Ile Gly Tyr Ile His Tyr Thr Gly Ser Thr Asn Tyr Asn Pro Ala Leu
    50                  55                  60

Arg Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ile Tyr Asn Gly Asn Ser Phe Pro Tyr Trp Gly Gln Gly Thr
            100                 105                 110

Thr Val Thr Val Ser Ser
        115
```

<210> SEQ ID NO 19
<211> LENGTH: 354
<212> TYPE: DNA
<213> ORGANISM: Artificial sequence
<220> FEATURE:
<223> OTHER INFORMATION: Synthesized polynucleotide

<400> SEQUENCE: 19

```
caggtgcagc tgcaggagag cggccccggc ctggtgaagc ccagccagac cctgagcctg    60
acctgcaccg tgagcggcgg cagcatcagc agcggctaca actggcactg gatccggcag   120
ccccccggca agggcctgga gtggatcggc tacatccact acaccggcag caccaactac   180
aaccccgccc tgcggagccg ggtgaccatc agcgtggaca ccagcaagaa ccagttcagc   240
ctgaagctga gcagcgtgac cgccgccgac accgccgtgt actactgcgc ccggatctac   300
aacggcaaca gcttccccta ctggggccag ggcaccaccg tgaccgtgag cagc         354
```

<210> SEQ ID NO 20
<211> LENGTH: 114
<212> TYPE: PRT

```
<213> ORGANISM: Artificial sequence
<220> FEATURE:
<223> OTHER INFORMATION: Synthesized polypeptide

<400> SEQUENCE: 20
```

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Leu Thr Phe Gly Gly Gly Thr Lys Val Glu Ile
            100                 105                 110

Lys Arg

```
<210> SEQ ID NO 21
<211> LENGTH: 342
<212> TYPE: DNA
<213> ORGANISM: Artificial sequence
<220> FEATURE:
<223> OTHER INFORMATION: Synthesized polynucleotide

<400> SEQUENCE: 21
```
gacatcgtga tgacccagag ccccgacagc ctggccgtga gcctgggcga gcgggccacc      60
atcaactgca agagcagcca gagcctgctg aacagcggca accagaagaa ctacctgacc     120
tggtaccagc agaagcccgg ccagcccccc aagctgctga tctactgggc cagcacccgg     180
gagagcggcg tgcccgaccg gttcagcggc agcggcagcg gcaccgactt caccctgacc     240
atcagcagcc tgcaggccga ggacgtggcc gtgtactact gccagaacga ctacagctac     300
cccctgacct tcggcggcgg caccaaggtg gagatcaagc gg                        342

```
<210> SEQ ID NO 22
<211> LENGTH: 118
<212> TYPE: PRT
<213> ORGANISM: Artificial sequence
<220> FEATURE:
<223> OTHER INFORMATION: Synthesized polypeptide

<400> SEQUENCE: 22
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Thr Met His Trp Val Arg Gln Ala Pro Gly Gln Gly Leu Glu Trp Met
        35                  40                  45

Gly Tyr Ile Asn Pro Ala Ser Gly Tyr Thr Asn Tyr Asn Gln Lys Phe
    50                  55                  60

Lys Asp Arg Val Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Tyr Tyr Gly Asn Ser Phe Ala Tyr Trp Gly Gln Gly Thr
            100                 105                 110

Leu Val Thr Val Ser Ser
        115

<210> SEQ ID NO 23
<211> LENGTH: 354
<212> TYPE: DNA
<213> ORGANISM: Artificial sequence
<220> FEATURE:
<223> OTHER INFORMATION: Synthesized polynucleotide

<400> SEQUENCE: 23
caggtgcagc tggtgcagag cggcgccgag gtgaagaagc ccggcgccag cgtgaaggtg      60
agctgcaagg ccagcggcta caccttcacc agctacacca tgcactgggt gcggcaggcc     120
cccggccagg gcctggagtg gatgggctac atcaaccccg ccagcggcta caccaactac     180
aaccagaagt tcaaggaccg ggtgaccatg acccgggaca ccagcaccag caccgcctac     240
atggagctga gcagcctgcg gagcgaggac accgccgtgt actactgcgc ccggatctac     300
tacggcaaca gcttcgccta ctggggccag ggcaccctgg tgaccgtgag cagc           354

<210> SEQ ID NO 24
<211> LENGTH: 473
<212> TYPE: PRT
<213> ORGANISM: Artificial sequence
<220> FEATURE:
<223> OTHER INFORMATION: Synthesized polypeptide

<400> SEQUENCE: 24

Gln Val Gln Leu Gln Glu Ser Gly Pro Gly Leu Ile Lys Pro Ser Gln
1               5                   10                  15

Thr Leu Ser Leu Thr Cys Thr Val Ser Gly Gly Ser Ile Ser Ser Gly
            20                  25                  30

Tyr Asn Trp His Trp Ile Arg Gln Pro Pro Gly Lys Gly Leu Glu Trp
        35                  40                  45

Ile Gly Tyr Ile His Tyr Thr Gly Ser Thr Asn Tyr Asn Pro Ala Leu
    50                  55                  60

Arg Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Ile Tyr Tyr Cys
                85                  90                  95

Ala Arg Ile Tyr Asn Gly Asn Ser Phe Pro Tyr Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Asp Ile Val Met Thr Gln Ser Pro Asp Ser Leu
    130                 135                 140

Ala Val Ser Leu Gly Glu Arg Ala Thr Ile Asn Cys Lys Ser Ser Gln
145                 150                 155                 160

Ser Leu Phe Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Ser Gly Ser Gly Ser Gly Thr
        195                 200                 205

Asp Phe Thr Leu Thr Ile Ser Ser Leu Gln Ala Glu Asp Val Ala Val
    210                 215                 220

-continued

Tyr Tyr Cys Gln Asn Ala Tyr Ser Phe Pro Tyr Thr Phe Gly Gly Gly
225                 230                 235                 240

Thr Lys Leu Glu Ile Lys Arg Thr Thr Thr Pro Ala Pro Arg Pro Pro
            245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
            275                 280                 285

Phe Ala Cys Asp Phe Trp Val Leu Val Val Gly Val Leu Ala
290                 295                 300

Cys Tyr Ser Leu Leu Val Thr Val Ala Phe Ile Ile Phe Trp Val Arg
305                 310                 315                 320

Ser Lys Arg Ser Arg Leu Leu His Ser Asp Tyr Met Asn Met Thr Pro
            325                 330                 335

Arg Arg Pro Gly Pro Thr Arg Lys His Tyr Gln Pro Tyr Ala Pro Pro
            340                 345                 350

Arg Asp Phe Ala Ala Tyr Arg Ser Arg Val Lys Phe Ser Arg Ser Ala
            355                 360                 365

Asp Ala Pro Ala Tyr Gln Gln Gly Gln Asn Gln Leu Tyr Asn Glu Leu
370                 375                 380

Asn Leu Gly Arg Arg Glu Glu Tyr Asp Val Leu Asp Lys Arg Arg Gly
385                 390                 395                 400

Arg Asp Pro Glu Met Gly Gly Lys Pro Gln Arg Arg Lys Asn Pro Gln
            405                 410                 415

Glu Gly Leu Tyr Asn Glu Leu Gln Lys Asp Lys Met Ala Glu Ala Tyr
            420                 425                 430

Ser Glu Ile Gly Met Lys Gly Glu Arg Arg Arg Gly Lys Gly His Asp
            435                 440                 445

Gly Leu Tyr Gln Gly Leu Ser Thr Ala Thr Lys Asp Thr Tyr Asp Ala
450                 455                 460

Leu His Met Gln Ala Leu Pro Pro Arg
465                 470

<210> SEQ ID NO 25
<211> LENGTH: 471
<212> TYPE: PRT
<213> ORGANISM: Artificial sequence
<220> FEATURE:
<223> OTHER INFORMATION: Synthesized polypeptide

<400> SEQUENCE: 25

Gln Val Gln Leu Gln Glu Ser Gly Pro Gly Leu Ile Lys Pro Ser Gln
1               5                   10                  15

Thr Leu Ser Leu Thr Cys Thr Val Ser Gly Gly Ser Ile Ser Ser Gly
            20                  25                  30

Tyr Asn Trp His Trp Ile Arg Gln Pro Pro Gly Lys Gly Leu Glu Trp
        35                  40                  45

Ile Gly Tyr Ile His Tyr Thr Gly Ser Thr Asn Tyr Asn Pro Ala Leu
    50                  55                  60

Arg Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Ile Tyr Tyr Cys
                85                  90                  95

Ala Arg Ile Tyr Asn Gly Asn Ser Phe Pro Tyr Trp Gly Gln Gly Thr
            100                 105                 110

```
Thr Val Thr Val Ser Gly Gly Gly Gly Gly Gly Ser
        115                 120                 125

Gly Gly Gly Gly Ser Asp Ile Val Met Thr Gln Ser Pro Asp Ser Leu
130                 135                 140

Ala Val Ser Leu Gly Glu Arg Ala Thr Ile Asn Cys Lys Ser Ser Gln
145                 150                 155                 160

Ser Leu Phe Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Ser Gly Ser Gly Ser Gly Thr
        195                 200                 205

Asp Phe Thr Leu Thr Ile Ser Ser Leu Gln Ala Glu Asp Val Ala Val
    210                 215                 220

Tyr Tyr Cys Gln Asn Ala Tyr Ser Phe Pro Tyr Thr Phe Gly Gly Gly
225                 230                 235                 240

Thr Lys Leu Glu Ile Lys Arg Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
        275                 280                 285

Phe Ala Cys Asp Ile Tyr Ile Trp Ala Pro Leu Ala Gly Thr Cys Gly
    290                 295                 300

Val Leu Leu Leu Ser Leu Val Ile Thr Leu Tyr Cys Lys Arg Gly Arg
305                 310                 315                 320

Lys Lys Leu Leu Tyr Ile Phe Lys Gln Pro Phe Met Arg Pro Val Gln
                325                 330                 335

Thr Thr Gln Glu Glu Asp Gly Cys Ser Cys Arg Phe Pro Glu Glu Glu
            340                 345                 350

Glu Gly Gly Cys Glu Leu Arg Val Lys Phe Ser Arg Ser Ala Asp Ala
        355                 360                 365

Pro Ala Tyr Gln Gln Gly Gln Asn Gln Leu Tyr Asn Glu Leu Asn Leu
    370                 375                 380

Gly Arg Arg Glu Glu Tyr Asp Val Leu Asp Lys Arg Arg Gly Arg Asp
385                 390                 395                 400

Pro Glu Met Gly Gly Lys Pro Gln Arg Arg Lys Asn Pro Gln Glu Gly
                405                 410                 415

Leu Tyr Asn Glu Leu Gln Lys Asp Lys Met Ala Glu Ala Tyr Ser Glu
            420                 425                 430

Ile Gly Met Lys Gly Glu Arg Arg Arg Gly Lys Gly His Asp Gly Leu
        435                 440                 445

Tyr Gln Gly Leu Ser Thr Ala Thr Lys Asp Thr Tyr Asp Ala Leu His
    450                 455                 460

Met Gln Ala Leu Pro Pro Arg
465                 470

<210> SEQ ID NO 26
<211> LENGTH: 515
<212> TYPE: PRT
<213> ORGANISM: Artificial sequence
<220> FEATURE:
<223> OTHER INFORMATION: Synthesized polypeptide

<400> SEQUENCE: 26
```

Gln Val Gln Leu Gln Glu Ser Gly Pro Gly Leu Ile Lys Pro Ser Gln
1               5                   10                  15

Thr Leu Ser Leu Thr Cys Thr Val Ser Gly Gly Ser Ile Ser Ser Gly
            20                  25                  30

Tyr Asn Trp His Trp Ile Arg Gln Pro Pro Gly Lys Gly Leu Glu Trp
        35                  40                  45

Ile Gly Tyr Ile His Tyr Thr Gly Ser Thr Asn Tyr Asn Pro Ala Leu
50                  55                  60

Arg Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Ile Tyr Tyr Cys
                85                  90                  95

Ala Arg Ile Tyr Asn Gly Asn Ser Phe Pro Tyr Trp Gly Gln Gly Thr
                100                 105                 110

Thr Val Thr Val Ser Ser Gly Gly Gly Gly Ser Gly Gly Gly Gly Ser
            115                 120                 125

Gly Gly Gly Gly Ser Asp Ile Val Met Thr Gln Ser Pro Asp Ser Leu
130                 135                 140

Ala Val Ser Leu Gly Glu Arg Ala Thr Ile Asn Cys Lys Ser Ser Gln
145                 150                 155                 160

Ser Leu Phe Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
                180                 185                 190

Arg Glu Ser Gly Val Pro Asp Arg Phe Ser Gly Ser Gly Ser Gly Thr
                195                 200                 205

Asp Phe Thr Leu Thr Ile Ser Ser Leu Gln Ala Glu Asp Val Ala Val
        210                 215                 220

Tyr Tyr Cys Gln Asn Ala Tyr Ser Phe Pro Tyr Thr Phe Gly Gly Gly
225                 230                 235                 240

Thr Lys Leu Glu Ile Lys Arg Thr Thr Thr Pro Ala Pro Arg Pro Pro
                245                 250                 255

Thr Pro Ala Pro Thr Ile Ala Ser Gln Pro Leu Ser Leu Arg Pro Glu
                260                 265                 270

Ala Cys Arg Pro Ala Ala Gly Gly Ala Val His Thr Arg Gly Leu Asp
                275                 280                 285

Phe Ala Cys Asp Phe Trp Val Leu Val Val Val Gly Gly Val Leu Ala
        290                 295                 300

Cys Tyr Ser Leu Leu Val Thr Val Ala Phe Ile Ile Phe Trp Val Arg
305                 310                 315                 320

Ser Lys Arg Ser Arg Leu Leu His Ser Asp Tyr Met Asn Met Thr Pro
                325                 330                 335

Arg Arg Pro Gly Pro Thr Arg Lys His Tyr Gln Pro Tyr Ala Pro Pro
                340                 345                 350

Arg Asp Phe Ala Ala Tyr Arg Ser Lys Arg Gly Arg Lys Lys Leu Leu
                355                 360                 365

Tyr Ile Phe Lys Gln Pro Phe Met Arg Pro Val Gln Thr Thr Gln Glu
370                 375                 380

Glu Asp Gly Cys Ser Cys Arg Phe Pro Glu Glu Glu Glu Gly Gly Cys
385                 390                 395                 400

Glu Leu Arg Val Lys Phe Ser Arg Ser Ala Asp Ala Pro Ala Tyr Gln
                405                 410                 415

Gln Gly Gln Asn Gln Leu Tyr Asn Glu Leu Asn Leu Gly Arg Arg Glu
            420                 425                 430

Glu Tyr Asp Val Leu Asp Lys Arg Arg Gly Arg Asp Pro Glu Met Gly
            435                 440                 445

Gly Lys Pro Gln Arg Arg Lys Asn Pro Gln Glu Gly Leu Tyr Asn Glu
            450                 455                 460

Leu Gln Lys Asp Lys Met Ala Glu Ala Tyr Ser Glu Ile Gly Met Lys
465                 470                 475                 480

Gly Glu Arg Arg Arg Gly Lys Gly His Asp Gly Leu Tyr Gln Gly Leu
                485                 490                 495

Ser Thr Ala Thr Lys Asp Thr Tyr Asp Ala Leu His Met Gln Ala Leu
            500                 505                 510

Pro Pro Arg
        515

<210> SEQ ID NO 27
<211> LENGTH: 473
<212> TYPE: PRT
<213> ORGANISM: Artificial sequence
<220> FEATURE:
<223> OTHER INFORMATION: Synthesized polypeptide

<400> SEQUENCE: 27

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Tyr Asn Trp His Trp Ile Arg Gln Pro Pro Gly Lys Gly Leu Glu Trp
            35                  40                  45

Ile Gly Tyr Ile His Tyr Thr Gly Ser Thr Asn Tyr Asn Pro Ala Leu
    50                  55                  60

Arg Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ile Tyr Asn Gly Asn Ser Phe Pro Tyr Trp Gly Gln Gly Thr
            100                 105                 110

Thr Val Thr Val Ser Ser Gly Gly Gly Gly Ser Gly Gly Gly Gly Ser
            115                 120                 125

Gly Gly Gly Gly Ser Asp Ile Val Met Thr Gln Ser Pro Asp Ser Leu
        130                 135                 140

Ala Val Ser Leu Gly Glu Arg Ala Thr Ile Asn Cys Lys Ser Ser Gln
145                 150                 155                 160

Ser Leu Phe Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Ser Gly Ser Gly Ser Gly Thr
            195                 200                 205

Asp Phe Thr Leu Thr Ile Ser Ser Leu Gln Ala Glu Asp Val Ala Val
        210                 215                 220

Tyr Tyr Cys Gln Asn Ala Tyr Ser Phe Pro Tyr Thr Phe Gly Gly Gly
225                 230                 235                 240

Thr Lys Leu Glu Ile Lys Arg Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
            275                 280                 285

Phe Ala Cys Asp Phe Trp Val Leu Val Val Val Gly Gly Val Leu Ala
290                 295                 300

Cys Tyr Ser Leu Leu Val Thr Val Ala Phe Ile Ile Phe Trp Val Arg
305                 310                 315                 320

Ser Lys Arg Ser Arg Leu Leu His Ser Asp Tyr Met Asn Met Thr Pro
            325                 330                 335

Arg Arg Pro Gly Pro Thr Arg Lys His Tyr Gln Pro Tyr Ala Pro Pro
            340                 345                 350

Arg Asp Phe Ala Ala Tyr Arg Ser Arg Val Lys Phe Ser Arg Ser Ala
            355                 360                 365

Asp Ala Pro Ala Tyr Gln Gln Gly Gln Asn Gln Leu Tyr Asn Glu Leu
            370                 375                 380

Asn Leu Gly Arg Arg Glu Glu Tyr Asp Val Leu Asp Lys Arg Arg Gly
385                 390                 395                 400

Arg Asp Pro Glu Met Gly Gly Lys Pro Gln Arg Arg Lys Asn Pro Gln
            405                 410                 415

Glu Gly Leu Tyr Asn Glu Leu Gln Lys Asp Lys Met Ala Glu Ala Tyr
            420                 425                 430

Ser Glu Ile Gly Met Lys Gly Glu Arg Arg Arg Gly Lys Gly His Asp
            435                 440                 445

Gly Leu Tyr Gln Gly Leu Ser Thr Ala Thr Lys Asp Thr Tyr Asp Ala
            450                 455                 460

Leu His Met Gln Ala Leu Pro Pro Arg
465                 470

<210> SEQ ID NO 28
<211> LENGTH: 471
<212> TYPE: PRT
<213> ORGANISM: Artificial sequence
<220> FEATURE:
<223> OTHER INFORMATION: Synthesized polypeptide

<400> SEQUENCE: 28

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Tyr Asn Trp His Trp Ile Arg Gln Pro Pro Gly Lys Gly Leu Glu Trp
        35                  40                  45

Ile Gly Tyr Ile His Tyr Thr Gly Ser Thr Asn Tyr Asn Pro Ala Leu
    50                  55                  60

Arg Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ile Tyr Asn Gly Asn Ser Phe Pro Tyr Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Asp Ile Val Met Thr Gln Ser Pro Asp Ser Leu
    130                 135                 140

Ala Val Ser Leu Gly Glu Arg Ala Thr Ile Asn Cys Lys Ser Ser Gln
145                 150                 155                 160

Ser Leu Phe Asn Ser Gly Asn Gln Lys Asn Tyr Leu Thr Trp Tyr Gln
            165                 170                 175

Gln Lys Pro Gly Gln Pro Pro Lys Leu Leu Ile Tyr Trp Ala Ser Thr
        180                 185                 190

Arg Glu Ser Gly Val Pro Asp Arg Phe Ser Gly Ser Gly Ser Gly Thr
    195                 200                 205

Asp Phe Thr Leu Thr Ile Ser Ser Leu Gln Ala Glu Asp Val Ala Val
210                 215                 220

Tyr Tyr Cys Gln Asn Ala Tyr Ser Phe Pro Tyr Thr Phe Gly Gly Gly
225                 230                 235                 240

Thr Lys Leu Glu Ile Lys Arg Thr Thr Thr Pro Ala Pro Arg Pro Pro
            245                 250                 255

Thr Pro Ala Pro Thr Ile Ala Ser Gln Pro Leu Ser Leu Arg Pro Glu
        260                 265                 270

Ala Cys Arg Pro Ala Ala Gly Gly Ala Val His Thr Arg Gly Leu Asp
    275                 280                 285

Phe Ala Cys Asp Ile Tyr Ile Trp Ala Pro Leu Ala Gly Thr Cys Gly
290                 295                 300

Val Leu Leu Leu Ser Leu Val Ile Thr Leu Tyr Cys Lys Arg Gly Arg
305                 310                 315                 320

Lys Lys Leu Leu Tyr Ile Phe Lys Gln Pro Phe Met Arg Pro Val Gln
            325                 330                 335

Thr Thr Gln Glu Glu Asp Gly Cys Ser Cys Arg Phe Pro Glu Glu Glu
        340                 345                 350

Glu Gly Gly Cys Glu Leu Arg Val Lys Phe Ser Arg Ser Ala Asp Ala
    355                 360                 365

Pro Ala Tyr Gln Gln Gly Gln Asn Gln Leu Tyr Asn Glu Leu Asn Leu
370                 375                 380

Gly Arg Arg Glu Glu Tyr Asp Val Leu Asp Lys Arg Arg Gly Arg Asp
385                 390                 395                 400

Pro Glu Met Gly Gly Lys Pro Gln Arg Arg Lys Asn Pro Gln Glu Gly
            405                 410                 415

Leu Tyr Asn Glu Leu Gln Lys Asp Lys Met Ala Glu Ala Tyr Ser Glu
        420                 425                 430

Ile Gly Met Lys Gly Glu Arg Arg Arg Gly Lys Gly His Asp Gly Leu
    435                 440                 445

Tyr Gln Gly Leu Ser Thr Ala Thr Lys Asp Thr Tyr Asp Ala Leu His
450                 455                 460

Met Gln Ala Leu Pro Pro Arg
465                 470

<210> SEQ ID NO 29
<211> LENGTH: 515
<212> TYPE: PRT
<213> ORGANISM: Artificial sequence
<220> FEATURE:
<223> OTHER INFORMATION: Synthesized polypeptide

<400> SEQUENCE: 29

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

-continued

Tyr Asn Trp His Trp Ile Arg Gln Pro Pro Gly Lys Gly Leu Glu Trp
             35                  40                  45

Ile Gly Tyr Ile His Tyr Thr Gly Ser Thr Asn Tyr Asn Pro Ala Leu
 50                  55                  60

Arg Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Ile Tyr Asn Gly Asn Ser Phe Pro Tyr Trp Gly Gln Gly Thr
                100                 105                 110

Thr Val Thr Val Ser Ser Gly Gly Gly Gly Ser Gly Gly Gly Gly Ser
            115                 120                 125

Gly Gly Gly Gly Ser Asp Ile Val Met Thr Gln Ser Pro Asp Ser Leu
    130                 135                 140

Ala Val Ser Leu Gly Glu Arg Ala Thr Ile Asn Cys Lys Ser Ser Gln
145                 150                 155                 160

Ser Leu Phe Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Ser Gly Ser Gly Ser Gly Thr
        195                 200                 205

Asp Phe Thr Leu Thr Ile Ser Ser Leu Gln Ala Glu Asp Val Ala Val
    210                 215                 220

Tyr Tyr Cys Gln Asn Ala Tyr Ser Phe Pro Tyr Thr Phe Gly Gly Gly
225                 230                 235                 240

Thr Lys Leu Glu Ile Lys Arg Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
        275                 280                 285

Phe Ala Cys Asp Phe Trp Val Leu Val Val Val Gly Gly Val Leu Ala
    290                 295                 300

Cys Tyr Ser Leu Leu Val Thr Val Ala Phe Ile Ile Phe Trp Val Arg
305                 310                 315                 320

Ser Lys Arg Ser Arg Leu Leu His Ser Asp Tyr Met Asn Met Thr Pro
                325                 330                 335

Arg Arg Pro Gly Pro Thr Arg Lys His Tyr Gln Pro Tyr Ala Pro Pro
            340                 345                 350

Arg Asp Phe Ala Ala Tyr Arg Ser Lys Arg Gly Arg Lys Lys Leu Leu
        355                 360                 365

Tyr Ile Phe Lys Gln Pro Phe Met Arg Pro Val Gln Thr Thr Gln Glu
    370                 375                 380

Glu Asp Gly Cys Ser Cys Arg Phe Pro Glu Glu Glu Glu Gly Gly Cys
385                 390                 395                 400

Glu Leu Arg Val Lys Phe Ser Arg Ser Ala Asp Ala Pro Ala Tyr Gln
                405                 410                 415

Gln Gly Gln Asn Gln Leu Tyr Asn Glu Leu Asn Leu Gly Arg Arg Glu
            420                 425                 430

Glu Tyr Asp Val Leu Asp Lys Arg Arg Gly Arg Asp Pro Glu Met Gly
        435                 440                 445

Gly Lys Pro Gln Arg Arg Lys Asn Pro Gln Glu Gly Leu Tyr Asn Glu

```
            450                 455                 460
Leu Gln Lys Asp Lys Met Ala Glu Ala Tyr Ser Glu Ile Gly Met Lys
465                 470                 475                 480

Gly Glu Arg Arg Gly Lys Gly His Asp Gly Leu Tyr Gln Gly Leu
                485                 490                 495

Ser Thr Ala Thr Lys Asp Thr Tyr Asp Ala Leu His Met Gln Ala Leu
                500                 505                 510

Pro Pro Arg
        515

<210> SEQ ID NO 30
<211> LENGTH: 473
<212> TYPE: PRT
<213> ORGANISM: Artificial sequence
<220> FEATURE:
<223> OTHER INFORMATION: Synthesized polypeptide

<400> SEQUENCE: 30

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Thr Met His Trp Val Arg Gln Ala Pro Gly Gln Gly Leu Glu Trp Met
            35                  40                  45

Gly Tyr Ile Asn Pro Ala Ser Gly Tyr Thr Asn Tyr Asn Gln Lys Phe
        50                  55                  60

Lys Asp Arg Val Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Tyr Tyr Gly Asn Ser Phe Ala Tyr Trp Gly Gln Gly Thr
            100                 105                 110

Leu Val Thr Val Ser Ser Gly Gly Gly Ser Gly Gly Gly Gly Ser
        115                 120                 125

Gly Gly Gly Gly Ser Asp Ile Val Met Thr Gln Ser Pro Asp Ser Leu
130                 135                 140

Ala Val Ser Leu Gly Glu Arg Ala Thr Ile Asn Cys Lys Ser Ser Gln
145                 150                 155                 160

Ser Leu Leu Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Ser Gly Ser Gly Ser Gly Thr
        195                 200                 205

Asp Phe Thr Leu Thr Ile Ser Ser Leu Gln Ala Glu Asp Val Ala Val
    210                 215                 220

Tyr Tyr Cys Gln Asn Asp Tyr Ser Tyr Pro Leu Thr Phe Gly Gly Gly
225                 230                 235                 240

Thr Lys Val Glu Ile Lys Arg Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
        275                 280                 285

Phe Ala Cys Asp Phe Trp Val Leu Val Val Val Gly Gly Val Leu Ala
```

```
Cys Tyr Ser Leu Leu Val Thr Val Ala Phe Ile Ile Phe Trp Val Arg
305                 310                 315                 320

Ser Lys Arg Ser Arg Leu Leu His Ser Asp Tyr Met Asn Met Thr Pro
                325                 330                 335

Arg Arg Pro Gly Pro Thr Arg Lys His Tyr Gln Pro Tyr Ala Pro Pro
            340                 345                 350

Arg Asp Phe Ala Ala Tyr Arg Ser Arg Val Lys Phe Ser Arg Ser Ala
        355                 360                 365

Asp Ala Pro Ala Tyr Gln Gln Gly Gln Asn Gln Leu Tyr Asn Glu Leu
    370                 375                 380

Asn Leu Gly Arg Arg Glu Glu Tyr Asp Val Leu Asp Lys Arg Arg Gly
385                 390                 395                 400

Arg Asp Pro Glu Met Gly Gly Lys Pro Gln Arg Arg Lys Asn Pro Gln
                405                 410                 415

Glu Gly Leu Tyr Asn Glu Leu Gln Lys Asp Lys Met Ala Glu Ala Tyr
                420                 425                 430

Ser Glu Ile Gly Met Lys Gly Glu Arg Arg Arg Gly Lys Gly His Asp
            435                 440                 445

Gly Leu Tyr Gln Gly Leu Ser Thr Ala Thr Lys Asp Thr Tyr Asp Ala
        450                 455                 460

Leu His Met Gln Ala Leu Pro Pro Arg
465                 470

<210> SEQ ID NO 31
<211> LENGTH: 471
<212> TYPE: PRT
<213> ORGANISM: Artificial sequence
<220> FEATURE:
<223> OTHER INFORMATION: Synthesized polypeptide

<400> SEQUENCE: 31

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Thr Met His Trp Val Arg Gln Ala Pro Gly Gln Gly Leu Glu Trp Met
            35                  40                  45

Gly Tyr Ile Asn Pro Ala Ser Gly Tyr Thr Asn Tyr Asn Gln Lys Phe
        50                  55                  60

Lys Asp Arg Val Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Tyr Tyr Gly Asn Ser Phe Ala Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Asp Ile Val Met Thr Gln Ser Pro Asp Ser Leu
    130                 135                 140

Ala Val Ser Leu Gly Glu Arg Ala Thr Ile Asn Cys Lys Ser Ser Gln
145                 150                 155                 160

Ser Leu Leu Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
```

```
                180             185             190
Arg Glu Ser Gly Val Pro Asp Arg Phe Ser Gly Ser Gly Ser Gly Thr
            195                 200                 205

Asp Phe Thr Leu Thr Ile Ser Ser Leu Gln Ala Glu Asp Val Ala Val
210                 215                 220

Tyr Tyr Cys Gln Asn Asp Tyr Ser Tyr Pro Leu Thr Phe Gly Gly Gly
225                 230                 235                 240

Thr Lys Val Glu Ile Lys Arg Thr Thr Thr Pro Ala Pro Arg Pro Pro
            245                 250                 255

Thr Pro Ala Pro Thr Ile Ala Ser Gln Pro Leu Ser Leu Arg Pro Glu
        260                 265                 270

Ala Cys Arg Pro Ala Ala Gly Gly Ala Val His Thr Arg Gly Leu Asp
            275                 280                 285

Phe Ala Cys Asp Ile Tyr Ile Trp Ala Pro Leu Ala Gly Thr Cys Gly
        290                 295                 300

Val Leu Leu Leu Ser Leu Val Ile Thr Leu Tyr Cys Lys Arg Gly Arg
305                 310                 315                 320

Lys Lys Leu Leu Tyr Ile Phe Lys Gln Pro Phe Met Arg Pro Val Gln
            325                 330                 335

Thr Thr Gln Glu Glu Asp Gly Cys Ser Cys Arg Phe Pro Glu Glu Glu
        340                 345                 350

Glu Gly Gly Cys Glu Leu Arg Val Lys Phe Ser Arg Ser Ala Asp Ala
            355                 360                 365

Pro Ala Tyr Gln Gln Gly Gln Asn Gln Leu Tyr Asn Glu Leu Asn Leu
        370                 375                 380

Gly Arg Arg Glu Glu Tyr Asp Val Leu Asp Lys Arg Arg Gly Arg Asp
385                 390                 395                 400

Pro Glu Met Gly Gly Lys Pro Gln Arg Arg Lys Asn Pro Gln Glu Gly
            405                 410                 415

Leu Tyr Asn Glu Leu Gln Lys Asp Lys Met Ala Glu Ala Tyr Ser Glu
        420                 425                 430

Ile Gly Met Lys Gly Glu Arg Arg Arg Gly Lys Gly His Asp Gly Leu
            435                 440                 445

Tyr Gln Gly Leu Ser Thr Ala Thr Lys Asp Thr Tyr Asp Ala Leu His
        450                 455                 460

Met Gln Ala Leu Pro Pro Arg
465                 470

<210> SEQ ID NO 32
<211> LENGTH: 515
<212> TYPE: PRT
<213> ORGANISM: Artificial sequence
<220> FEATURE:
<223> OTHER INFORMATION: Synthesized polypeptide

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Thr Met His Trp Val Arg Gln Ala Pro Gly Gln Gly Leu Glu Trp Met
        35                  40                  45

Gly Tyr Ile Asn Pro Ala Ser Gly Tyr Thr Asn Tyr Asn Gln Lys Phe
    50                  55                  60

Lys Asp Arg Val Thr Met Thr Arg Asp Thr Ser Thr Ser Thr Ala Tyr
```

```
                65                  70                  75                  80
        Met Glu Leu Ser Ser Leu Arg Ser Glu Asp Thr Ala Val Tyr Tyr Cys
                            85                  90                  95

Ala Arg Ile Tyr Tyr Gly Asn Ser Phe Ala Tyr Trp Gly Gln Gly Thr
                        100                 105                 110

Leu Val Thr Val Ser Ser Gly Gly Gly Ser Gly Gly Gly Ser
                    115                 120                 125

Gly Gly Gly Gly Ser Asp Ile Val Met Thr Gln Ser Pro Asp Ser Leu
                130                 135                 140

Ala Val Ser Leu Gly Glu Arg Ala Thr Ile Asn Cys Lys Ser Ser Gln
        145                 150                 155                 160

Ser Leu Leu Asn Ser Gly Asn Gln Lys Asn Tyr Leu Thr Trp Tyr Gln
                        165                 170                 175

Gln Lys Pro Gly Gln Pro Pro Lys Leu Leu Ile Tyr Trp Ala Ser Thr
                    180                 185                 190

Arg Glu Ser Gly Val Pro Asp Arg Phe Ser Gly Ser Gly Ser Gly Thr
                195                 200                 205

Asp Phe Thr Leu Thr Ile Ser Ser Leu Gln Ala Glu Asp Val Ala Val
                210                 215                 220

Tyr Tyr Cys Gln Asn Asp Tyr Ser Tyr Pro Leu Thr Phe Gly Gly Gly
        225                 230                 235                 240

Thr Lys Val Glu Ile Lys Arg Thr Thr Thr Pro Ala Pro Arg Pro Pro
                        245                 250                 255

Thr Pro Ala Pro Thr Ile Ala Ser Gln Pro Leu Ser Leu Arg Pro Glu
                    260                 265                 270

Ala Cys Arg Pro Ala Ala Gly Gly Ala Val His Thr Arg Gly Leu Asp
                275                 280                 285

Phe Ala Cys Asp Phe Trp Val Leu Val Val Val Gly Gly Val Leu Ala
                290                 295                 300

Cys Tyr Ser Leu Leu Val Thr Val Ala Phe Ile Ile Phe Trp Val Arg
        305                 310                 315                 320

Ser Lys Arg Ser Arg Leu Leu His Ser Asp Tyr Met Asn Met Thr Pro
                        325                 330                 335

Arg Arg Pro Gly Pro Thr Arg Lys His Tyr Gln Pro Tyr Ala Pro Pro
                    340                 345                 350

Arg Asp Phe Ala Ala Tyr Arg Ser Lys Arg Gly Arg Lys Lys Leu Leu
                355                 360                 365

Tyr Ile Phe Lys Gln Pro Phe Met Arg Pro Val Gln Thr Thr Gln Glu
                370                 375                 380

Glu Asp Gly Cys Ser Cys Arg Phe Pro Glu Glu Glu Gly Gly Cys
        385                 390                 395                 400

Glu Leu Arg Val Lys Phe Ser Arg Ser Ala Asp Ala Pro Ala Tyr Gln
                        405                 410                 415

Gln Gly Gln Asn Gln Leu Tyr Asn Glu Leu Asn Leu Gly Arg Arg Glu
                    420                 425                 430

Glu Tyr Asp Val Leu Asp Lys Arg Arg Gly Arg Asp Pro Glu Met Gly
                435                 440                 445

Gly Lys Pro Gln Arg Arg Lys Asn Pro Gln Glu Gly Leu Tyr Asn Glu
                450                 455                 460

Leu Gln Lys Asp Lys Met Ala Glu Ala Tyr Ser Glu Ile Gly Met Lys
        465                 470                 475                 480

Gly Glu Arg Arg Arg Gly Lys Gly His Asp Gly Leu Tyr Gln Gly Leu
                        485                 490                 495
```

```
Ser Thr Ala Thr Lys Asp Thr Tyr Asp Ala Leu His Met Gln Ala Leu
            500                 505                 510

Pro Pro Arg
        515

<210> SEQ ID NO 33
<211> LENGTH: 261
<212> TYPE: PRT
<213> ORGANISM: Artificial sequence
<220> FEATURE:
<223> OTHER INFORMATION: Synthesized polypeptide

<400> SEQUENCE: 33

Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
        35                  40                  45

Leu Trp Arg Ser Cys Val Arg Glu Ser Ser Gly Phe Thr Glu Cys Arg
    50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260

<210> SEQ ID NO 34
<211> LENGTH: 261
<212> TYPE: PRT
<213> ORGANISM: Artificial sequence
<220> FEATURE:
<223> OTHER INFORMATION: Synthesized polypeptide

<400> SEQUENCE: 34

Met Ser Thr Thr Thr Cys Gln Val Val Ala Phe Leu Leu Ser Ile Leu
```

```
                1               5                  10                 15
            Gly Leu Ala Gly Cys Ile Ala Ala Thr Gly Met Asp Met Trp Ser Thr
                            20                  25                  30

Gln Asp Leu Tyr Asp Asn Pro Val Thr Ser Val Phe Gln Tyr Glu Gly
                        35                  40                  45

Leu Trp Arg Ser Cys Val Arg Gln Ser Ser Gly Phe Thr Glu Cys Arg
                50                  55                  60

Pro Tyr Phe Thr Ile Leu Gly Leu Pro Ala Met Leu Gln Ala Val Arg
            65                  70                  75                  80

Ala Leu Met Ile Val Gly Ile Val Leu Gly Ala Ile Gly Leu Leu Val
                            85                  90                  95

Ser Ile Phe Ala Leu Lys Cys Ile Arg Ile Gly Ser Met Glu Asp Ser
                            100                 105                 110

Ala Lys Ala Asn Met Thr Leu Thr Ser Gly Ile Met Phe Ile Val Ser
                        115                 120                 125

Gly Leu Cys Ala Ile Ala Gly Val Ser Val Phe Ala Asn Met Leu Val
                    130                 135                 140

Thr Asn Phe Trp Met Ser Thr Ala Asn Met Tyr Thr Gly Met Gly Gly
            145                 150                 155                 160

Met Val Gln Thr Val Gln Thr Arg Tyr Thr Phe Gly Ala Ala Leu Phe
                            165                 170                 175

Val Gly Trp Val Ala Gly Gly Leu Thr Leu Ile Gly Gly Val Met Met
                        180                 185                 190

Cys Ile Ala Cys Arg Gly Leu Ala Pro Glu Glu Thr Asn Tyr Lys Ala
                    195                 200                 205

Val Ser Tyr His Ala Ser Gly His Ser Val Ala Tyr Lys Pro Gly Gly
                210                 215                 220

Phe Lys Ala Ser Thr Gly Phe Gly Ser Asn Thr Lys Asn Lys Lys Ile
            225                 230                 235                 240

Tyr Asp Gly Gly Ala Arg Thr Glu Asp Glu Val Gln Ser Tyr Pro Ser
                            245                 250                 255

Lys His Asp Tyr Val
                        260

<210> SEQ ID NO 35
<211> LENGTH: 21
<212> TYPE: PRT
<213> ORGANISM: Artificial sequence
<220> FEATURE:
<223> OTHER INFORMATION: Synthesized polypeptide

<400> SEQUENCE: 35

Met Ala Leu Pro Val Thr Ala Leu Leu Leu Pro Leu Ala Leu Leu Leu
1               5                   10                  15

His Ala Ala Arg Pro
            20

<210> SEQ ID NO 36
<211> LENGTH: 63
<212> TYPE: DNA
<213> ORGANISM: Artificial sequence
<220> FEATURE:
<223> OTHER INFORMATION: Synthesized polynucleotide

<400> SEQUENCE: 36
atggccttac cagtgaccgc cttgctcctg ccgctggcct tgctgctcca cgccgccagg    60
ccg                                                                 63
```

<210> SEQ ID NO 37
<211> LENGTH: 45
<212> TYPE: PRT
<213> ORGANISM: Artificial sequence
<220> FEATURE:
<223> OTHER INFORMATION: Synthesized polypeptide

<400> SEQUENCE: 37

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 38
<211> LENGTH: 135
<212> TYPE: DNA
<213> ORGANISM: Artificial sequence
<220> FEATURE:
<223> OTHER INFORMATION: Synthesized polynucleotide

<400> SEQUENCE: 38
accacgacgc cagcgccgcg accaccaaca ccggcgccca ccatcgcgtc gcagcccctg      60
tccctgcgcc agaggcgtg ccggccagcg gcggggggcg cagtgcacac gaggggggctg    120 gacttcgcct gtgat                                                     135

<210> SEQ ID NO 39
<211> LENGTH: 27
<212> TYPE: PRT
<213> ORGANISM: Artificial sequence
<220> FEATURE:
<223> OTHER INFORMATION: Synthesized polypeptide

<400> SEQUENCE: 39

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 40
<211> LENGTH: 81
<212> TYPE: DNA
<213> ORGANISM: Artificial sequence
<220> FEATURE:
<223> OTHER INFORMATION: Synthesized polynucleotide

<400> SEQUENCE: 40
ttttgggtgc tggtggtggt tggtggagtc ctggcttgct atagcttgct agtaacagtg      60
gcctttatta ttttctgggt g                                                81

<210> SEQ ID NO 41
<211> LENGTH: 41
<212> TYPE: PRT
<213> ORGANISM: Artificial sequence
<220> FEATURE:
<223> OTHER INFORMATION: Synthesized polypeptide

<400> SEQUENCE: 41

Arg Ser Lys Arg Ser Arg Leu Leu His Ser Asp Tyr Met Asn Met Thr
1               5                   10                  15

```
Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40
```

<210> SEQ ID NO 42
<211> LENGTH: 123
<212> TYPE: DNA
<213> ORGANISM: Artificial sequence
<220> FEATURE:
<223> OTHER INFORMATION: Synthesized polynucleotide

<400> SEQUENCE: 42

```
aggagtaaga ggagcaggct cctgcacagt gactacatga acatgactcc ccgccgcccc    60
gggccaaccc gcaagcatta ccagccctat gccccaccac gcgacttcgc agcctatcgc   120
tcc                                                                 123
```

<210> SEQ ID NO 43
<211> LENGTH: 113
<212> TYPE: PRT
<213> ORGANISM: Artificial sequence
<220> FEATURE:
<223> OTHER INFORMATION: Synthesized polypeptide

<400> SEQUENCE: 43

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg
```

<210> SEQ ID NO 44
<211> LENGTH: 339
<212> TYPE: DNA
<213> ORGANISM: Artificial sequence
<220> FEATURE:
<223> OTHER INFORMATION: Synthesized polynucleotide

<400> SEQUENCE: 44

```
agagtgaagt tcagcaggag cgcagacgcc cccgcgtacc agcagggcca gaaccagctc    60
tataacgagc tcaatctagg acgaagagag gagtacgatg tttttggacaa gagacgtggc   120 cgggaccctg agatggggggg aaagccgcag agaaggaaga accctcagga aggcctgtac   180
aatgaactgc agaaagataa gatggcggag gcctacagtg agattgggat gaaaggcgag   240
cgccggaggg gcaaggggca cgatggcctt taccagggtc tcagtacagc caccaaggac   300
acctacgacg cccttcacat gcaggccctg cccctcgc                            339
```

<210> SEQ ID NO 45

<211> LENGTH: 24
<212> TYPE: PRT
<213> ORGANISM: Artificial sequence
<220> FEATURE:
<223> OTHER INFORMATION: Synthesized polypeptide

<400> SEQUENCE: 45

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 46
<211> LENGTH: 72
<212> TYPE: DNA
<213> ORGANISM: Artificial sequence
<220> FEATURE:
<223> OTHER INFORMATION: Synthesized polynucleotide

<400> SEQUENCE: 46
atctacatct gggcgccctt ggccgggact tgtggggtcc ttctcctgtc actggttatc    60 acccttact gc                                                         72

<210> SEQ ID NO 47
<211> LENGTH: 42
<212> TYPE: PRT
<213> ORGANISM: Artificial sequence
<220> FEATURE:
<223> OTHER INFORMATION: Synthesized polypeptide

<400> SEQUENCE: 47

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 48
<211> LENGTH: 126
<212> TYPE: DNA
<213> ORGANISM: Artificial sequence
<220> FEATURE:
<223> OTHER INFORMATION: Synthesized polynucleotide

<400> SEQUENCE: 48
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                              126

<210> SEQ ID NO 49
<211> LENGTH: 20
<212> TYPE: DNA
<213> ORGANISM: Artificial sequence
<220> FEATURE:
<223> OTHER INFORMATION: Synthesized polynucleotide

<400> SEQUENCE: 49
ctgagcagcg tgaccgccgc                                                20

<210> SEQ ID NO 50
<211> LENGTH: 20
<212> TYPE: DNA

<213> ORGANISM: Artificial sequence
<220> FEATURE:
<223> OTHER INFORMATION: Synthesized polynucleotide

<400> SEQUENCE: 50
tggagtggat cggctacatc					20

<210> SEQ ID NO 51
<211> LENGTH: 20
<212> TYPE: DNA
<213> ORGANISM: Artificial sequence
<220> FEATURE:
<223> OTHER INFORMATION: Synthesized polynucleotide

<400> SEQUENCE: 51
agtagtagat ggcggtgtcg					20

<210> SEQ ID NO 52
<211> LENGTH: 114
<212> TYPE: PRT
<213> ORGANISM: Artificial sequence
<220> FEATURE:
<223> OTHER INFORMATION: Synthesized polypeptide

<400> SEQUENCE: 52

Asp Ile Val Met Thr Gln Ser Pro Ser Ser Leu Thr Val Thr Pro Gly
1               5                   10                  15

Glu Lys Val Thr Met Thr Cys Lys Ser Ser Gln Ser Leu Phe Asn Ser
            20                  25                  30

Gly Asn Gln Lys Asn Tyr Leu Thr Trp Tyr Gln Gln Arg Pro Gly Gln
        35                  40                  45

Pro Pro Lys Met Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Phe Tyr Cys Gln Asn
                85                  90                  95

Ala Tyr Ser Phe Pro Tyr Thr Phe Gly Gly Gly Thr Lys Leu Glu Ile
            100                 105                 110

Lys Arg

<210> SEQ ID NO 53
<211> LENGTH: 118
<212> TYPE: PRT
<213> ORGANISM: Artificial sequence
<220> FEATURE:
<223> OTHER INFORMATION: Synthesized polypeptide

<400> SEQUENCE: 53

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Asn Trp His Trp Ile Arg Gln Phe Pro Gly Asn Lys Met Glu Trp
        35                  40                  45

Met Gly Tyr Ile His Tyr Thr Gly Ser Thr Asn Tyr Asn Pro Ser Leu
    50                  55                  60

Arg Ser Arg Ile Ser Ile Thr Arg Asp Thr Ser Lys Asn Gln Phe Phe
65                  70                  75                  80

Leu Gln Leu Asn Ser Val Thr Thr Asp Asp Thr Ala Thr Tyr Tyr Cys

```
                            85                  90                  95
Thr Arg Ile Tyr Asn Gly Asn Ser Phe Pro Tyr Trp Gly Gln Gly Thr
                100                 105                 110

Ser Val Thr Val Ser Ser
        115

<210> SEQ ID NO 54
<211> LENGTH: 247
<212> TYPE: PRT
<213> ORGANISM: Artificial sequence
<220> FEATURE:
<223> OTHER INFORMATION: Synthesized polypeptide

<400> SEQUENCE: 54

Gln Val Gln Leu Gln Glu Ser Gly Pro Gly Leu Ile Lys Pro Ser Gln
1               5                   10                  15

Thr Leu Ser Leu Thr Cys Thr Val Ser Gly Gly Ser Ile Ser Ser Gly
            20                  25                  30

Tyr Asn Trp His Trp Ile Arg Gln Pro Pro Gly Lys Gly Leu Glu Trp
        35                  40                  45

Ile Gly Tyr Ile His Tyr Thr Gly Ser Thr Asn Tyr Asn Pro Ala Leu
    50                  55                  60

Arg Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Ile Tyr Tyr Cys
                85                  90                  95

Ala Arg Ile Tyr Asn Gly Asn Ser Phe Pro Tyr Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Asp Ile Val Met Thr Gln Ser Pro Asp Ser Leu
    130                 135                 140

Ala Val Ser Leu Gly Glu Arg Ala Thr Ile Asn Cys Lys Ser Ser Gln
145                 150                 155                 160

Ser Leu Phe Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Ser Gly Ser Gly Ser Gly Thr
        195                 200                 205

Asp Phe Thr Leu Thr Ile Ser Ser Leu Gln Ala Glu Asp Val Ala Val
    210                 215                 220

Tyr Tyr Cys Gln Asn Ala Tyr Ser Phe Pro Tyr Thr Phe Gly Gly Gly
225                 230                 235                 240

Thr Lys Leu Glu Ile Lys Arg
                245

<210> SEQ ID NO 55
<211> LENGTH: 741
<212> TYPE: DNA
<213> ORGANISM: Artificial sequence
<220> FEATURE:
<223> OTHER INFORMATION: Synthesized polynucleotide

<400> SEQUENCE: 55
caggtgcagc tgcaggagag cggccccggc ctgatcaagc ccagccagac cctgagcctg     60
acctgcaccg tgagcggcgg cagcatcagc agcggctaca actggcactg gatccggcag    120
```

```
cccccggca   agggcctgga   gtggatcggc   tacatccact   acaccggcag   caccaactac    180
aaccccgccc  tgcggagccg   ggtgaccatc   agcgtggaca   ccagcaagaa   ccagttcagc    240
ctgaagctga  gcagcgtgac   cgccgccgac   accgccatct   actactgcgc   ccggatctac    300
aacggcaaca  gcttccccta   ctggggccag   ggcaccaccg   tgaccgtgag   cagcggtgga    360
ggcggttcag  gcggaggtgg   ttctggcggt   ggcggatcgg   acatcgtgat   gacccagagc    420
cccgacagcc  tggccgtgag   cctgggcgag   cgggccacca   tcaactgcaa   gagcagccag    480
agcctgttca  acagcggcaa   ccagaagaac   tacctgacct   ggtaccagca   gaagcccggc    540 cagccccca   agctgctgat   ctactgggcc   agcacccggg   agagcggcgt   gcccgaccgg    600
ttcagcggca  gcggcagcgg   caccgacttc   accctgacca   tcagcagcct   gcaggccgag    660
gacgtggccg  tgtactactg   ccagaacgcc   tacagcttcc   cctacacctt   cggcggcggc    720
accaagctgg  agatcaagcg   g                                                   741
```

<210> SEQ ID NO 56
<211> LENGTH: 247
<212> TYPE: PRT
<213> ORGANISM: Artificial sequence
<220> FEATURE:
<223> OTHER INFORMATION: Synthesized polypeptide

<400> SEQUENCE: 56

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Tyr Asn Trp His Trp Ile Arg Gln Pro Pro Gly Lys Gly Leu Glu Trp
        35                  40                  45

Ile Gly Tyr Ile His Tyr Thr Gly Ser Thr Asn Tyr Asn Pro Ala Leu
    50                  55                  60

Arg Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ile Tyr Asn Gly Asn Ser Phe Pro Tyr Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Asp Ile Val Met Thr Gln Ser Pro Asp Ser Leu
    130                 135                 140

Ala Val Ser Leu Gly Glu Arg Ala Thr Ile Asn Cys Lys Ser Ser Gln
145                 150                 155                 160

Ser Leu Phe Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Ser Gly Ser Gly Ser Gly Thr
        195                 200                 205

Asp Phe Thr Leu Thr Ile Ser Ser Leu Gln Ala Glu Asp Val Ala Val
    210                 215                 220

Tyr Tyr Cys Gln Asn Ala Tyr Ser Phe Pro Tyr Thr Phe Gly Gly Gly
225                 230                 235                 240

Thr Lys Leu Glu Ile Lys Arg
```

<210> SEQ ID NO 57
<211> LENGTH: 247
<212> TYPE: PRT
<213> ORGANISM: Artificial sequence
<220> FEATURE:
<223> OTHER INFORMATION: Synthesized polypeptide

<400> SEQUENCE: 57

```
Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Asn Trp His Trp Ile Arg Gln Phe Pro Gly Asn Lys Met Glu Trp
        35                  40                  45

Met Gly Tyr Ile His Tyr Thr Gly Ser Thr Asn Tyr Asn Pro Ser Leu
    50                  55                  60

Arg Ser Arg Ile Ser Ile Thr Arg Asp Thr Ser Lys Asn Gln Phe Phe
65                  70                  75                  80

Leu Gln Leu Asn Ser Val Thr Thr Asp Asp Thr Ala Thr Tyr Tyr Cys
                85                  90                  95

Thr Arg Ile Tyr Asn Gly Asn Ser Phe Pro Tyr Trp Gly Gln Gly Thr
            100                 105                 110

Ser Val Thr Val Ser Ser Gly Gly Gly Gly Ser Gly Gly Gly Gly Ser
        115                 120                 125

Gly Gly Gly Gly Ser Asp Ile Val Met Thr Gln Ser Pro Ser Ser Leu
    130                 135                 140

Thr Val Thr Pro Gly Glu Lys Val Thr Met Thr Cys Lys Ser Ser Gln
145                 150                 155                 160

Ser Leu Phe Asn Ser Gly Asn Gln Lys Asn Tyr Leu Thr Trp Tyr Gln
                165                 170                 175

Gln Arg Pro Gly Gln Pro Pro Lys Met Leu Ile Tyr Trp Ala Ser Thr
            180                 185                 190

Arg Glu Ser Gly Val Pro Asp Arg Phe Thr Gly Ser Gly Ser Gly Thr
        195                 200                 205

Asp Phe Thr Leu Thr Ile Ser Ser Val Gln Ala Glu Asp Leu Ala Val
    210                 215                 220

Phe Tyr Cys Gln Asn Ala Tyr Ser Phe Pro Tyr Thr Phe Gly Gly Gly
225                 230                 235                 240

Thr Lys Leu Glu Ile Lys Arg
                245
```

<210> SEQ ID NO 58
<211> LENGTH: 247
<212> TYPE: PRT
<213> ORGANISM: Artificial sequence
<220> FEATURE:
<223> OTHER INFORMATION: Synthesized polypeptide

<400> SEQUENCE: 58

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Thr Met His Trp Val Arg Gln Ala Pro Gly Gln Gly Leu Glu Trp Met
        35                  40                  45
```

Gly Tyr Ile Asn Pro Ala Ser Gly Tyr Thr Asn Tyr Asn Gln Lys Phe
            50                  55                  60

Lys Asp Arg Val Thr Met Thr Arg Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ile Tyr Tyr Gly Asn Ser Phe Ala Tyr Trp Gly Gln Gly Thr
            100                 105                 110

Leu Val Thr Val Ser Ser Gly Gly Gly Ser Gly Gly Gly Gly Ser
            115                 120                 125

Gly Gly Gly Gly Ser Asp Ile Val Met Thr Gln Ser Pro Asp Ser Leu
        130                 135                 140

Ala Val Ser Leu Gly Glu Arg Ala Thr Ile Asn Cys Lys Ser Ser Gln
145                 150                 155                 160

Ser Leu Leu Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Ser Gly Ser Gly Ser Gly Thr
        195                 200                 205

Asp Phe Thr Leu Thr Ile Ser Ser Leu Gln Ala Glu Asp Val Ala Val
210                 215                 220

Tyr Tyr Cys Gln Asn Asp Tyr Ser Tyr Pro Leu Thr Phe Gly Gly Gly
225                 230                 235                 240

Thr Lys Val Glu Ile Lys Arg
                245

<210> SEQ ID NO 59
<211> LENGTH: 27
<212> TYPE: PRT
<213> ORGANISM: Artificial sequence
<220> FEATURE:
<223> OTHER INFORMATION: Synthesized polypeptide

<400> SEQUENCE: 59

Met Ala Ser Pro Leu Thr Arg Phe Leu Ser Leu Asn Leu Leu Leu Leu
 1               5                  10                  15

Gly Glu Ser Ile Ile Leu Gly Ser Gly Glu Ala
            20                  25

<210> SEQ ID NO 60
<211> LENGTH: 81
<212> TYPE: DNA
<213> ORGANISM: Artificial sequence
<220> FEATURE:
<223> OTHER INFORMATION: Synthesized polynucleotide

<400> SEQUENCE: 60
atggcctcac cgttgacccg ctttctgtcg ctgaacctgc tgctgctggg tgagtcgatt      60
atcctgggga gtggagaagc t                                               81

<210> SEQ ID NO 61
<211> LENGTH: 72
<212> TYPE: PRT
<213> ORGANISM: Artificial sequence
<220> FEATURE:
<223> OTHER INFORMATION: Synthesized polypeptide

<400> SEQUENCE: 61

```
Thr Thr Thr Lys Pro Val Leu Arg Thr Pro Ser Pro Val His Pro Thr
1               5                   10                  15

Gly Thr Ser Gln Pro Gln Arg Pro Glu Asp Cys Arg Pro Arg Gly Ser
            20                  25                  30

Val Lys Gly Thr Gly Leu Asp Phe Ala Cys Asp Ile Tyr Ile Trp Ala
        35                  40                  45

Pro Leu Ala Gly Ile Cys Val Ala Leu Leu Leu Ser Leu Ile Ile Thr
    50                  55                  60

Leu Ile Cys Tyr His Arg Ser Arg
65                  70
```

<210> SEQ ID NO 62
<211> LENGTH: 216
<212> TYPE: DNA
<213> ORGANISM: Artificial sequence
<220> FEATURE:
<223> OTHER INFORMATION: Synthesized polynucleotide

<400> SEQUENCE: 62
actactacca agccagtgct gcgaactccc tcacctgtgc accctaccgg gacatctcag      60
ccccagagac cagaagattg tcggccccgt ggctcagtga aggggaccgg attggacttc    120
gcctgtgata tttacatctg gcacccttg gccggaatct gcgtggccct tctgctgtcc    180
ttgatcatca ctctcatctg ctaccacagg agccga                              216

<210> SEQ ID NO 63
<211> LENGTH: 45
<212> TYPE: PRT
<213> ORGANISM: Artificial sequence
<220> FEATURE:
<223> OTHER INFORMATION: Synthesized polypeptide

<400> SEQUENCE: 63

```
Lys Trp Ile Arg Lys Lys Phe Pro His Ile Phe Lys Gln Pro Phe Lys
1               5                   10                  15

Lys Thr Thr Gly Ala Ala Gln Glu Glu Asp Ala Cys Ser Cys Arg Cys
            20                  25                  30

Pro Gln Glu Glu Glu Gly Gly Gly Gly Gly Tyr Glu Leu
            35                  40                  45
```

<210> SEQ ID NO 64
<211> LENGTH: 135
<212> TYPE: DNA
<213> ORGANISM: Artificial sequence
<220> FEATURE:
<223> OTHER INFORMATION: Synthesized polynucleotide

<400> SEQUENCE: 64
aaatggatca ggaaaaaatt cccccacata ttcaagcaac catttaagaa gaccactgga      60
gcagctcaag aggaagatgc ttgtagctgc cgatgtccac aggaagaaga aggaggagga    120
ggaggctatg agctg                                                     135

<210> SEQ ID NO 65
<211> LENGTH: 107
<212> TYPE: PRT
<213> ORGANISM: Artificial sequence
<220> FEATURE:
<223> OTHER INFORMATION: Synthesized polypeptide

<400> SEQUENCE: 65

Ser Arg Ser Ala Glu Thr Ala Ala Asn Leu Gln Asp Pro Asn Gln Leu

```
1               5                   10                  15
Tyr Asn Glu Leu Asn Leu Gly Arg Arg Glu Glu Tyr Asp Val Leu Glu
            20                  25                  30

Lys Lys Arg Ala Arg Asp Pro Glu Met Gly Gly Lys Gln Gln Arg Arg
        35                  40                  45

Arg Asn Pro Gln Glu Gly Val Tyr Asn Ala Leu Gln Lys Asp Lys Met
    50                  55                  60

Ala Glu Ala Tyr Ser Glu Ile Gly Thr Lys Gly Glu Arg Arg Arg Gly
65                  70                  75                  80

Lys Gly His Asp Gly Leu Tyr Gln Gly Leu Ser Thr Ala Thr Lys Asp
                85                  90                  95

Thr Tyr Asp Ala Leu His Met Gln Thr Leu Ala
            100                 105
```

<210> SEQ ID NO 66
<211> LENGTH: 321
<212> TYPE: DNA
<213> ORGANISM: Artificial sequence
<220> FEATURE:
<223> OTHER INFORMATION: Synthesized polynucleotide

<400> SEQUENCE: 66

```
agcaggagtg cagagactgc tgccaacctg caggaccccca accagctcta caatgagctc    60
aatctagggc gaagagagga atatgacgtc ttggagaaga gcgggctcg ggatccagag     120
atgggaggca acagcagag gaggaggaac ccccaggaag gcgtatacaa tgcactgcag     180
aaagacaaga tggcagaagc ctacagtgag atcggcacaa aaggcgagag gcggagaggc    240
aaggggcacg atggccttta ccagggtctc agcactgcca ccaaggacac ctatgatgcc    300
ctgcatatgc agaccctggc c                                              321
```

<210> SEQ ID NO 67
<211> LENGTH: 795
<212> TYPE: DNA
<213> ORGANISM: Artificial sequence
<220> FEATURE:
<223> OTHER INFORMATION: Synthesized polynucleotide

<400> SEQUENCE: 67

```
atgtcggtga ccgcctgcca gggcttgggg tttgtggtgt cactgatcgg gtttgcgggc    60
atcattgcag ccacttgtat ggaccagtgg agcacccagg atttatacaa caacccggtg   120
accgctgtat tcaactacca agggctatgg cgttcatgcg tccgagagag ctctggcttc   180
accgagtgcc gaggctactt cacccctgttg gggttgccag ccatgctgca agctgtacga   240
gccctgatga tcgtgggcat tgttctgggg gtcatcggta tcctcgtgtc catcttcgcc   300
ctgaagtgca ttcgcattgg tagcatggat gactctgcca aggccaagat gactctgact   360
tctgggatct tgttcatcat ctccggcatc tgtgcaatca ttggtgtgtc tgtgtttgcc   420
aacatgctgg tgaccaactt ctggatgtcc acagctaaca tgtacagcgg catgggcggc   480
atgggtggca tggtgcagac cgttcagacc aggtacacct ttggtgcagc tctgttcgtg   540
ggctggttg ctggaggcct cacccctgatt ggggagtga tgatgtgcat cgcctgccgt   600
ggcctgacac cagatgacag caacttcaaa gctgtgtctt accatgcctc tggccaaaat   660
gttgcctaca ggcctggagg ctttaaggcc agcactggct ttgggtccaa caccagaaac   720
aagaagatct acgatggggg tgcccgcaca gaagacgatg aacagtctca tcctaccaag   780
tatgactatg tgtag                                                    795
```

```
<210> SEQ ID NO 68
<211> LENGTH: 17
<212> TYPE: PRT
<213> ORGANISM: Artificial sequence
<220> FEATURE:
<223> OTHER INFORMATION: Synthesized polypeptide

<400> SEQUENCE: 68

Tyr Ile Asn Pro Ala Ser Gly Tyr Thr Asn Tyr Asn Gln Lys Phe Lys
1               5                   10                  15

Asp
```